US009518083B2

(12) United States Patent
Franzoso et al.

(10) Patent No.: US 9,518,083 B2
(45) Date of Patent: *Dec. 13, 2016

(54) GADD45BETA TARGETING AGENTS

(71) Applicant: Imperial Innovations Limited, London (GB)

(72) Inventors: Guido Franzoso, London (GB); Albert Andrzej Jaxa-Chamiec, London (GB); Caroline Minli Rachel Low, London (GB); Simona Maria Monti, Naples (IT); Menotti Ruvo, Naples (IT); Laura Tornatore, London (GB); Catherine Jane Tralau-Stewart, London (GB)

(73) Assignee: Imperial Innovations Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/618,613

(22) Filed: Feb. 10, 2015

(65) Prior Publication Data

US 2015/0368294 A1    Dec. 24, 2015

Related U.S. Application Data

(63) Continuation of application No. 13/502,781, filed as application No. PCT/GB2010/001970 on Oct. 22, 2010, now Pat. No. 8,993,717.

(30) Foreign Application Priority Data

Oct. 22, 2009  (GB) ................................. 09185794

(51) Int. Cl.
| | |
|---|---|
| *A61K 38/00* | (2006.01) |
| *A61P 9/10* | (2006.01) |
| *A61P 27/02* | (2006.01) |
| *C07K 5/08* | (2006.01) |
| *C07K 5/065* | (2006.01) |
| *C07K 5/072* | (2006.01) |
| *C07K 5/087* | (2006.01) |
| *C07K 5/107* | (2006.01) |

(52) U.S. Cl.
CPC ............ *C07K 5/08* (2013.01); *C07K 5/06078* (2013.01); *C07K 5/06104* (2013.01); *C07K 5/06113* (2013.01); *C07K 5/0812* (2013.01); *C07K 5/1016* (2013.01); *A61K 38/00* (2013.01)

(58) Field of Classification Search
CPC ................................. A61K 38/00; A61K 8/64
See application file for complete search history.

(56) References Cited

U.S. PATENT DOCUMENTS

| 4,950,651 A | 8/1990 | Suli et al. |
|---|---|---|
| 2003/0077262 A1 | 4/2003 | Franzoso et al. |
| 2003/0162223 A1 | 8/2003 | Lowery et al. |
| 2004/0101916 A1 | 5/2004 | Yen |
| 2005/0265970 A1 | 12/2005 | Franzoso et al. |
| 2006/0166891 A1 | 7/2006 | Sircar et al. |
| 2007/0032430 A1 | 2/2007 | Fogelman et al. |
| 2008/0095821 A1 | 4/2008 | Fogelman et al. |
| 2008/0146496 A1 | 6/2008 | Haskell-Luevano |
| 2009/0312396 A1 | 12/2009 | Byth et al. |

FOREIGN PATENT DOCUMENTS

| CN | 101153053 | | 4/2008 | |
|---|---|---|---|---|
| EP | 1388537 | A1 | 2/2004 | |
| JP | 58-88349 | | 5/1983 | |
| JP | 2004-533846 | | 11/2004 | |
| JP | 2005-537465 | | 12/2005 | |
| JP | 2007-534612 | | 11/2007 | |
| WO | WO 03/006492 | A2 | 1/2003 | |
| WO | 2004013306 | A2 | 2/2004 | |
| WO | 2004094471 | A2 | 11/2004 | |
| WO | 2006049597 | A1 | 5/2006 | |
| WO | 2006074501 | A1 | 7/2006 | |
| WO | 2006086321 | A2 | 8/2006 | |
| WO | WO 2008021088 | A2 * | 2/2008 | ........... A61K 31/165 |
| WO | WO2008104387 | A2 | 9/2008 | |
| WO | 2009073725 | A2 | 6/2009 | |
| WO | WO2009099677 | A2 | 8/2009 | |
| WO | WO2011048390 | A2 | 4/2011 | |
| WO | WO2011147987 | A1 | 12/2011 | |

OTHER PUBLICATIONS

D'Angelo Velia et al., "High Erk-1 Activation and Gadd45a Expression as Prognostic Markers in High Risk Pediatric Haemolymphoproliferative Diseases," Journal of Experimental & Clinical Cancer Research, vol. 28, No. 1, Mar. 19, 2009, p. 39, XP021052996.

Zenmyo Michihisa et al., "Gadd45beta Expression in Chondrosarcoma: A Pilot Study for Diagnostic and Biological Implications in Histological Grading," Diagnostic Pathology, vol. 5, No. 1, Oct. 13, 2010, p. 69, XP021081043, Biomed Central Ltd., LO.

De Smaele Enrico et al., "Induction of Gadd45beta by NF-KappaB Downregulates Pro-Apoptotic JNK Signalling," Nature: International Weekly Jounal of Science, vol. 414, No. 6861, Nov. 15, 2001, pp. 308-313, XP002460070 Nature Publishing Group, United Kingdom.

Liebermann Dan A. et al., "Gadd45 Stress Sensors in Malignancy and Leukemia," PubMed Cental (PMC), Author Manuscript, Critical Reviews in Oncogenesis, vol. 16, No. 1-2, 2011, XP002685638.

International Search Report and Written Opinion, Application No. PCT/GB2012/050947, Date of Mailing Nov. 9, 2012.

(Continued)

*Primary Examiner* — Hasan Syed Ahmed
*Assistant Examiner* — Kaipeen Yang
(74) *Attorney, Agent, or Firm* — RatnerPrestia

(57) ABSTRACT

Compounds based around tetrapeptide, tripeptide and dipeptide moieties and corresponding peptiod moieties. Related methods and pharmaceutical compositions for use in treatment of cancer, inflammatory diseases, and other disorders.

2 Claims, 36 Drawing Sheets

(56) References Cited

OTHER PUBLICATIONS

Registry (STN) [online], CAS Registry No. 1196972-23-2; Nov. 12, 2009.
Registry (STN) [online], CAS Registry No. 1196971-47-7; Nov. 12, 2009.
del Mar Contreras M. et al. "Novel casein-derived peptides with antihypertensive activity" International Dairy Journal (2009) 19(10): 566-573.
Strøm M.B. et al. "The Pharmacophore of Short Cationic Antibacterial Peptides" Journal of Medicinal Chemistry (2003) 46(9): 1567-1570.
Gao Y. et al. "Structure-activity relationship of the novel bivalent and C-terminal modified analogues of endomorphin-2" Bioorganic & Medicinal Chemistry Letters (2005) 15(7): 1847-1850.
Fujikawa M. et al. "QSAR study on permeability of hydrophobic compounds with artificial membranes" Bioorganic & Medicinal Chemistry (2007) 15(11): 3756-3767.
Vig B.S. et al. "Human PEPT1 Pharmacophore Distinguishes between Dipeptide Transport and Binding" J. Med. Chem. (2006) 49(12): 3636-3644.
Holmes D.F. et al. "The Use of l-Menthoxyacetyl Chloride for the Resolution of Amino Acids" Journal of the American Chemical Society (1934) 56(10): 2093-2094.
Chen Y.-J. et al. "Highly diastereoselective synthesis of arylglycine derivatives via TFA-promoted Friedel-Crafts reactions of phenols with cyclic glyoxylate imines" Tetrahedron (2003) 59(38): 7609-7614.
Papa S. et al. "Insights into the Structural Basis of the GADD45β-mediated Inactivation of the JNK Kinase, MKK7/JNKK2" Journal of Biological Chemistry (2007) 282(26): 19029-19041.
Australian Search Report; Application No. 2010309594, issued May 28, 2015.
Takedatsu Hiroko et al., "Immunological evaluation of vaccination of peptides derived from epithelial cancer-related antigens in two patients with hematological malignancy," International Journal of Oncology Jun. 2005, vol. 26, No. 6, Jun. 1, 2005, pp. 1605-1612, XP008171531, ISSN: 1019-6439.
Eriksson B. et al., "High-dose treatment with lanreotide of patients with advanced neuroendocrine gastrointestinal tumors: Clinical and biological effects," Annals of Oncology, Oxford University Press, GB vol. 8 No. 10, Oct. 1, 1997, pp. 1041-1044, XP019228669, ISSN: 1569-8041, DOI: 10.1023/A:1008205415035.
Araya et al., "Antitumor effects of cationic synthetic peptides derived from Lys49 phospholipase A2 homologues of snake venoms," Cell Biology International, Academic Press, GB, vol. 31, No. 3, Feb. 21, 2007, pp. 263-268, XP005894319, ISSN: 1065-6995, DOI:10.1016/J.Cellbi. Nov. 7, 2006.
Carsten Grundker et al., "Gonadotropin-releasing hormone receptor-targeted gene therapy of gynecologic cancers," Molecular Cancer Therapeutics, vol. 4, No. 2, Feb. 1, 2005, pp. 225-231, XP55136542, ISSN: 1535-7163.
European Search Report Application No. 10781977.3, Date Feb. 9, 2014.
Registry (STN) [online], CAS Registry No. 41046-26-8; Nov. 16, 1984.
Registry (STN) [online], CAS Registry No. 42166-92-7; Nov. 16, 1984.
Registry (STN) [online], CAS Registry No. 122978-92-1; Sep. 29, 1989.
Registry (STN) [online], CAS Registry No. 132144-98-0; Feb. 15, 1991.
Registry (STN) [online], CAS Registry No. 138771-70-7; Feb. 7, 1992.
Registry (STN) [online], CAS Registry No. 138771-71-8; Feb. 7, 1992.
Registry (STN) [online], CAS Registry No. 138771-72-9; Feb. 7, 1992.
Registry (STN) [online], CAS Registry No. 138771-73-0; Feb. 7, 1992.
Registry (STN) [online], CAS Registry No. 138848-28-9; Feb. 7, 1992.
Registry (STN) [online], CAS Registry No. 140834-76-0; Apr. 26, 1992.
Registry (STN) [online], CAS Registry No. 140835-00-3; Apr. 26, 1992.
Registry (STN) [online], CAS Registry No. 140835-01-4; Apr. 26, 1992.
Registry (STN) [online], CAS Registry No. 141238-41-7; May 8, 1992.
Registry (STN) [online], CAS Registry No. 141238-42-8; May 8, 1992.
Registry (STN) [online], CAS Registry No. 167773-77-5; Sep. 15, 1995.
Registry (STN) [online], CAS Registry No. 167773-78-6; Sep. 15, 1995.
Registry (STN) [online], CAS Registry No. 167983-61-1; Sep. 22, 1995.
Registry (STN) [online], CAS Registry No. 168110-38-1; Sep. 28, 1995.
Registry (STN) [online], CAS Registry No. 168110-40-5; Sep. 28, 1995.
Registry (STN) [online], CAS Registry No. 168251-73-8; Oct. 3, 1995.
Registry (STN) [online], CAS Registry No. 169029-50-9; Oct. 18, 1995.
Registry (STN) [online], CAS Registry No. 169107-06-6; Oct. 19, 1995.
Registry (STN) [online], CAS Registry No. 177959-01-2; Jul. 2, 1996.
Registry (STN) [online], CAS Registry No. 177959-06-7; Jul. 2, 1996.
Registry (STN) [online], CAS Registry No. 178207-54-0; Jul. 10, 1996.
Registry (STN) [online], CAS Registry No. 178207-56-2, Jul. 10, 1996.
Registry (STN) [online], CAS Registry No. 179383-68-7; Aug. 9, 1996.
Registry (STN) [online], CAS Registry No. 182687-56-5; Nov. 5, 1996.
Registry (STN) [online], CAS Registry No. 182637-60-1; Nov. 5, 1996.
Registry (STN) [online], CAS Registry No. 183238-18-8; Nov. 21, 1996.
Registry (STN) [online], CAS Registry No. 183238-21-3; Nov. 21, 1996.
Registry (STN) [online], CAS Registry No. 183238-22-4; Nov. 21, 1996.
Registry (STN) [online], CAS Registry No. 183238-23-5; Nov. 21, 1996.
Registry (STN) [online], CAS Registry No. 183238-24-6; Nov. 21, 1996.
Registry (STN) [online], CAS Registry No. 184713-36-8; Jan. 7, 1997.
Registry (STN) [online], CAS Registry No. 184713-41-5; Jan. 7, 1997.
Registry (STN) [online], CAS Registry No. 184713-42-6; Jan. 7, 1997.
Registry (STN) [online], CAS Registry No. 186086-95-3; Feb. 13, 1997.
Registry (STN) [online], CAS Registry No. 217958-93-5; Jan. 24, 1999.
Registry (STN) [online], CAS Registry No. 219902-63-3; Feb. 23, 1999.
Registry (STN) [online], CAS Registry No. 239119-74-5; Sep. 15, 1999.
Registry (STN) [online], CAS Registry No. 321180-15-8; Feb. 9, 2001.
Registry (STN) [online], CAS Registry No. 321180-17-0; Feb. 9, 2001.
Registry (STN) [online], CAS Registry No. 475497-49-5; Dec. 9, 2002.

(56) References Cited

OTHER PUBLICATIONS

Registry (STN) [online], CAS Registry No. 475497-73-5; Dec. 9, 2002.
Registry (STN) [online], CAS Registry No. 475497-97-3; Dec. 9, 2002.
Registry (STN) [online], CAS Registry No. 475498-21-6; Dec. 9, 2002.
Registry (STN) [online], CAS Registry No. 475499-09-3; Dec. 9, 2002.
Registry (STN) [online], CAS Registry No. 475499-81-1; Dec. 9, 2002.
Registry (STN) [online], CAS Registry No. 909032-36-6; Sep. 28, 2006.
Lin et al., Can J. Physiol Pharmacol, 82:1018-25 (2004).
Tornatore et al., Cancer Cell, 26:495-508 (2014).
Watanabe et al., Oral Therapeutics and Pharmacology, 22(1):25-31 (2003).

* cited by examiner

A

B

C

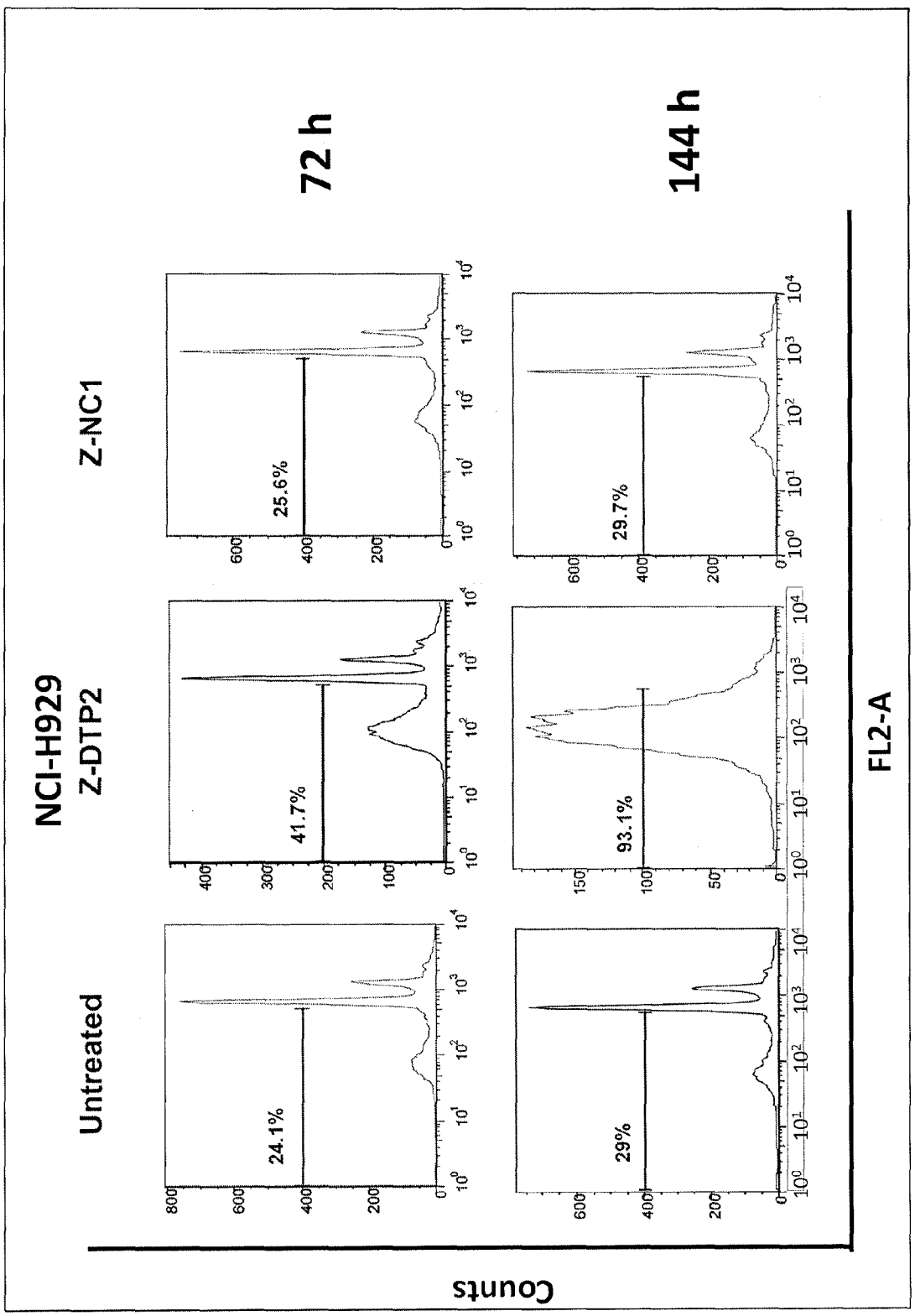

A

B

C

A

B

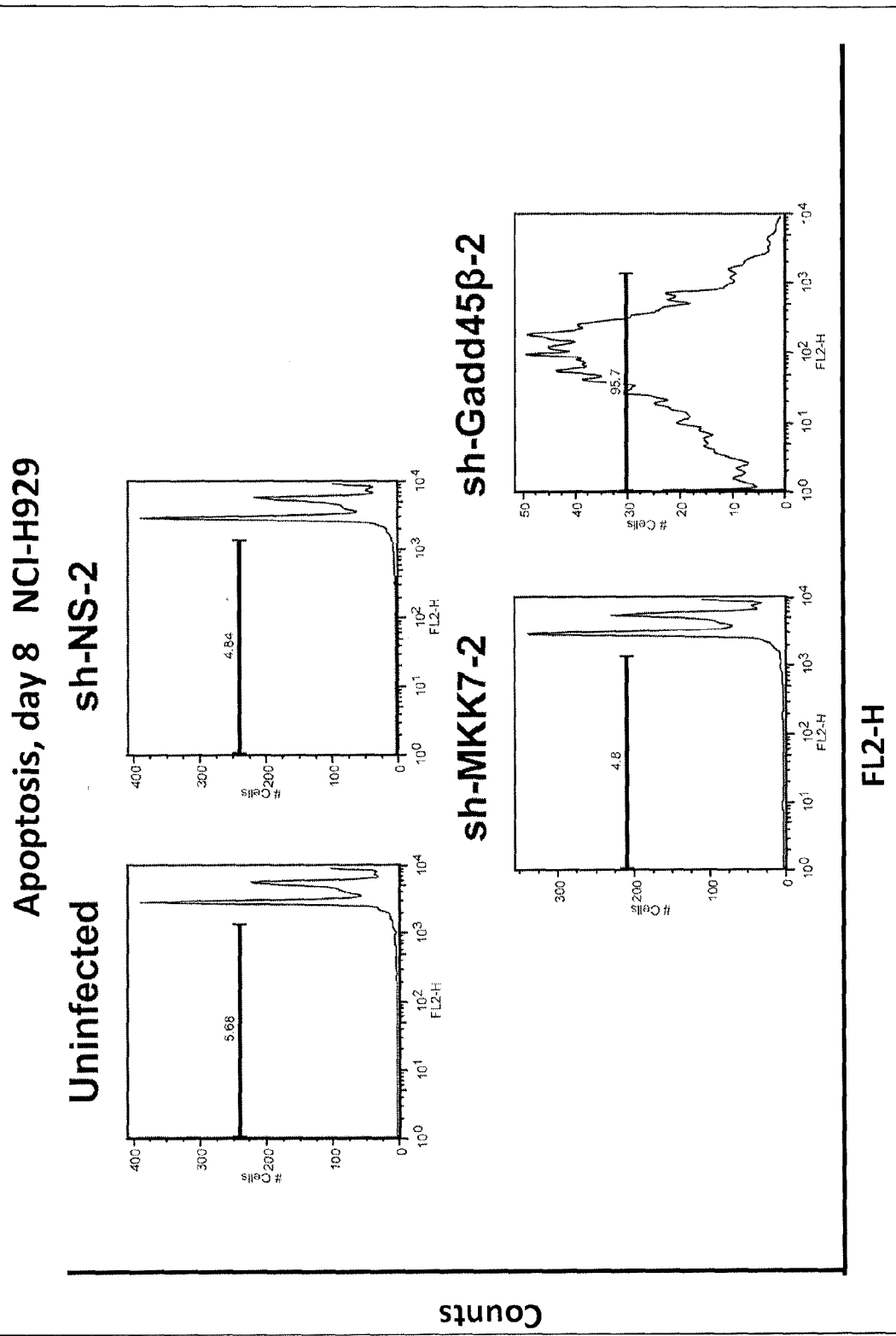

Cell Cycle, day 8  NCI-H929

Uninfected sh-NS-2 sh-MKK7-2

SEQUENCE LISTING

```
<160> NUMBER OF SEQ ID NOS: 227

<210> SEQ ID NO 1
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: residues 1 - 4 are D-amino acids
<220> FEATURE:
<221> NAME/KEY: MOD_RES
<222> LOCATION: (1)..(1)
<223> OTHER INFORMATION: benzyloxycarbonyl N-terminal group
<220> FEATURE:
<221> NAME/KEY: MOD_RES
<222> LOCATION: (4)..(4)
<223> OTHER INFORMATION: AMINATION

<400> SEQUENCE: 1

Tyr Glu Arg Phe
1

<210> SEQ ID NO 2
<211> LENGTH: 4
<212> TYPE: PRT
<213> ORGANISM: artificial sequence
<220> FEATURE:
<223> OTHER INFORMATION: therapeutic agent

<400> SEQUENCE: 2

Tyr Asp His Phe
1

<210> SEQ ID NO 3
<211> LENGTH: 4
<212> TYPE: PRT
<213> ORGANISM: artificial sequence
<220> FEATURE:
<223> OTHER INFORMATION: therapeutic agent

<400> SEQUENCE: 3

Tyr Glu Arg Phe
1

<210> SEQ ID NO 4
<211> LENGTH: 4
<212> TYPE: PRT
<213> ORGANISM: artificial sequence
<220> FEATURE:
<223> OTHER INFORMATION: therapeutic agent

<400> SEQUENCE: 4
```

Tyr Glu His Phe
1

<210> SEQ ID NO 5
<211> LENGTH: 4
<212> TYPE: PRT
<213> ORGANISM: artificial sequence
<220> FEATURE:
<223> OTHER INFORMATION: therapeutic agent

<400> SEQUENCE: 5

Trp Asp His Phe
1

<210> SEQ ID NO 6
<211> LENGTH: 4
<212> TYPE: PRT
<213> ORGANISM: artificial sequence
<220> FEATURE:
<223> OTHER INFORMATION: therapeutic agent

<400> SEQUENCE: 6

Trp Glu His Phe
1

<210> SEQ ID NO 7
<211> LENGTH: 4
<212> TYPE: PRT
<213> ORGANISM: artificial sequence
<220> FEATURE:
<223> OTHER INFORMATION: therapeutic agent

<400> SEQUENCE: 7

Tyr Asp Arg Phe
1

<210> SEQ ID NO 8
<211> LENGTH: 4
<212> TYPE: PRT
<213> ORGANISM: artificial sequence
<220> FEATURE:
<223> OTHER INFORMATION: therapeutic agent

<400> SEQUENCE: 8

Tyr Asp Lys Phe
1

<210> SEQ ID NO 9
<211> LENGTH: 4
<212> TYPE: PRT
<213> ORGANISM: artificial sequence
<220> FEATURE:
<223> OTHER INFORMATION: therapeutic agent

<400> SEQUENCE: 9

Tyr Glu Lys Phe
1

<210> SEQ ID NO 10
<211> LENGTH: 4
<212> TYPE: PRT
<213> ORGANISM: artificial sequence
<220> FEATURE:
<223> OTHER INFORMATION: therapeutic agent

<400> SEQUENCE: 10

Trp Glu Lys Phe
1

<210> SEQ ID NO 11
<211> LENGTH: 4
<212> TYPE: PRT
<213> ORGANISM: artificial sequence
<220> FEATURE:
<223> OTHER INFORMATION: therapeutic agent

<400> SEQUENCE: 11

Trp Glu Arg Phe
1

<210> SEQ ID NO 12
<211> LENGTH: 4
<212> TYPE: PRT
<213> ORGANISM: artificial sequence
<220> FEATURE:
<223> OTHER INFORMATION: therapeutic agent

<400> SEQUENCE: 12

Trp Asp Lys Phe
1

<210> SEQ ID NO 13
<211> LENGTH: 4
<212> TYPE: PRT
<213> ORGANISM: artificial sequence
<220> FEATURE:
<223> OTHER INFORMATION: therapeutic agent

<400> SEQUENCE: 13

Trp Asp Arg Phe
1

<210> SEQ ID NO 14
<211> LENGTH: 4
<212> TYPE: PRT
<213> ORGANISM: artificial sequence
<220> FEATURE:
<223> OTHER INFORMATION: therapeutic agent

<400> SEQUENCE: 14

Tyr Asp His Trp
1

<210> SEQ ID NO 15
<211> LENGTH: 4
<212> TYPE: PRT
<213> ORGANISM: artificial sequence
<220> FEATURE:
<223> OTHER INFORMATION: therapeutic agent

<400> SEQUENCE: 15

Tyr Glu His Trp
1

<210> SEQ ID NO 16
<211> LENGTH: 4
<212> TYPE: PRT
<213> ORGANISM: artificial sequence
<220> FEATURE:
<223> OTHER INFORMATION: therapeutic agent

<400> SEQUENCE: 16

Trp Asp His Trp

```
<210> SEQ ID NO 17
<211> LENGTH: 4
<212> TYPE: PRT
<213> ORGANISM: artificial sequence
<220> FEATURE:
<223> OTHER INFORMATION: therapeutic agent

<400> SEQUENCE: 17

Trp Glu His Trp
1

<210> SEQ ID NO 18
<211> LENGTH: 4
<212> TYPE: PRT
<213> ORGANISM: artificial sequence
<220> FEATURE:
<223> OTHER INFORMATION: therapeutic agent

<400> SEQUENCE: 18

Tyr Asp Arg Trp
1

<210> SEQ ID NO 19
<211> LENGTH: 4
<212> TYPE: PRT
<213> ORGANISM: artificial sequence
<220> FEATURE:
<223> OTHER INFORMATION: therapeutic agent

<400> SEQUENCE: 19

Tyr Asp Lys Trp
1

<210> SEQ ID NO 20
<211> LENGTH: 4
<212> TYPE: PRT
<213> ORGANISM: artificial sequence
<220> FEATURE:
<223> OTHER INFORMATION: therapeutic agent

<400> SEQUENCE: 20

Tyr Glu Lys Trp
1

<210> SEQ ID NO 21
<211> LENGTH: 4
<212> TYPE: PRT
<213> ORGANISM: artificial sequence
<220> FEATURE:
<223> OTHER INFORMATION: therapeutic agent

<400> SEQUENCE: 21

Tyr Glu Arg Trp
1

<210> SEQ ID NO 22
<211> LENGTH: 4
<212> TYPE: PRT
<213> ORGANISM: artificial sequence
<220> FEATURE:
<223> OTHER INFORMATION: therapeutic agent

<400> SEQUENCE: 22

Trp Glu Lys Trp
1
```

```
<210> SEQ ID NO 23
<211> LENGTH: 4
<212> TYPE: PRT
<213> ORGANISM: artificial sequence
<220> FEATURE:
<223> OTHER INFORMATION: therapeutic agent

<400> SEQUENCE: 23

Trp Glu Arg Trp
1

<210> SEQ ID NO 24
<211> LENGTH: 4
<212> TYPE: PRT
<213> ORGANISM: artificial sequence
<220> FEATURE:
<223> OTHER INFORMATION: therapeutic agent

<400> SEQUENCE: 24

Trp Asp Lys Trp
1

<210> SEQ ID NO 25
<211> LENGTH: 4
<212> TYPE: PRT
<213> ORGANISM: artificial sequence
<220> FEATURE:
<223> OTHER INFORMATION: therapeutic agent

<400> SEQUENCE: 25

Trp Asp Lys Trp
1

<210> SEQ ID NO 26
<211> LENGTH: 4
<212> TYPE: PRT
<213> ORGANISM: artificial sequence
<220> FEATURE:
<223> OTHER INFORMATION: therapeutic agent

<400> SEQUENCE: 26

Tyr Asp His Tyr
1

<210> SEQ ID NO 27
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: residues 1 - 4 are D-amino acids

<400> SEQUENCE: 27

Tyr Glu Arg Phe
1

<210> SEQ ID NO 28
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
```

-continued

<222> LOCATION: (1)..(4)
<223> OTHER INFORMATION: residues 1 - 4 are D-amino acids

<400> SEQUENCE: 28

Tyr Asp His Phe
1

<210> SEQ ID NO 29
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: residues 1 - 4 are D-amino acids

<400> SEQUENCE: 29

Trp Glu Arg Phe
1

<210> SEQ ID NO 30
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: misc_feature
<222> LOCATION: (1)..(4)
<223> OTHER INFORMATION: residues 1 - 4 are D-amino acids

<400> SEQUENCE: 30

Trp Glu His Phe
1

<210> SEQ ID NO 31
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: misc_feature
<222> LOCATION: (1)..(4)
<223> OTHER INFORMATION: residues 1 - 4 are D-amino acids

<400> SEQUENCE: 31

Tyr Asp Arg Phe
1

<210> SEQ ID NO 32
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: residues 1 - 4 are D-amino acids

<400> SEQUENCE: 32

Tyr Asp His Tyr
1

<210> SEQ ID NO 33
<211> LENGTH: 4

```
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: residues 1 - 4 are D-amino acids

<400> SEQUENCE: 33

Tyr Glu Arg Tyr
1

<210> SEQ ID NO 34
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: residues 1 - 4 are D-amino acids

<400> SEQUENCE: 34

Trp Asp His Phe
1

<210> SEQ ID NO 35
<211> LENGTH: 4
<212> TYPE: PRT
<213> ORGANISM: artificial sequence
<220> FEATURE:
<223> OTHER INFORMATION: therapeutic sequence
<220> FEATURE:
<221> NAME/KEY: MISC_FEATURE
<222> LOCATION: (1)..(4)
<223> OTHER INFORMATION: residues 1 - 4 are D-amino acids

<400> SEQUENCE: 35

Trp Glu Arg Phe
1

<210> SEQ ID NO 36
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: residues 1 - 4 are D-amino acids

<400> SEQUENCE: 36

Tyr Asp Lys Phe
1

<210> SEQ ID NO 37
<211> LENGTH: 5
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
```

```
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 37

Phe Tyr Glu Arg Phe
1               5

<210> SEQ ID NO 38
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 38

Tyr Asp His Phe
1

<210> SEQ ID NO 39
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 39

Tyr Asp Lys Phe
1

<210> SEQ ID NO 40
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
```

```
<223> OTHER INFORMATION: ACETYLATION
<220> FEATURE:
<221> NAME/KEY: MOD_RES
<222> LOCATION: (1)..(1)
<223> OTHER INFORMATION: AMIDATION

<400> SEQUENCE: 40

Tyr Glu Lys Phe
1

<210> SEQ ID NO 41
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 41

Tyr Glu His Phe
1

<210> SEQ ID NO 42
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 42

Tyr Asp Arg Phe
1

<210> SEQ ID NO 43
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: ACETYLATION
```

```
<220> FEATURE:
<221> NAME/KEY: MOD_RES
<222> LOCATION: (4)..(4)
<223> OTHER INFORMATION: AMIDATION

<400> SEQUENCE: 43

Trp Glu His Phe
1

<210> SEQ ID NO 44
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 44

Trp Glu Lys Phe
1

<210> SEQ ID NO 45
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 45

Trp Glu His Phe
1

<210> SEQ ID NO 46
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: ACETYLATION
<220> FEATURE:
```

<221> NAME/KEY: MOD_RES
<222> LOCATION: (4)..(4)
<223> OTHER INFORMATION: AMIDATION

<400> SEQUENCE: 46

Trp Asp Lys Phe
1

<210> SEQ ID NO 47
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 47

Tyr Glu Arg Tyr
1

<210> SEQ ID NO 48
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 48

Thr Asp Lys Tyr
1

<210> SEQ ID NO 49
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES

```
<222> LOCATION: (4)..(4)
<223> OTHER INFORMATION: AMIDATION

<400> SEQUENCE: 49

Tyr Glu Lys Tyr
1

<210> SEQ ID NO 50
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 50

Tyr Glu His Tyr
1

<210> SEQ ID NO 51
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 51

Tyr Asp Arg Tyr
1

<210> SEQ ID NO 52
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
```

```
<223> OTHER INFORMATION: AMIDATION

<400> SEQUENCE: 52

Trp Glu His Tyr
1

<210> SEQ ID NO 53
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: D/L configuration no specified. both
      configurations encompassed
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 53

Trp Glu Lys Tyr
1

<210> SEQ ID NO 54
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 54

Trp Asp His Tyr
1

<210> SEQ ID NO 55
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
```

```
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 55

Trp Glu Lys Tyr
1

<210> SEQ ID NO 56
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MISC_FEATURE
<222> LOCATION: (1)..(4)
<223> OTHER INFORMATION: INTERNAL LACTAM
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 56

Tyr Glu Lys Phe
1

<210> SEQ ID NO 57
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 57

Tyr Gln Arg Phe
1

<210> SEQ ID NO 58
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
```

```
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 58

Tyr Met Arg Phe
1

<210> SEQ ID NO 59
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 59

Tyr Leu Arg Phe
1

<210> SEQ ID NO 60
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: Benzyloxycarbonyl-Tyr
<220> FEATURE:
<221> NAME/KEY: MOD_RES
<222> LOCATION: (4)..(4)
<223> OTHER INFORMATION: AMIDATION

<400> SEQUENCE: 60

Tyr Glu Arg Phe
1

<210> SEQ ID NO 61
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
```

```
<221> NAME/KEY: MOD_RES
<222> LOCATION: (1)..(1)
<223> OTHER INFORMATION: Benzyloxycarbonyl-Tyr
<220> FEATURE:
<221> NAME/KEY: MOD_RES
<222> LOCATION: (4)..(4)
<223> OTHER INFORMATION: AMIDATION

<400> SEQUENCE: 61

Tyr Asp His Phe
1

<210> SEQ ID NO 62
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: Benzyloxycarbonyl-Tyr
<220> FEATURE:
<221> NAME/KEY: MOD_RES
<222> LOCATION: (2)..(2)
<223> OTHER INFORMATION: 4-methyl ester aspartic acid (Asp(OMe))
<220> FEATURE:
<221> NAME/KEY: MOD_RES
<222> LOCATION: (4)..(4)
<223> OTHER INFORMATION: AMIDATION

<400> SEQUENCE: 62

Tyr Asp His Phe
1

<210> SEQ ID NO 63
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: (3-Methoxy,4-hydroxy-benzoyl)-Tyr
<220> FEATURE:
<221> NAME/KEY: MOD_RES
<222> LOCATION: (4)..(4)
<223> OTHER INFORMATION: AMIDATION

<400> SEQUENCE: 63

Tyr Glu Arg Phe
1

<210> SEQ ID NO 64
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
```

```
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: (3-Methoxy,4-hydroxy-benzoyl)-Tyr
<220> FEATURE:
<221> NAME/KEY: MOD_RES
<222> LOCATION: (4)..(4)
<223> OTHER INFORMATION: AMIDATION

<400> SEQUENCE: 64

Tyr Asp His Phe
1

<210> SEQ ID NO 65
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: N-(3-Methoxy,4-hydroxy-benzoyl)ation
<220> FEATURE:
<221> NAME/KEY: MOD_RES
<222> LOCATION: (2)..(2)
<223> OTHER INFORMATION: 4-methyl ester aspartic acid  (Asp(OMe))
<220> FEATURE:
<221> NAME/KEY: MOD_RES
<222> LOCATION: (4)..(4)
<223> OTHER INFORMATION: AMIDATION

<400> SEQUENCE: 65

Tyr Asp His Phe
1

<210> SEQ ID NO 66
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: Fluorenylmethyloxycarbonyl-Tyr
<220> FEATURE:
<221> NAME/KEY: MOD_RES
<222> LOCATION: (4)..(4)
<223> OTHER INFORMATION: AMIDATION

<400> SEQUENCE: 66

Tyr Glu Arg Phe
1

<210> SEQ ID NO 67
<211> LENGTH: 4
<212> TYPE: PRT
<213> ORGANISM: artificial sequence
<220> FEATURE:
<223> OTHER INFORMATION: therapeutic agent
```

```
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: Fluorenylmethyloxycarbonyl-Tyr
<220> FEATURE:
<221> NAME/KEY: MOD_RES
<222> LOCATION: (4)..(4)
<223> OTHER INFORMATION: AMIDATION

<400> SEQUENCE: 67

Tyr Asp His Phe
1

<210> SEQ ID NO 68
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: Fluorenylmethyloxycarbonyl-Tyr
<220> FEATURE:
<221> NAME/KEY: MOD_RES
<222> LOCATION: (2)..(2)
<223> OTHER INFORMATION: 4-methyl ester aspartic acid (Asp(OMe))
<220> FEATURE:
<221> NAME/KEY: MOD_RES
<222> LOCATION: (4)..(4)
<223> OTHER INFORMATION: AMIDATION

<400> SEQUENCE: 68

Tyr Asp His Phe
1

<210> SEQ ID NO 69
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: Fluorenylmethyloxycarbonyl-Tyr
<220> FEATURE:
<221> NAME/KEY: MOD_RES
<222> LOCATION: (2)..(2)
<223> OTHER INFORMATION: 4-methyl ester aspartic acid (Asp(OMe))
<220> FEATURE:
<221> NAME/KEY: MOD_RES
<222> LOCATION: (4)..(4)
<223> OTHER INFORMATION: AMIDATION

<400> SEQUENCE: 69

Tyr Asp His Phe
1
```

```
<210> SEQ ID NO 70
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: Myristyl-Tyr
<220> FEATURE:
<221> NAME/KEY: MOD_RES
<222> LOCATION: (4)..(4)
<223> OTHER INFORMATION: AMIDATION

<400> SEQUENCE: 70

Tyr Glu Arg Phe
1

<210> SEQ ID NO 71
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: Myristyl-Tyr
<220> FEATURE:
<221> NAME/KEY: MOD_RES
<222> LOCATION: (4)..(4)
<223> OTHER INFORMATION: AMIDATION

<400> SEQUENCE: 71

Tyr Asp His Phe
1

<210> SEQ ID NO 72
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: Myristyl-Tyr
<220> FEATURE:
<221> NAME/KEY: MOD_RES
<222> LOCATION: (2)..(2)
<223> OTHER INFORMATION: 4-methyl ester aspartic acid
<220> FEATURE:
<221> NAME/KEY: MOD_RES
<222> LOCATION: (4)..(4)
<223> OTHER INFORMATION: AMIDATION

<400> SEQUENCE: 72
```

```
Tyr Asp His Phe
1

<210> SEQ ID NO 73
<211> LENGTH: 9
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(9)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (9)..(9)
<223> OTHER INFORMATION: AMIDATION

<400> SEQUENCE: 73

Tyr Glu Arg Phe Gly Tyr Asp Arg Phe
1               5

<210> SEQ ID NO 74
<211> LENGTH: 9
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(9)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (9)..(9)
<223> OTHER INFORMATION: AMIDATION

<400> SEQUENCE: 74

Tyr Asp His Phe Gly Tyr Asp His Phe
1               5

<210> SEQ ID NO 75
<211> LENGTH: 7
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(7)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (7)..(7)
<223> OTHER INFORMATION: AMIDATION

<400> SEQUENCE: 75

Tyr Arg Phe Gly Tyr Arg Phe
```

```
<210> SEQ ID NO 76
<211> LENGTH: 9
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(9)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: 4-methyl ester aspartic acid
<220> FEATURE:
<221> NAME/KEY: MOD_RES
<222> LOCATION: (7)..(7)
<223> OTHER INFORMATION: 4-methyl ester aspartic acid
<220> FEATURE:
<221> NAME/KEY: MOD_RES
<222> LOCATION: (9)..(9)
<223> OTHER INFORMATION: AMIDATION

<400> SEQUENCE: 76

Tyr Asp His Phe Gly Tyr Asp His Phe
1               5

<210> SEQ ID NO 77
<211> LENGTH: 9
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(9)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: benzyloxycarbonyl-Tyr
<220> FEATURE:
<221> NAME/KEY: MOD_RES
<222> LOCATION: (9)..(9)
<223> OTHER INFORMATION: AMIDATION

<400> SEQUENCE: 77

Tyr Glu Arg Phe Gly Tyr Glu Arg Phe
1               5

<210> SEQ ID NO 78
<211> LENGTH: 9
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(9)
<223> OTHER INFORMATION: D or L amino acid configuration not specified.
      Both configurations encompassed.
<220> FEATURE:
<221> NAME/KEY: MOD_RES
<222> LOCATION: (1)..(9)
<223> OTHER INFORMATION: benzyloxycarbonyl-Tyr
<220> FEATURE:
```

```
<221> NAME/KEY: MOD_RES
<222> LOCATION: (9)..(9)
<223> OTHER INFORMATION: AMIDATION

<400> SEQUENCE: 78

Tyr Asp His Phe Gly Tyr Asp His Phe
1               5

<210> SEQ ID NO 79
<211> LENGTH: 7
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(7)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: benzyloxycarbonyl-Tyr
<220> FEATURE:
<221> NAME/KEY: MOD_RES
<222> LOCATION: (7)..(7)
<223> OTHER INFORMATION: AMIDATION

<400> SEQUENCE: 79

Tyr Asp Phe Gly Tyr Asp Phe
1               5

<210> SEQ ID NO 80
<211> LENGTH: 9
<212> TYPE: PRT
<213> ORGANISM: artificial sequence
<220> FEATURE:
<223> OTHER INFORMATION: therapeutic ageny
<220> FEATURE:
<221> NAME/KEY: MISC_FEATURE
<222> LOCATION: (1)..(9)
<223> OTHER INFORMATION: D or L amino acid configuration not specified.
      Both configurations encompassed.
<220> FEATURE:
<221> NAME/KEY: MOD_RES
<222> LOCATION: (1)..(1)
<223> OTHER INFORMATION: benzyloxycarbonyl-Tyr
<220> FEATURE:
<221> NAME/KEY: MOD_RES
<222> LOCATION: (2)..(2)
<223> OTHER INFORMATION: 4-methyl ester aspartic acid
<220> FEATURE:
<221> NAME/KEY: MOD_RES
<222> LOCATION: (7)..(7)
<223> OTHER INFORMATION: 4-methyl ester aspartic acid
<220> FEATURE:
<221> NAME/KEY: MOD_RES
<222> LOCATION: (9)..(9)
<223> OTHER INFORMATION: AMIDATION

<400> SEQUENCE: 80

Tyr Asp His Phe Gly Tyr Asp His Phe
1               5

<210> SEQ ID NO 81
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
```

```
<223> OTHER INFORMATION: residues 1 to 4 are D-amino acids
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 81

Tyr Asp His Gln
1

<210> SEQ ID NO 82
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: residues 1 to 4 are D-amino acids
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 82

Tyr Asp His Ala
1

<210> SEQ ID NO 83
<211> LENGTH: 4
<212> TYPE: PRT
<213> ORGANISM: Artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: residues 1 to 4 are D-amino acids
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 83

Tyr Glu Lys Trp
1

<210> SEQ ID NO 84
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: residues 1 to 4 are D-amino acids
<220> FEATURE:
<221> NAME/KEY: MOD_RES
<222> LOCATION: (1)..(1)
```

```
<223> OTHER INFORMATION: ACETYLATION
<220> FEATURE:
<221> NAME/KEY: MOD_RES
<222> LOCATION: (1)..(1)
<223> OTHER INFORMATION: AMIDATION

<400> SEQUENCE: 84

Tyr Asp Lys Trp
1

<210> SEQ ID NO 85
<211> LENGTH: 4
<212> TYPE: PRT
<213> ORGANISM: Artificial Sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 85

Trp Asp His Phe
1

<210> SEQ ID NO 86
<211> LENGTH: 4
<212> TYPE: PRT
<213> ORGANISM: Artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 86

Trp Glu Arg Phe
1

<210> SEQ ID NO 87
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 87

Trp Asp Arg Phe
1

<210> SEQ ID NO 88
<211> LENGTH: 4
<212> TYPE: PRT
<213> ORGANISM: artificial sequence
```

```
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 88

Tyr Asp His Trp
1

<210> SEQ ID NO 89
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 89

Tyr Asp His Trp
1

<210> SEQ ID NO 90
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 90

Tyr Glu His Trp
1

<210> SEQ ID NO 91
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 91

Trp Asp His Trp
1
```

```
<210> SEQ ID NO 92
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 92

Trp Glu His Trp
1

<210> SEQ ID NO 93
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 93

Tyr Asp Arg Trp
1

<210> SEQ ID NO 94
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 94

Tyr Asp Lys Trp
1

<210> SEQ ID NO 95
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION
```

```
<400> SEQUENCE: 95

Tyr Glu Lys Trp
1

<210> SEQ ID NO 96
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 96

Tyr Glu Arg Trp
1

<210> SEQ ID NO 97
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 97

Trp Glu Lys Trp
1

<210> SEQ ID NO 98
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 98

Trp Glu Arg Trp
1

<210> SEQ ID NO 99
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: ACETYLATION
```

```
<220> FEATURE:
<221> NAME/KEY: MOD_RES
<222> LOCATION: (4)..(4)
<223> OTHER INFORMATION: AMIDATION

<400> SEQUENCE: 99

Trp Asp Lys Trp
1

<210> SEQ ID NO 100
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 100

Trp Asp Arg Trp
1

<210> SEQ ID NO 101
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 101

Tyr Asp His Gln
1

<210> SEQ ID NO 102
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 102

Ala Glu Arg Phe
1

<210> SEQ ID NO 103
<211> LENGTH: 4
<212> TYPE: PRT
<213> ORGANISM: artificial sequence
<220> FEATURE:
```

```
<223> OTHER INFORMATION: therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 103

Tyr Ala Arg Phe
1

<210> SEQ ID NO 104
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 104

Tyr Glu Ala Phe
1

<210> SEQ ID NO 105
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 105

Tyr Glu Arg Ala
1

<210> SEQ ID NO 106
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 106

Pro Glu Arg Phe
1
```

```
<210> SEQ ID NO 107
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 107

Tyr Glu Pro Phe
 1

<210> SEQ ID NO 108
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 108

Tyr Pro Arg Phe
 1

<210> SEQ ID NO 109
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 109

Tyr Glu Arg Pro
 1

<210> SEQ ID NO 110
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: benzoic acid-Tyr
<220> FEATURE:
<221> NAME/KEY: MOD_RES
<222> LOCATION: (4)..(4)
<223> OTHER INFORMATION: AMIDATION

<400> SEQUENCE: 110
```

Tyr Asp His Gln
1

<210> SEQ ID NO 111
<211> LENGTH: 4
<212> TYPE: PRT
<213> ORGANISM: artificial sequence
<220> FEATURE:
<223> OTHER INFORMATION: benzyloxycarbonyl-Tyr 4-methyl ester aspartic
      acid (Asp(OMe))
<220> FEATURE:
<221> NAME/KEY: MOD_RES
<222> LOCATION: (1)..(1)
<223> OTHER INFORMATION: benzyloxycarbonyl-Tyr
<220> FEATURE:
<221> NAME/KEY: MOD_RES
<222> LOCATION: (2)..(2)
<223> OTHER INFORMATION: 4-methyl ester aspartic acid (Asp(OMe))
<220> FEATURE:
<221> NAME/KEY: MOD_RES
<222> LOCATION: (4)..(4)
<223> OTHER INFORMATION: AMIDATION

<400> SEQUENCE: 111

Tyr Asp His Gln
1

<210> SEQ ID NO 112
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: 2-Chlorobenzyloxycarbonyl-Tyr
<220> FEATURE:
<221> NAME/KEY: MOD_RES
<222> LOCATION: (4)..(4)
<223> OTHER INFORMATION: AMIDATION

<400> SEQUENCE: 112

Tyr Glu Arg Phe
1

<210> SEQ ID NO 113
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: 2-Chlorobenzyloxycarbonyl-Tyr
<220> FEATURE:
<221> NAME/KEY: MOD_RES
<222> LOCATION: (4)..(4)
<223> OTHER INFORMATION: AMIDATION

<400> SEQUENCE: 113

Tyr Asp His Phe
1

<210> SEQ ID NO 114
<211> LENGTH: 4
<212> TYPE: PRT
<213> ORGANISM: artificial sequence
<220> FEATURE:
<223> OTHER INFORMATION: therapeutic agent

```
<220> FEATURE:
<221> NAME/KEY: MOD_RES
<222> LOCATION: (1)..(1)
<223> OTHER INFORMATION: 2-Chlorobenzyloxycarbonyl-Tyr
<220> FEATURE:
<221> NAME/KEY: MOD_RES
<222> LOCATION: (4)..(4)
<223> OTHER INFORMATION: AMIDATION

<400> SEQUENCE: 114

Tyr Asp His Gln
1

<210> SEQ ID NO 115
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (4)..(4)
<223> OTHER INFORMATION: AMIDATION
<220> FEATURE:
<221> NAME/KEY: MOD_RES
<222> LOCATION: (4)..(4)
<223> OTHER INFORMATION: (3-Methoxy,4-hydroxy-benzoyl)-Tyr

<400> SEQUENCE: 115

Tyr Asp His Gln
1

<210> SEQ ID NO 116
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: (3-Methoxy,4-hydroxy-benzoyl)-Tyr
<220> FEATURE:
<221> NAME/KEY: MOD_RES
<222> LOCATION: (4)..(4)
<223> OTHER INFORMATION: AMIDATION

<400> SEQUENCE: 116

Tyr Asp Phe Gln
1

<210> SEQ ID NO 117
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 117

Tyr Tyr Arg Phe
1

<210> SEQ ID NO 118
```

```
<211> LENGTH: 5
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (5)..(5)
<223> OTHER INFORMATION: AMIDATION

<400> SEQUENCE: 118

Tyr Tyr Glu Arg Phe
1               5

<210> SEQ ID NO 119
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 119

Tyr Asn Arg Phe
1

<210> SEQ ID NO 120
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (4)..(4)
<223> OTHER INFORMATION: AMIDATION
<220> FEATURE:
<221> NAME/KEY: MOD_RES
<222> LOCATION: (4)..(4)
<223> OTHER INFORMATION: benzyloxycarbonyl-Tyr

<400> SEQUENCE: 120

Tyr Asn Arg Phe
1

<210> SEQ ID NO 121
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 121
```

```
Tyr Met Arg Phe
1

<210> SEQ ID NO 122
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: benzyloxycarbonyl-Tyr
<220> FEATURE:
<221> NAME/KEY: MOD_RES
<222> LOCATION: (4)..(4)
<223> OTHER INFORMATION: AMIDATION

<400> SEQUENCE: 122

Tyr Met Arg Phe
1

<210> SEQ ID NO 123
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 123

Tyr Asn Arg Phe
1

<210> SEQ ID NO 124
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: benzyloxycarbonyl-Tyr
<220> FEATURE:
<221> NAME/KEY: MOD_RES
<222> LOCATION: (4)..(4)
<223> OTHER INFORMATION: AMIDATION

<400> SEQUENCE: 124

Tyr Asn Arg Phe
1

<210> SEQ ID NO 125
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
```

```
<222> LOCATION: (4)..(4)
<223> OTHER INFORMATION: AMIDATION

<400> SEQUENCE: 125

Tyr Leu Arg Phe
1

<210> SEQ ID NO 126
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: benzyloxycarbonyl-Tyr
<220> FEATURE:
<221> NAME/KEY: MOD_RES
<222> LOCATION: (4)..(4)
<223> OTHER INFORMATION: AMIDATION

<400> SEQUENCE: 126

Tyr Leu Arg Phe
1

<210> SEQ ID NO 127
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: benzyloxycarbonyl-Tyr
<220> FEATURE:
<221> NAME/KEY: MOD_RES
<222> LOCATION: (4)..(4)
<223> OTHER INFORMATION: AMIDATION

<400> SEQUENCE: 127

Tyr Asp His Gln
1

<210> SEQ ID NO 128
<211> LENGTH: 5
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: benzyloxycarbonyl-Tyr
<220> FEATURE:
<221> NAME/KEY: MOD_RES
<222> LOCATION: (5)..(5)
<223> OTHER INFORMATION: AMIDATION

<400> SEQUENCE: 128

Tyr Tyr Asp His Gln
1               5

<210> SEQ ID NO 129
<211> LENGTH: 19
<212> TYPE: DNA
<213> ORGANISM: artificial sequence
<220> FEATURE:
<223> OTHER INFORMATION: targeting sequence
```

<400> SEQUENCE: 129
cagtcgcgtt tgcgactgg                                                      19

<210> SEQ ID NO 130
<211> LENGTH: 55
<212> TYPE: DNA
<213> ORGANISM: artificial sequence
<220> FEATURE:
<223> OTHER INFORMATION: forward primer

<400> SEQUENCE: 130
tcagtcgcgt ttgcgactgg ttcaagagac cagtcgcaaa cgcgactgtt ttttc             55

<210> SEQ ID NO 131
<211> LENGTH: 59
<212> TYPE: DNA
<213> ORGANISM: artificial sequence
<220> FEATURE:
<223> OTHER INFORMATION: backward primer

<400> SEQUENCE: 131
tcgagaaaaa acagtcgcgt ttgcgactgg tctcttgaac cagtcgcaaa cgcgactga         59

<210> SEQ ID NO 132
<211> LENGTH: 19
<212> TYPE: DNA
<213> ORGANISM: artificial sequence
<220> FEATURE:
<223> OTHER INFORMATION: targeting sequence

<400> SEQUENCE: 132
aagtatggtg agcacgcgt                                                      19

<210> SEQ ID NO 133
<211> LENGTH: 55
<212> TYPE: DNA
<213> ORGANISM: artificial sequence
<220> FEATURE:
<223> OTHER INFORMATION: forward primer

<400> SEQUENCE: 133
taagtatggt gagcacgcgt ttcaagagaa cgcgtgctca ccatactttt ttttc             55

<210> SEQ ID NO 134
<211> LENGTH: 59
<212> TYPE: DNA
<213> ORGANISM: artificial sequence
<220> FEATURE:
<223> OTHER INFORMATION: backward primer

<400> SEQUENCE: 134
tcgagaaaaa aaagtatggt gagcacgcgt tctcttgaaa cgcgtgctca ccatactta         59

<210> SEQ ID NO 135
<211> LENGTH: 19
<212> TYPE: DNA
<213> ORGANISM: artificial sequence
<220> FEATURE:
<223> OTHER INFORMATION: targeting sequence

<400> SEQUENCE: 135
ccaagttgat gaatgtgga                                                      19

<210> SEQ ID NO 136
<211> LENGTH: 55

```
<212> TYPE: DNA
<213> ORGANISM: artificial sequence
<220> FEATURE:
<223> OTHER INFORMATION: forward primer

<400> SEQUENCE: 136
tccactgtct tcccttccta ttcaagagat aggaagggaa gacagtggtt ttttc        55

<210> SEQ ID NO 137
<211> LENGTH: 56
<212> TYPE: DNA
<213> ORGANISM: artificial sequence
<220> FEATURE:
<223> OTHER INFORMATION: backward primer

<400> SEQUENCE: 137
gaaaaaacca agttgatgaa tgtggatctc ttgaatccac attcatcaac ttggat       56

<210> SEQ ID NO 138
<211> LENGTH: 19
<212> TYPE: DNA
<213> ORGANISM: artificial sequence
<220> FEATURE:
<223> OTHER INFORMATION: targeting sequence

<400> SEQUENCE: 138
cagaagatgc agacggtga                                                19

<210> SEQ ID NO 139
<211> LENGTH: 55
<212> TYPE: DNA
<213> ORGANISM: artificial sequence
<220> FEATURE:
<223> OTHER INFORMATION: forward primer

<400> SEQUENCE: 139
tcagaagatg cagacggtga ttcaagagat caccgtctgc atcttctgtt ttttc         55

<210> SEQ ID NO 140
<211> LENGTH: 59
<212> TYPE: DNA
<213> ORGANISM: artificial sequence
<220> FEATURE:
<223> OTHER INFORMATION: backward primer

<400> SEQUENCE: 140
tcgagaaaaa acagaagatg cagacggtga tctcttgaat caccgtctgc atcttctga    59

<210> SEQ ID NO 141
<211> LENGTH: 19
<212> TYPE: DNA
<213> ORGANISM: artificial sequence
<220> FEATURE:
<223> OTHER INFORMATION: targeting sequence

<400> SEQUENCE: 141
caaatccact tcacgctca                                                19

<210> SEQ ID NO 142
<211> LENGTH: 55
<212> TYPE: DNA
<213> ORGANISM: artificial sequence
<220> FEATURE:
<223> OTHER INFORMATION: forward primer

<400> SEQUENCE: 142
```
tcaaatccac ttcacgctca ttcaagagat gagcgtgaag tggatttgtt ttttc        55

<210> SEQ ID NO 143
<211> LENGTH: 59
<212> TYPE: DNA
<213> ORGANISM: artificial sequence
<220> FEATURE:
<223> OTHER INFORMATION: backward primer

<400> SEQUENCE: 143
tcgagaaaaa acaaatccac ttcacgctca tctcttgaat gagcgtgaag tggatttga    59

<210> SEQ ID NO 144
<211> LENGTH: 19
<212> TYPE: DNA
<213> ORGANISM: artificial sequence
<220> FEATURE:
<223> OTHER INFORMATION: targeting sequence

<400> SEQUENCE: 144
gatcacagga agagaccaa                                                19

<210> SEQ ID NO 145
<211> LENGTH: 55
<212> TYPE: DNA
<213> ORGANISM: artificial sequence
<220> FEATURE:
<223> OTHER INFORMATION: forward primer

<400> SEQUENCE: 145
tgatcacagg aagagaccaa ttcaagagat tggtctcttc ctgtgatctt ttttc        55

<210> SEQ ID NO 146
<211> LENGTH: 59
<212> TYPE: DNA
<213> ORGANISM: artificial sequence
<220> FEATURE:
<223> OTHER INFORMATION: backward primer

<400> SEQUENCE: 146
tcgagaaaaa agatcacagg aagagaccaa tctcttgaat tggtctcttc ctgtgatca    59

<210> SEQ ID NO 147
<211> LENGTH: 19
<212> TYPE: DNA
<213> ORGANISM: artificial sequence
<220> FEATURE:
<223> OTHER INFORMATION: targeting sequence

<400> SEQUENCE: 147
gcattgagat tgaccagaa                                                19

<210> SEQ ID NO 148
<211> LENGTH: 55
<212> TYPE: DNA
<213> ORGANISM: artificial sequence
<220> FEATURE:
<223> OTHER INFORMATION: forward primer

<400> SEQUENCE: 148
tgcattgaga ttgaccagaa ttcaagagat tctggtcaat ctcaatgctt ttttc        55

<210> SEQ ID NO 149
<211> LENGTH: 55
<212> TYPE: DNA
<213> ORGANISM: artificial sequence

```
<220> FEATURE:
<223> OTHER INFORMATION: backward primer

<400> SEQUENCE: 149
tgcattgaga ttgaccagaa ttcaagagat tctggtcaat ctcaatgctt ttttc      55

<210> SEQ ID NO 150
<211> LENGTH: 21
<212> TYPE: DNA
<213> ORGANISM: artificial sequence
<220> FEATURE:
<223> OTHER INFORMATION: forward primer

<400> SEQUENCE: 150
ctccttaatg tcacgcacga t                                           21

<210> SEQ ID NO 151
<211> LENGTH: 20
<212> TYPE: DNA
<213> ORGANISM: artificial sequence
<220> FEATURE:
<223> OTHER INFORMATION: backward primer

<400> SEQUENCE: 151
gtccgtgtga gggttctgta                                             20

<210> SEQ ID NO 152
<211> LENGTH: 21
<212> TYPE: DNA
<213> ORGANISM: artificial sequence
<220> FEATURE:
<223> OTHER INFORMATION: forward primer

<400> SEQUENCE: 152
catgtacgtt gctatccagg c                                           21

<210> SEQ ID NO 153
<211> LENGTH: 21
<212> TYPE: DNA
<213> ORGANISM: artificial sequence
<220> FEATURE:
<223> OTHER INFORMATION: backward primer

<400> SEQUENCE: 153
ctccttaatg tcacgcacga t                                           21

<210> SEQ ID NO 154
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (4)..(4)
<223> OTHER INFORMATION: AMIDATION
<220> FEATURE:
<221> NAME/KEY: MOD_RES
<222> LOCATION: (4)..(4)
<223> OTHER INFORMATION: benzoic acid-Tyr

<400> SEQUENCE: 154

Tyr Glu Arg Phe
1

<210> SEQ ID NO 155
<211> LENGTH: 4
```

```
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: bezoic acid-Tyr
<220> FEATURE:
<221> NAME/KEY: MOD_RES
<222> LOCATION: (4)..(4)
<223> OTHER INFORMATION: AMIDATION

<400> SEQUENCE: 155

Tyr Asp His Phe
1

<210> SEQ ID NO 156
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: Fmoc(betaAla)2-Gln
<220> FEATURE:
<221> NAME/KEY: MISC_FEATURE
<222> LOCATION: (2)..(4)
<223> OTHER INFORMATION: residues 2, 3 and 4 may be substituted by any
      amino acid
<220> FEATURE:
<221> NAME/KEY: MOD_RES
<222> LOCATION: (4)..(4)
<223> OTHER INFORMATION: AMIDATION

<400> SEQUENCE: 156

Gln Ala Ala Ala
1

<210> SEQ ID NO 157
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: Fmoc(betaAla)2-Ser
<220> FEATURE:
<221> NAME/KEY: MISC_FEATURE
<222> LOCATION: (2)..(4)
<223> OTHER INFORMATION: residues 2, 3 and 4 may be substituted by any
      amino acid
<220> FEATURE:
<221> NAME/KEY: MOD_RES
<222> LOCATION: (4)..(4)
<223> OTHER INFORMATION: AMIDATION

<400> SEQUENCE: 157

Ser Ala Ala Ala
1

<210> SEQ ID NO 158
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
```

```
<222> LOCATION: (1)..(1)
<223> OTHER INFORMATION: Fmoc(betaAla)2-Arg
<220> FEATURE:
<221> NAME/KEY: MISC_FEATURE
<222> LOCATION: (2)..(4)
<223> OTHER INFORMATION: residues 2, 3 and 4 may be substituted by any
      amino acid
<220> FEATURE:
<221> NAME/KEY: MOD_RES
<222> LOCATION: (4)..(4)
<223> OTHER INFORMATION: AMIDATION

<400> SEQUENCE: 158

Arg Ala Ala Ala
1

<210> SEQ ID NO 159
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: Fmoc(betaAla)2-Ala
<220> FEATURE:
<221> NAME/KEY: misc_feature
<222> LOCATION: (2)..(4)
<223> OTHER INFORMATION: residues 2, 3, 4 may be substituted by any
      naturally occurring amino acid
<220> FEATURE:
<221> NAME/KEY: MOD_RES
<222> LOCATION: (4)..(4)
<223> OTHER INFORMATION: AMIDATION

<400> SEQUENCE: 159

Ala Ala Ala Ala
1

<210> SEQ ID NO 160
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MISC_FEATURE
<222> LOCATION: (2)..(4)
<223> OTHER INFORMATION: residues 2, 3 and 4 may be substituated by any
      amino acid
<220> FEATURE:
<221> NAME/KEY: MOD_RES
<222> LOCATION: (4)..(4)
<223> OTHER INFORMATION: AMIDATION

<400> SEQUENCE: 160

Tyr Ala Ala Ala
1

<210> SEQ ID NO 161
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
```

```
<223> OTHER INFORMATION: Fmoc(betaAla)2-Pro
<220> FEATURE:
<221> NAME/KEY: MISC_FEATURE
<222> LOCATION: (2)..(4)
<223> OTHER INFORMATION: residues 2, 3 and 4 may be substituted by any
      amino acid
<220> FEATURE:
<221> NAME/KEY: MOD_RES
<222> LOCATION: (4)..(4)
<223> OTHER INFORMATION: AMIDATION

<400> SEQUENCE: 161

Pro Ala Ala Ala
1

<210> SEQ ID NO 162
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: Fmoc(betaAla)2-Met
<220> FEATURE:
<221> NAME/KEY: MISC_FEATURE
<222> LOCATION: (2)..(4)
<223> OTHER INFORMATION: residues 2, 3 and 4 may be substituted by any
      amino acid
<220> FEATURE:
<221> NAME/KEY: MOD_RES
<222> LOCATION: (4)..(4)
<223> OTHER INFORMATION: AMIDATION

<400> SEQUENCE: 162

Met Ala Ala Ala
1

<210> SEQ ID NO 163
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: Fmoc(betaAla)2-
<220> FEATURE:
<221> NAME/KEY: MISC_FEATURE
<222> LOCATION: (2)..(4)
<223> OTHER INFORMATION: residues 2, 3 and 4 may be substituted by any
      amino acid
<220> FEATURE:
<221> NAME/KEY: MOD_RES
<222> LOCATION: (4)..(4)
<223> OTHER INFORMATION: AMIDATION

<400> SEQUENCE: 163

Cys Ala Ala Ala
1

<210> SEQ ID NO 164
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: Fmoc(betaAla)2-
```

```
<220> FEATURE:
<221> NAME/KEY: MOD_RES
<222> LOCATION: (1)..(1)
<223> OTHER INFORMATION: Fmoc(betaAla)2-Pha
<220> FEATURE:
<221> NAME/KEY: MISC_FEATURE
<222> LOCATION: (2)..(4)
<223> OTHER INFORMATION: residues 2, 3 and 4 may be substituted by any
      amino acid
<220> FEATURE:
<221> NAME/KEY: MOD_RES
<222> LOCATION: (4)..(4)
<223> OTHER INFORMATION: AMIDATION

<400> SEQUENCE: 164

Phe Ala Ala Ala
1

<210> SEQ ID NO 165
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MOD_RES
<222> LOCATION: (4)..(4)
<223> OTHER INFORMATION: AMIDATION

<400> SEQUENCE: 165

Tyr Asp His Gln
1

<210> SEQ ID NO 166
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: Fmoc(betaAla)2-Leu
<220> FEATURE:
<221> NAME/KEY: MISC_FEATURE
<222> LOCATION: (2)..(4)
<223> OTHER INFORMATION: residues 2, 3 and 4 may be substituted by any
      amino acid
<220> FEATURE:
<221> NAME/KEY: MOD_RES
<222> LOCATION: (4)..(4)
<223> OTHER INFORMATION: AMIDATION

<400> SEQUENCE: 166

Leu Ala Ala Ala
1

<210> SEQ ID NO 167
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: Fmoc(betaAla)2-His
<220> FEATURE:
<221> NAME/KEY: MISC_FEATURE
```

```
<222> LOCATION: (2)..(4)
<223> OTHER INFORMATION: residues 2, 3 and 4 may be substituted by any
      amino acid
<220> FEATURE:
<221> NAME/KEY: MOD_RES
<222> LOCATION: (4)..(4)
<223> OTHER INFORMATION: AMIDATION

<400> SEQUENCE: 167

His Ala Ala Ala
1

<210> SEQ ID NO 168
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: Fmoc(betaAla)2-Asp
<220> FEATURE:
<221> NAME/KEY: misc_feature
<222> LOCATION: (2)..(4)
<223> OTHER INFORMATION: residues 2, 3, 4 may be substituted by any
      naturally ocuring amino acid
<220> FEATURE:
<221> NAME/KEY: MOD_RES
<222> LOCATION: (4)..(4)
<223> OTHER INFORMATION: AMIDATION

<400> SEQUENCE: 168

Asp Ala Ala Ala
1

<210> SEQ ID NO 169
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MISC_FEATURE
<222> LOCATION: (3)..(4)
<223> OTHER INFORMATION: residues 3 and 4 may be substituted by any
      amino acid
<220> FEATURE:
<221> NAME/KEY: MOD_RES
<222> LOCATION: (4)..(4)
<223> OTHER INFORMATION: AMIDATION

<400> SEQUENCE: 169

Tyr Ser Ala Ala
1

<210> SEQ ID NO 170
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MISC_FEATURE
<222> LOCATION: (3)..(4)
```

<223> OTHER INFORMATION: residues 3 and 4 may be substituted by any
      amino acid
<220> FEATURE:
<221> NAME/KEY: MOD_RES
<222> LOCATION: (4)..(4)
<223> OTHER INFORMATION: AMIDATION

<400> SEQUENCE: 170

Tyr Arg Ala Ala
1

<210> SEQ ID NO 171
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MISC_FEATURE
<222> LOCATION: (3)..(4)
<223> OTHER INFORMATION: residues 3 and 4 may be substituted by any
      amino acid
<220> FEATURE:
<221> NAME/KEY: MOD_RES
<222> LOCATION: (4)..(4)
<223> OTHER INFORMATION: AMIDATION

<400> SEQUENCE: 171

Tyr Ala Ala Ala
1

<210> SEQ ID NO 172
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MISC_FEATURE
<222> LOCATION: (3)..(4)
<223> OTHER INFORMATION: residues 3 and 4 may be substituted by any
      amino acid
<220> FEATURE:
<221> NAME/KEY: MOD_RES
<222> LOCATION: (4)..(4)
<223> OTHER INFORMATION: AMIDATION

<400> SEQUENCE: 172

Tyr Tyr Ala Ala
1

<210> SEQ ID NO 173
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MISC_FEATURE
<222> LOCATION: (3)..(4)
<223> OTHER INFORMATION: residues 3 and 4 may be substituted by any

```
        amino acid
<220> FEATURE:
<221> NAME/KEY: MOD_RES
<222> LOCATION: (4)..(4)
<223> OTHER INFORMATION: AMIDATION

<400> SEQUENCE: 173

Tyr Pro Ala Ala
1

<210> SEQ ID NO 174
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MISC_FEATURE
<222> LOCATION: (3)..(4)
<223> OTHER INFORMATION: residues 3 and 4 may be substituted by any
        amino acid
<220> FEATURE:
<221> NAME/KEY: MOD_RES
<222> LOCATION: (4)..(4)
<223> OTHER INFORMATION: AMIDATION

<400> SEQUENCE: 174

Tyr Met Ala Ala
1

<210> SEQ ID NO 175
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MISC_FEATURE
<222> LOCATION: (3)..(4)
<223> OTHER INFORMATION: residues 3 and 4 may be substituted by any
        amino acid
<220> FEATURE:
<221> NAME/KEY: MOD_RES
<222> LOCATION: (4)..(4)
<223> OTHER INFORMATION: AMIDATION

<400> SEQUENCE: 175

Tyr Cys Ala Ala
1

<210> SEQ ID NO 176
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MISC_FEATURE
<222> LOCATION: (3)..(4)
<223> OTHER INFORMATION: residues 3 and 4 may be substituted by any
        amino acid
```

```
<220> FEATURE:
<221> NAME/KEY: MOD_RES
<222> LOCATION: (4)..(4)
<223> OTHER INFORMATION: AMIDATION

<400> SEQUENCE: 176

Tyr Phe Ala Ala
1

<210> SEQ ID NO 177
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MISC_FEATURE
<222> LOCATION: (3)..(4)
<223> OTHER INFORMATION: residues 3 and 4 may be substituted by any
     amino acid
<220> FEATURE:
<221> NAME/KEY: MOD_RES
<222> LOCATION: (4)..(4)
<223> OTHER INFORMATION: AMIDATION

<400> SEQUENCE: 177

Tyr Leu Ala Ala
1

<210> SEQ ID NO 178
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MISC_FEATURE
<222> LOCATION: (3)..(4)
<223> OTHER INFORMATION: residues 3 and 4 may be substituted by any
     amino acid
<220> FEATURE:
<221> NAME/KEY: MOD_RES
<222> LOCATION: (4)..(4)
<223> OTHER INFORMATION: AMIDATION

<400> SEQUENCE: 178

Tyr His Ala Ala
1

<210> SEQ ID NO 179
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MISC_FEATURE
<222> LOCATION: (3)..(4)
<223> OTHER INFORMATION: residues 3 and 4 may be substituted by any
     amino acid
<220> FEATURE:
```

```
<221> NAME/KEY: MOD_RES
<222> LOCATION: (4)..(4)
<223> OTHER INFORMATION: AMIDATION

<400> SEQUENCE: 179

Tyr Asp Ala Ala
1

<210> SEQ ID NO 180
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MOD_RES
<222> LOCATION: (4)..(4)
<223> OTHER INFORMATION: AMIDATION
<220> FEATURE:
<221> NAME/KEY: MISC_FEATURE
<222> LOCATION: (4)..(4)
<223> OTHER INFORMATION: residue 4 may be substituted by any amino acid

<400> SEQUENCE: 180

Tyr Asp Gln Ala
1

<210> SEQ ID NO 181
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MOD_RES
<222> LOCATION: (4)..(4)
<223> OTHER INFORMATION: AMIDATION
<220> FEATURE:
<221> NAME/KEY: MISC_FEATURE
<222> LOCATION: (4)..(4)
<223> OTHER INFORMATION: residue 4 may be substituted by any amino acid

<400> SEQUENCE: 181

Tyr Asp Ser Ala
1

<210> SEQ ID NO 182
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MOD_RES
<222> LOCATION: (4)..(4)
<223> OTHER INFORMATION: AMIDATION
<220> FEATURE:
<221> NAME/KEY: MISC_FEATURE
<222> LOCATION: (4)..(4)
<223> OTHER INFORMATION: residue 4 may be substituted by any amino acid
```

```
<400> SEQUENCE: 182

Thr Asp Arg Ala
1

<210> SEQ ID NO 183
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MOD_RES
<222> LOCATION: (4)..(4)
<223> OTHER INFORMATION: AMIDATION
<220> FEATURE:
<221> NAME/KEY: MISC_FEATURE
<222> LOCATION: (4)..(4)
<223> OTHER INFORMATION: residue 4 may be substituted by any amino acid

<400> SEQUENCE: 183

Tyr Asp Ala Ala
1

<210> SEQ ID NO 184
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MOD_RES
<222> LOCATION: (4)..(4)
<223> OTHER INFORMATION: AMIDATION
<220> FEATURE:
<221> NAME/KEY: MISC_FEATURE
<222> LOCATION: (4)..(4)
<223> OTHER INFORMATION: residue 4 may be substituted by any amino acid

<400> SEQUENCE: 184

Tyr Asp Tyr Ala
1

<210> SEQ ID NO 185
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MOD_RES
<222> LOCATION: (4)..(4)
<223> OTHER INFORMATION: AMIDATION
<220> FEATURE:
<221> NAME/KEY: MISC_FEATURE
<222> LOCATION: (4)..(4)
<223> OTHER INFORMATION: residue 4 may be substituted by any amino acid

<400> SEQUENCE: 185

Tyr Asp Pro Ala
1
```

```
<210> SEQ ID NO 186
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MOD_RES
<222> LOCATION: (4)..(4)
<223> OTHER INFORMATION: AMIDATION
<220> FEATURE:
<221> NAME/KEY: MISC_FEATURE
<222> LOCATION: (4)..(4)
<223> OTHER INFORMATION: residue 4 may be substituted by any amino acid

<400> SEQUENCE: 186

Tyr Asp Met Ala
1

<210> SEQ ID NO 187
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MOD_RES
<222> LOCATION: (4)..(4)
<223> OTHER INFORMATION: AMIDATION
<220> FEATURE:
<221> NAME/KEY: MISC_FEATURE
<222> LOCATION: (4)..(4)
<223> OTHER INFORMATION: X is any amino acid

<400> SEQUENCE: 187

Tyr Asp Cys Glx
1

<210> SEQ ID NO 188
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MOD_RES
<222> LOCATION: (4)..(4)
<223> OTHER INFORMATION: AMIDATION
<220> FEATURE:
<221> NAME/KEY: MISC_FEATURE
<222> LOCATION: (4)..(4)
<223> OTHER INFORMATION: residue 4 may be substituted by any amino acid

<400> SEQUENCE: 188

Tyr Asp Phe Ala
1

<210> SEQ ID NO 189
<211> LENGTH: 4
```

```
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MOD_RES
<222> LOCATION: (4)..(4)
<223> OTHER INFORMATION: AMIDATION
<220> FEATURE:
<221> NAME/KEY: MISC_FEATURE
<222> LOCATION: (4)..(4)
<223> OTHER INFORMATION: residue 4 may be substituted by any amino acid

<400> SEQUENCE: 189

Tyr Asp Leu Ala
1

<210> SEQ ID NO 190
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MOD_RES
<222> LOCATION: (4)..(4)
<223> OTHER INFORMATION: AMIDATION
<220> FEATURE:
<221> NAME/KEY: MISC_FEATURE
<222> LOCATION: (4)..(4)
<223> OTHER INFORMATION: residue 4 may be substituted by any amino acid

<400> SEQUENCE: 190

Tyr Asp His Ala
1

<210> SEQ ID NO 191
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MOD_RES
<222> LOCATION: (4)..(4)
<223> OTHER INFORMATION: AMIDATION
<220> FEATURE:
<221> NAME/KEY: MISC_FEATURE
<222> LOCATION: (4)..(4)
<223> OTHER INFORMATION: residue 4 may be substituted by any amino acid

<400> SEQUENCE: 191

Tyr Asp Asp Ala
1

<210> SEQ ID NO 192
<211> LENGTH: 4
<212> TYPE: PRT
<213> ORGANISM: artificial sequence
<220> FEATURE:
<223> OTHER INFORMATION: therapeutic agent
```

```
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MOD_RES
<222> LOCATION: (4)..(4)
<223> OTHER INFORMATION: AMIDATION

<400> SEQUENCE: 192

Tyr Asp His Gln
1

<210> SEQ ID NO 193
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MOD_RES
<222> LOCATION: (4)..(4)
<223> OTHER INFORMATION: AMIDATION

<400> SEQUENCE: 193

Tyr Asp His Ser
1

<210> SEQ ID NO 194
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MOD_RES
<222> LOCATION: (4)..(4)
<223> OTHER INFORMATION: AMIDATION

<400> SEQUENCE: 194

Tyr Asp His Arg
1

<210> SEQ ID NO 195
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MOD_RES
<222> LOCATION: (4)..(4)
<223> OTHER INFORMATION: AMIDATION

<400> SEQUENCE: 195

Tyr Asp His Ala
1

<210> SEQ ID NO 196
```

```
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MOD_RES
<222> LOCATION: (4)..(4)
<223> OTHER INFORMATION: AMIDATION

<400> SEQUENCE: 196

Tyr Asp His Tyr
1

<210> SEQ ID NO 197
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MOD_RES
<222> LOCATION: (4)..(4)
<223> OTHER INFORMATION: AMIDATION

<400> SEQUENCE: 197

Tyr Asp His Pro
1

<210> SEQ ID NO 198
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MOD_RES
<222> LOCATION: (4)..(4)
<223> OTHER INFORMATION: AMIDATION

<400> SEQUENCE: 198

Tyr Asp His Met
1

<210> SEQ ID NO 199
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MOD_RES
<222> LOCATION: (4)..(4)
<223> OTHER INFORMATION: AMIDATION

<400> SEQUENCE: 199
```

Tyr Asp His Cys
1

<210> SEQ ID NO 200
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MOD_RES
<222> LOCATION: (4)..(4)
<223> OTHER INFORMATION: AMIDATION

<400> SEQUENCE: 200

Tyr Asp His Phe
1

<210> SEQ ID NO 201
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MOD_RES
<222> LOCATION: (4)..(4)
<223> OTHER INFORMATION: AMIDATION

<400> SEQUENCE: 201

Tyr Asp His Leu
1

<210> SEQ ID NO 202
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MOD_RES
<222> LOCATION: (4)..(4)
<223> OTHER INFORMATION: AMIDATION

<400> SEQUENCE: 202

Tyr Asp His His
1

<210> SEQ ID NO 203
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: Fmoc(betaAla)2-Tyr
<220> FEATURE:
<221> NAME/KEY: MOD_RES

```
<222> LOCATION: (4)..(4)
<223> OTHER INFORMATION: AMIDATION

<400> SEQUENCE: 203

Tyr Asp His Asp
1

<210> SEQ ID NO 204
<211> LENGTH: 5
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (5)..(5)
<223> OTHER INFORMATION: AMIDATION
<220> FEATURE:
<221> NAME/KEY: MOD_RES
<222> LOCATION: (5)..(5)
<223> OTHER INFORMATION: benzyloxycarbonyl-Lys

<400> SEQUENCE: 204

Tyr Glu Arg Phe Lys
1               5

<210> SEQ ID NO 205
<211> LENGTH: 5
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (5)..(5)
<223> OTHER INFORMATION: benzyloxycarbonyl-Lys
<220> FEATURE:
<221> NAME/KEY: MOD_RES
<222> LOCATION: (5)..(5)
<223> OTHER INFORMATION: AMIDATION

<400> SEQUENCE: 205

Tyr Asp His Phe Lys
1               5

<210> SEQ ID NO 206
<211> LENGTH: 5
<212> TYPE: PRT
<213> ORGANISM: artificial sequence
<220> FEATURE:
<223> OTHER INFORMATION: therapeutic agent
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (5)..(5)
<223> OTHER INFORMATION: AMIDATION
<220> FEATURE:
<221> NAME/KEY: MOD_RES
<222> LOCATION: (5)..(5)
<223> OTHER INFORMATION: benzyloxycarbonyl-Lys

<400> SEQUENCE: 206
```

Tyr Asp His Gln Lys
1               5

<210> SEQ ID NO 207
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: residues 1 - 4 are D amino acids

<400> SEQUENCE: 207

Tyr Glu His Phe
1

<210> SEQ ID NO 208
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: residues 1 - 4 are D amino acids

<400> SEQUENCE: 208

Tyr Asp Lys Phe
1

<210> SEQ ID NO 209
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: residues 1 - 4 are D amino acids

<400> SEQUENCE: 209

Trp Glu His Phe
1

<210> SEQ ID NO 210
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: residues 1 - 4 are D amino acids

<400> SEQUENCE: 210

Tyr Glu Lys Phe
1

<210> SEQ ID NO 211
<211> LENGTH: 4
<212> TYPE: PRT
<213> ORGANISM: artificial sequence
<220> FEATURE:
<223> OTHER INFORMATION: therapeutic agent

```
<220> FEATURE:
<221> NAME/KEY: MISC_FEATURE
<222> LOCATION: (1)..(4)
<223> OTHER INFORMATION: residues 1 - 4 are D amino acids

<400> SEQUENCE: 211

Trp Glu Lys Phe
1

<210> SEQ ID NO 212
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: residues 1 - 4 are D amino acids

<400> SEQUENCE: 212

Trp Asp Lys Phe
1

<210> SEQ ID NO 213
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: residues 1 - 4 are D amino acids

<400> SEQUENCE: 213

Tyr Asp His Trp
1

<210> SEQ ID NO 214
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: residues 1 - 4 are D amino acids

<400> SEQUENCE: 214

Tyr Glu His Trp
1

<210> SEQ ID NO 215
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: residues 1 - 4 are D amino acids

<400> SEQUENCE: 215

Trp Asp His Trp
1
```

```
<210> SEQ ID NO 216
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: residues 1 - 4 are D amino acids

<400> SEQUENCE: 216

Trp Glu His Trp
1

<210> SEQ ID NO 217
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: residues 1 - 4 are D amino acids

<400> SEQUENCE: 217

Tyr Asp Asp Trp
1

<210> SEQ ID NO 218
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: residues 1 - 4 are D amino acids

<400> SEQUENCE: 218

Tyr Asp Lys Trp
1

<210> SEQ ID NO 219
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: residues 1 - 4 are D amino acids

<400> SEQUENCE: 219

Tyr Glu Lys Trp
1

<210> SEQ ID NO 220
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: residues 1 - 4 are D amino acids
```

```
<400> SEQUENCE: 220

Tyr Glu Arg Trp
1

<210> SEQ ID NO 221
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: residues 1 - 4 are D amino acids

<400> SEQUENCE: 221

Trp Glu Lys Trp
1

<210> SEQ ID NO 222
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: residues 1 - 4 are D amino acids

<400> SEQUENCE: 222

Trp Glu Arg Trp
1

<210> SEQ ID NO 223
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: residues 1 - 4 are D amino acids

<400> SEQUENCE: 223

Trp Glu Lys Trp
1

<210> SEQ ID NO 224
<211> LENGTH: 4
<212> TYPE: PRT
<213> ORGANISM: artificial sequence
<220> FEATURE:
<223> OTHER INFORMATION: therapeutic agent
<220> FEATURE:
<221> NAME/KEY: MISC_FEATURE
<222> LOCATION: (1)..(4)
<223> OTHER INFORMATION: residues 1 - 4 are D amino acids

<400> SEQUENCE: 224

Trp Gln Arg Trp
1

<210> SEQ ID NO 225
<211> LENGTH: 4
<212> TYPE: PRT
<213> ORGANISM: artificial sequence
<220> FEATURE:
```

```
-continued

<223> OTHER INFORMATION: therapeutic agent
<220> FEATURE:
<221> NAME/KEY: MISC_FEATURE
<222> LOCATION: (1)..(4)
<223> OTHER INFORMATION: residues 1 - 4 are D amino acids

<400> SEQUENCE: 225

Trp Asn Lys Trp
1

<210> SEQ ID NO 226
<211> LENGTH: 5
<212> TYPE: PRT
<213> ORGANISM: artificial sequence
<220> FEATURE:
<223> OTHER INFORMATION: cleavable linker

<400> SEQUENCE: 226

Asp Asp Asp Asp Tyr
1               5

<210> SEQ ID NO 227
<211> LENGTH: 5
<212> TYPE: PRT
<213> ORGANISM: artificial sequence
<220> FEATURE:
<223> OTHER INFORMATION: cleavable linker

<400> SEQUENCE: 227

His Pro Phe His Leu
1               5
```

GADD45BETA TARGETING AGENTS

The work leading to this invention was supported in part by National Institutes of Health R01 Grants CA84040 and CA098583.

FIELD OF INVENTION

The invention relates to cancer and other diseases and disorders for example inflammatory diseases and disorders and to therapeutic modulation thereof. In particular, the invention relates to compounds based on short peptides capable of modulating programmed cell death (PCD) and proliferation of cancer cells, and pro-inflammatory/auto-immune cells.

BACKGROUND OF THE INVENTION

The induction of apoptosis has long been considered as a method of targeting cancer cells as well as pro-inflammatory, autoimmune cells, and other diseased cells. There are a number of cellular pathways involved in triggering cell death including the c-Jun N-terminal kinase JNK pathway. JNKs are responsive to cytokines and stress stimuli such as ultraviolet irradiation, heat shock and osmotic shock. Also activated in the response to cytokines and cellular stress is the NF-κB pathway. The NF-κB pathway can inhibit the JNK pathway by crosstalk mediated by Gadd45β and the JNK kinase, mitogen activated protein-kinase kinase 7 (MKK7/JNKK2). MKK7 activity is inhibited by Gadd45β, a member of the Gadd45 family of inducible factors and a direct transcriptional target of NF-κB. This means that Gadd45β mediates NF-κB suppression of JNK signalling by binding to MKK7 and inhibiting its activity. Papa, et al. 2004, Nature Cell Biology 6(2):1462153.

The use of NF-κB inhibitors has been proposed for use in the treatment of cancer and inflammatory diseases. However, because NF-κB has a number of activities including roles in PCD, immunity, inflammation and tissue development, it is preferred to inhibit specific functions of NF-κB rather than NF-κB itself.

The present invention relates to the inhibition of Gadd45β which is known to be up-regulated in a number of cancers and also in chronic inflammatory and hereditary disorders.

Multiple myeloma (MM), also known as plasma cell myeloma or Kahler's disease, is a cancer of plasma cells. Multiple myeloma is currently incurable, although temporary remissions can be induced by use of steroids, chemotherapy, thalidomide, proteasome inhibitors (PIs), e.g. bortezomib, melphalan, and stem cell transplants. According to the American Cancer Society, there are approximately 45,000 people in the United States living with multiple myeloma with approximately 15,000 new cases being diagnosed each year in the United States. The average survival time from diagnosis is approximately three years. Multiple myeloma is the second most prevalent blood cancer after non-Hodgkin's lymphoma and represents approximately 1% of all cancers and approximately 2% of all cancer deaths. The incidence of multiple myeloma appears to be increasing and there is also some evidence that the age of onset of the disease is falling. Thus, there is a clear need for improved treatments for multiple myeloma.

Nearly all multiple myeloma primary tumours and multiple myeloma cell lines display constitutive NF-κB activity. Blocking the activity of NF-κB causes multiple myeloma cell death. A major barrier to achieving long-term cancer treatment results with NF-κB targeting strategies is lack of specificity, and therefore poor treatment tolerability. This is due to the pleiotropic functions of NF-κB and of the proteasome. There is a need for a radically new therapeutic approach which is more specific, safer, and therefore more effective.

One of NF-κB's key functions in multiple myeloma is to promote survival. It has been shown (De Smaele, et al. (2001) Nature 414:306-313) that NF-κB affords cyto-protection by suppressing the JNK MAPK cascade by means of Gadd45β, a member of the Gadd45 family of inducible factors. Gadd45β is up-regulated by NF-κB in response to various stimuli and promotes survival by directly targeting the JNK kinase MKK7 (Papa, et al. 2004 Nature Cell Biology 6:146-153, Papa, et al. 2007) J. Biol. Chem. 282: 19029-19041, Papa, et al. (2008) J. Clin. Invest. 118:191-1923).

Proteasome inhibitors (PIs) and direct NF-κB inhibitors kill multiple myeloma cells by activating the JNK pathway, but are unsuitable for curative multiple myeloma therapy because of their indiscriminate effects on NF-κB and/or indiscriminate effects on the proteasome which prevents them being used at fully inhibitory curative doses.

In addition to multiple myeloma, Gadd45β is expressed at high levels in other tumours including diffuse large B-cell lymphoma, Burkitt's lymphoma, promonocytic leukaemia and other leukemias, as well as some solid tumours including hepatocellular carcinoma, bladder cancer, brain and central nervous system cancer, breast cancer, head and neck cancer, lung cancer, and prostate cancer. Therefore, inhibiting Gadd45β in these tumours may induce cancer cell death and so have beneficial therapeutic effects. Many haematological malignancies (including multiple myeloma, mantle cell lymphoma, MALT lymphoma, diffuse large B-cell lymphoma, Hodgkin's lymphoma, myelodysplastic syndrome, adult T-cell leukaemia (HTLV-1), chronic lymphocytic leukaemia, chronic myeloid leukaemia, acute myelogenic leukaemia, and acute lymphocytic leukaemia) and solid tumours (including breast cancer, cervical cancer, renal cancer, lung cancer, colon cancer, liver cancer, oesophageal cancer, gastric cancer, laryngeal cancer, thyroid cancer, parathyroid cancer, bladder cancer, ovarian cancer, prostate cancer, pancreatic cancer and many other cancers) are also known to exhibit constitutive NF-κB activation providing pro-survival signals to the cells at the expense of PCD which could otherwise lead to increased tumour cell death (V. Baud and M. Karin 2009, Nat. Rev. Drug Disc. 8: 33-40). Constitutive NF-κB activity is also found in melanoma, cylindroma, squamous cell carcinoma (skin, and head and neck), oral carcinoma, endometrial carcinoma, retinoblastoma, astrocytoma, and glioblastoma (V. Baud and M. Karin 2009, Nat. Rev. Drug Disc. 8: 33-40). Inhibiting Gadd45β in these tumours featuring aberrantly high constitutive NF-κB activity could also produce beneficial therapeutic effects by inducing programmed cell death in the cancerous cells. The present invention is based on the realisation that targeting the discreet pro-survival functions of NF-κB in cell survival via Gadd45β provides safer, more effective, therapy than does targeting NF-κB directly for a range of diseases and disorders including cancer and also other diseases characterised by aberrant cell survival or diseases which could be treated by the induction of increased PCD (such as autoimmune diseases, chronic inflammatory diseases, degenerative diseases and ischemic and vascular diseases).

A broad range of diseases and disorders depend on the activity of NF-κB. Indeed, the pathogenesis of virtually every known human disease or disorder is now being considered to depend on inflammation, and hence to involve NF-κB. This functions as a masterswitch of the inflammatory response, coordinating expression of an array of over 200 genes encoding cytokines, receptors, transcription factors, chemokines, pro-inflammatory enzymes, and other factors, including pro-survival factors, which initiate and sustain inflammation. The compounds of the invention inhibit the discrete pro-survival activity of NF-κB in inflammation. Therefore, diseases and disorders amenable to treatment with these compounds include, apart from conventional chronic inflammatory diseases (such as inflammatory bowel disease, rheumatoid arthritis, and psoriasis), other diseases and disorders that depend on a significant inflammatory component. Examples of such diseases and disorders, which are being treated with anti-inflammatory agents or NF-κB-inhibiting agents or have been proposed as suitable for treatment with NF-κB inhibitors and could also be treated with a compound of the invention, include:

1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) or adenovirus; or eosinophilic esophagitis;

2. bone and joints: arthritides associated with or including osteoarthritis/osteoarthrosis, both primary and secondary to, for example, congenital hip dysplasia; cervical and lumbar spondylitis, and low back and neck pain; osteoporosis; rheumatoid arthritis and Still's disease; seronegative spondyloarthropathies including ankylosing spondylitis, psoriatic arthritis, reactive arthritis and undifferentiated spondarthropathy; septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositis and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; low back pain; Familial Mediterranean fever, Muckle-Wells syndrome, and Familial Hibernian Fever, Kikuchi disease; drug-induced arthalgias, tendonititides, and myopathies;

3. pain and connective tissue remodelling of musculoskeletal disorders due to injury [for example sports injury] or disease: arthitides (for example rheumatoid arthritis, osteoarthritis, gout or crystal arthropathy), other joint disease (such as intervertebral disc degeneration or temporomandibular joint degeneration), bone remodelling disease (such as osteoporosis, Paget's disease or osteonecrosis), polychondritis, scleroderma, mixed connective tissue disorder, spondyloarthropathies or periodontal disease (such as periodontitis);

4. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia greata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;

5. eyes: blepharitis; conjunctivitis, including perennial and vernal allergic conjunctivitis; iritis; anterior and posterior uveitis; choroiditis; autoimmune; degenerative or inflammatory disorders affecting the retina; ophthalmitis including sympathetic ophthalmitis; sarcoidosis; infections including viral, fungal, and bacterial;

6. gastrointestinal tract: glossitis, gingivitis, periodontitis; oesophagitis, including reflux; eosinophilic gastro-enteritis, mastocytosis, Crohn's disease, colitis including ulcerative colitis, proctitis, pruritis ani; coeliac disease, irritable bowel syndrome, and food-related allergies which may have effects remote from the gut (for example migraine, rhinitis or eczema);

7. abdominal: hepatitis, including autoimmune, alcoholic and viral; fibrosis and cirrhosis of the liver; cholecystitis; pancreatitis, both acute and chronic;

8. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);

9. allograft rejection: acute and chronic following, for example, transplantation of kidney, heart, liver, lung, bone marrow, skin or cornea or following blood transfusion; or chronic graft versus host disease;

10. CNS: Atzheimer's disease and other dementing disorders including CJD and nvCJD; amyloidosis; multiple sclerosis and other demyelinating syndromes; cerebral atherosclerosis and vasculitis; temporal arteritis; myasthenia gravis; acute and chronic pain (acute, intermittent or persistent, whether of central or peripheral origin) including visceral pain, headache, migraine, trigeminal neuralgia, atypical facial pain, joint and bone pain, pain arising from cancer and tumor invasion, neuropathic pain syndromes including diabetic, post-herpetic, and HIV-associated neuropathies; neurosarcoidosis; central and peripheral nervous system complications of malignant, infectious or autoimmune processes;

11. other auto-immune and allergic disorders including Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome;
12. other disorders with an inflammatory or immunological component; including acquired immune deficiency syndrome (AIDS), leprosy, Sezary syndrome, and paraneoplastic syndromes;
13. cardiovascular: atherosclerosis, affecting the coronary and peripheral circulation; pericarditis; myocarditis, inflammatory and auto-immune cardiomyopathies including myocardial sarcoid; ischaemic reperfusion injuries; endocarditis, valvulitis, and aortitis including infective (for example syphilitic); vasculitides; disorders of the proximal and peripheral veins including phlebitis and thrombosis, including deep vein thrombosis and complications of varicose veins;
14. gastrointestinal tract: Coeliac disease, proctitis, eosinopilic gastro-enteritis, mastocytosis, Crohn's disease, ulcerative colitis, microscopic colitis, indeterminant colitis, irritable bowel disorder, irritable bowel syndrome, non-inflammatory diarrhea, food-related allergies which have effects remote from the gut, e.g., migraine, rhinitis and eczema.

The present invention relates to novel inhibitors of the Gadd45β/MKK7 complex and/or signalling of that complex which may be used to inhibit the pro-survival function of NF-κB in cancer, inflammation, autoimmunity and degenerative, ischemic and vascular disorders.

SUMMARY OF INVENTION

According to a first aspect of the invention there is provided a compound of formula I:

$$X_1\text{-}A\text{-}X_2 \quad \quad \text{I:}$$

wherein,
A is A'''',
   or A''-[M-A'-]$_n$ M-A''';
A'' is A'',
  A'''
  or $Z_1$—$Y_2$—$Y_3$—$Z_4$, wherein $Y_2$—$Y_3$ is an oligopeptide moiety or an oligopeptoid moiety having the residues $Y_2$—$Y_3$ and $Z_1$ is attached to the N-terminal nitrogen of $Y_2$—$Y_3$ and $Z_4$ is attached to the C-terminal carbon of $Y_2$—$Y_3$;
A'' is A',
  or $Y_1$—$Y_2$—$Y_3$—$Z_4$, wherein $Y_1$—$Y_2$—$Y_3$ is an oligopeptoid moiety or an oligopeptoid moiety comprising the residues: $Y_1$—$Y_2$—$Y_3$ and $Z_4$ is attached to the C-terminal carbon of $Y_1$—$Y_2$—$Y_3$;
A''' is A',
  or $Z_1$—$Y_2$—$Y_3$—$Y_4$, wherein $Y_2$—$Y_3$—$Y_4$ is an oligopeptoid moiety or an oligopeptoid moiety comprising the residues $Y_2$—$Y_3$—$Y_4$ and $Z_1$ is attached to the N-terminal nitrogen of $Y_2$—$Y_3$—$Y_4$;
each occurrence of A' is independently an oligopeptide moiety or an oligopeptoid moiety comprising the residues $Y_1$—$Y_2$—$Y_3$—$Y_4$;
n is an integer from 0 to 18
$Y_1$ and $Y_4$ are independently amino acid residues or residues of amino acid derivatives having aromatic side chains
$Y_2$ is an amino acid residue or a residue of an amino acid derivative or is absent, $Y_3$ is an amino acid residue or a residue of an amino acid derivative or is absent;
$Z_1$ is a group of formula II:

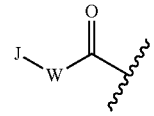

(II)

which is linked to the N-terminal nitrogen of $Y_2$,
W is absent, or an oxygen, or a nitrogen, or an alkylene group of from one to three carbons,
which alkylene group of from one to three carbons is optionally substituted by at least one substituent selected from alkyl of from one to four carbons, or 5-10 membered carbocyclic or heterocyclic aromatic group;
J is a 5-10 membered carbocyclic or heterocyclic aromatic group,
which aromatic group is optionally substituted by at least one substituent selected from hydroxyl, halogen, alkyl of from one to four carbons, or alkoxy of from one to four carbon atoms;
$Z_4$ represents a group of formula III:

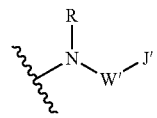

(III)

which is linked to the C-terminal carbon of $Y_3$,
R is hydrogen or alkyl of from one to four carbons;
W' is absent or an alkylene group of from one to three carbons, which alkylene group of from one to three carbons is optionally substituted by at least one substituent selected from alkyl of from one to four carbons, or 5-10 membered carbocyclic or heterocyclic aromatic group;
J' is a 3-10 membered aliphatic carbocyclic group or a 5-10 membered carbocyclic or heterocyclic aromatic group, which aliphatic or aromatic group is optionally substituted by at least one substituent selected from hydroxyl, halogen, alkyl of from one to four carbons, or alkoxy of from one to four carbon atoms;
M is a peptide bond between preceding oligopeptide or oligopeptoid moiety (A', A'' or A''') and following oligopeptide or oligopeptide moiety (A', A'' or A''') or a linker moiety attached via an amide bond, an ester bond, an ether bond, or a thioether bond to the terminal carboxylic group of preceding oligopeptide or oligopeptoid moiety (A', A'' or A''') and via an amide bond, an ester bond, an ether bond, or a thioether bond to the terminal amino group of following oligopeptoid moiety (A', A'' or A''');
$X_1$ is absent, or is a moiety added to the -amino terminal of A in order to block the free amino group;
$X_2$ is absent or is a moiety added to the carboxyl terminal of A in order to block the free carboxyl group;
with the proviso that $X_1$ is absent if A comprises $Z_1$ and $X_2$ is absent if A comprises $Z_4$;
or derivatives thereof, said derivatives being selected from the group consisting of:
  a) oligomers or multimers of molecules of the compound of formula I, said oligomers and multimers comprising two or more molecules of the compound of formula I each linked to a common scaffold moiety via an amide bond formed between an amino or carboxylic acid group present in molecules of the compound of formula I and an opposite amino or carboxylic acid group on a scaffold moiety said scaffold moiety participating in at least 2 amide bonds, b) derivatives comprising a molecule of the compound of formula I or an oligomer or multimer thereof as defined above in part a) conjugated via an amide bond, an ester bond, an ether bond or a thioether bond to:
PEG,
PEG-based compounds,
cell-penetrating peptides,
fluorescent dyes,
biotin or other tag moiety,
fatty acids,
nanoparticles of discrete size
or chelating ligands complexed with metallic or radioactive ions.

c) derivatives comprising a molecule of the compound of formula I or an oligomer or multimer thereof as defined in part a) which has been modified by amidation, glycosylation, carbamylation, acylation, sulfation, phosphorylation, cyclization, lipidation, pegylation or linkage to a peptide or peptiod fusion partner to make a fusion peptide or fusion peptiod.

and d) salts and solvates of a molecule of the compound of formula I or of a derivative thereof as defined in part a) or b) above.

According to a second aspect of the invention, there is provided a pharmaceutical composition comprising a compound according the first aspect of the invention and a pharmaceutically acceptable carrier.

According to a third aspect of the invention, there is provided a method of treating a disease or disorder characterised by increased NF-κB activity and/or expression and/or increased Gadd45β activity and/or expression comprising administering a therapeutically effective amount of a compound according to the first aspect of the invention or a pharmaceutical composition according to the second aspect of the invention to a subject in need thereof.

According to a fourth aspect of the invention, there is provided a compound according to the first aspect of the invention or a composition according to the second aspect of the invention for use as a medicament.

According to a fifth aspect of the invention, there is provided use of a compound according to the first aspect of the invention or a pharmaceutical composition according to the second aspect of the invention for the manufacture of a medicament for the treatment of a disease or disorder characterised by increased NF-κB activity and/or expression and/or increased Gadd45β activity and/or expression.

BRIEF EXPLANATION OF DRAWINGS

FIG. 16, Gadd45β and MKK7 gene silencing), and confirm the essential role that Gadd45β plays in multiple myeloma cell survival. Together, they also further validate=Gadd45β as therapeutic target in multiple myeloma.

FIGS. 7, 8, and 12, multiple myeloma cell line sensitivity to Z-DTP-induced killing and Gadd45β expression) (FIG. 18A, FIG. 18B, FIG. 18C). No significant induction of apoptosis was observed in the same multiple myeloma cell lines in the absence of lentiviral infection (uninfected) or after expression of MKK7-specific sh-RNAs (i.e. sh-MKK7-1 and sh-MKK7-2) or non-specific sh-RNAs (i.e. sh-NS-1 and sh-NS-2). Multiple myeloma cell lines were infected with sh-RNA-expressing pLentiLox.3.7 lentiviruses, and eGFP$^+$ multiple myeloma cells (that is cells infected with lentivirus) were sorted using a BD FACSAria™ II cell sorter as in FIG. 16. PI nuclear staining assays were performed 10 days after cell sorting, corresponding to day 8 in FIG. 16. The percentages of apoptotic cells (that is cells exhibiting sub-$G_1$ DNA content) are depicted in the histograms. (FIG. 18A) Importantly, the levels of apoptosis induced by the different Gadd45β-specific sh-RNAs (that is sh-Gadd45β-1, sh-Gadd45β-2, and sh-Gadd45β-3) correlate with the levels of Gadd45β downregulation induced by each of these Gadd45β-specific sh-RNAs (data not shown). (FIG. 18A, FIG. 18B, FIG. 18C) These data further establish the target specificity of Z-DTPs for the Gadd45β/MKK7 complex in multiple myeloma cells (see also FIGS. 7, 8 and 9, killing assays with Z-DTPs; FIG. 12, statistically significant correlation between Gadd45β expression and cancer cell sensitivity to Z-DTP-induced killing; FIGS. 16 and 17, induction of multiple myeloma cell killing by the downregulation of Gadd45β, but not of MKK7), and confirm the essential role that Gadd45β plays in multiple myeloma cell survival. Together, they further validate Gadd45β as a therapeutic target in multiple myeloma.

(FIG. 19 A, FIG. 19 B) Cell-cycle analyses could not be performed with Gadd45β-specific sh-RNAs in the ARH-77 (FIG. 19 A) and NCI-H929 (FIG. 19 B) multiple myeloma cell lines, due to the induction of massive apoptosis in these cells (see FIGS. 18A and 18B).

NOTE ON NOMENCLATURE USED HEREIN

Figure 1:
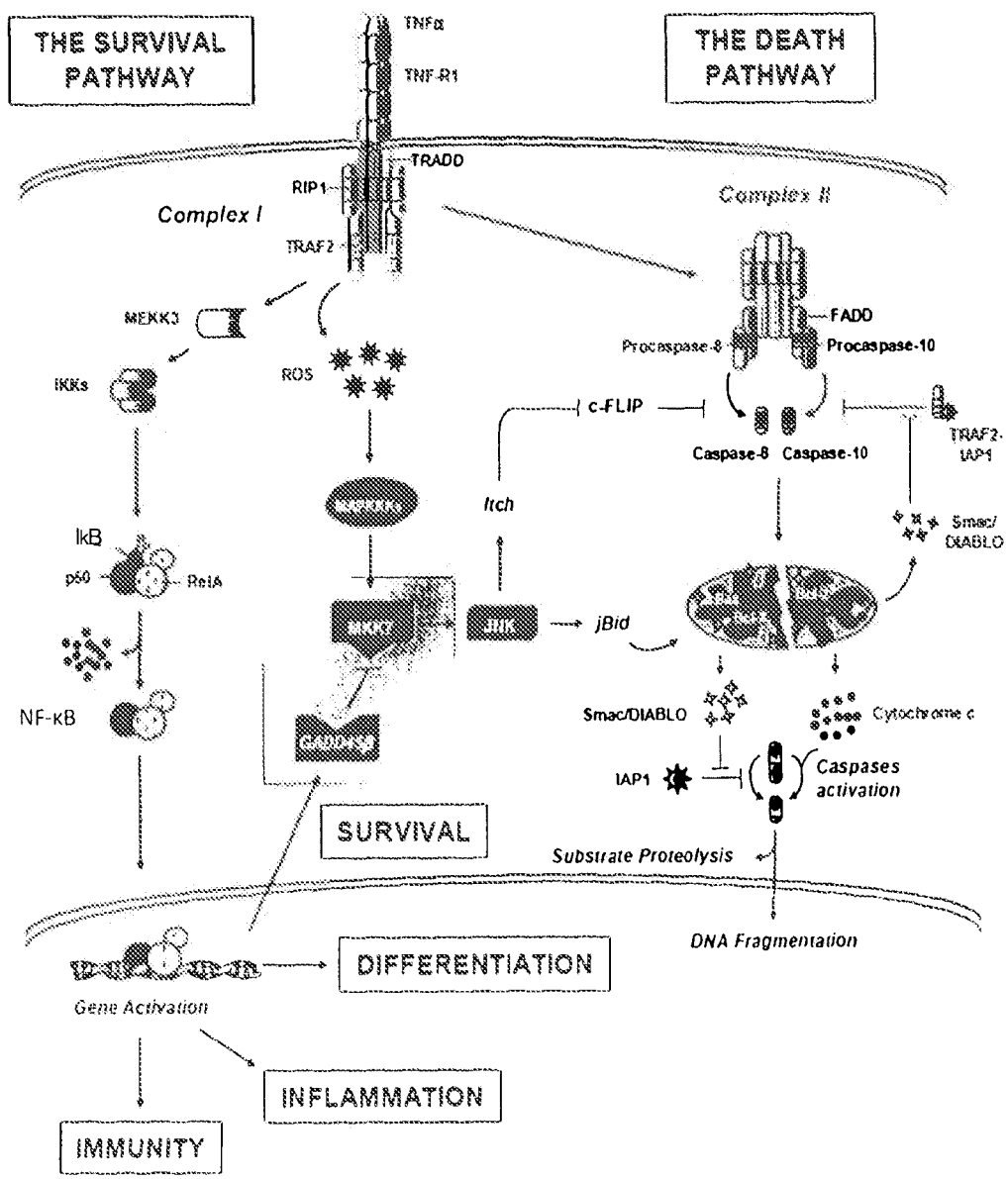
FIG. 1. Schematic representation of the protective crosstalk between the NF-κB and JNK pathways in the context of TNF-R1 signalling. It can be seen that Gadd45β mediates crosstalk between the survival pathway induced by NF-κB and the death pathway induced by MKK7 and JNK. Inhibition of this crosstalk by blocking Gadd45β allows MKK7 to activate JNK thus triggering a death pathway in tumour cells.
Figure 2:
FIG. 2. Model of the Gadd45β-MKK7 complex. The model was built as reported in the reference by Papa S. et al. 2007, J Biol Chem 282: 19029-19041. The model was further refined using the crystallographic structure of MKK7 (pdb: 2DYL) and a structure of Gadd45β modelled on the crystallographic structure of Gadd45γ (pdb: 3FFM).

In various parts of this specification, compounds are refereed to by a signifying code such as LTP, DTP, LNC, DTP1 etc. Codes containing "NC" describe compounds which are negative controls not encompassed within the scope of the invention. Codes containing "TP" (which is an abbreviation of for tetra or tri-peptide/peptoids, although it should be noted that some of the compounds are based on di-peptide/peptiod motifs) are within the scope of the invention. The "L" or "D" prefix denotes residues in the L or D optical configuration. A numeric suffix denotes a specific numbered compound detailed elsewhere. The prefix "Z" as in "Z-DTP" denotes a benzyloxycarbonyl N-terminal group. The "m" prefix as in "mDTP" denotes any modification of a DTP aimed at improving cellular uptake, cellular activity, and/or PK profile, such as the removal of the N and/or C terminus (e.g. as in mDTP1), the removal of the Z group and of the Arg or Glu residues of Z-DTP2 as in mDTP2 and mDTP3, respectively (further examples are provided in FIG. 13).

DETAILED DESCRIPTION OF THE INVENTION

The strategy underlining the present invention arises from an understanding that NF-κB-JNK crosstalk also controls survival versus programmed death of cells including cancer cells which would otherwise have died. Significantly, Gadd45β is up-regulated in cancerous cells in response to NF-κB activation and is expressed constitutively at high levels in multiple myeloma cells and other tumours, including diffuse large B-cell lymphoma, Burkitt's lymphoma, promonocytic leukaemia and other leukemias, as well as in some solid tumours, including hepatocellular carcinoma, bladder cancer, brain and central nervous system cancer, breast cancer, head and neck cancer, lung cancer, and prostate cancer. The present invention is based on the strategy of promoting programmed cell death by delivering Gadd45β/MKK7-targeting compounds that prevent NF-κB-JNK crosstalk thereby enhancing JNK cytotoxic signalling in cells. Products and methods of the present invention may be especially relevant to treatment of disorders characterised by aberrant up-regulation of Gadd45β. They are also relevant to diseases and disorders where Gadd45β may not necessarily be aberrantly up-regulated, but where NF-κB is aberrantly up-regulated or activated and where an inductor of programmed cell death via Gadd45β-MKK7 signalling may provide a treatment.

Examples of these diseases featuring aberrant up-regulation or activation of NF-κB and where an inductor of programmed cell death via Gadd45β-MKK7 signalling may provide a treatment include: haematological malignancies (such as multiple myeloma, mantle cell lymphoma, MALT lymphoma, diffuse large B-cell lymphoma, Hodgkin's lymphoma, myelodysplastic syndrome, adult T-cell leukaemia (HTLV-1), chronic lymphocytic leukaemia, chronic myeloid leukaemia, acute myelogenic leukaemia, and acute lymphocytic leukaemia), solid tumours (such as breast cancer, cervical cancer, renal cancer, lung cancer, colon cancer, liver cancer, oesophageal cancer, gastric cancer, laryngeal cancer, thyroid cancer, parathyroid cancer, bladder cancer, ovarian cancer, prostate cancer, pancreatic cancer and many other cancers), other cancers (such as melanoma, cylindroma, squamous cell carcinoma [skin, and head and neck], oral carcinoma, endometrial carcinoma, retinoblastoma, astrocytoma, and glioblastoma), and other diseases and disorders such as autoimmune diseases, chronic inflammatory diseases, degenerative diseases, ischemic diseases, and vascular diseases.

A broad range of diseases and disorders depend on the activity of NF-κB. Indeed, the pathogenesis of virtually every known human disease or disorder is now being considered to depend on inflammation, and hence to involve NF-κB. This functions as a masterswitch of the inflammatory response, coordinating expression of an array of over 200 genes encoding cytokines, receptors, transcription factors, chemokines, pro-inflammatory enzymes, and other factors, including pro-survival factors, which initiate and sustain inflammation. The compounds of the invention inhibit the discrete pro-survival activity of NF-κB in inflammation. Therefore, diseases and disorders amenable to treatment with these compounds include, apart from conventional chronic inflammatory diseases (such as inflammatory bowel disease, rheumatoid arthritis, and psoriasis), other diseases and disorders that depend on a significant inflammatory component. Examples of such diseases and disorders, which are being treated with anti-inflammatory agents or NF-κB-inhibiting agents or have been proposed as suitable for treatment with NF-κB inhibitors and could also be treated with a compound of the invention, include:

1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) or adenovirus; or eosinophilic esophagitis;

2. bone and joints: arthritides associated with or including osteoarthritis/osteoarthrosis, both primary and secondary to, for example, congenital hip dysplasia; cervical and lumbar spondylitis, and low back and neck pain; osteoporosis; rheumatoid arthritis and Still's disease; seronegative spondyloarthropathies including ankylosing spondylitis, psoriatic arthritis, reactive arthritis and undifferentiated spondarthropathy; septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositits and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; low back pain; Familial Mediterranean fever, Muckle-Wells syndrome, and Familial Hibernian Fever, Kikuchi disease; drug-induced arthalgias, tendonititides, and myopathies;

3. pain and connective tissue remodelling of musculoskeletal disorders due to injury [for example sports injury] or disease: arthitides (for example rheumatoid arthritis, osteoarthritis, gout or crystal arthropathy), other joint disease (such as intervertebral disc degeneration or temporomandibular joint degeneration), bone remodelling disease (such as osteoporosis, Paget's disease or osteonecrosis), polychondritits, scleroderma, mixed connective tissue disorder, spondyloarthropathies or periodontal disease (such as periodontitis);

4. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia greata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;

5. eyes: blepharitis; conjunctivitis, including perennial and vernal allergic conjunctivitis; iritis; anterior and posterior uveitis; choroiditis; autoimmune; degenerative or inflammatory disorders affecting the retina; ophthalmitis including sympathetic ophthalmitis; sarcoidosis; infections including viral, fungal, and bacterial;

6. gastrointestinal tract: glossitis, gingivitis, periodontitis; oesophagitis, including reflux; eosinophilic gastro-enteritis, mastocytosis, Crohn's disease, colitis including ulcerative colitis, proctitis, pruritis ani; coeliac disease, irritable bowel syndrome, and food-related allergies which may have effects remote from the gut (for example migraine, rhinitis or eczema);

7. abdominal: hepatitis, including autoimmune, alcoholic and viral; fibrosis and cirrhosis of the liver; cholecystitis; pancreatitis, both acute and chronic;

8. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);

9. allograft rejection: acute and chronic following, for example, transplantation of kidney, heart, liver, lung, bone marrow, skin or cornea or following blood transfusion; or chronic graft versus host disease;

10. CNS: Atzheimer's disease and other dementing disorders including CJD and nvCJD; amyloidosis; multiple sclerosis and other demyelinating syndromes; cerebral atherosclerosis and vasculitis; temporal arteritis; myasthenia gravis; acute and chronic pain (acute, intermittent or persistent, whether of central or peripheral origin) including visceral pain, headache, migraine, trigeminal neuralgia, atypical facial pain, joint and bone pain, pain arising from cancer and tumor invasion, neuropathic pain syndromes including diabetic, post-herpetic, and HIV-associated neuropathies; neurosarcoidosis; central and peripheral nervous system complications of malignant, infectious or autoimmune processes;

11. other auto-immune and allergic disorders including Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome;

12. other disorders with an inflammatory or immunological component; including acquired immune deficiency syndrome (AIDS), leprosy, Sezary syndrome, and paraneoplastic syndromes;

13. cardiovascular: atherosclerosis, affecting the coronary and peripheral circulation; pericarditis; myocarditis, inflammatory and auto-immune cardiomyopathies including myocardial sarcoid; ischaemic reperfusion injuries; endocarditis, valvulitis, and aortitis including infective (for example syphilitic); vasculitides; disorders of the proximal and peripheral veins including phlebitis and thrombosis, including deep vein thrombosis and complications of varicose veins;

14. gastrointestinal tract: Coeliac disease, proctitis, eosinopilic gastro-enteritis, mastocytosis, Crohn's disease, ulcerative colitis, microscopic colitis, indeterminant colitis, irritable bowel disorder, irritable bowel syndrome, non-inflammatory diarrhea, food-related allergies which have effects remote from the gut, e.g., migraine, rhinitis and eczema.

To this end the inventors have developed a number of synthetic molecules based on D-enantiomers of tetrapeptides, tripeptides, dipeptides and similar peptide-mimetics including peptoid moeties that disrupt the Gadd45β/MKK7 interaction. Importantly, these compounds show Gadd45β inhibitory activity without suppressing MKK7 kinase function. This is important because it confirms that the compounds of the invention can induce JNK cytotoxic signalling via inhibition of Gadd45β/MKK7 complexes.

The synthetic molecules do not bind Gadd45β nor MKK7 in isolation, but they bind to one or another protein when the proteins are in contact with each other in the bound or unbound state, presumably by recognizing a surface that becomes available on Gadd45β, MKK7, and/or a complex of the two proteins only when Gadd45β and MKK7 come in contact with each other, and consequently inducing a conformational modification in one of the two proteins or in the complex as whole that triggers the dissociation of the complex. This property is of particular interest, since it ensures that the compounds have a very high specificity for the target (i.e. the Gadd45β/MKK7 complex) and reduce the probability that the compounds of the invention can interact and so affect proteins that have a structure similar to that of Gadd45β or MKK7. This property—which establish that the therapeutic target of the compounds of the invention is the interface between two proteins (i.e. Gadd45β and MKK7)—also ensures that the compounds of the invention will not block the global biological activities of Gadd45β or MKK7 in vivo, but rather will selectively interfere with the biological functions that Gadd45β or MKK7 have as part of the Gadd45β/MKK7 complex.

Remarkably, compounds of the invention have been shown to induce apoptosis in multiple myeloma cell lines and primary tumour cells, and other tumour B-cell lines, including diffuse large B-cell lymphoma and Burkitt's lymphoma cell lines, as well as other cancers such as promonocytic leukaemia, with $IC_{50}$s in the low nanomolar range, but to have no activity on tumour T-cell lines or on normal cells such as untransformed fibroblasts, bone marrow stromal cells (BMSCs), peripheral blood mononuclear cells (PB-MNCs), and mesenkymal stem cells (MSCs), or in purified primary B- and T-lymphocytes from mice, even when used at very high concentrations (that is 100 μM). This is evidence for their having specificity in their cytotoxic activity for cells with abnormally constitutively active NF-κB. Importantly, compounds of the invention are resistant to proteolysis, soluble and stable in biological fluids retaining full inhibitory activity after prolonged incubation with human serum and therefore appear suitable candidates for systemic use.

The compounds of the invention show high target specificity for the Gadd45β/MKK7 complex in cells. This is shown by the findings that: 1) In a large panel of tumour cell lines there is a highly significant statistical correlation between levels of Gadd45β expression and cancer cell sensitivity to Z-/mDTP-induced killing; 2) sh-RNA-mediated downregulation of Gadd45β induces apoptosis in Z-/mDTP-sensitive but not in Z-/mDTP-resistant cancer cell lines, and the kinetics of apoptosis induction by Gadd45β-specific sh-RNAs in these cell lines is similar to those observed with Z-/mDTPs; 3) the sh-RNA-mediated downregulation of MKK7 renders Z-/mDTP-sensitive cancer cell lines completely resistant to Z-/mDTP-induced killing; 4) the therapeutic target of the invention is the interface between two proteins, Gadd45β and MKK7—which further provides potential for high target selectivity, a key advantage of our solution over existing therapies. These data, together with the low toxicity of Z-/mDTPs to normal cells and the findings that knockout ablation of Gadd45β is well tolerated in mice, indicate that targeting the discreet pro-survival functions of NF-κB in cell survival via Z-/mDTP-mediated inhibition of Gadd45β/MKK7 can provide a therapy that is more specific, less toxic, and hence more effective than therapies targeting the NF-κB pathway and/or the proteasome.

Furthermore, compounds of the invention have no toxicity to normal cells and inhibition of Gadd45β appears to have no or few side effects because Gadd45β knock-out mice are viable and apparently healthy, indicating that complete Gadd45β inactivation is well tolerated in vivo. Compounds of the invention are also stable, soluble, cell-permeable and therefore suitable for the treatment of multiple myeloma, diffuse large B-cell lymphoma and other cancers that depend on NF-κB for their survival. They are also useful for the treatment of chronic inflammatory and autoimmune diseases especially those mediated by NF-κB. Compounds of the invention also have PK profiles which are attractive for therapeutic use.

The invention also relates to the development of clinically useful assays to predict Z-/mDTP therapy response in patients. The data with a large panel of tumour cell lines show that sensitivity to Z-/mDTP-induced killing correlates with a high degree of significance with Gadd45β expression levels (p<0.01), thus establishing the high specificity of Z-/mDTPs' cytotoxic action for Gadd45β. Furthermore, knocking down Gadd45β induces apoptosis in multiple myeloma cells, whereas knocking down MKK7 renders these cells completely resistant to Z-/mDTP-induced killing Together, these data indicate that, should Z-/mDTP therapy enter the clinic, it will be possible to predict patient responder populations via simple and cost-effective qRT-PCR analysis.

According to a first aspect of the invention there is provided a compound of formula I:

    I:

wherein,

A is A'''',
or A''-[M-A'-]$_n$ M-A''';
A'' is A',
A'''
or $Z_1$—$Y_2$—$Y_3$—$Z_4$, wherein $Y_2$—$Y_3$ is an oligopeptide moiety or an oligopeptoid moiety having the residues $Y_2$—$Y_3$ and $Z_1$ is attached to the N-terminal nitrogen of $Y_2$—$Y_3$ and $Z_4$ is attached to the C-terminal carbon of $Y_2$—$Y_3$;

A'' is A',
or $Y_1$—$Y_2$—$Y_3$—$Z_4$, wherein $Y_1$—$Y_2$—$Y_3$ is an oligopeptoid moiety or an oligopeptoid moiety comprising the residues: $Y_1$—$Y_2$—$Y_3$ and $Z_4$ is attached to the C-terminal carbon of $Y_1$—$Y_2$—$Y_3$;

A''' is A',
or $Z_1$—$Y_2$—$Y_3$—$Y_4$, wherein $Y_2$—$Y_3$—$Y_4$ is an oligopeptoid moiety or an oligopeptoid moiety comprising the residues $Y_2$—$Y_3$—$Y_4$ and $Z_1$ is attached to the N-terminal nitrogen of $Y_2$—$Y_3$—$Y_4$;

each occurrence of A' is independently an oligopeptide moiety or an oligopeptoid moiety comprising the residues $Y_1$—$Y_2$—$Y_3$—$Y_4$;

n is an integer from 0 to 18

$Y_1$ and $Y_4$ are independently amino acid residues or residues of amino acid derivatives having aromatic side chains; according to certain embodiments each side chain comprises an alkylene group of from one to three carbons which is substituted once or twice with a 5 to 10 membered carbocyclic or heterocyclic aromatic group and optionally further substituted by alkyl of from 1 to 4 carbon atoms; said aromatic group is optionally substituted by at least one substituent selected from hydroxyl, halogen or C1 to C4 alkyl or C1 to C4 alkoxy.

$Y_2$ is absent or is an amino acid residue or a residue of an amino acid derivative preferably any of the 20 natural amino acids in the L or D configuration and/or preferably an amino acid residue or a residue of an amino acid derivative having a side chain carrying preferably a negative charge in aqueous solution at pH7;

$Y_3$ is an amino acid residue or a residue of an amino acid derivative preferably any of the 20 natural amino acids in the L or D configuration and/or preferably an amino acid residue or a residue of an amino acid derivative having a side chain carrying preferably a positive charge in aqueous solution at pH7, Where $Y_2$ and $Y_3$ are both present in certain embodiments they are preferably such that a salt-bridge is able to form between the respective positive and negative charges of the side chains and/or are such that the distance between the aromatic centres on $Y_1$ and $Y_4$, or on $X_1$ and $X_4$, or on $X_1$ and $Y_4$, or on $Y_1$ and $X_4$ is no higher than 10 or 20 Angstroms and no smaller than 3 Angstroms. Preferably the side chains of $Y_2$ and $Y_3$ consist of no more than 30 atoms. $Y_2$ and $Y_3$ may be naturally occurring amino acids or N-methyl-amino acids in the L- or D-configuration.

$Z_1$ is a group of formula II:

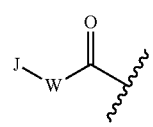    (II)

which is linked to the N-terminal nitrogen of $Y_2$,

W is absent, or a oxygen, or a nitrogen, or an alkylene group of from one to three carbons, which alkylene group of from one to three carbons is optionally substituted by at least one substituent selected from alkyl of from one to four carbons, or 5-10 membered carbocyclic or heterocyclic aromatic group;
J is a 5-10 membered carbocyclic or heterocyclic aromatic group, which aromatic group is optionally substituted by at least one substituent selected from hydroxyl, halogen, alkyl of from one to four carbons, or alkoxy of from one to four carbon atoms;
$Z_4$ represents a group of formula III:

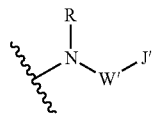

(III)

which is linked to the C-terminal carbon of $Y_3$,
R is hydrogen or alkyl of from one to four carbons;
W' is absent or an alkylene group of from one to three carbons,
which alkylene group of from one to three carbons is optionally substituted by at least one substituent selected from alkyl of from one to four carbons, or 5-10 membered carbocyclic or heterocyclic aromatic group;
J' is a 3-10 membered aliphatic carbocyclic group or a 5-10 membered carbocyclic or heterocyclic aromatic group, which aliphatic or aromatic group is optionally substituted by at least one substituent selected from hydroxyl, halogen, alkyl of from one to four carbons, or alkoxy of from one to four carbon atoms;
M is a peptide bond between preceding oligopeptide or oligopeptoid moiety (A', A" or A''') and following oligopeptide or oligopeptoid moiety (A', A" or A''') or a linker moiety attached via an amide bond, an ester bond, an ether bond, or a thioether bond to the terminal carboxylic group of preceding oligopeptide or oligopeptoid moiety (A', A" or A''') and via an amide bond, an ester bond, an ether bond, or a thioether bond to the terminal amino group of following oligopeptide or oligopeptoid moiety (A', A" or A''');
$X_1$ is absent, or is a moiety added to the amino terminal of A in order to block the free amino group;
$X_2$ is absent or is a moiety added to the carboxyl terminal of A in order to block the free carboxylic group;
According to certain embodiments W is absent or an alkylene of from 1 to 3 carbons.

Preferably $X_1$ and $X_2$ are moieties of no more than 30 (or more preferably 20 or 10) atoms,
with the proviso that $X_1$ is absent if A comprises $Z_1$ and $X_2$ is absent if A comprises $Z_4$ (i.e., if there are no free amino or carboxyl groups at the termini of the molecule, $X_1$ and $X_2$ are not required);
or derivatives thereof, said derivatives being selected from the group consisting of:
  a) oligomers or multimers of molecules of the compound of formula I, said oligomers and multimers comprising two or more molecules of the compound of formula I each linked to a common scaffold moiety via an amide bond formed between an amino or carboxylic acid group present in molecules of the compound of formula I and an opposite amino or carboxylic acid group on a scaffold moiety said scaffold moiety participating in at least 2 amide bonds;
  b) derivatives comprising a molecule of the compound of formula I or an oligomer or multimer thereof as defined above in part a) conjugated via an amide bond, an ester bond, an ether bond or a thioether bond to:
    PEG,
    PEG-based compounds,
    cell-penetrating peptides,
    fluorescent dyes,
    biotin or other tag moiety,
    fatty acids,
    nanoparticles of discrete size,
    or chelating ligands complexed with metallic or radioactive ions.
  c) derivatives comprising a molecule of the compound of formula I or an oligomer or multimer thereof as defined in part a) which has been modified by amidation, glycosylation, carbamylation, acylation, sulfation, phosphorylation, cyclization, lipidation, pegylation or linkage to a peptide or peptoid fusion partner to make a fusion peptide or fusion peptoid.
and
  d) salts and solvates of a molecule of the compound of formula I or of a derivative thereof as defined in part a) or b) above.

According to certain embodiments:
$Y_1$ is D-tryptophan,
L-tryptophan,
D-tyrosine,
L-tyrosine,
D-3,3-diphenyl-alanine,
L-3,3-diphenyl-alanine,
D-H-3-(4-pyridyl) alanine,
L-H-3-(4-pyridyl) alanine,
D-H-3-(3-pyridyl) alanine,
L-H-3-(3-pyridyl) alanine,
D-H-3-(2-pyridyl) alanine,
L-H-3-(2-pyridyl) alanine,
D-2-amino-4-phenyl-butirric acid,
L-2-amino-4-phenyl-butirric acid,
D-H-4-hydroxy-phenyl-glycine,
L-H-4-hydroxy-phenyl-glycine,
D-3-(2-furyl)-alanine,
L-3-(2-furyl)-alanine,
L-homoPhenylalanine,
D-homoPhenylalanine,
D-3-(4-quinolyl)-alanine,
L-3-(4-quinolyl)-alanine;
D-naphtyl-alanine
L-naphtyl-alanine
p-hydroxy-Benzoic acid
p-hydroxy-phenyl-acetic-acid
3-(p-hydroxy-phenyl)-propionic-acid
or N-methyl-derivatives in L- or D-configuration of any above
Alternatively $Y_1$ may be:
D-phenylalanine,
L-phenylalanine,
D-tryptophan,
L-tryptophan,
D-tyrosine,
L-tyrosine,
D-3,3-diphenyl-alanine,
L-3,3-diphenyl-alanine,
D-H-3-(4-pyridyl) alanine,
L-H-3-(4-pyridyl) alanine,
D-H-3-(3-pyridyl) alanine,
L-H-3-(3-pyridyl) alanine,
D-H-3-(2-pyridyl) alanine,
L-H-3-(2-pyridyl) alanine, D-2-amino-4-phenyl-butirric acid,
L-2-amino-4-phenyl-butirric acid,
D-phenyl-glycine,
L-phenyl-glycine,
D-H-4-hydroxy-phenyl-glycine,
L-H-4-hydroxy-phenyl-glycine,
D-3-(2-furyl)-alanine,
L-3-(2-furyl)-alanine,
L-Cyclohexylalanine,
D-Cyclohexylalanine,
L-homoPhenylalanine,
D-homoPhenylalanine,
D-3-(4-quinolyl)-alanine,
L-3-(4-quinolyl)-alanine;
D-naphtyl-alanine
or L-naphtyl-alanine
According to certain embodiments:
$Y_2$ is absent
   D-glutamic acid,
   L-glutamic acid,
   D-aspartic acid,
   L-aspartic acid,
   L-Leucine
   D-Leucine
   L-Glutamine
   D-Glutamine
   L-Methionine
   D-Methionine
   D-2-amino-heptanedioic acid,
   L-2-amino-heptanedioic acid,
   a methyl or ethyl ester of any thereof,
   L-homoserine,
   D-homoserine;
   or N-methyl-derivatives in L- or D-configuration of any
     above
Alternatively $Y_2$ may be:
D-glutamic acid,
L-glutamic acid,
D-aspartic acid,
L-aspartic acid,
D-2-amino-heptanedioic acid,
L-2-amino-heptanedioic acid,
a methyl or ethyl ester of any thereof,
L-homoserine,
or D-homoserine;
According to certain embodiments:
$Y_3$ is D-arginine,
   L-arginine,
   L-Proline
   D-Proline
   D-histidine,
   L-histidine,
   D-lysine,
   D-α,β-diaminopropionic acid (D-Dap),
   L-α,β-diaminopropionic acid (L-Dap),
   L-α,δ-diaminobutirric acid (L-Dab),
   L-α,δ-diaminobutirric acid (L-Dab),
   L-ornitine,
   D-ornitine,
   L-lysine;
   or N-methyl-derivatives in L- or D-configuration of any
     above
Alternatively $Y_3$ may be
D-arginine,
L-arginine,
D-histidine,
L-histidine,
D-lysine,
D-α,β-diaminopropionic acid (D-Dap),
L-α,β-diaminopropionic acid (L-Dap),
L-α,δ-diaminobutirric acid (L-Dab),
L-α,δ-diaminobutirric acid (L-Dab),
L-ornitine,
D-ornitine,
or L-lysine;
According to certain embodiments:
$Y_4$ is
   D-phenylalanine,
   L-phenylalanine,
   D-tryptophan,
   L-tryptophan,
   D-tyrosine,
   L-tyrosine,
   D-3,3-diphenyl-alanine,
   L-3,3-diphenyl-alanine,
   D-H-3-(4-pyridyl) alanine,
   L-H-3-(4-pyridyl) alanine,
   D-H-3-(3-pyridyl) alanine,
   L-H-3-(3-pyridyl) alanine,
   D-H-3-(2-pyridyl) alanine,
   L-H-3-(2-pyridyl) alanine,
   D-2-amino-4-phenyl-butirric acid,
   L-2-amino-4-phenyl-butirric acid,
   D-phenyl-glycine,
   L-phenyl-glycine,
   D-H-4-hydroxy-phenyl-glycine,
   L-H-4-hydroxy-phenyl-glycine,
   D-3-(2-furyl)-alanine,
   L-3-(2-furyl)-alanine,
   L-homoPhenylalanine,
   D-homoPhenylalanine,
   D-3-(4-quinolyl)-alanine,
   L-3-(4-quinolyl)-alanine;
   D-naphtyl-alanine
   L-naphtyl-alanine
   Their N-methyl-derivatives in L- or
   D-configuration
   aniline
   benzylamine
   or 2-phenyl-ethyl-amine
Alternatively $Y_4$ may be
D-phenylalanine,
L-phenylalanine,
D-tryptophan,
L-tryptophan,
D-tyrosine,
L-tyrosine,
D-3,3-diphenyl-alanine,
L-3,3-diphenyl-alanine,
D-H-3-(4-pyridyl) alanine,
L-H-3-(4-pyridyl) alanine,
D-H-3-(3-pyridyl) alanine,
L-H-3-(3-pyridyl) alanine,
D-H-3-(2-pyridyl) alanine,
L-H-3-(2-pyridyl) alanine,
D-2-amino-4-phenyl-butirric acid,
L-2-amino-4-phenyl-butirric acid,
D-phenyl-glycine,
L-phenyl-glycine,
D-H-4-hydroxy-phenyl-glycine,
L-H-4-hydroxy-phenyl-glycine,
D-3-(2-furyl)-alanine,
L-3-(2-furyl)-alanine,
L-Cyclohexylalanine, D-Cyclohexylalanine,
L-homoPhenylalanine,
D-homoPhenylalanine,
D-3-(4-quinolyl)-alanine,
L-3-(4-quinolyl)-alanine;
D-naphtyl-alanine
or L-naphtyl-alanine According to certain preferred embodiments $Y_1$, $Y_2$, $Y_3$ and $Y_4$ are all as described above. According to certain embodiments $Y_1$, $Y_2$, $Y_3$ and $Y_4$ are all described above with the proviso that $Y_2$ is
D-glutamic acid,
L-glutamic acid,
D-aspartic acid,
L-aspartic acid,
D-2-amino-heptanedioic acid,
L-2-amino-heptanedioic acid,
a methyl or ethyl ester of any thereof;
L-homoserine,
L-Leucine
D-Leucine
L-Glutamine
D-Glutamine
L-Methionine
D-Methionine
D-homoserine,
or N-methyl-derivatives in L- or D-configuration of any above and $Y_3$ is
D-arginine,
L-arginine,
D-histidine,
L-histidine,
D-lysine,
L-lysine;
L-Proline
D-Proline
D-α,β-diaminopropionic acid (D-Dap),
L-α,β-diaminopropionic acid (L-Dap),
D-α,δ-diaminobutirric acid (D-Dab),
L-α,δ-diaminobutirric acid (L-Dab),
D-ornitine
L-ornitine
or N-methyl-derivatives in L- or D-configuration of any above According to certain embodiments $Y_1$ and $Y_2$ are both as described above but one or both of $Y_2$ and $Y_3$ are absent. According to certain embodiments M is a peptide bond.

According to certain embodiments $X_1$ is a hydrogen or $X_1$ is one of the following groups added to the amino terminal of the oligopeptide sequence so as to form an amide bond:
acetyl,
benzyloxycarbonyl,
2-chloro-benzyloxycarbonyl,
3-methoxy,4-hydroxy-benzoyl,
3-hydroxy,4-methoxy-benzoyl,
benzoyl,
or fluorenylmethoxycarbonyl;
$X_2$ is an hydroxyl group or is one of the following groups added to the carbonyl acid terminal of the oligopeptide sequence so as to form an amide bond:
amine,
D-phenylalanine,
L-phenylalanine,
D-tryptophan,
L-tryptophan,
D-tyrosine,
L-tyrosine
D-3,3-diphenyl-alanine,
L-3,3-diphenyl-alanine,
D-H-3-(4-pyridyl)-alanine,
L-H-3-(4-pyridyl)-alanine,
D-H-3-(3-pyridyl)-alanine,
L-H-3-(3-pyridyl)-alanine,
D-H-3-(2-pyridyl)-alanine,
L-H-3-(2-pyridyl)-alanine,
D-2-amino-4-phenyl-butirric acid,
L-2-amino-4-phenyl-butirric acid,
D-phenyl-glycine,
L-phenyl-glycine,
D-H-4-hydroxy-phenyl-glycine,
L-H-4-hydroxy-phenyl-glycine,
D-3-(2-furyl)-alanine,
L-3-(2-furyl)-alanine,
L-Cyclohexylalanine,
D-Cyclohexylalanine,
L-homoPhenylalanine,
D-homoPhenylalanine,
D-3-(4-quinolyl)-alanine,
L-3-(4-quinolyl)-alanine;
D-naphtyl-alanine
L-naphtyl-alanine
Or N-methyl-derivatives in L- or D-configuration of any above According to certain embodiments:
$Z_1$ Is 4-hydroxy-benzoyl,
(4-hydroxy-phenyl)-acetyl
3-(4-hydroxy-phenyl)-propionyl
benzoyl,
benzyloxycarbonyl,
2-phenyl-acetyl
3-phenyl-propionyl
3,3-diphenyl-propionyl
3-(1H-Indol-3yl)-propionyl
(1H-Indol-3-yl)-acetyl
Furan-2-yl-acetyl
Furan-3-yl-acetyl
3-pyridin-4-yl-propionyl
3-pyridin-3-yl-propionyl
3-pyridin-2-yl-propionyl
3-pyrimidin-4-yl-propionyl
3-pyridazin-4-yl-propionyl
3-[1,3,5]Triazin-2-yl-propionyl
2-pyridin-4-yl-acetyl
2-pyridin-3-yl-acetyl
2-pyridin-2-yl-acetyl
2-pyrimidin-4-yl-acetyl
2-pyridazin-4-yl-acetyl
2-[1,3,5]Triazin-2-yl-acetyl
Naphthalen-1-yl-acetyl
Naphthalen-2-yl-acetyl
2-Naphthalen-1-yl-propionyl
or 2-Naphthalen-2-yl-propionyl $Y_2$ is D-glutamic acid,
L-glutamic acid,
D-aspartic acid,
L-aspartic acid,
L-Leucine,
D-Leucine,
L-Glutamine,
D-Glutamine,
L-Methionine,
D-Methionine,
D-2-amino-heptanedioic acid, L-2-amino-heptanedioic acid,
a methyl or ethyl ester of any thereof;
L-homoserine;
D-homoserine;
or N-methyl-derivatives in L- or D-configuration of any above $Y_3$ is D-arginine,
L-arginine,
D-histidine,
L-histidine,
L-proline,
D-proline,
D-lysine,
L-lysine;
D-α,β-diaminopropionic acid (D-Dap),
L-α,β-diaminopropionic acid (L-Dap),
D-α,δ-diaminobutirric acid (D-Dab),
L-α,δ-diaminobutirric acid (L-Dab),
D-ornitine
L-ornitine
or N-methyl-derivatives in L- or D-configuration of any above $Z_4$ is phenylamine,
benzylamine,
Phenetylamine
Cyclohexyl-amine
2-cyclohexyl-ethylamine
3-cyclohexyl-propylamine
4-(2-amino-ethyl)-phenol
4-amino-phenol
4-aminomethyl-phenol
1H-Indol-3-yl-amine
2-(1H-Indol-3-yl)-ethylamine
C-(1H-Indol-3-yl)-methylamine
2,2-diphenyl-ethylamine
2,2-dipyridin-4-yl-ethylamine
2-pyridin-4-yl-ethylamine
2-pyridin-3-yl-ethylamine
2-pyridin-2-yl-ethylamine
2-pyrimidin-4-yl-ethylamine
2-[1,3,5]Triazin-2-yl-ethylamine
C-furan-2-yl-methylamine
C-furan-3-yl-methylamine
or C-Naphthalen-2-yl-methylamine.

According to the convention all peptides and peptoids and regions thereof are described from the N terminus to the C terminus.

n may be 0, 1, 2, 3, 4, 5, 6, 7, 8, 9, 10, 11, 12, 13, 14, 15, 16, 17 or 18. According to certain preferred embodiments n=0.

According to certain preferred embodiments A is A'. In such embodiments the compound is therefore essentially a tetrapeptide, a tripeptide, or a dipeptide (or a corresponding peptoid) with optional blocking groups $X_1$ and $X_2$ at one or more of the termini.

Oligopeptides

Oligopeptides are short polymers formed by the condensation of α-amino acids (referred to herein as simply "amino acids"). The link between one amino acid residue and the next is known as a peptide bond or an amide bond.

Amino-Acids

As used herein the term "amino acid" includes the 20 standard amino acids (Isoleucine, Alanine, Leucine, Asparagine, Lysine, Aspartic Acid, Methionine, Cysteine, Phenylalanine, Glutamic Acid, Threonine, Glutamine, Tryptophan, Glycine, Valine, Proline, Serine, Tyrosine, Arginine and Histidine) in both their D and L optical configurations. It also includes synthetic α-amino acids in both D and L forms. According to certain embodiments the D configuration is preferred.

Amino Acid Derivatives

As used herein this term includes N-substituted glycines which differ from α-amino acids in that their side chains are appended to nitrogen atoms along the molecule's backbone, rather than to the α-carbons (as they are in amino acids). Also included in the term are methyl and ethyl esters of α-amino acids, β-amino acids and N-methylated α-amino acids.

Oligopeptoids

Strictly speaking, the term "oligopeptide" relates to oligomers of α-amino acids only. An analogous oligomer incorporating (at all or some residue positions) an amino acid derivate (for example an N-substituted glycine) is known as an oligopeptoid.

Derivatives

Preferably, derivatives of the compound of the first aspect of the invention are functional derivatives. The term "functional derivative" is used herein to denote a chemical derivative of a compound of formula (I) having the same physiological function (as the corresponding unmodified compounds of formula (I) or alternatively having the same in vitro function in a functional assay (for example, in one of the assays described in one of the examples disclosed herein).

Derivatives of the compound of the invention may comprise the structure of formula (I) modified by well known processes including amidation, glycosylation, carbamylation, acylation, for example acetylation, sulfation, phosphorylation, cyclization, lipidization and pegylation. The structure of formula (I) may be modified at random positions within the molecule, or at predetermined positions within the molecule and may include one, two, three or more attached chemical moieties. Derivatives include compounds in which the N-terminal $NH_2$ group is replaced with another group, for example a methoxy group. A compound of the invention may be a fusion protein, whereby the structure of formula (I) is fused to another protein or polypeptide (the fusion partner) using methods known in the art. Any suitable peptide or protein can be used as the fusion partner (e.g., serum albumin, carbonic anhydrase, glutathione-S-transferase or thioredoxin, etc.). Preferred fusion partners will not have an adverse biological activity in vivo. Such fusion proteins may be made by linking the carboxy-terminus of the fusion partner to the amino-terminus of the structure of formula (I) or vice versa. Optionally, a cleavable linker may be used to link the structure of formula (I) to the fusion partner. A resulting cleavable fusion protein may be cleaved in vivo such that an active form of a compound of the invention is released. Examples of such cleavable linkers include, but are not limited to, the linkers D-D-D-D-Y [SEQ ID NO.: 227], G-P-R, A-G-G and H-P-F-H-L [SEQ ID NO.: 228], which can be cleaved by enterokinase, thrombin, ubiquitin cleaving enzyme and renin, respectively. See, e.g., U.S. Pat. No. 6,410,707.

A compound of the invention may be a physiologically functional derivative of the structure of formula (I). The term "physiologically functional derivative" is used herein to denote a chemical derivative of a compound of formula (I) having the same physiological function as the corresponding unmodified compound of formula (I). For example, a physiologically functionally derivative may be convertible in the body to a compound of formula (I). According to the present invention, examples of physiologically functional derivatives include esters, amides, and carbamates; preferably esters and amides. Pharmaceutically acceptable esters and amides of the compounds of the invention may comprise a $C_{1-20}$ alkyl-, $C_{2-20}$ alkenyl-, $C_{5-10}$ aryl-, $C_{5-10}$ or $C_{1-20}$ alkyl-, or amino acid-ester or -amide attached at an appropriate site, for example at an acid group. Examples of suitable moieties are hydrophobic substituents with 4 to 26 carbon atoms, preferably 5 to 19 carbon atoms. Suitable lipid groups include, but are not limited to, the following: lauroyl ($Ci_2H_{23}$), palmityl ($C_{15}H_{31}$), oleyl ($C_{15}H_{29}$), stearyl ($C_{17}H_{35}$), cholate; and deoxycholate.

Methods for lipidization of sulfhydryl-containing compounds with fatty acid derivatives are disclosed in U.S. Pat. No. 5,936,092; U.S. Pat. No. 6,093,692; and U.S. Pat. No. 6,225,445. Fatty acid derivatives of a compound of the invention comprising a compound of the invention linked to fatty acid via a disulfide linkage may be used for delivery of a compound of the invention to neuronal cells and tissues. Lipidisation markedly increases the absorption of the compounds relative to the rate of absorption of the corresponding unlipidised compounds, as well as prolonging blood and tissue retention of the compounds. Moreover, the disulfide linkage in lipidised derivative is relatively labile in the cells and thus facilitates intracellular release of the molecule from the fatty acid moieties. Suitable lipid-containing moieties are hydrophobic substituents with 4 to 26 carbon atoms, preferably 5 to 19 carbon atoms. Suitable lipid groups include, but are not limited to, the following: palmityl ($C_{15}H_{31}$), oleyl ($C_{15}H_{29}$), stearyl ($C_{17}H_{35}$), cholate; and deoxycholate.

Cyclization methods include cyclization through the formation of a disulfide bridge and head-to-tail cyclization using a cyclization resin. Cyclized peptides may have enhanced stability, including increased resistance to enzymatic degradation, as a result of their conformational constraints. Cyclization may in particular be expedient where the uncyclized peptide includes an N-terminal cysteine group. Suitable cyclized peptides include monomeric and dimeric head-to-tail cyclized structures. Cyclized peptides may include one or more additional residues, especially an additional cysteine incorporated for the purpose of formation of a disulfide bond or a side chain incorporated for the purpose of resin-based cyclization.

A compound of the invention may be a pegylated structure of formula (I). Pegylated compounds of the invention may provide additional advantages such as increased solubility, stability and circulating time of the polypeptide, or decreased immunogenicity (see U.S. Pat. No. 4,179,337).

Chemical moieties for derivitization of a compound of the invention may also be selected from water soluble polymers such as polyethylene glycol, ethylene glycol/propylene glycol copolymers, carboxymethylcellulose, dextran, polyvinyl alcohol and the like. A polymer moiety for derivatisation of a compound of the invention may be of any molecular weight, and may be branched or unbranched. Polymers of other molecular weights may be used, depending on the desired therapeutic profile, for example the duration of sustained release desired, the effects, if any on biological activity, the ease in handling, the degree or lack of antigenicity and other known effects of the polyethylene glycol to a therapeutic protein or analog. For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

Salts and solvates of compounds of the invention that are suitable for use in a medicament are those wherein a counterion or associated solvent is pharmaceutically acceptable. However, salts and solvates having non-pharmaceutically acceptable counterions or associated solvents are within the scope of the present invention, for example, for use as intermediates in the preparation of the compounds of formula (I) and their pharmaceutically acceptable salts or solvates.

Suitable salts according to the invention include those formed with organic or inorganic acids or bases. Pharmaceutically acceptable acid addition salts include those formed with hydrochloric, hydrobromic, sulphuric, nitric, citric, tartaric, acetic, phosphoric, lactic, pyruvic, acetic, trifluoroacetic, succinic, perchloric, fumaric, maleic, glycollic, lactic, salicylic, oxaloacetic, methanesulfonic, ethanesulfonic, p-toluenesulfonic, formic, benzoic, malonic, naphthalene-2-sulfonic, benzenesulfonic, and isetliionic acids. Other acids such as oxalic, while not in themselves pharmaceutically acceptable, may be useful as intermediates in obtaining the compounds of the invention and their pharmaceutical acceptable salts. Pharmaceutically acceptable salts with bases include ammonium salts, alkali metal salts, for example potassium and sodium salts, alkaline earth metal salts, for example calcium and magnesium salts, and salts with organic bases, for example dicyclohexylamine and N-methyl-D-glucomine.

Those skilled in the art of organic chemistry will appreciate that many organic compounds can form complexes with solvents in which they are reacted or from which they are precipitated or crystallized. Such complexes are known as "solvates". For example, a complex with water is known as a "hydrate". The present invention provides solvates of compounds of the invention.

According to certain preferred embodiments, the compound as a half-life in the human circulation of at least 0.1, 0.2, 0.5, 1, 2, 3, 4, 5, 6, 7, 8, 9, 10, 11 or most preferably at least 12 hours.

Preferably, the compound retains at least 20, 30, 40, 50, 60, 70, 80, 90 or most preferably 99% of its capacity to bind to Gadd45β and/or MKK7 (and/or an association of both) as assessed in an in vitro binding assay, or at least 20, 30, 40, 50, 60, 70, 80, 90 or most preferably 99% of its capacity to block the Gadd45β interaction with MKK7 as assessed in an in vitro competitive binding assay following incubation in normal human serum for at 24 hours at 37 degrees Celsius.

Alternatively or additionally, the compound has at least one of the following activities:
  a) The ability to inhibit at least 20, 30, 40, 50, 60, 70, 80, 90 or most preferably 99% of the MKK7 interactions with Gadd45β under the assay conditions described in the examples.
  b) The ability in vitro to kill at least 20, 30, 40, 50, 60, 70, 80, 90 or most preferably 99% of cells in a culture of a human myeloma cell line selected from the group consisting of U266, KMS-11, NCI-H929, ARH-77, JJN-3, KMS-12, KMS-18, and KMS-27, or of a culture of the DLBCL cell line LY-3, or of a culture of the pro-monocytic cell line U937, or of a culture of the Burkitt's lymphoma cell line BJAB or a culture of primary tumour cells (for example primary multiple myeloma tumour cells) under conditions in which at least 90% of the T-cell line JURKAT is not killed.

According to certain preferred embodiments the oligopeptide core moiety of the compound, identified as A in Formula I has an amino acid sequence selected from the group consisting of:

(L-Tyr)-(L-Asp)-(L-His)-(L-Phe), [SEQ ID NO.: 2]

(L-Tyr)-(L-Glu)-(L-Arg)-(L-Phe), [SEQ ID NO.: 3]

(L-Tyr)-(L-Glu)-(L-His)-(L-Phe), [SEQ ID NO.: 4]

(L-Trp)-(L-Asp)-(L-His)-(L-Phe), [SEQ ID NO.: 5]

(L-Trp)-(L-Glu)-(L-His)-(L-Phe), [SEQ ID NO.: 6]

(L-Tyr)-(L-Asp)-(L-Arg)-(L-Phe), [SEQ ID NO.: 7]

(L-Tyr)-(L-Asp)-(L-Lys)-(L-Phe), [SEQ ID NO.: 8]

(L-Tyr)-(L-Glu)-(L-Lys)-(L-Phe), [SEQ ID NO.: 9]

(L-Trp)-(L-Glu)-(L-Lys)-(L-Phe), [SEQ ID NO.: 10]

(L-Trp)-(L-Glu)-(L-Arg)-(L-Phe), [SEQ ID NO.: 11]

(L-Trp)-(L-Asp)-(L-Lys)-(L-Phe), [SEQ ID NO.: 12]

(L-Trp)-(L-Asp)-(L-Arg)-(L-Phe), [SEQ ID NO.: 13]

(L-Tyr)-(L-Asp)-(L-His)-(L-Trp), [SEQ ID NO.: 14]

(L-Tyr)-(L-Glu)-(L-His)-(L-Trp), [SEQ ID NO.: 15]

(L-Trp)-(L-Asp)-(L-His)-(L-Trp), [SEQ ID NO.: 16]

(L-Trp)-(L-Glu)-(L-His)-(L-Trp), [SEQ ID NO.: 17]

(L-Tyr)-(L-Asp)-(L-Arg)-(L-Trp), [SEQ ID NO.: 18]

(L-Tyr)-(L-Asp)-(L-Lys)-(L-Trp), [SEQ ID NO.: 19]

(L-Tyr)-(L-Glu)-(L-Lys)-(L-Trp), [SEQ ID NO.: 20]

(L-Tyr)-(L-Glu)-(L-Arg)-(L-Trp), [SEQ ID NO.: 21]

(L-Trp)-(L-Glu)-(L-Lys)-(L-Trp), [SEQ ID NO.: 22]

(L-Trp)-(L-Glu)-(L-Arg)-(L-Trp), [SEQ ID NO.: 23]

(L-Trp)-(L-Asp)-(L-Lys)-(L-Trp), [SEQ ID NO.: 24]

(L-Trp)-(L-Asp)-(L-Arg)-(L-Trp), [SEQ ID NO.: 25]

(L-Tyr)-(L-Asp)-(L-His)-(L-Tyr), [SEQ ID NO.: 26]

(D-Tyr)-(D-Glu)-(D-Arg)-(D-Phe), [SEQ ID NO.: 27]

(D-Tyr)-(D-Asp)-(D-His)-(D-Phe), [SEQ ID NO.: 28]

(D-Trp)-(D-Glu)-(D-Arg)-(D-Phe), [SEQ ID NO.: 29]

(D-Trp)-(D-Asp)-(D-His)-(D-Phe), [SEQ ID NO.: 30]

(D-Tyr)-(D-Asp)-(D-Arg)-(D-Phe), [SEQ ID NO.: 31]

(D-Tyr)-(D-Asp)-(D-His)-(D-Tyr), [SEQ ID NO.: 32]

(D-Tyr)-(D-Glu)-(D-Arg)-(D-Tyr), [SEQ ID NO.: 33]

(D-Trp)-(D-Asp)-(D-His)-(D-Typ), [SEQ ID NO.: 34]

(D-Trp)-(D-Glu)-(D-Arg)-(D-Typ), [SEQ ID NO.: 35]

(D-Tyr)-(D-Asp)-(D-Lys)-(D-Phe), [SEQ ID NO.: 36]

(D-Tyr)-(D-Glu)-(D-His)-(D-Phe), [SEQ ID NO.: 208]

(D-Tyr)-(D-Asp)-(D-Lys)-(D-Phe), [SEQ ID NO.: 209]

(D-Trp)-(D-Glu)-(D-His)-(D-Phe), [SEQ ID NO.: 210]

(D-Tyr)-(D-Glu)-(D-Lys)-(D-Phe), [SEQ ID NO.: 211]

(D-Trp)-(D-Glu)-(D-Lys)-(D-Phe), [SEQ ID NO.: 212]

(D-Trp)-(D-Asp)-(D-Lys)-(D-Phe), [SEQ ID NO.: 213]

(D-Tyr)-(D-Asp)-(D-His)-(D-Trp), [SEQ ID NO.: 214]

(D-Tyr)-(D-Glu)-(D-His)-(D-Trp), [SEQ ID NO.: 215]

(D-Trp)-(D-Asp)-(D-His)-(D-Trp), [SEQ ID NO.: 216]

(D-Trp)-(D-Glu)-(D-His)-(D-Trp), [SEQ ID NO.: 217]

(D-Tyr)-(D-Asp)-(D-Arg)-(D-Trp), [SEQ ID NO.: 218]

(D-Tyr)-(D-Asp)-(D-Lys)-(D-Trp), [SEQ ID NO.: 219]

(D-Tyr)-(D-Glu)-(D-Lys)-(D-Trp), [SEQ ID NO.: 220]

(D-Tyr)-(D-Glu)-(D-Arg)-(D-Trp), [SEQ ID NO.: 221]

(D-Trp)-(D-Glu)-(D-Lys)-(D-Trp), [SEQ ID NO.: 222]

(D-Trp)-(D-Glu)-(D-Arg)-(D-Trp), [SEQ ID NO.: 223]

(D-Trp)-(D-Asp)-(D-Lys)-(D-Trp), [SEQ ID NO.: 224]

-continued (D-Trp)-(D-Gln)-(D-Arg)-(D-Trp), [SEQ ID NO.: 225]

(D-Trp)-(D-Asn)-(D-Lys)-(D-Trp), [SEQ ID NO.: 226]

(L-Tyr)-(L-Asp)-(L-Phe), (D-Tyr)-(D-Asp)-(D-Phe), (L-Tyr)-(L-Glu)-(L-Phe), (L-Tyr)-(L-Arg)-(L-Phe), (D-Tyr)-(D-Arg)-(D-Phe), (D-Tyr)-(D-Glu)-(D-Phe), (D-Tyr)-(D-Pro)-(D-Phe)

(D-Tyr)-(D-Leu)-(D-Phe), (D-Tyr)-(D-Asp)-(D-Tyr), (D-Tyr)-(D-Glu)-(D-Tyr), (D-Tyr)-(D-Arg)-(D-Tyr), (D-Tyr)-(D-Pro)-(D-Tyr), (D-Tyr)-(D-Leu)-(D-Tyr), (D-Phe)-(D-Pro)-(D-Phe)

(D-Phe)-(D-Leu)-(D-Phe), (D-Phe)-(D-Arg)-(D-Tyr)

(D-Phe)-(D-Glu)-(D-Tyr), (D-Phe)-(D-Asp)-(D-Tyr), (D-Phe)-(D-Pro)-(D-Tyr)

(D-Phe)-(D-Leu)-(D-Tyr)

(D-Tyr)-(D-Pro)-(D-Trp)

(D-Tyr)-(D-Leu)-(D-Trp), (D-Tyr)-(D-Asp)-(D-Trp), (D-Tyr)-(D-Glu)-(D-Trp), (D-Tyr)-(D-Arg)-(D-Trp), (D-Tyr)-(D-Pro)-(D-Trp), (D-Tyr)-(D-Leu)-(D-Trp), (D-Phe)-(D-Pro)-(D-Trp)

(D-Phe)-(D-Leu)-(D-Trp), (D-Phe)-(D-Arg)-(D-Trp)

(D-Phe)-(D-Glu)-(D-Trp), (D-Phe)-(D-Asp)-(D-Trp), (D-Phe)-(D-Pro)-(D-Trp) and (D-Phe)-(D-Leu)-(D-Trp)

In other embodiments the A moiety is selected from the group consisting of:
p-hydroxybenzoic acid-(L-Glu)-(L-Arg)-aniline
p-hydroxybenzoic acid-(D-Glu)-(L-Arg)-aniline
p-hydroxybenzoic acid-(L-Glu)-(D-Arg)-aniline
p-hydroxybenzoic acid-(D-Glu)-(D-Arg)-aniline
p-hydroxybenzoic acid-(L-Glu)-(L-Arg)-benzylamine
p-hydroxybenzoic acid-(D-Glu)-(L-Arg)-benzylamine
p-hydroxybenzoic acid-(L-Glu)-(D-Arg)-benzylamine
p-hydroxybenzoic acid-(D-Glu)-(D-Arg)-benzylamine
p-hydroxybenzoic acid-(L-Glu)-(L-Arg)-2-phenyl-ethyl-amine
p-hydroxybenzoic acid-(D-Glu)-(L-Arg)-2-phenyl-ethyl-amine
p-hydroxybenzoic acid-(L-Glu)-(D-Arg)-2-phenyl-ethyl-amine
p-hydroxybenzoic acid-(D-Glu)-(D-Arg)-2-phenyl-ethyl-amine
2-(4-hydroxy-phenyl) acetic acid-(L-Glu)-(L-Arg)-aniline
2-(4-hydroxy-phenyl) acetic acid-(D-Glu)-(L-Arg)-aniline
2-(4-hydroxy-phenyl) acetic acid-(L-Glu)-(D-Arg)-aniline
2-(4-hydroxy-phenyl) acetic acid-(D-Glu)-(D-Arg)-aniline
2-(4-hydroxy-phenyl) acetic acid-(L-Glu)-(L-Arg)-benzylamine
2-(4-hydroxy-phenyl) acetic acid-(D-Glu)-(L-Arg)-benzylamine
2-(4-hydroxy-phenyl) acetic acid-(L-Glu)-(D-Arg)-benzylamine
2-(4-hydroxy-phenyl acetic acid-(D-Glu)-(D-Arg)-benzylamine
2-(4-hydroxy-phenyl) acetic acid-(L-Glu)-(L-Arg)-2-phenyl-ethyl-amine
2-(4-hydroxy-phenyl) acetic acid-(D-Glu)-(L-Arg)-2-phenyl-ethyl-amine
2-(4-hydroxy-phenyl) acetic acid-(L-Glu)-(D-Arg)-2-phenyl-ethyl-amine
2-(4-hydroxy-phenyl) acetic acid-(D-Glu)-(D-Arg)-2-phenyl-ethyl-amine
3-(4-hydroxy-phenyl) propionic acid-(L-Glu)-(L-Arg)-aniline
3-(4-hydroxy-phenyl) propionic acid-(D-Glu)-(L-Arg)-aniline
3-(4-hydroxy-phenyl) propionic acid-(L-Glu)-(D-Arg)-aniline
3-(4-hydroxy-phenyl) propionic acid-(D-Glu)-(D-Arg)-aniline
3-(4-hydroxy-phenyl) propionic acid-(L-Glu)-(L-Arg)-benzylamine
3-(4-hydroxy-phenyl) propionic acid-(D-Glu)-(L-Arg)-benzylamine
3-(4-hydroxy-phenyl) propionic acid-(L-Glu)-(D-Arg)-benzylamine
3-(4-hydroxy-phenyl) propionic acid-(D-Glu)-(D-Arg)-benzylamine
3-(4-hydroxy-phenyl) propionic acid-(L-Glu)-(L-Arg)-2-phenyl-ethyl-amine
3-(4-hydroxy-phenyl) propionic acid-(D-Glu)-(L-Arg)-2-phenyl-ethyl-amine
3-(4-hydroxy-phenyl) propionic acid-(L-Glu)-(D-Arg)-2-phenyl-ethyl-amine
3-(4-hydroxy-phenyl) propionic acid-(D-Glu)-(D-Arg)-2-phenyl-ethyl-amine
p-hydroxybenzoic acid-(L-Arg)-aniline
p-hydroxybenzoic acid-(D-Arg)-aniline
p-hydroxybenzoic acid-(L-Glu)-aniline
p-hydroxybenzoic acid-(D-Glu)-aniline
p-hydroxybenzoic acid-(L-Arg)-benzylamine
p-hydroxybenzoic acid-(D-Arg)-benzylamine
p-hydroxybenzoic acid-(L-Glu)-benzylamine
p-hydroxybenzoic acid-(D-Glu)-benzylamine
p-hydroxybenzoic acid-(L-Arg)-2-phenyl-ethyl-amine
p-hydroxybenzoic acid-(D-Arg)-2-phenyl-ethyl-amine
p-hydroxybenzoic acid-(D-Glu)-2-phenyl-ethyl-amine p-hydroxybenzoic acid-(L-Glu)-2-phenyl-ethyl-amine
2-(4-hydroxy-phenyl) acetic acid-(L-Arg)-aniline
2-(4-hydroxy-phenyl) acetic acid-(D-Arg)-aniline
2-(4-hydroxy-phenyl) acetic acid-(L-Glu)-aniline
2-(4-hydroxy-phenyl) acetic acid-(D-Glu)-aniline
2-(4-hydroxy-phenyl) acetic acid-(D-Arg)-benzylamine
2-(4-hydroxy-phenyl) acetic acid-(L-Arg)-benzylamine
2-(4-hydroxy-phenyl) acetic acid-(D-Glu)-benzylamine
2-(4-hydroxy-phenyl) acetic acid-(L-Glu)-benzylamine
2-(4-hydroxy-phenyl) acetic acid-(L-Arg)-2-phenyl-ethyl-amine
2-(4-hydroxy-phenyl) acetic acid-(D-Arg)-2-phenyl-ethyl-amine
2-(4-hydroxy-phenyl) acetic acid-(L-Glu)-2-phenyl-ethyl-amine
2-(4-hydroxy-phenyl) acetic acid-(D-Glu)-2-phenyl-ethyl-amine
3-(4-hydroxy-phenyl) propionic acid-(L-Arg)-aniline
3-(4-hydroxy-phenyl) propionic acid-(D-Arg)-aniline
3-(4-hydroxy-phenyl) propionic acid-(L-Glu)-aniline
3-(4-hydroxy-phenyl) propionic acid-(D-Glu)-aniline
3-(4-hydroxy-phenyl) propionic acid-(L-Arg)-benzylamine
3-(4-hydroxy-phenyl) propionic acid-(D-Arg)-benzylamine
3-(4-hydroxy-phenyl) propionic acid-(L-Glu)-benzylamine
3-(4-hydroxy-phenyl) propionic acid-(D-Glu)-benzylamine
3-(4-hydroxy-phenyl) propionic acid-(L-Arg)-2-phenyl-ethyl-amine
3-(4-hydroxy-phenyl) propionic acid-(D-Arg)-2-phenyl-ethyl-amine
3-(4-hydroxy-phenyl) propionic acid-(L-Glu)-2-phenyl-ethyl-amine
3-(4-hydroxy-phenyl) propionic acid-(D-Glu)-2-phenyl-ethyl-amine Alternatively, the moiety labelled as A' in Formula I may be an oligopeptide having an amino acid sequence selected from the group listed directly above.

According to certain embodiments the A' moiety is a peptide or peptoid moiety having the residues $Xaa_1$-$Xaa_2$-$Xaa_3$-$Xaa_4$ wherein:

Xaa$_1$ is L-Tyr, D-Tyr, N-methyl-L-Tyr, N-methyl-D-Tyr, p-hydroxybenzoic acid, 2-(4-hydroxy-phenyl) acetic acid, 3-(4-hydroxy-phenyl) propionic acid or acetyl Xaa$_2$ is L-Glu, D-Glu, L-Asp or D-Asp, N-methyl-L-Glu, N-methyl-D-Glu, N-methyl-L-Asp, N-methyl-D-Asp, L-Pro, D-Pro, N-methyl-L-Pro, N-methyl-D-Pro, L-Leu, D-Leu, N-methyl-L-Leu, N-methyl-D-Leu, or absent Xaa$_3$ is L-Arg, D-Arg, L-His or D-His, L-Lys, D-Lys, N-methyl-L-Arg, N-methyl-D-Arg, N-methyl-L-His, N-methyl-D-His, N-methyl-L-Lys, N-methyl-D-Lys, or absent; and Xaa$_4$ is aniline, benzylamine, 2-phenyl-ethyl-amine, L-Phe or D-Phe, N-methyl-L-Phe, N-methyl-D-Phe, L-Trp, D-Trp, N-methyl-L-Trp, N-methyl-D-Trp.

According to certain embodiments either Xaa$_2$ or Xaa$_3$ are absent but not both Xaa$_2$ and Xaa$_3$. According to other embodiments Xaa$_2$ and Xaa$_3$ are both absent.

M may be simply an amide bond between adjacent peptide or peptoid moieties. Alternatively, it may be a molecular moiety introduced as a spacer and attached to adjacent peptide or peptoid moieties by amide bonds.

M may be an additional amino acid. Preferably it is an additional amino acid with a non-bulky side chain, for example glycine, alanine or serine or derivatives of any thereof. Alternatively M may be a non-amino acid moiety, for example, ε-aminocaproic acid, 3-amino-propionic acid, 4-amino-butirric acid. Other moieties can be methyl-amine, ethyl-amine, propyl-amine, butyl-amine, methylene, di-methylene, tri-methylene or tetra-methylene. In all cases M should be such that its presence does not materially interfere with binding between the A' moiety and Gadd45β and/or MKK7. The extent of potential interference may be assessed by use of an in vitro binding assay as disclosed herein.

Oligomers and Multimers

The first aspect of the invention encompasses, oligomers or multimers of molecules of the compound of formula I, said oligomers and multimers comprising two or more molecules of the compound of formula I each linked to a common scaffold moiety via an amide bond formed between an amine or carboxylic acid group present in molecules of the compound of formula I and an opposite amino or carboxylic acid group on a scaffold moiety said scaffold moiety participating in at least 2 amide bonds.

According to certain embodiments the common scaffold may be the amino acid lysine. Lysine is a tri-functional amino acid, having in addition to the functional groups which define it as an amino acid, an amino group on its side claim. This tri-functional nature allows it to form three amide bonds with peptides, peptoids or similar molecules. Other tri-functional amino acids which may be used as a common scaffold include D-α,β-diaminopropionic acid (D-Dap), L-α,β-diaminopropionic acid (L-Dap), L-α,δ-diaminobutirric acid (L-Dab), L-α,δ-diaminobutirric acid (L-Dab), and L-ornitine, D-ornitine. Other tri-functional non-standard amino acids may also be used in accordance with the invention. The common scaffold may also comprise branched peptides, peptoids or similar molecules which incorporate tri-functional amino acids within their sequence and have at least three functionally active terminal groups able to form amide bonds.

Cell-Penetrating Peptides.

According to certain embodiments the compounds of formula I are conjugated to a cell penetrating peptide (CPP). Such peptides may be attached to a compound of formula I either via one or more covalent bonds or by non-covalent associations.

CPPs may either directly penetrate the plasmalemma, for example the CPP may be Tat or a derivative, a peptide derived from the Antennapedia sequence, or a poly-arginine tag, a PTD-4 peptide, or a functionally equivalent cell-permeable peptide (Ho A, Schwarze S R, Mermelstein S J, Waksman G, Dowdy S F 2001 Synthetic protein transduction domains: enhanced transduction potential in vitro and in vivo. Cancer Res 61:474-477).

Alternatively, the CPP may enter the cell by mediating endocytosis or through mediating the formation of transitory membrane-spanning structures. For a discussion of cell penetrating peptides, the reader is directed to Wagstaff et al. (2006). Curr. Med. Chem. 13:171-1387 and references therein.

According to certain embodiments compounds of the invention may be conjugated to nano-particles (for example nano-Gold) in order to promote cellular uptake Fluorescent Dyes, Tag Moieties and Lipidated Derivatives.

Compounds of formula I may be conjugated to fluorescent dyes in order that their penetration into target tissues or cells may be monitored. Fluorescent dyes may be obtained with amino groups (i.e., succinimides, isothiocyanates, hydrazines), carboxyl groups (i.e., carbodiimides), thiol groups (i.e., maleimides and acetyl bromides) and azide groups which may be used to selectively react with the peptide moieties of compounds of formula I. Examples of fluorescent dyes include fluoresceine and its derivates, rhodamine and its derivatives.

Compounds of formula I may be conjugated to nanoparticles of discrete size such those described in Chithrani D B, Mol Membr Biol. 2010 Oct. 7, (Epub ahead of print) with a discrete size of up to 100 nm, whereby the peptides or their derivatives can be attached by a disulphide bridge to allow specific release within the reducing environment of the cytosol. Also peptide-nanoparticles conjugated via amide, ether, ester, thioether bonds can be used for the same purpose given the low toxicity of these compounds. Nanoparticles will favour cell uptake as well as will provide a mean to visualize and quantify cell uptake by fluorescence techniques (Schrand A M, Lin J B, Hens S C, Hussain S M., Nanoscale. 2010 Sep. 27, Epub ahead of print).

Tag moieties may be attached by similar means and similarly allow for monitoring of the success of targeting to tissues and cells.

Fatty acid derivatives of a compound of the invention comprising a compound of formula I linked to a fatty acid via a disulfide linkage may be used for delivery of a compound of the invention to cells and tissues. Lipidisation markedly increases the absorption of the compounds relative to the rate of absorption of the corresponding unlipidised compounds, as well as prolonging blood and tissue retention of the compounds. Moreover, the disulfide linkage in lipidised derivative is relatively labile in the cells and thus facilitates intracellular release of the molecule from the fatty acid moieties. Suitable lipid-containing moieties are hydrophobic substituents with 4 to 26 carbon atoms, preferably 5 to 19 carbon atoms. Suitable lipid groups include, but are not limited to, the following: palmityl ($C_{15}H_{31}$), oleyl ($C_{15}H_{29}$), stearyl ($C_{17}H_{35}$), cholate; linolate, and deoxycholate.

Ion Conjugates

The invention also encompasses compounds of formula I functionally attached to metallic or radioactive ions. This attachment is typically achieved by the conjugation of an ion chelating agent (for example EDTA) which is chelated with the ion. By such means radioactive ions (for example $^{99m}Tc$, $^{111}In$, $^{64}Cu$, $^{67}Cu$, $^{89}Sr$, $^{90}Y$, $^{117m}Sn$, $^{153}Sm$, $^{186}Re$, $^{188}Re$, or $^{177}Lu$) may be delivered to target cells as radiotherapy. Non-radioactive metallic ions (for example ions of gadolinium) may be used as a NMR-detectable marker.

Salts and Solvates

Salts and solvates of compounds of the invention that are suitable for use in a medicament are those wherein a counterion or associated solvent is pharmaceutically acceptable. However, salts and solvates having non-pharmaceutically acceptable counterions or associated solvents are within the scope of the present invention, for example, for use as intermediates in the preparation of the compounds of formula (I) and their pharmaceutically acceptable salts or solvates.

Suitable salts according to the invention include those formed with organic or inorganic acids or bases. Pharmaceutically acceptable acid addition salts include those formed with hydrochloric, hydrobromic, sulphuric, nitric, citric, tartaric, acetic, phosphoric, lactic, pyruvic, acetic, trifluoroacetic, succinic, perchloric, fumaric, maleic, glycollic, lactic, salicylic, oxaloacetic, methanesulfonic, ethanesulfonic, p-toluenesulfonic, formic, benzoic, malonic, naphthalene-2-sulfonic, benzenesulfonic, and isethionic acids. Other acids such as oxalic, while not in themselves pharmaceutically acceptable, may be useful as intermediates in obtaining the compounds of the invention and their pharmaceutical acceptable salts. Pharmaceutically acceptable salts with bases include ammonium salts, alkali metal salts, for example potassium and sodium salts, alkaline earth metal salts, for example calcium and magnesium salts, and salts with organic bases, for example dicyclohexylamine and N-methyl-D-glucosamine.

Those skilled in the art of organic chemistry will appreciate that many organic compounds can form complexes with solvents in which they are reacted or from which they are precipitated or crystallized. Such complexes are known as "solvates". For example, a complex with water is known as a "hydrate". The present invention provides solvates of compounds of the invention.

Examples of preferred molecules of formula I are given below. Where the L/D configuration of an amino acid residue is not specified, both configurations are encompassed Acetyl-Tyr-Glu-Arg-Phe-$NH_2$ [SEQ ID NO.: 37]
para-hydroxybenzoic acid-Glu-Arg-aniline
para-hydroxybenzoic acid-Glu-Arg-benzylamine
para-hydroxybenzoic acid-Glu-Arg-2-phenyl-ethyl-amine
2-(4-hydroxyphenyl) acetic acid-Glu-Arg-aniline
2-(4-hydroxyphenyl) acetic acid-Glu-Arg-benzylamine
2-(4-hydroxyphenyl) acetic acid-Glu-Arg-2-phenyl-ethyl-amine
3-(4-hydroxyphenyl) acetic acid-Glu-Arg-3-aniline
3-(4-hydroxyphenyl) acetic acid-Glu-Arg-benzylamine
3-(4-hydroxyphenyl) acetic acid-Glu-Arg-2-phenyl-ethyl-amine
Acetyl-Tyr-Asp-His-Phe-$NH_2$ [SEQ ID NO.: 38]
para-hydroxybenzoic-acid-Asp-His-aniline
para-hydroxybenzoic-acid-Asp-His-benzylamine
para-hydroxybenzoic-acid-Asp-His-3-phenyl-propyl-amine
2-(4-hydroxyphenyl) acetic acid-Asp-His-aniline
2-(4-hydroxyphenyl) acetic acid-Asp-His-benzylamine
2-(4-hydroxyphenyl) acetic acid-Asp-His-2-phenyl-ethyl-amine
3-(4-hydroxyphenyl) propionic acid-Asp-His-aniline
3-(4-hydroxyphenyl) propionic acid-Asp-His-benzylamine
3-(4-hydroxyphenyl) propionic acid-Asp-His-2-phenyl-ethyl-amine
Acetyl-Tyr-Asp-Lys-Phe-$NH_2$ [SEQ ID NO.: 39]
Acetyl-Tyr-Glu-Lys-Phe-$NH_2$ [SEQ ID NO.: 40]
Acetyl-Tyr-Glu-His-Phe-$NH_2$ [SEQ ID NO.: 41]
Acetyl-Tyr-Asp-Arg-Phe-$NH_2$, [SEQ ID NO.: 42]
Acetyl-Trp-Glu-His-Phe-$NH_2$, [SEQ ID NO.: 43]
Acetyl-Trp-Glu-Lys-Phe-$NH_2$, [SEQ ID NO.: 44]
Acetyl-Trp-Asp-His-Phe-$NH_2$, [SEQ ID NO.: 45]
Acetyl-Trp-Asp-Lys-Phe-$NH_2$, [SEQ ID NO.: 46]
Acetyl-Tyr-Glu-Arg-Tyr-$NH_2$ [SEQ ID NO.: 47]
Acetyl-Tyr-Asp-Lys-Tyr-$NH_2$ [SEQ ID NO.: 48]
Acetyl-Tyr-Glu-Lys-Tyr-$NH_2$ [SEQ ID NO.: 49]
Acetyl-Tyr-Glu-His-Tyr-$NH_2$ [SEQ ID NO.: 50]
Acetyl-Tyr-Asp-Arg-Tyr-$NH_2$, [SEQ ID NO.: 51]
Acetyl-Trp-Glu-His-Tyr-$NH_2$, [SEQ ID NO.: 52]
Acetyl-Trp-Glu-Lys-Tyr-$NH_2$, [SEQ ID NO.: 53]
Acetyl-Trp-Asp-His-Tyr-$NH_2$, [SEQ ID NO.: 54]
Acetyl-Trp-Asp-Lys-Tyr-$NH_2$, [SEQ ID NO.: 55]
internal lactam of acetyl-Tyr-Glu-Lys-Phe-$NH_2$ [SEQ ID NO.: 56]
Acetyl-Tyr-Gln-Arg-Phe-$NH_2$ [SEQ ID NO.: 57]
Acetyl-Tyr-Met-Arg-Phe-$NH_2$ [SEQ ID NO.: 58]
Acetyl-Tyr-Leu-Arg-Phe-$NH_2$ [SEQ ID NO.: 59]
Acetyl-Tyr-Arg-Phe-$NH_2$,
Acetyl-Tyr-Arg-Tyr-$NH_2$,
Acetyl-Tyr-Glu-Phe-$NH_2$,
Acetyl-Tyr-Glu-Tyr-$NH_2$,
Acetyl-Tyr-Asp-Phe-$NH_2$, Acetyl-Tyr-Asp-Tyr-NH$_2$,
Acetyl-Tyr-Pro-Phe-NH$_2$,
Acetyl-Tyr-Lys-Phe-NH$_2$,
Acetyl-Tyr-His-Phe-NH$_2$,
H-Tyr-Arg-Phe-NH$_2$,
H-Tyr-Arg-Tyr-NH$_2$,
H-Tyr-Glu-Phe-NH$_2$,
H-Tyr-Glu-Tyr-NH$_2$,
H-Tyr-Asp-Phe-NH$_2$,
H-Tyr-Asp-Tyr-NH$_2$,
H-Tyr-Pro-Phe-NH$_2$,
H-Tyr-Lys-Phe-NH$_2$,
H-Tyr-His-Phe-NH$_2$,
Benzyloxycarbonyl-Tyr-Arg-Phe-NH$_2$,
Benzyloxycarbonyl-Tyr-Arg-Tyr-NH$_2$,
Benzyloxycarbonyl-Tyr-Glu-Phe-NH$_2$,
Benzyloxycarbonyl-Tyr-Glu-Tyr-NH$_2$,
Benzyloxycarbonyl-Tyr-Asp-Phe-NH$_2$,
Benzyloxycarbonyl-Tyr-Asp-Tyr-NH$_2$,
Benzyloxycarbonyl-Tyr-Pro-Phe-NH$_2$,
Benzyloxycarbonyl-Tyr-Lys-Phe-NH$_2$,
Benzyloxycarbonyl-Tyr-His-Phe-NH$_2$,
Benzyloxycarbonyl-Tyr-Glu-Arg-Phe-NH$_2$, [SEQ ID NO.: 60]
Benzyloxycarbonyl-Tyr-Asp-His-Phe-NH$_2$, [SEQ ID NO.: 61]
Benzyloxycarbonyl-Tyr-Asp(OMe)-His-Phe-NH$_2$, [SEQ ID NO.: 62]
Benzyloxycarbonyl-Tyr-Arg-Phe-NH$_2$,
Benzyloxycarbonyl-Tyr-Glu-Phe-NH$_2$,
Benzyloxycarbonyl-(N-methyl)Tyr-(N-methyl)Arg-(N-methyl)Phe-NH$_2$,
Benzyloxycarbonyl-(N-methyl)Tyr-Glu-(N-methyl)Phe-NH$_2$,
Benzyloxycarbonyl-Tyr-(N-methyl)Arg-(N-methyl)Phe-NH$_2$,
Benzyloxycarbonyl-(N-methyl)Tyr-(N-methyl)Arg-Phe-NH$_2$,
Benzyloxycarbonyl-Tyr-Glu-(N-methyl)Phe-NH$_2$,
Benzyloxycarbonyl-Tyr-(N-methyl)Glu-Phe-NH$_2$,
Benzyloxycarbonyl-(N-methyl)Tyr-Glu-Phe-NH$_2$,
Acetyl-(N-methyl)Tyr-(N-methyl)Arg-(N-methyl)Phe-NH$_2$,
Acetyl-(N-methyl)Tyr-Glu-(N-methyl)Phe-NH$_2$,
Acetyl-Tyr-(N-methyl)Arg-(N-methyl)Phe-NH$_2$,
Acetyl-(N-methyl)Tyr-(N-methyl)Arg-Phe-NH$_2$,
Acetyl-Tyr-Glu-(N-methyl)Phe-NH$_2$,
Acetyl-Tyr-(N-methyl)Glu-Phe-NH$_2$,
Acetyl-(N-methyl)Tyr-Glu-Phe-NH$_2$,
H—(N-methyl)Tyr-(N-methyl)Arg-(N-methyl)Phe-NH$_2$,
H—(N-methyl)Tyr-Glu-(N-methyl)Phe-NH$_2$,
H-Tyr-(N-methyl)Arg-(N-methyl)Phe-NH$_2$,
H—(N-methyl)Tyr-(N-methyl)Arg-Phe-NH$_2$,
H-Tyr-Glu-(N-methyl)Phe-NH$_2$,
H-Tyr-(N-methyl)Glu-Phe-NH$_2$,
H—(N-methyl)Tyr-Glu-Phe-NH$_2$,
Acetyl-Tyr-Glu-(β-homo)Phe-NH$_2$,
Acetyl-Tyr-(β-homo)Glu-Phe-NH$_2$,
Acetyl-(β-homo)Tyr-Glu-Phe-NH$_2$,
Acetyl-Tyr-Phe-NH$_2$,
Acetyl-Phe-Tyr-NH$_2$,
Benzyloxycarbonyl-Tyr-Phe-NH$_2$,
Benzyloxycarbonyl-Phe-Tyr-NH$_2$,
H-Tyr-Phe-NH$_2$,
H-Phe-Tyr-NH$_2$,
(3-Methoxy,4-hydroxy-benzoyl)-Tyr-Glu-Arg-Phe-NH$_2$, [SEQ ID NO.: 63]
(3-Methoxy,4-hydroxy-benzoyl)-Tyr-Asp-His-Phe-NH$_2$, [SEQ ID NO.: 64]
(3-Methoxy,4-hydroxy-benzoyl)-Tyr-Asp(OMe)-His-Phe-NH$_2$, [SEQ ID NO.: 65]
(3-Methoxy,4-hydroxy-benzoyl)-Tyr-Arg-Phe-NH$_2$,
(3-Methoxy,4-hydroxy-benzoyl)-Tyr-Glu-Phe-NH$_2$,
Fluorenylmethyloxycarbonyl-Tyr-Glu-Arg-Phe-NH$_2$, [SEQ ID NO.: 66]
Fluorenylmethyloxycarbonyl-Tyr-Asp-His-Phe-NH$_2$, [SEQ ID NO.: 67]
Fluorenylmethyloxycarbonyl-Tyr-Asp(OMe)-His-Phe-NH$_2$, [SEQ ID NO.: 68]
Fluorenylmethyloxycarbonyl-Tyr-Asp(OMe)-His-Phe-NH$_2$ [SEQ ID NO.: 69]
Fluorenylmethyloxycarbonyl-Tyr-Arg-Phe-NH$_2$,
Fluorenylmethyloxycarbonyl-Tyr-Glu-Phe-NH$_2$,
Myristyl-Tyr-Glu-Arg-Phe-NH$_2$, [SEQ ID NO.: 70]
Myristyl-Tyr-Asp-His-Phe-NH$_2$, [SEQ ID NO.: 71]
Myristyl-Tyr-Arg-Phe-NH$_2$,
Myristyl-Tyr-Glu-Phe-NH$_2$,
Myristyl-Tyr-Asp(OMe)-His-Phe-NH$_2$, [SEQ ID NO.: 72]
Acetyl-Tyr-Glu-Arg-Phe-Gly-Tyr-Glu-Arg-Phe-NH$_2$, [SEQ ID NO.: 73]
Acetyl-Tyr-Asp-His-Phe-Gly-Tyr-Asp-His-Phe-NH$_2$, [SEQ ID NO.: 74]
Acetyl-Tyr-Arg-Phe-Gly-Tyr-Arg-Phe-NH$_2$, [SEQ ID NO.: 75]
Acetyl-Tyr-Asp(OMe)-His-Phe-Gly-Tyr-Asp(OMe)-His-Phe-NH$_2$, [SEQ ID NO.: 76]
benzyloxycarbonyl-Tyr-Glu-Arg-Phe-Gly-Tyr-Glu-Arg-Phe-NH$_2$, [SEQ ID NO.: 77]
benzyloxycarbonyl-Tyr-Asp-His-Phe-Gly-Tyr-Asp-His-Phe-NH$_2$, [SEQ ID NO.: 78]
benzyloxycarbonyl-Tyr-Arg-Phe-Gly-Tyr-Arg-Phe-NH$_2$, [SEQ ID NO.: 79]
benzyloxycarbonyl-Tyr-Asp(OMe)-His-Phe-Gly-Tyr-Asp(OMe)-His-Phe-NH$_2$, [SEQ ID NO.: 80]
Further examples of compounds of the invention include:

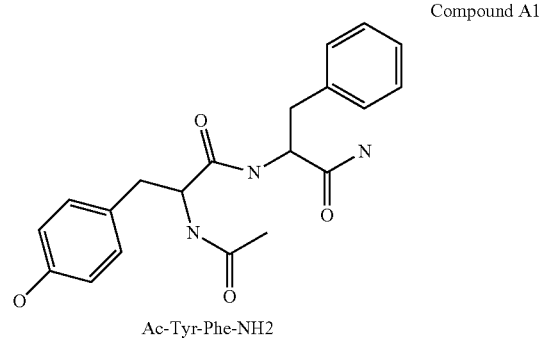

Compound A1

Ac-Tyr-Phe-NH2

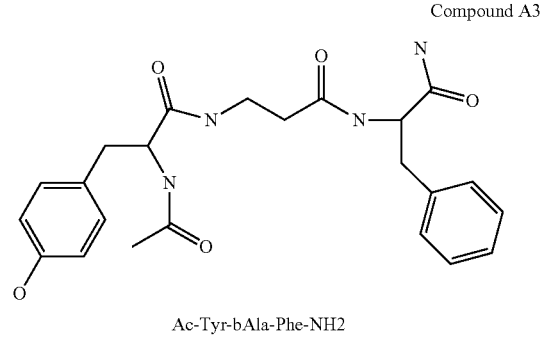

Compound A3

Ac-Tyr-bAla-Phe-NH2

-continued

Compound A6

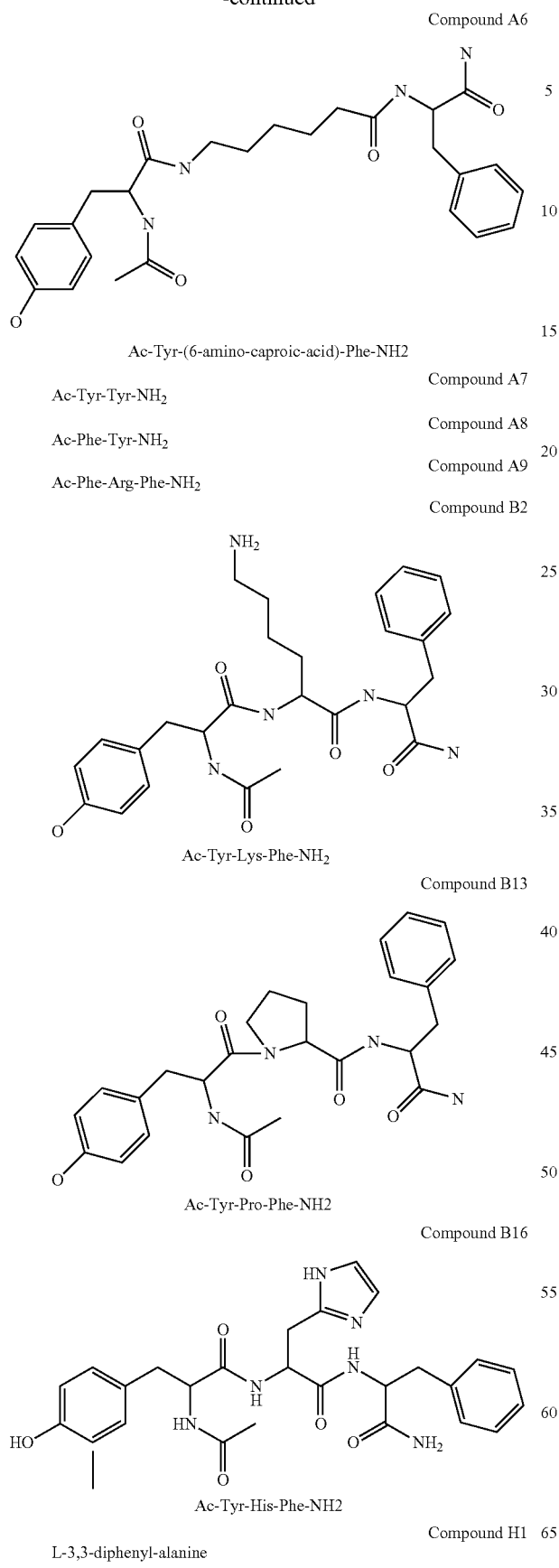

Ac-Tyr-(6-amino-caproic-acid)-Phe-NH2

Compound A7
Ac-Tyr-Tyr-NH₂

Compound A8
Ac-Phe-Tyr-NH₂

Compound A9
Ac-Phe-Arg-Phe-NH₂

Compound B2

Ac-Tyr-Lys-Phe-NH₂

Compound B13

Ac-Tyr-Pro-Phe-NH₂

Compound B16

Ac-Tyr-His-Phe-NH₂

Compound H1
L-3,3-diphenyl-alanine

Compound H2
L—H-3(4-pyridyl) alanine

Compound H3
L—H-4-hydroxy-phenyl-glycine

Compound H4
L-2-amino-4-phenyl-butirric acid

Compound H5
L-phenyl-glycine

Compound H6
L—H-4-hydroxy-phenyl-glycine

Compound H7
L-homoPhenylalanine

Compound H8
L-3-(2-furyl)-alanine

Compound H9
L-3-(4-quinolyl)-alanine

Compound H10
L-naphtyl-alanine

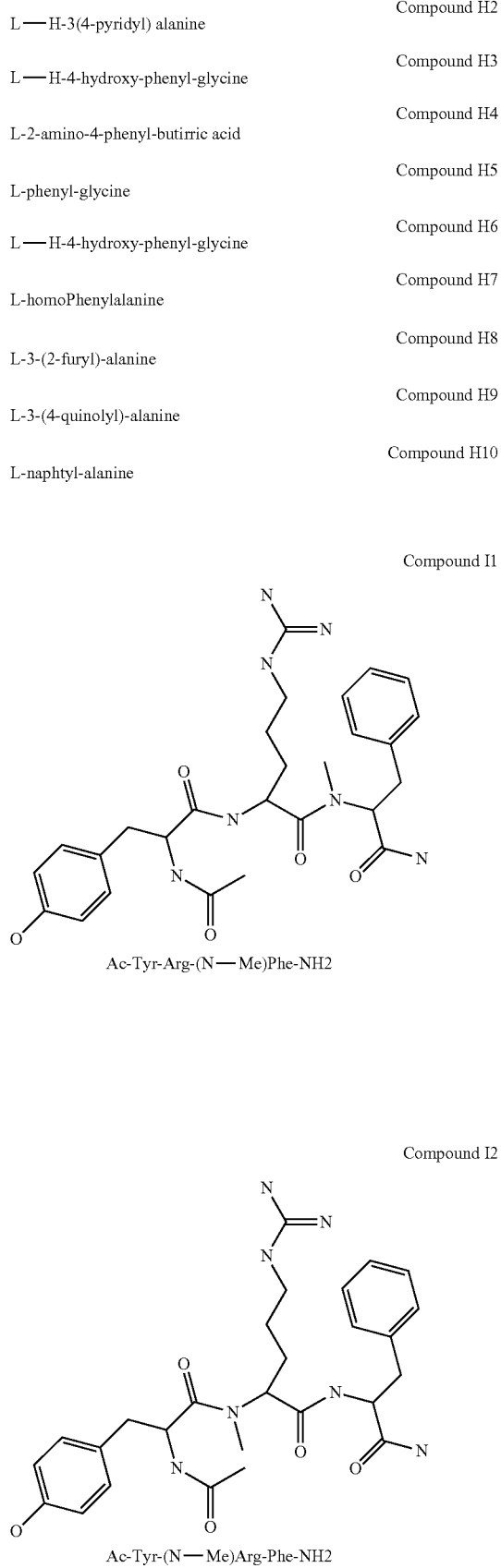

Compound I1

Ac-Tyr-Arg-(N—Me)Phe-NH2

Compound I2

Ac-Tyr-(N—Me)Arg-Phe-NH2

-continued
Compound I3
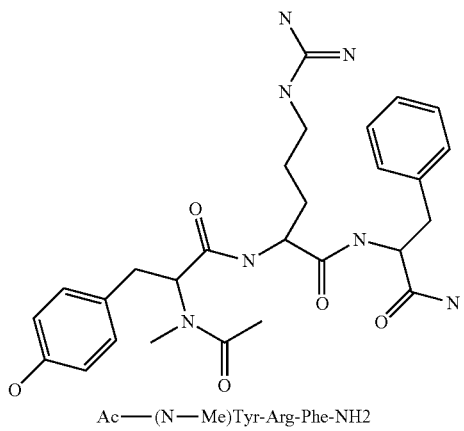
Ac—(N—Me)Tyr-Arg-Phe-NH2
Compound I4
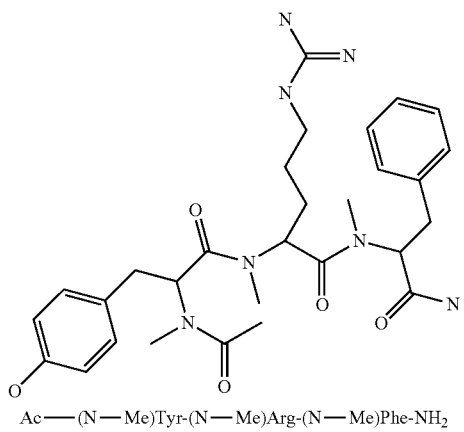
Ac—(N—Me)Tyr-(N—Me)Arg-(N—Me)Phe-NH$_2$
Compound I5
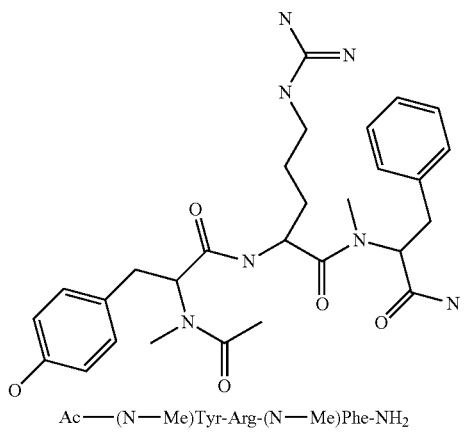
Ac—(N—Me)Tyr-Arg-(N—Me)Phe-NH$_2$
-continued
Compound O1
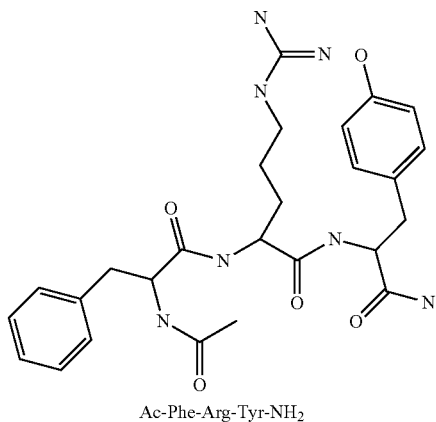
Ac-Phe-Arg-Tyr-NH$_2$
Compound O2
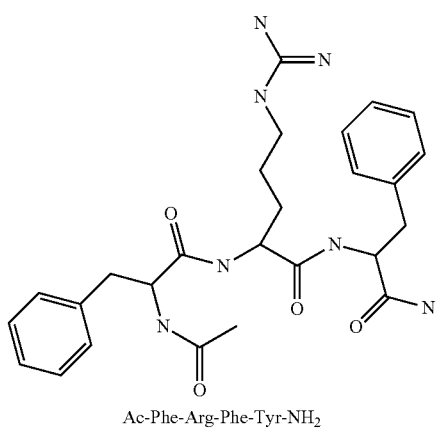
Ac-Phe-Arg-Phe-Tyr-NH$_2$
Compound O3
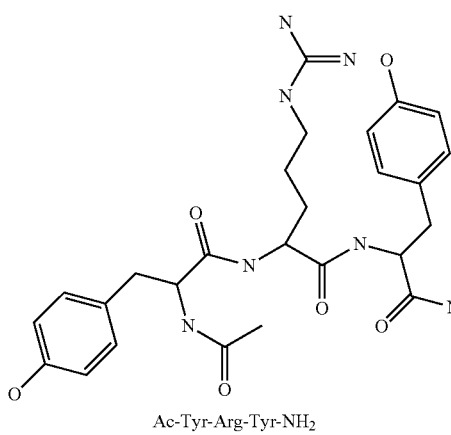
Ac-Tyr-Arg-Tyr-NH$_2$ Compound O5

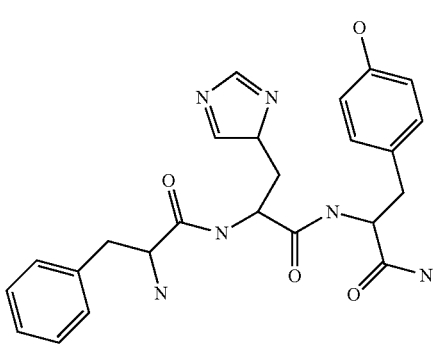

H-Phe-His-Tyr-NH₂

Compound O7

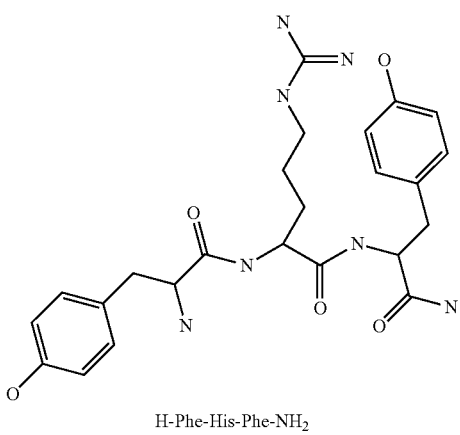

H-Phe-His-Phe-NH₂

Compound O8
H-Phe-Arg-Tyr-NH₂

Compound O9
H-Phe-Arg-Phe-NH₂

Compound O10
H-Tyr-Arg-Tyr-NH₂

Compound P1
4-(hydroxyl)-phenyl-acetic acid-Arg-3-phenyl-ethylamine

Compound P2
4-(hydroxyl)-phenyl-acetic acid-His-3-phenyl-ethyl-amine

Compound P3
4-(hydroxyl)-phenyl-acetic acid-Glu-3-phenyl-ethylamine

Compound G1

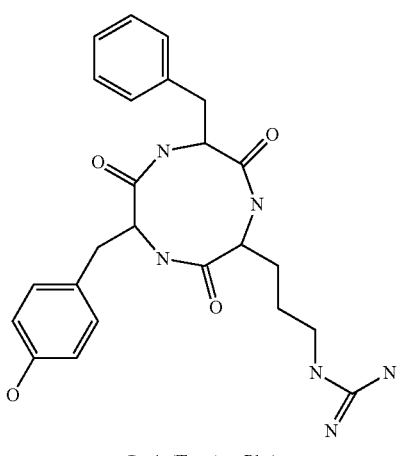

Cyclo(Tyr-Arg-Phe)

Compound G2
Cyclo(Phe-Arg-Tyr)

Compound G3

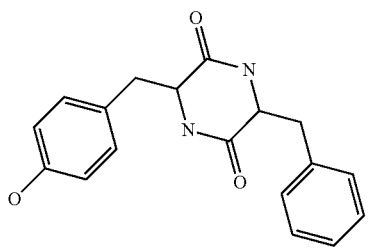

Cyclo(Tyr-Phe)

Compound N1
Nanogolds-Tyr-Arg-Phe-NH₂

According to certain embodiments compounds disclosed specifically herein, including in the examples, are preferred compounds or are preferred embodiments of the A' moiety of formula I. The present invention contemplates the multimer versions or the specific compounds explicitly disclosed herein. For example the present invention contemplates the 3 or 4 residue peptide or peptoid moieties of the specific compounds disclosed herein as corresponding to the A, A', A'', A''' or A'''' moiety of compounds of formula I.

Pharmaceutical Compositions

According to a second aspect of the invention, there is provided a pharmaceutical composition comprising a compound according to the first aspect of the invention and a pharmaceutically acceptable carrier.

While it is possible for the active ingredient to be administered alone, it is preferable for it to be present in a pharmaceutical formulation or composition. Accordingly, the invention provides a pharmaceutical formulation comprising a compound of formula (I), or derivative thereof, or a salt or solvate thereof, as defined above and a pharmaceutically acceptable carrier. Pharmaceutical compositions of the invention may take the form of a pharmaceutical formulation as described below.

The pharmaceutical formulations according to the invention include those suitable for oral, parenteral (including subcutaneous, intradermal, intramuscular, intravenous, and intraarticular), inhalation (including fine particle dusts or mists which may be generated by means of various types of metered does pressurized aerosols, nebulizers or insufflators), rectal and topical (including dermal, transdermal, transmucosal, buccal, sublingual, and intraocular) administration, although the most suitable route may depend upon, for example, the condition and disorder of the recipient.

The formulations may conveniently be presented in unit dosage form and may be prepared by any of the methods well known in the art of pharmacy. All methods include the step of bringing the active ingredient into association with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste. Various pharmaceutically acceptable carriers and their formulation are described in standard formulation treatises, e.g., *Remington's Pharmaceutical Sciences* by E. W. Martin. See also Wang, Y. J. and Hanson, M. A., *Journal of Parenteral Science and Technology*, Technical Report No. 10, Supp. 42:2S, 1988.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Preferably, compositions according to the invention are suitable for subcutaneous administration, for example by injection.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The compounds of formula (I) or variant, derivative, salt or solvate thereof can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use. Extemporaneous injection solutions and suspensions may be prepared from sterile powders, granules and tablets of the kind previously described. Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor. An aqueous carrier may be, for example, an isotonic buffer solution at a pH of from about 3.0 to about 8.0, preferably at a pH of from about 3.5 to about 7.4, for example from 3.5 to 6.0, for example from 3.5 to about 5.0. Useful buffers include sodium citrate-citric acid and sodium phosphate-phosphoric acid, and sodium acetate/acetic acid buffers. The composition preferably does not include oxidizing agents and other compounds that are known to be deleterious to the compound of formula I and related molecules. Excipients that can be included are, for instance, other proteins, such as human serum albumin or plasma preparations. If desired, the pharmaceutical composition may also contain minor amounts of non-toxic auxiliary substances, such as wetting or emulsifying agents, preservatives, and pH buffering agents and the like, for example sodium acetate or sorbitan monolaurate.

Exemplary compositions for nasal aerosol or inhalation administration include solutions in saline, which can contain, for example, benzyl alcohol or other suitable preservatives, absorption promoters to enhance bioavailability, and/or other solubilizing or dispersing agents such as those known in the art. Conveniently in compositions for nasal aerosol or inhalation administration the compound of the invention is delivered in the form of an aerosol spray presentation from a pressurized pack or a nebulizer, with the use of a suitable propellant, e.g., dichlorodifluoro-methane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g., gelatin for use in an inhaler or insufflator can be formulated to contain a powder mix of the compound and a suitable powder base, for example lactose or starch. In one specific, non-limiting example, a compound of the invention is administered as an aerosol from a metered dose valve, through an aerosol adapter also known as an actuator. Optionally, a stabilizer is also included, and/or porous particles for deep lung delivery are included (e.g., see U.S. Pat. No. 6,447,743).

Formulations for rectal administration may be presented as a retention enema or a suppository with the usual carriers such as cocoa butter, synthetic glyceride esters or polyethylene glycol. Such carriers are typically solid at ordinary temperatures, but liquefy and/or dissolve in the rectal cavity to release the drug.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerine or sucrose and acacia. Exemplary compositions for topical administration include a topical carrier such as Plastibase (mineral oil gelled with polyethylene).

Preferred unit dosage formulations are those containing an effective dose, as hereinbefore recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavouring agents.

The compounds of the invention are also suitably administered as sustained-release systems. Suitable examples of sustained-release systems of the invention include suitable polymeric materials, for example semi-permeable polymer matrices in the form of shaped articles, e.g., films, or mirocapsules; suitable hydrophobic materials, for example as an emulsion in an acceptable oil; or ion exchange resins; and sparingly soluble derivatives of the compound of the invention, for example, a sparingly soluble salt. Sustained-release systems may be administered orally; rectally; parenterally; intravaginally; intraperitoneally; topically, for example as a powder, ointment, gel, drop or transdermal patch; bucally; or as an oral or nasal spray.

Preparations for administration can be suitably formulated to give controlled release of compounds of the invention. For example, the pharmaceutical compositions may be in the form of particles comprising one or more of biodegradable polymers, polysaccharide jellifying and/or bioadhesive polymers, amphiphilic polymers, agents capable of modifying the interface properties of the particles of the compound of formula (I). These compositions exhibit certain biocompatibility features which allow a controlled release of the active substance. See U.S. Pat. No. 5,700,486.

A compound of the invention may be delivered by way of a pump (see Langer, supra; Sefton, *CRC Crit. Ref Biomed. Eng.* 14:201, 1987; Buchwald et al., *Surgery* 88:507, 1980; Saudek et al., *N. Engl. J. Med.* 321:574, 1989) or by a continuous subcutaneous infusions, for example, using a mini-pump. An intravenous bag solution may also be employed. Other controlled release systems are discussed in the review by Langer (*Science* 249:1527-1533, 1990). In another aspect of the disclosure, compounds of the invention are delivered by way of an implanted pump, described, for example, in U.S. Pat. No. 6,436,091; U.S. Pat. No. 5,939,380; U.S. Pat. No. 5,993,414.

Implantable drug infusion devices are used to provide patients with a constant and long term dosage or infusion of a drug or any other therapeutic agent. Essentially such device may be categorized as either active or passive. A compound of the present invention may be formulated as a depot preparation. Such a long acting depot formulation can be administered by implantation, for example subcutaneously or intramuscularly; or by intramuscular injection. Thus, for example, the compounds can be formulated with suitable polymeric or hydrophobic materials, for example as an emulsion in an acceptable oil; or ion exchange resins; or as a sparingly soluble derivatives, for example, as a sparingly soluble salt.

A therapeutically effective amount of a compound of the invention may be administered as a single pulse dose, as a bolus dose, or as pulse doses administered over time. Thus, in pulse doses, a bolus administration of a compound of the invention is provided, followed by a time period wherein no a compound of the invention is administered to the subject, followed by a second bolus administration. In specific, non-limiting examples, pulse doses of a compound of the invention are administered during the course of a day, during the course of a week, or during the course of a month.

In one embodiment, a therapeutically effective amount of a compound of the invention is administered with a therapeutically effective amount of another agent, for example a further anti-neoplastic chemotherapeutic agent (for example, thalidomide, dexamethasone, bortezomib, lenalidomide, melphalan, cisplatinum, doxorubicin, 5-FU, etc) or an agent to treat anaemia (for example erythropoietin), or an agent to prevent bone fractures (for example a bisphosphonate such as pamidronate or zoledronic acid).

The therapeutically effective amount of a compound of the invention will be dependent on the molecule utilized, the subject being treated, the severity and type of the affliction, and the manner and route of administration.

According to the third aspect of the invention, there is provided a method of treating a disorder or disease comprising administering a compound according to the first and second aspect of the invention or a pharmaceutical composition according to the second aspect of the invention administering a therapeutically effective amount of a compound according to the first aspect of the invention or a pharmaceutical composition according to the second aspect of the invention to a subject in need thereof.

Disorders and Diseases

The compounds, compositions and methods of the invention are suitable for the treatment or prevention of diseases and disorders which are either characterised by aberrant increased expression or activity of Gadd45β or which are characterised by aberrant activation of the NF-κB pathway and are amenable to treatment by the induction of Programmed Cell Death by the inhibition of Gadd45β activity.

Diseases suitable for treatment or prevention include cancer. Preferably the cancer is a cancer expressing raised levels of Gadd45β relative to corresponding normal healthy cells or tissues. Cancers known to express aberrantly high levels of Gadd45β and so suitable for treatment with the compounds of the invention include: multiple myeloma, diffuse large B-cell lymphoma, Burkitt's lymphoma, promonocytic leukaemia and other leukemias, as well as solid tumours such as hepatocellular carcinoma, bladder cancer, brain and central nervous system cancer, breast cancer, head and neck cancer, lung cancer, and prostate cancer. According to certain embodiments the cancer is a cancer that depends on NF-κB for its survival. Specific such cancers that depend on NF-κB for survival and so are suitable for treatment or prevention include: multiple myeloma, mantle cell lymphoma, MALT lymphoma, Hodgkin's lymphoma, diffuse large B-cell lymphoma, Burkitt's lymphoma, promonocytic leukaemia, myelodysplastic syndrome, adult T-cell leukaemia (HTLV-1), chronic lymphocytic leukaemia, chronic myelogenous leukemia, acute myelogenic leukaemia, acute lymphoblastic leukemia, colitis-associated cancer, colon cancer, liver cancer (for example hapatocellular carcinoma) cervical cancer, renal cancer, lung cancer, oesophageal cancer, gastric cancer, laryngeal cancer, prostate cancer, pancreatic cancer, thyroid cancer, parathyroid cancer, bladder cancer, ovarian cancer, breast cancer, melanoma, cylindroma, squamous cell carcinoma (skin, and head and neck), oral carcinoma, endometrial carcinoma, retinoblastoma, astrocytoma, and glioblastoma. According to certain preferred embodiments the cancer is multiple myeloma. According to certain embodiments, cells taken from the subject (for example biopsied from a subject's cancer or extracted from the subjects blood or other body fuild into which they may have been released by the cancer) may be tested for NF-κB activation and/or elevated level of Gadd45β activity in order to determine the cancer's suitability to treatment by methods, compounds and compositions of the invention.

Other diseases and disorders suitable for treatment or prevention include autoimmune disease (for example multiple sclerosis, lupus, type-I diabetes), allergic disease (for example asthma), chronic inflammatory disease (for example inflammatory bowel disease, rheumatoid arthritis, psoriasis, ulcerative colitis), genetic disease (for example, incontinentia pigmenti, anhidrotic ectodermal dysplasia with immunodeficiency and cylindromatosis), ischemic and vascular disease (for example atherosclerosis, angina pectoris, stroke, myocardial infarction), and degenerative disease (for example Alzheimer's and Parkinson disease), liver diseases such as liver fibrosis and liver cirrhosis A broad range of diseases and disorders depend on the activity of NF-κB. Indeed, the pathogenesis of virtually every known human disease or disorder is now being considered to depend on inflammation, and hence to involve NF-κB. This functions as a masterswitch of the inflammatory response, coordinating expression of an array of over 200 genes encoding cytokines, receptors, transcription factors, chemokines, pro-inflammatory enzymes, and other factors, including pro-survival factors, which initiate and sustain inflammation. The compounds of the invention inhibit the discrete pro-survival activity of NF-κB in inflammation. Therefore, diseases and disorders amenable to treatment with these compounds include, apart from conventional chronic inflammatory diseases (such as inflammatory bowel disease, rheumatoid arthritis, and psoriasis), other diseases and disorders that depend on a significant inflammatory component. Examples of such diseases and disorders, which are being treated with anti-inflammatory agents or NF-κB-inhibiting agents or have been proposed as suitable for treatment with NF-κB inhibitors and could also be treated with a compound of the invention, include:

1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) or adenovirus; or eosinophilic esophagitis;

2. bone and joints: arthritides associated with or including osteoarthritis/osteoarthrosis, both primary and secondary to, for example, congenital hip dysplasia; cervical and lumbar spondylitis, and low back and neck pain; osteoporosis; rheumatoid arthritis and Still's disease; seronegative spondyloarthropathies including ankylosing spondylitis, psoriatic arthritis, reactive arthritis and undifferentiated spondarthropathy; septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositits and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; low back pain; Familial Mediterranean fever, Muckle-Wells syndrome, and Familial Hibernian Fever, Kikuchi disease; drug-induced arthalgias, tendonititides, and myopathies;

3. pain and connective tissue remodelling of musculoskeletal disorders due to injury [for example sports injury] or disease: arthitides (for example rheumatoid arthritis, osteoarthritis, gout or crystal arthropathy), other joint disease (such as intervertebral disc degeneration or temporomandibular joint degeneration), bone remodelling disease (such as osteoporosis, Paget's disease or osteonecrosis), polychondritits, scleroderma, mixed connective tissue disorder, spondyloarthropathies or periodontal disease (such as periodontitis);

4. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia greata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;

5. eyes: blepharitis; conjunctivitis, including perennial and vernal allergic conjunctivitis; iritis; anterior and posterior uveitis; choroiditis; autoimmune; degenerative or inflammatory disorders affecting the retina; ophthalmitis including sympathetic ophthalmitis; sarcoidosis; infections including viral, fungal, and bacterial;

6. gastrointestinal tract: glossitis, gingivitis, periodontitis; oesophagitis, including reflux; eosinophilic gastro-enteritis, mastocytosis, Crohn's disease, colitis including ulcerative colitis, proctitis, pruritis ani; coeliac disease, irritable bowel syndrome, and food-related allergies which may have effects remote from the gut (for example migraine, rhinitis or eczema);

7. abdominal: hepatitis, including autoimmune, alcoholic and viral; fibrosis and cirrhosis of the liver; cholecystitis; pancreatitis, both acute and chronic;

8. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);
9. allograft rejection: acute and chronic following, for example, transplantation of kidney, heart, liver, lung, bone marrow, skin or cornea or following blood transfusion; or chronic graft versus host disease;
10. CNS: Atzheimer's disease and other dementing disorders including CJD and nvCJD; amyloidosis; multiple sclerosis and other demyelinating syndromes; cerebral atherosclerosis and vasculitis; temporal arteritis; myasthenia gravis; acute and chronic pain (acute, intermittent or persistent, whether of central or peripheral origin) including visceral pain, headache, migraine, trigeminal neuralgia, atypical facial pain, joint and bone pain, pain arising from cancer and tumor invasion, neuropathic pain syndromes including diabetic, post-herpetic, and HIV-associated neuropathies; neurosarcoidosis; central and peripheral nervous system complications of malignant, infectious or autoimmune processes;
11. other auto-immune and allergic disorders including Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome;
12. other disorders with an inflammatory or immunological component; including acquired immune deficiency syndrome (AIDS), leprosy, Sezary syndrome, and paraneoplastic syndromes;
13. cardiovascular: atherosclerosis, affecting the coronary and peripheral circulation; pericarditis; myocarditis, inflammatory and auto-immune cardiomyopathies including myocardial sarcoid; ischaemic reperfusion injuries; endocarditis, valvulitis, and aortitis including infective (for example syphilitic); vasculitides; disorders of the proximal and peripheral veins including phlebitis and thrombosis, including deep vein thrombosis and complications of varicose veins;
14. gastrointestinal tract: Coeliac disease, proctitis, eosinopilic gastro-enteritis, mastocytosis, Crohn's disease, ulcerative colitis, microscopic colitis, indeterminant colitis, irritable bowel disorder, irritable bowel syndrome, non-inflammatory diarrhea, food-related allergies which have effects remote from the gut, e.g., migraine, rhinitis and eczema.

According to a forth aspect of the invention, there is provided a compound according to the first aspect of the invention or a composition according to the second aspect of the invention for use as a medicament.

According to a fifth aspect of the invention, there is provided use of a compound according to the first aspect of the invention or a pharmaceutical composition according to the second aspect of the invention for the manufacture of a medicament for the treatment of a disease or disorder. Said disease or disorder and subject being defined in certain preferred embodiments as described above in reference to the third aspect of the invention.

Preferably products, methods of the invention are for the treatment of diseases and disorders in humans.

Theranostic Aspects of the Invention

The invention encompasses in various embodiments methods of treatment, use of compounds or compositions of the invention of the manufacture of a medicament and compounds or compositions of the invention for therapeutic use.

According to certain embodiments the invention may also encompass:
a) Methods of treating or preventing a disease or disorder as stated above wherein the disease or disorder is a cancer in an individual subject and that subject's suspected cancer has been previously sampled (for example by taking a tissue biopsy or body fluid such as blood or sputum) and determined to show elevated levels of Gadd45β expression and/or activity and/or elevated levels of NF-κB expression and/or activity.
b) Compounds or compositions of the invention for use as a medicament for treatment of tissues of an individual previously determined to show elevated levels of Gadd45β expression and/or activity and/or elevated levels of NF-κB expression and/or activity.
c) Use of compounds or compositions of the invention for the manufacture of a medicament for the treatment of a disease or disorder which is either characterised by aberrant increased expression and/or activity of Gadd45β or which are characterised by aberrant activation of the NF-κB pathway and are amenable to treatment by the induction of Programmed Cell Death by the inhibition of Gadd45β activity wherein the disease or disorder is a cancer wherein said cancer cells have previously been determined to show elevated levels of Gadd45β expression and/or activity.

"Elevated levels" may mean elevated by at least 10%, at least 20%, at least 30%, at least 50%, at least 75%, at least 100%, at least 200%, at least 300%, at least 400%, at least 500%, at least 600%, at least 700%, at least 800%, at least 900%, or at least 1,000% compared to levels in control healthy tissue of the same origin and optionally obtained from the same subject or from a healthy subject. Levels of expression and activity may be determined by any method known in the art including RT-PCR, Southern blotting, Northern blotting, Western blotting, ELISA, radio-immuno assay, kinase assay and other binding, functional, and/or expression assays.

This theranostic aspect of the invention is primarily illustrated by the results presented in FIGS. 12A and 12B. The results shown here demonstrate that, in a panel of 29 cancer cell lines of different tissues of origin, cancer cell sensitivity to Z-DTP-induced killing correlates with a very high degree of statistical significance with levels of endogenus Gadd45β expression, as assessed by qRT-PCR assays. Indeed, the correlation plot of Gadd45β expression versus the percentage of cell survival/proliferation after treatment with Z-DTP2 shows that the significance of the correlation coefficient between the 2 parameters' domain is very high ($p<0.01$) (Pearson correlation). Strikingly, the only multiple myeloma cell line (out of a total of 9 multiple myeloma cell lines tested) which is refractory to Z-/mDTP-induced killing, as well as to cell death induced by the sh-RNA-mediated silencing of Gadd45β (FIGS. 16, 17, and 18), is the RPMI-8226 cell line, which expresses the lowest—almost undetectable—levels of Gadd45β (FIG. 12A). These data indicate that should DTP-based therapy enter the clinic, it will be possible to predict patient responder populations via simple and cost-effective qRT-PCR analysis. For example, primary cell from multiple myeloma patients can be analyzed for levels of Gadd45β expression, and patients with high levels of this expression can be deemed as those who will receive the most benefit from treatment with the compounds of the invention. Hence, an important aspect of the invention is a theranostic aspect—that is the application of a clinically useful assay to predict DTPs' therapy response in patients.

Figure 20:
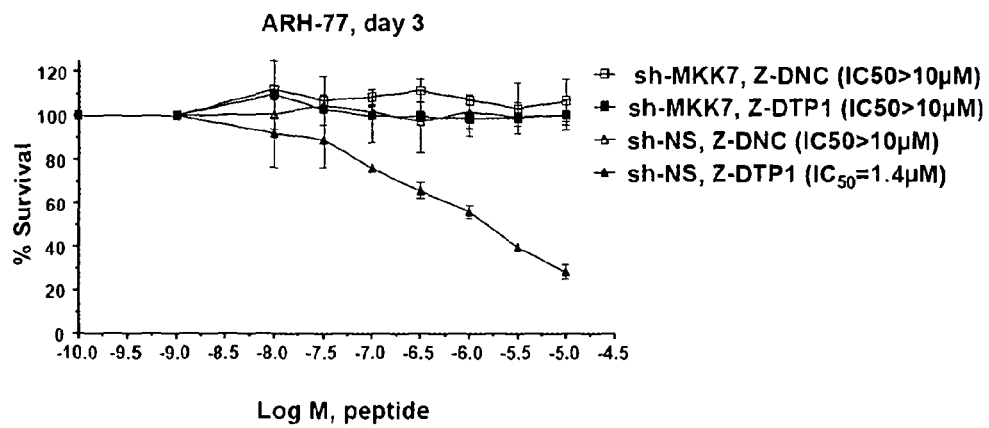
FIG. 20. (A, B, C) The sh-RNA-mediated silencing of MKK7 renders the representative Z-DTP-sensitive cell line, ARH-77, resistant to Z-/mDTP-induced killing. [$^3$H]Thymidine incorporation assays showing the $IC_{50}$s of D-isomer negative control tetrapeptide (Z-DNC) (A, B, C), Z-DTP1 (A), Z-DTP2 (B), or mDTP3 (C) in ARH-77 multiple myeloma cells expressing either MKK7-specific (sh-MKK7) or non-specific sh-RNAs (sh-NS). Treatments of ARH-77 cells with Z-DNC, Z-DTP1, Z-DTP2, or mDTP3 were for 3 days. It can be seen that sh-NS-expressing ARH-77 cells are highly sensitive to Z-/mDTP-induced killing—shown by the $IC_{50}$ values of 1.4 μM (Z-DTP1; A), 302 nM (Z-DTP2; B), and 303 nM (mDTP3; C)—similar to what is seen in the uninfected, parental ARH-77 cells (see Table IV). (A, B, C) In contrast, sh-MKK7-expressing ARH-77 cells have become completely resistant to Z-/mDTP-induced killing—shown by the $IC_{50}$ values>10 μM—similar to what is seen in Z-DNC-treated ARH-77 cells. $IC_{50}$s were calculated as described in the Examples, using increasing concentrations of Z-DNC (A, B, C), Z-DTP1 (A), Z-DTP2 (B), and mDTP3 (C), ranging from 0.01 to 10 μM. Reported in the graphs are the percentages of the counts per minute (c.p.m.), a measure of cell proliferation, obtained with peptide treated cells relative to the c.p.m. values obtained with untreated cells. Similar data were obtained with additional Z-/mDTP-sensitive multiple myeloma cell lines, including the U266, KMS-11, and KMS-12 cell lines (data not shown). (A, B, C) These data demonstrate the very high target specificity of Z-/mDTPs for the Gadd45β/MKK7 complex in multiple myeloma cells (see also FIG. 12, correlation between Gadd45β expression and cancer cell sensitivity to Z-DTP-induced killing).
Figure 20:
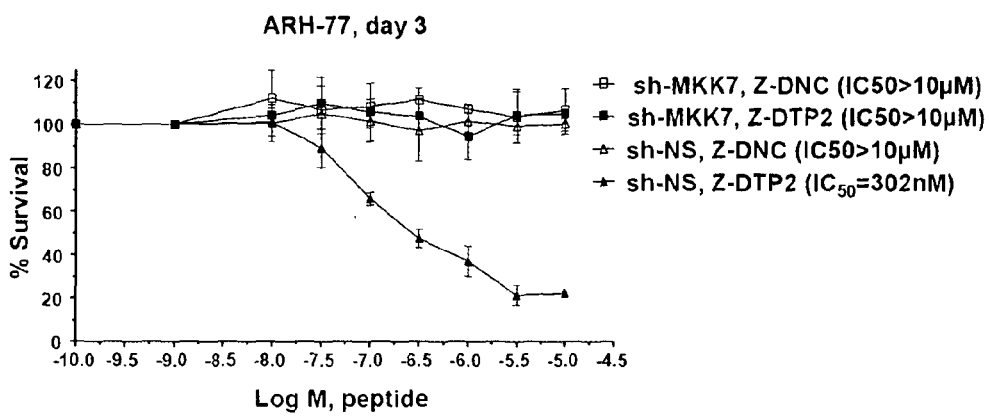
Figure 20:
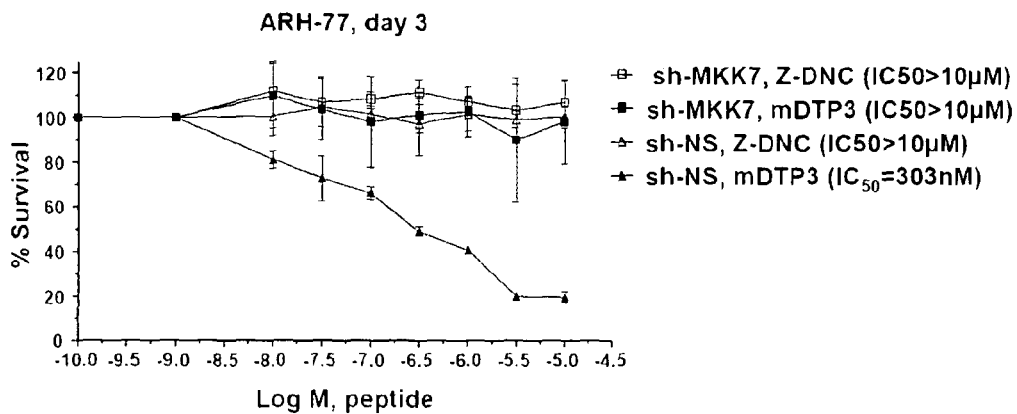

This theranostic aspect of the invention is also supported by the very high target specificity of the compounds of the invention in cells for the Gadd45β/MKK7 complex. This indicates that the higher the levels of expression of the target (i.e. Gadd45β) in cells, the higher will be the probability that such cells will depend on Gadd45β for survival, hence the higher will be the probability that such cells will be sensitive to Z-/mDTP-induced killing. This high specificity of Z-/mDTPs is demonstrated by the findings that: 1) In a large panel of tumour cell lines there is a highly significant statistical correlation between levels of Gadd45β expression and cancer cell sensitivity to Z-/mDTP-induced killing (FIG. 12); 2) the sh-RNA-mediated downregulation of Gadd45β rapidly induces apoptosis in Z-/mDTP-sensitive but not in Z-/mDTP-resistant cancer cell lines (FIGS. 16, 17, 18), and the kinetics of apoptosis induction by Gadd45β-specific sh-RNAs in these cell lines is similar to those observed with Z-/mDTPs (FIGS. 7A, 8B, and 8C); 3) the sh-RNA-mediated downregulation of MKK7 renders Z-/mDTP-sensitive cancer cell lines completely resistant to Z-/mDTP-induced killing (FIGS. 20A, 20B, and 20C); 4) the therapeutic target of the invention is the interface between two proteins, Gadd45β and MKK7 (FIGS. 21A, 21B, 21C, and 21D)—which further provides potential for high target selectivity, a key advantage of our solution over existing therapies. These data, together with the low toxicity of Z-/mDTPs to normal cells and the findings that knockout ablation of Gadd45β is well tolerated in mice (see reference by Papa, et al. (2008) J. Clin. Invest. 118:191-1923), indicate that targeting the discreet pro-survival functions of NF-κB in cell survival via Z-/mDTP-mediated inhibition of Gadd45β/MKK7 can provide a therapy that is more specific, less toxic, and hence more effective than therapies targeting the NF-κB pathway and/or the proteasome.

EXAMPLES

The following non-limiting examples illustrate the invention.

Example 1

Synthesis of Z-DTP2

By way of example, the synthesis of Z-DTP2 is reported. Z-DTP2 comprises a tetrapeptide core made up of D-tyrosine, D-glutamine, D-arginine, D-phenylalanine with benzyloxycarbonyl (that is a Z group) bonded to the N-terminus by means of an amide bond and an amino group bonded to the C-terminus by means of an amide bond.

Materials and Methods

Z-DTP2 was manually prepared following the Fmoc/tBu solid phase method (Fields G. B. and Noble R. L. 1990 *Int J Pept Protein Res;* 35: 161-214; Bodansky, M. and Bodansky A. 1995). The practice of peptide synthesis, 2nd edn., Springer Verlag, Berlin) and starting from 500 μmoles (1000 mg) of Rink amide polystyrene resin (Fmoc-RINK-AM-resin, GL Biochem, Shangai, China, Cat. 49001), having a substitution of 0.50 mmoles/g. The resin was placed in a 30 mL polypropylene vessel endowed with a 20 μm teflon septum, a polypropylene upper cap and a lower luer-lock polypropylene cap. The resin was swollen with 10.0 mL of a 50:50 dichloromethane (DCM):dimethyl formamide (DMF) mixture (both from LabScan, Stillorgan, Ireland; DCM cat. No H6508L; DMF cat. No H33H11X) for 20 minutes. Then after solvent removal under vacuum, the Fmoc group was cleaved by treatment with 5.0 mL of a DMF-Piperidine 8:2 mixture (Piperidine, Pip, cat. No Cat. No 80641; Sigma-Aldrich, Milan, Italy) for 20 minutes at room temperature (RT). The reactant was removed under vacuum and the resin washed 3 times with 5.0 mL of DMF. Then, 2.5 mmoles, 0.97 g, of Fmoc-D-Phe-OH (GL Biochem, Shangai. Cat. N. 35702) were dissolved in 5.0 mL of DMF (final conc. 0.5 M) and activated with 5.0 mL of a 0.5 M solution of Benzotriazole-1-yl-oxy-tris-pyrrolidino-phosphonium hexafluorophosphate (PyBOP, Novabiochem, cat. No 01-62-0016) in DCM, and 0.90 mL of di-iso-propyl-ethylamine (5.0 mmoles; DIEA, Sigma-Aldrich, cat. No D-3887). The solution of activated aminoacid was poured onto the resin and left under vigorous stirring for 30 minutes. The solution was drained under vacuum and the resin washed 3 times with 5.0 mL of DMF. The Fmoc group on the α-$NH_2$ was removed as described earlier using a 8:2 DMF-Pip solution (5.0 mL) for 20 minutes and extensive washing with 5.0 mL of DMF (3 times). A solution of Fmoc-D-Arg(Pbf)-OH (2.5 mmoles, 1.6 g in 5.0 mL DMF; GL Biochem, Shangai, Cat. N. 36404) was activated as described using 2.5 mmoles of PyBOP and 5.0 mmoles of pure DIEA. The solution was transferred onto the resin and left under stirring for 30 minutes. After cleavage of the Fmoc groups with 5.0 mL of a 8:2 DMF-Pip solution and washing with DMF (3 times, 5.0 mL), a solution of Fmoc-(D)-Glu (tBu)-OH 0.50 M in DMF (2.5 mmoles, 1.1 g in 5.0 mL DMF; GL Biochem, Shangai, Cat. N. 36605) preactivated with PyBOP and DIEA as described above, was added to the resin and the reaction was left to proceed for 30 minutes at room temperature. Following draining of the aminoacid, the Fmoc-group was removed as described above (20 minute treatment with 8:2 DMF:Pip, 5.0 mL) and the resin washed 3 times with 5.0 mL of DMF. 2.5 mmoles of Fmoc-(D)-Tyr (tBu)-OH (1.2 g, GL Biochem, Shangai, Cat. N. 36906) dissolved in 5.0 mL of DMF was preactivated with PyBOP and DIEA as reported above, was transferred onto the resin and left under stirring for 45 minutes. The aminoacid solution was removed by vacuum draining, then the resin was washed 5 times with 5.0 mL of DMF. 5 mmoles of Z-OSu (benzyloxycarbonyl-N-hydroxy-succinimide, GL Biochem, Shangai, Cat. N. 10502) were dissolved in 10 mL of DMF and added to the resin. 2.4 mL of DIEA were added and the reaction was left under stirring over night. After draining of the solution, the resin was extensively washed with DMF, DCM, methyl alcohol (MeOH, LabScan, Cat. No C2517), and ethyl ether ($Et_2O$, LabScan, Cat. No A3509E), and dried under vacuum and weighted. The weight was 1.1 g. To cleave the peptide, the resin was treated with 10.0 mL of a mixture composed of TFA-$H_2O$-TIS 90:5:5 (v/v/v) mixture (TFA, trifluoroacetic acid, Sigma-Aldrich, Italy Cat. No 91700; TIS, tri-iso-propylsilane, Sigma-Aldrich, cat. N. 23,378-1) for 3 hours at RT. The resin was removed by filtration, then 20 mL of cold $Et_2O$ was added to the trifluoroacetic solution, leading to the formation of a white precipitate. After removal of the solvents by centrifugation, the precipitate was washed with 10.0 mL of cold $Et_2O$, dissolved in 10.0 mL of $H_2O$/$CH_3CN$ 50:50 (v/v) and lyophilized. The peptide was characterized by LC-MS using a narrow bore 50×2 mm ID ONYX C18 column (Phenomenex, Torrance, Calif., USA), equilibrated at 600 μL/min with 5% $CH_3CN$, 0.05% TFA. The analysis was carried out applying a gradient of $CH_3CN$, 0.05% TFA from 5% to 70% over 3 minutes. The peptide was purified by semi-preparative RP-HPLC using a 10×1 cm C18 ONYX column (Phenomenex, Torrance, Calif., USA), equilibrated at 20 mL/min, injecting 20 mg in each run. A gradient from 5% to 65% over 8 minutes was applied to elute the peptide. Pure fractions were pooled and characterized by LC-MS. The determined MW of Peptide A was 746.8 amu (theor. 746.83 amu) and the product was more than 95% pure (HPLC). A yield of around 60% was achieved after purification of all the crude product.

Example 2

Dose Dependent Inhibition of the Interaction Between Gadd45β and MKK7 with a Selection of Compounds of General Formula (I)

To evaluate the inhibitory properties of peptides, ELISA-based assays were performed. In these assays, a fusion protein of glutathione S-transferase (GST) and mitogen-activated protein kinase kinase 7 (MKK7) was coated onto wells of a 96-well plate, while biotinylated-hGadd45β was used in solution. hGadd45β was biotinylated using an EZ Link NHS-LC-biotin kit (Pierce, Rockford, Ill.), according to Tornatore et al. (Tornatore L., et al. (2008). J Mol Biol; 378:97-111).

Materials and Methods

Firstly, the association between Gadd45β and MKK7 was investigated by ELISA assays as also reported in Tornatore et al. (Tornatore L., et al. (2008). J Mol Biol; 378:97-111). The GST-fused full-length kinase was coated for 16 h at 4° C., at a concentration of 42 nM in buffer A (25 mM Tris pH 7.5, 150 mM NaCl, 1 mM DTT and 1 mM EDTA) into wells of a 96-well microtiter plate. Some wells were filled with buffer alone and were used as blanks After incubation for 16 h at 4° C., the solutions were removed and the wells were filled with 350 μL of a 1% (w/v) solution of NFDM (Non Fat Dry Milk) in PBS (phosphate buffered saline). The plate was incubated for 1 h at 37° C. in the dark. After washing with buffer T-PBS (PBS with 0.004% (v/v) Tween detergent), the wells were filled with 100 μL of biotinylated-hGadd45β at concentrations ranging from 8.4 nM to 168 nM. Each data point was performed in triplicate. Following incubation for 1 hr in the dark at 37° C. the solutions were removed and the wells were again washed with T-PBS. Then 100 μL of a 1:10,000 dilution of horseradish peroxidase-conjugated streptavidin dissolved in buffer was added to each well and the plate incubated for 1 hr at 37° C. in the dark. After removal of the enzyme solution and washing, 100 μL of the chromogenic substrate o-phenylendiamine (0.4 mg/mL in 50 mM sodium phosphate-citrate buffer, containing 0.4 mg/mL of urea in hydrogen peroxide) was added and the colour was allowed to develop in the dark for 5 min. The reaction was stopped by adding 50 μL of 2.5 M $H_2SO_4$. The absorbance at 490 nm was measured in all wells and the values were averaged after subtracting the corresponding blanks Bound protein was then detected as described above. The molar concentration of biotinylated-hGadd45β at which the half-maximal ELISA signal is detected corresponds to the dissociation constant ($K_D$) (Friguet B, Chaffotte A F, Djavadi-Ohaniance L, Goldberg M E. J Immunol Methods. 1985 Mar. 18; 77(2):305-19). Binding competition assays were performed by coating GST-MKK7 at 42 nM as described, a concentration of biotinylated-hGadd45β of 21 nM (pre-saturation conditions 1:0.5 mol/mol ratio) and, in a first test, using competitors at 21 nM. The binding of biotinylated hGadd45β to GST-MKK7 was analyzed in the presence of increasing amounts of competitor peptide (concentrations ranging from 0.01 nM to 100 nM), and the values obtained with the competitor were expressed as the percentage of the binding detected in the absence of competitor. Data of activity, expressed as percentage of inhibiting capacity at 21 nM under the assay conditions, are reported in the following Table I for a selected set of compounds according to the invention. According to the convention adopted in the table "L-Xaa" and "D-Xaa" refer to the L and D forms of amino acid Xaa.

Figure 3:
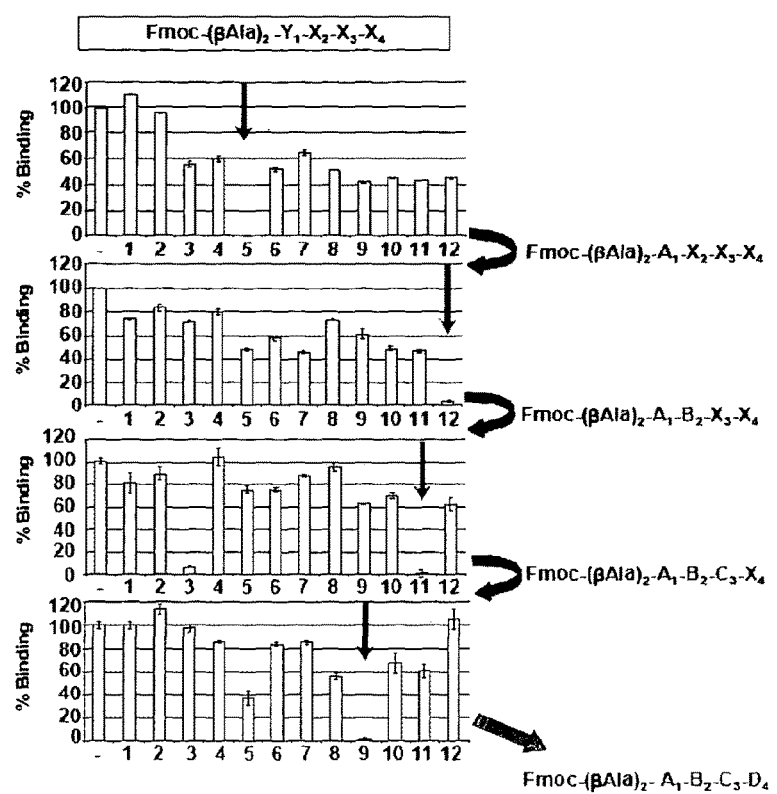
FIG. 3. (A) The ELISA screen used to isolate the lead D-tetrapeptides (DTPs) 1 and 2. Antagonists of the Gadd45β/MKK7 interaction were selected by screening a simplified combinatorial peptide library of general formula Fmoc-(βAla)$_2$-X$_1$—X$_2$—X$_3$—X$_4$—CONH$_2$ (see reference by Marasco et al. 2008, Curr. Protein Pept. Sci. 9:447-67) prepared using one of 12 amino acids at each position from X$_1$ to X$_4$. This library, containing a total of $12^4$=20,736 different peptides, was iteratively deconvoluted in four steps by ELISA competition assays, using at each step coated human MKK7 (42 nM), soluble biotin-labeled human (h)Gadd45β (21 nM) and each of the 12 sub-libraries at the nominal concentration of 42 nM (not shown). (B) The most active peptide of first generation was then used for the synthesis of a second-generation library. The screening of this library provided two highly active peptides (labelled in FIG. 3B as 1 and 8). (C) Optimized peptides were then freed of the Fmoc-(βAla)$_2$-tag and synthesized as D-isomers, yielding DTP1 and DTP2, which disrupted the Gadd45β/MKK7 interaction with IC$_{50}$ of 0.22 nM and 0.19 nM, respectively. It can also be seen that the L-isomers of these peptides (i.e. LTP1 and LTP2) exhibited IC$_{50}$s similar to those of DTPs in the ELISA competition assays, whereas the negative control peptides, LNC and DNC, displayed no detectable inhibitory effect on the formation of the Gadd45β/MKK7 complex. LNC, L-isomer negative control; LTP1, L-isomer tetrapeptide 1; LTP2, L-isomer tetrapeptide 2; DNC, D-isomer negative control.
Figure 3:
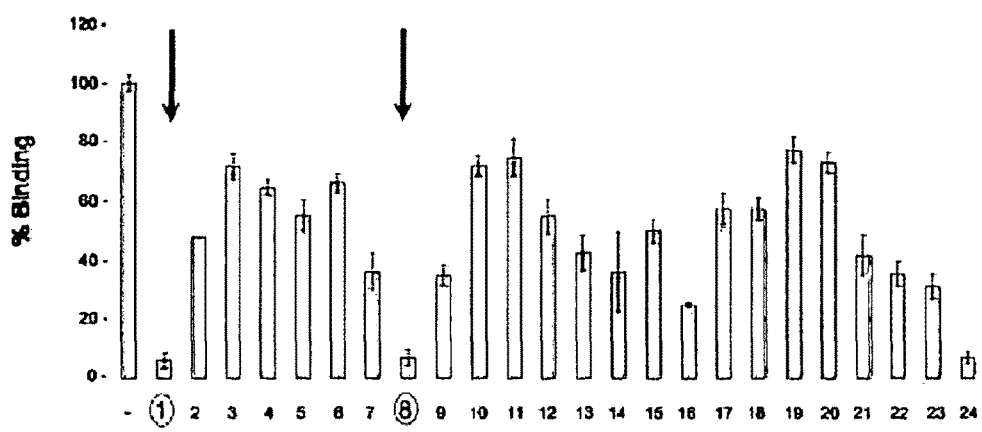
Figure 3:
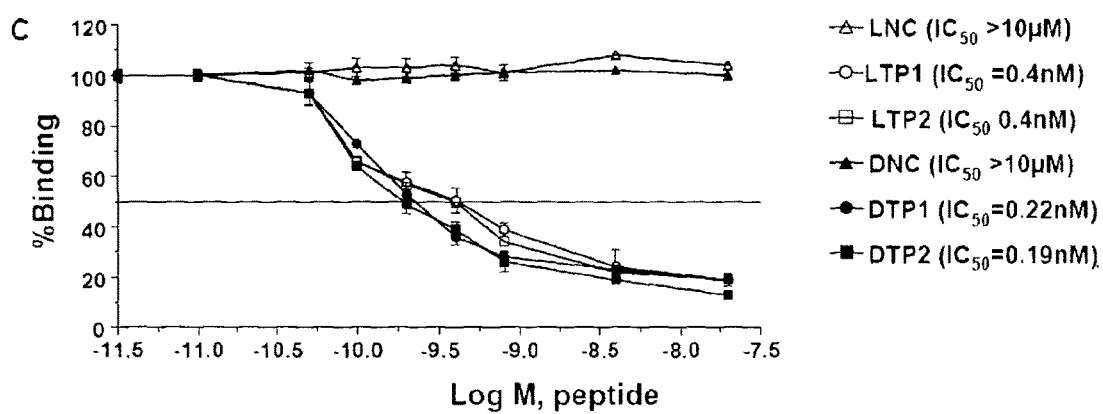

Data of $IC_{50}$ of selected compounds (i.e. the compound dose required to achieve a 50% reduction of Gadd45β binding to MKK7) are reported in FIG. 3C.

Example 3

Isolation of Lead Tetrapeptides

Materials and Methods

An ELISA screen was used to identify lead D-tetrapeptides from which preferred compounds of the invention could be derived. A simplified combinatorial peptide library (Marasco et al. 2008, Curr. Protein Pept. Sci. 9:447-67) was screened for antagonists of the Gadd45β/MKK7 interaction. This library contained a total of $12^4$=20,736 different tetrapeptides formed by combinations of the following amino acid residues Gln (Q), Ser (S), Arg (R), Ala (A), Tyr (Y), Pro (P), Met (M), Cys (C), Phe (F), Leu (L), His (H), Asp (D), and was iteratively deconvoluted in four steps by ELISA competition assays using at each step coated MKK7 (42 nM), soluble-biotin-hGadd45β (21 nM) and each of the 12 sub-libraries (42 nM). The results of this screen are shown in Table I above (wherein standard single letter amino acid residue codes are used and $X_2$, $X_3$ and $X_4$ represent mixtures of the 12 residues given above) (see also FIG. 3A). The resulting most active peptide described in Table I (i.e. Fmoc-(βAla)$_2$-YDHF-NH$_2$, also referred to as Fmoc-LTP1) was then subjected to several rounds of optimization and removal of the Fmoc-(βAla)$_2$-tag, yielding Ac-LTP1 and Ac-LTP2 (see Table II). These tetrapeptides were then resynthesized using D-isomers of the same amino acids, ultimately yielding the lead tetrapeptide 1 and 2 (DTP1 and DTP2), which disrupted the Gadd45β/MKK7 interaction with IC$_{50}$s of 0.22 nM and 0.19 nM, respectively (FIG. 3C).

```
Sequence of DTP1:
                                     [SEQ ID NO.: 38]
Acetyl-(D-Tyr)-(D-Asp)-(D-His)-(D-Phe)-NH2

Sequence of DTP2:
                                     [SEQ ID NO.: 37]
Acetyl-(D-Tyr)-(D-Glu)-(D-Arg)-(D-Phe)-NH2
```

Also the following sequences were selected as negative controls (NC):
Sequence of NC1: Acetyl-(D-Tyr)-(D-Asp)-(D-His)-(D-Gln)-NH$_2$ [SEQ ID NO.: 81]
Sequence of NC2: Acetyl-(L-Tyr)-(L-Asp)-(L-His)-(L-Ala)-NH$_2$ [SEQ ID NO.: 82]

```
Sequence of NC3:
                                     [SEQ ID NO.: 83]
Acetyl-(L-Tyr)-(L-Glu)-(L-Lys)-(L-Trp)-NH2

Sequence of NC4:
                                     [SEQ ID NO.: 84]
Acetyl-(L-Tyr)-(L-Asp)-(L-Lys)-(L-Trp)-NH2
```

FIGS. 3A, 3B and 3C show the ELISA competition binding assays. Percentage inhibition of acetylated peptides and/or modified peptides (that is peptides conjugated to either acetyl or other groups) are shown respectively in Tables II and III (which use standard single letter amino acid residue codes).

Example 4

Immunoprecipitation Assays

Materials and Methods

Human Embryonic Kidney (HEK-293) were cultured in Dulbecco's modified Eagle's medium (DMEM) supplemented with 10% fetal calf serum (FCS), 100 units/ml penicillin, 100 mg/mL streptomycin, and 1% glutamine. HEK-293 cells ($2.2 \times 10^6$) were seeded onto 10 cm² tissue-culture dishes, and the following day, were transfected with pcDNA-FLAG-MKK7 and pcDNA-HA-Gadd45β plasmids, using a standard $Ca_3(PO4)_2$ precipitation technique (Papa, S et al., (2004) Nat. Cell Biol. 6, 146-153). Forty-eight hours after transfection, the cells were washed once with PBS, then resuspended and incubated for 30 min at 4° C. in lysis buffer (20 mM HEPES, 350 mM NaCl, 20% glycerol, 1 mM $MgCl_2$, 0.2 mM EGTA, 1 mM DTT, 1 mM $Na_3VO_4$, and 50 mM NaF) supplemented with protease inhibitors (1 mM phenylmethylsulfonylfluoride, 10 µM chymostatin, 2 µg/ml aprotinin, and 2 µg/ml leupeptin) with occasional gentle shaking. The lysed cells were collected and then centrifuged at 45,000×g for 40 min. The resulting cleared cell lysates were used for further analysis.

Lead tetrapeptides DTP1 and DTP2 isolated in Example 3, together with negative control tetrapeptides (NC1, NC2, NC3 and NC4), were co-incubated with Gadd45β/MKK7 in order to demonstrate that the active D-tetrapeptides, but not the negative control tetrapeptides, disrupted the Gadd45β/MKK7 interaction. Immunoprecipitations were performed using essentially the same conditions described in Papa, S et al., (2004) Nat. Cell Biol. 6, 146-153 and the references therein, and an anti-FLAG antibody which precipitated FLAG-tagged MKK7. Western blots were developed using anti-MKK7 antibodies or anti-HA antibodies (binding to HA-hGadd45β), as indicated in FIG. 5 (bottom and top panels, respectively).

Results

Figure 4:
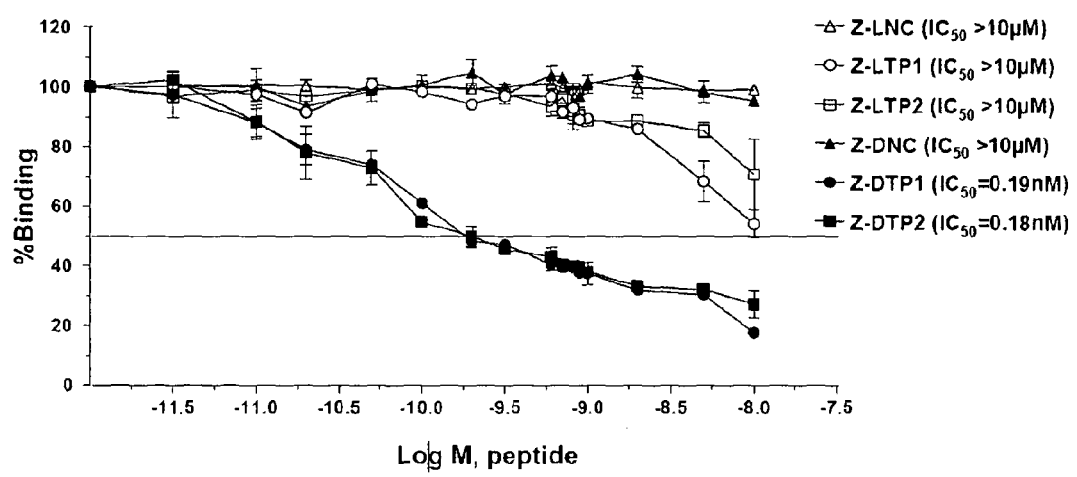
FIG. 4. Stability of Z-DTPs in biological fluids. ELISA competition assays showing that the Z-protected DTPs (Z-DTP1, Z-DTP2) retain full inhibitory activity after a 48-hr incubation with human serum at 37° C. (IC$_{50}$=0.19 nM, Z-DTP1; IC$_{50}$=0.18 nM, Z-DTP2), whereas the Z-protected LTPs (Z-LTP1, Z-LTP2) are almost completely inactivated after this treatment (IC$_{50}$s>10 μM). Assays were performed as in FIG. 3C, using coated MKK7, soluble biotin-hGadd45β, and the indicated concentrations of the tetrapeptides. Z-LNC and Z-DNC, L- and D-isomer negative controls, respectively.
Figure 5:
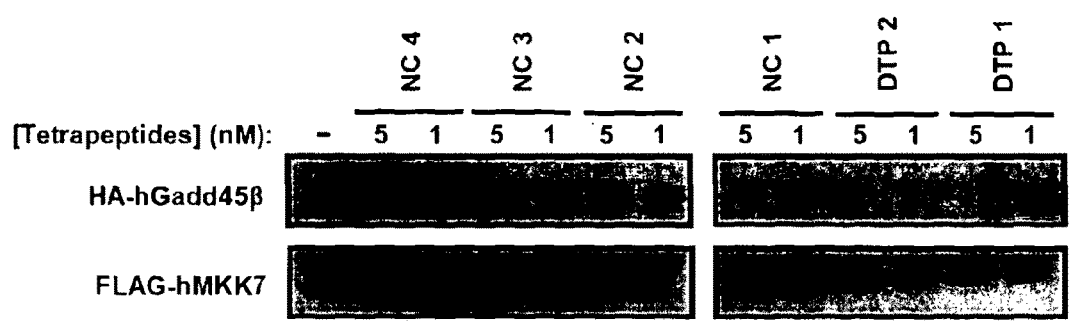
FIG. 5. Co-immunoprecipitation (co-IP) assays showing the effective and specific disruption of the Gadd45β/MMK7 interaction by D-tetrapeptides 1 and 2 (DTP1 and DTP2), but not by negative control (NC) D-tetrapeptides (NC1, NC2, NC3 and NC4). Co-IP was performed using anti-FLAG (MKK7) antibody, and western blots were developed using anti-HA (detecting HA-Gadd45β) (top) or anti-MKK7 (bottom) antibodies, as indicated.

Results are presented in FIG. 5. It can be seen from the western blots presented in FIG. 5 that there was a strong interaction between Gadd45β and MKK7 when co-immunoprecipitation was performed with lysates from HEK-293 cells transiently expressing HA-Gadd45β and FLAG-MKK7 and an anti-FLAG antibody (specifically binding to FLAG-tagged MKK7). This result was obtained when co-immunoprecipitations were performed either in the absence of tetrapeptides or in the presence of negative control (NC) D-tetrapeptides NC1, NC2, NC2 or NC4. When co-immunoprecipitations were performed in the presence of 1 or 5 nM of DTP1 or DTP2, however, the precipitated complex contained no or very little Gadd45β, indicating that the interaction between MKK7 and Gadd45β had been disrupted by the active DTP compounds, thereby leading to a reduction of Gadd45β in the co-immuno-precipitates. These data confirm and extend the result observed in the ELISA competition assays shown in FIGS. 3A, 3B and 3C and FIG. 4.

Example 5

Stability of DTPs in Human Serum

Materials and Methods

In FIG. 4, Gadd45β/MKK7 binding, competition ELISA assays were carried out to determine the stability of Z-conjugated D-tetrapeptides in human serum. For this purpose, the activities of the most active Gadd45β/MKK7 antagonists selected from the combinatorial library screen described in Example 3 (i.e. Z-LTP1, Z-LTP2, Z-DTP1, and Z-DTP2), as well as of one negative control L-tetrapeptide (i.e. Z-LNC) and the corresponding D-enantiomer (i.e. Z-DNC), were compared before and after a 48-hr pre-incubation with human serum at 37° C. in ELISA competition assays. ELISA were performed as described in FIG. 3 C. Briefly, 100 µl of 42 nM of recombinant GST-MKK7 in ELISA buffer (25 mM Tris pH 7.5, 150 mM NaCl, 1 mM DTT, 1 mM EDTA) were coated onto wells of 96-well plates by overnight incubation at 4° C. After blocking with 2% of NFDM for 1 hr at 37° C., plates were washed with TPBS, and then 21 nM of recombinant, biotinylated human (h)Gadd450 were added to the wells together with increasing concentrations of tetrapeptides which had either been subjected or had not been subjected to pre-incubation with human serum, as indicated. For a further discussion of the conditions used for the competition ELISA assay, the reader is directed to Tornatore et al 2008 JMB, 378: 97-111 and the references therein.

Results

FIG. 3C shows that the activities of DTP1 and DTP2 are comparable to those of their corresponding L-enantiomers (i.e. LTP1 and LTP2, respectively) in inhibiting the formation of the Gadd45β/MMK7 complex, as shown by a comparison the $IC_{50}$s of DTPs and LTPs in ELISA competition assays. FIG. 4 shows that no loss of activity occurs after a 48-hr incubation of Z-DTP1 or Z-DTP2 with human serum at 37° C. Indeed, the data show that after this pre-incubation, Z-DTPs but not Z-LTPs fully retain their ability to disrupt the Gadd45β-MKK7 interaction in ELISA competition assays. By comparing the $IC_{50}$s of the tetrapeptides after pre-incubation with serum and after no pre-incubation with serum, it can be seen that Z-DTP1 and Z-DTP2 are completely stable after pre-incubation with serum ($IC_{50}$=0.19 nM for Z-DTP1, and $IC_{50}$=0.18 nM for Z-DTP2), whereas Z-LTP1 and Z-LTP2 are not, as the latter tetrapeptides show significant loss of activity after pre-incubation with serum (see their $IC_{50}$s>10 µM). At all the concentrations tested, the inhibitory activities of the D-tetrapeptides that had been pre-incubated with serum were indistinguishable in these assays from those of the D-tetrapeptides that had not been subjected to this pre-incubation (FIGS. 3C and 4).

The comparison of the dose-dependent patterns shown in FIGS. 3C and 4 indicates that Z-DTP1 and Z-DTP2 are stable in human serum at 37° C. and so are suitable for systemic use, whereas Z-LTP1 and Z-LTP2 are not. It can also be seen that negative control tetrapeptides (e.g. Z-DNC and Z-LNC) lack any activity in the aforementioned competition ELISA assays, regardless of whether or not they had been pre-incubated with human serum (FIGS. 3C and 4). The data depicted in FIGS. 3C and 4 also show that the N-terminal addition of a benzyloxycarbonil (Z) group (in place of the acetyl group) does not compromises the ability of either DTP1 and DTP2 or of LTP1 and LTP2 to inhibit formation of the Gadd45β/MKK7 complex—yet the addition of a Z group markedly increases DTPs' cellular uptake (data not shown), hence markedly increases DTPs' cellular activity in tumour killing assays (see FIGS. 7A and 7B).

Example 6

Determination of the $IC_{50}$s of Z-DTPs in a Panel of Multiple Myeloma Cell Lines Materials and Methods To further examine the effects of D-tetrapeptide treatment on the survival/proliferation of multiple myeloma cell lines, the cells from the 8 multiple myeloma cell lines (out of the 9 multiple myeloma cell lines tested) that were sensitive to Z-DTP-induced killing (i.e. U266, KMS-11, NC1-H929, ARH-77, JJN-3, KMS-12, KMS-18, KMS-27 cells; see also FIGS. 8A, 8B, 8C, and 12) were treated with increasing concentrations (ranging from 0.01 to 10 µM) of Z-DTP1 or Z-DTP2 for 24, 72 or 144 hrs, as shown in Table IV. Cultures of multiple myeloma cells and treatments with Z-DTPs were carried out as described in Example 8 (see below). The effects of Z-DTPs on the survival/proliferation of multiple myeloma cells were evaluated by the use of [$^3$H]thymidine) incorporation assays, performed as also described in Example 8. The amount of cell proliferation measured with each of the Z-DTPs' concentrations used and with the untreated cultures (i.e. cultures incubated with medium alone), was expressed as counts per minute (c.p.m.)—which directly correlate with the extent of cell proliferation. All experiments were performed in triplicate. The mean concentrations of Z-DTP1 and Z-DTP2, as well as of their derivatives (e.g. mDTP3), that resulted in 50% inhibition of cell proliferation (i.e. $IC_{50}$) relative to the cell proliferation recorded with the untreated cultures were then determined. The $IC_{50}$s of Z-DTP1 and Z-DTP2 calculated for the 8 sensitive multiple myeloma cell lines tested at the times shown (i.e. day 1, 3 and 6) are reported in Table IV. The $IC_{50}$s of these two compounds, as well as those of 31 additional compounds (including those of Z-DTP2 derivatives such as mDTP3), calculated in KMS-11 and/or KMS-12 multiple myeloma cells at day 1, 3 and 6 are reported in Table V.

As it can be seen in Table IV, Z-DTP1 and Z-DTP2 markedly decreased [$^3$H]-TdR uptake in all the multiple myeloma cell lines tested in a dose-dependent fashion (except that in the RPMI-8226 cell line, which display very low levels of Gadd45β; further discussed below; see FIG. 12) (see also FIGS. 8A, 8B, 8C, and 12). Similar results were obtained in these multiple myeloma cell lines when the $IC_{50}$s of Z-DTP1 and Z-DTP2 were calculated using Trypan blue exclusion assays (measuring cell viability) (data not shown).

Results

As shown in Table IV, all the multiple myeloma cell lines tested exhibited high sensitivity to Z-DTP-afforded inhibition of cell survival/proliferation (see also FIGS. 8A, 8B, 8C, and 12). As in can also be seen in Table IV, however, these cell lines displayed variable sensitivity to Z-DTP1 and Z-DTP2. Indeed, some cell lines were already highly sensitive to Z-DTP-afforded inhibition of cell survival/proliferation after a 24-hr treatment with these compounds (e.g. see the $IC_{50}$=1.3 µM of KMS-12 cells, and the $IC_{50}$=2.88 µM of KMS-11 cells Z-DTP2 at 24 hrs), and all of them were highly sensitive to both Z-DTP1 and Z-DTP2 after treatment for 144 hrs, with $IC_{50}$s ranging from 10.1 nM to 4.9 µM for Z-DTP1, and from 10 nM to 4.5 µM for Z-DTP2, at this time point (Table IV). Of note, the Z-DTP2 derivative, mDTP3 (compound 17), was tested in KMS-11 and KMS-12 cell lines, and showed an improved cellular activity in these cell lines compared to Z-DTP1 and Z-DTP2, with $IC_{50}$s of 16 nM and 25 nM, respectively, at day 6, compared to the $IC_{50}$s of Z-DTP1 (i.e. 316 nM and 10.1 nM, respectively) and Z-DTP2 (i.e. 66 nM and 10 nM, respectively) (see Table V) (see also FIGS. 20A, 20B, and 20C). Hence, the active DTPs, but not negative control Z-DNCs, have strong cytotoxic activity in most multiple myeloma cell lines. Furthermore, our most recent derivatives (e.g. mDTP3) retain high potency in vitro, but show improved cellular activity in multiple myeloma cells, with substantially reduced MW (~500 versus >700), hence increased ligand efficiencies (see Table V) (see also FIG. 13).

Example 7

Restoration of Gadd45β-Inhibited MKK7 Catalytic Activity by Tetrapeptides

Materials and Methods

Figure 6:
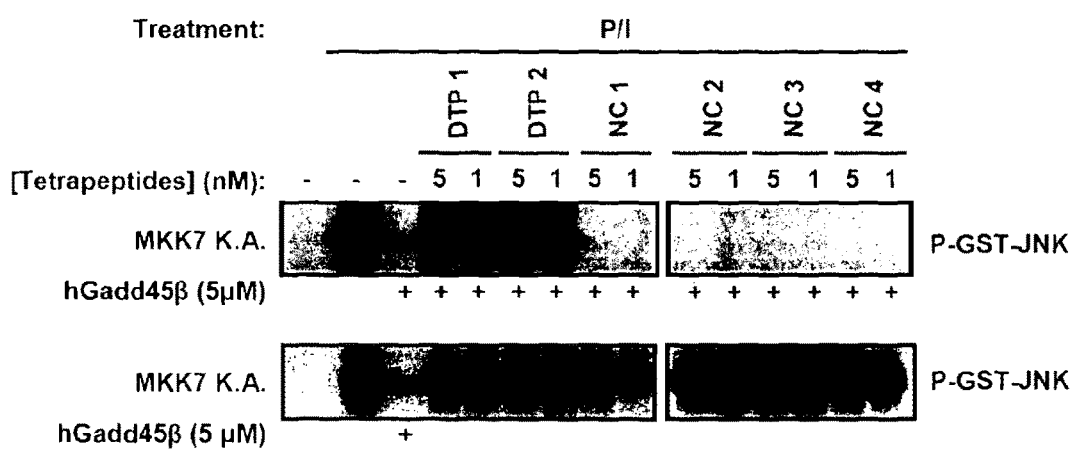
FIG. 6. MKK7 kinase assays showing the effective and specific disruption of the Gadd45β/MMK7 interaction and the restoration of MKK7 catalytic activity by D-tetrapeptides 1 and 2 (DTP1 and DTP2), but not by negative control (NC) D-tetrapeptides (NC1, NC2, NC3 and NC4). Active MKK7 was immunoprecipitated with anti-FLAG antibody from phorbol 12-myristate 13-acetate (PMA)/ionomycin (P/I)-treated HEK-293T cells and incubated with the D-tetrapeptides in the presence (top panel) or absence (bottom panel) of recombinant human (h)Gadd45β, as indicated. As shown, neither active lead D-tetrapeptides nor control NC tetrapeptides inhibited MKK7 catalytic activity when incubated with the kinase in the absence of Gadd45β (bottom panel).

In FIG. 6, transient transfection of pcDNA-FLAG-MKK7 in HEK-293 cells was performed using the method of $Ca_3(PO_4)_2$ precipitation, essentially as described in Papa, S et al., (2004) Nat. Cell Biol. 6, 146-153 and references therein. 36 hrs after transfection, the cells were treated with 100 ng/ml phorbol 12-myristate 13-acetate (PMA) and 1 µM ionomycin for 30 min at 37° C. Cell extracts were prepared as described in example 4 and used for immunoprecipitation with anti-FLAG antibodies (binding to FLAG-MKK7) as described in Papa, S et al., (2004) Nat. Cell Biol. 6, 146-153 and references therein. Briefly, 50 µg of cell lysate from PMA-ionomycin (P11)-treated or untreated, HEK-293 cells transiently expressing FLAG-MKK7 was incubated with 10 µl of anti-FLAG M2 Affinity Gel (SIGMA) for 4 hrs at 4° C. during rotation. The immunoprecipitates were then washed 3 times in lysis buffer and twice more in kinase buffer (10 mM HEPES, 5 mM $MgCl_2$, 1 mM $MnCl_2$, 12.5 mM β-glycerophosphate, 2 mM DTT, 4 mM NaF and 0.1 mM $Na_3VO_4$). MKK7 catalytic activity was finally measured in kinase assays by incubating FLAG-MKK7 immunoprecipitates at 30° C. for 20 min with 20 µl of kinase buffer containing 2 µM of recombinant GST-JNK1 and 5 µCi of [$\gamma$-$^{32}$P]ATP) (kinase reaction), as described in Papa, S et a., (2004) Nat. Cell Biol. 6, 146-153 and references therein.

In some reactions, to test the ability of D-tetrapeptide antagonists to disrupt the Gadd45β-MKK7 interaction and so release the catalytic activity of MKK7 from Gadd45β-afforded inhibition, FLAG-MKK7 immunoprecipitates were 1) first pre-incubated for 10 min at 30° C. with either 1 nM or 5 nM of DTP1, DTP2 or negative control (NC) D-tetrapeptides, NC1, NC2, NC3 and NC4, and 2) then incubated for another 10 min at 30° C. with or without 5 µM of a GST-fusion protein of recombinant human (h)Gadd45β (GST-hGadd45β; purified from bacterial lysates as described in Papa, S., (2007) J. Biol. Chem. 282, 19029-19041), before using them for the kinase reaction described above, as indicated in FIG. 6.

In all cases, kinase reactions were terminated by the addition of Laemmli sample buffer. Proteins were then resolved by 10% SDS-PAGE, and MKK7 kinase activity revealed by autoradiography. For a further discussion of MKK7 kinase assay conditions, the reader is directed to Papa, S et al., (2007) J. Biol. Chem. 282, 19029-19041 and Papa, S et al., (2004) Nat. Cell Biol. 6, 146-153 and the references therein.

Results

Results are shown in FIG. 6 wherein the intensity of a band corresponds to the degree of MKK kinase activity measured, as this intensity is proportional to the amount of [$\gamma$-$^{32}$P]ATP) incorporated by MKK7 into its substrate, GST-JNK1. As can be seen from FIGS. 3C, 4, and 5, incubation with DTP1 or DTP2 effectively and specifically disrupted the Gadd45β interaction with MKK7 and as a consequence, as can be seen from FIG. 6, fully restored the catalytic activity of MKK7, whereas incubation with negative control (NC) tetrapeptides NC1, NC2, NC3 or NC4 did not (FIG. 6, top panels). It can also be seen from FIG. 6 that neither the control tetrapeptides, NC1, NC2, NC3 and NC4, nor the active tetrapeptides, DTP1 and DTP2, afforded any inhibition of MKK7 catalytic activity when incubated with MKK7 in the absence of recombinant GST-hGadd4513 (FIG. 6, bottom panels). These results are consistent with those shown in FIGS. 3C, 4, and 5, where only DTP 1 and DTP2, but not NC1, NC2, NC3 or NC4 were capable of disrupting the MKK7-Gadd45β interaction in either ELISA or co-immunoprecipitation assays.

Example 8

Specific Killing of Tumour Cell Lines Featuring Constitutive NF-κB Activity and/or High Levels of Gadd45β Expression by Tetrapeptides Materials and Methods This example investigates the use of control tetrapeptides (that is Z-DNC, Z-LNC, and Ac-DNC) and in vitro bioactive lead tetrapeptides (that is Z-DTP1, Z-DTP2, Z-LTP2 and Ac-DTP2) for the killing of a large panel of human and murine tumour cell lines of various tissues of origin. The tumour cell lines tested include: the multiple myeloma cell lines U266, KMS-11, NC1-H929, ARH-77, JJN-3, KMS-12, KMS-18, KMS-27, RPMI-8226; the diffuse large B-cell lymphoma cell lines LY-3 and SUDHL6; the Burkitt's lymphoma cell lines BJAB, ST486, RAJI, RAMOS, Namalwa, and HS-SULTAN; the pro-monocytic leukaemia cell line U937; the T-cell leukaemia and lymphoma cell lines JURKAT, HUT-78, MT-2, MT-4, MOLT4, MT2-HTLV-I, and CEM; the breast cancer cell lines MCF7, MD-MDA-231, and MD-MDA-486; the pre-B-cell lymphoma cell lines NALM-6 (human) and 70Z/3 (mouse); the chronic myelogenic leukemia cell line K652; the B-cell lymphoma cell lines KARPAS (human) and A20 (mouse); the human embryonic kidney cell line HEK-293T. Tumour cell lines were cultured as described previously (Zazzeroni et al. 2003, Blood 102: 3270-3279) in RPMI-1640 (multiple myeloma, diffuse large B-cell lymphoma, Burkitt's lymphoma, pro-monocytic leukaemia, T-cell leukaemia and lymphoma, pre-B-cell lymphoma, chronic myelogenic leukemia, and B-cell lymphoma cell lines) or DMEM medium (breast cancer and embryonic kidney cell lines) supplemented with 10% fetal bovine serum (FBS), 1% glutamine, 100 U/mL penicillin, and 100 µg/mL streptomycin in a humidified atmosphere of 5% $CO_2$ at 37° C.

For proliferation inhibition assays (FIGS. 7, 8 and 9) and cell death assays (FIGS. 10A, 10B, 10C, 10D and 10 E), cells were seeded in wells of 96-well plates at a concentration of $1.0 \times 10^4$ cells/ml (proliferation assays) or in wells of 24-well plates at a concentration of $4 \times 10^5$ cells/ml (apoptosis assays) and cultured for up to 6 days. During this time, cells were cultured in medium alone (untreated cultures) or in medium supplemented with either control (e.g. Z-DNC) or active (e.g. Z-DTP2) tetrapeptides (treated cultures) to achieve a final concentration of the tetrapeptides in the cultures of 10 µM or 100 µM, as indicated. For the proliferation inhibition assays aimed at assessing the effects of the tetrapeptides on survival/proliferation of tumour cells, cultures were analyzed daily by either Trypan blue exclusion (discriminating between live and dead cells) and cell counting (data not shown) or [$^3$H]thymidine incorporation assays (FIGS. 7A, 7B, 7C, 8A, 8B, 8C and 9), as indicated. In these latter assays, the effects of Z-DTPs, Ac-DTPs and Z-LTPs on the survival/proliferation of tumour cell lines was investigated by measuring DNA synthesis using standard tritiated thymidine ([$^3$H]thymidine; [$^3$H]-TdR) uptake assays. In the analyses shown, cells were incubated for 24, 72, 120 or 144 hrs at 37° C. in the presence or absence of control or bioactive tetrapeptides, as indicated, then subjected to an additional incubation for 18 hrs with [$^3$H]-TdR (0.037 MBq/well, equivalent to 0.5 µCi/well). Cells were subsequently harvested onto glass fibre filter mats using a 96-well plate automated cell harvester, after which scintillation fluid was added, and [$^3$H]thymidine incorporation measured by liquid scintillation spectroscopy on a beta counter. The results are expressed as the percentages of the counts per minute (c.p.m.) (directly correlating with the extent of cell proliferation) measured with tetrapeptide-treated cultures relative to the c.p.m. measured with the corresponding cultures incubated with medium alone (untreated cells). All experiments were performed in triplicate. As it is further discussed later, Z-DTP2, Z-LTP2 and Ac-DTP2 yielded similar results to Z-DTP1, Z-LTP1 and Ac-DTP1, respectively, in these survival/proliferation assays, albeit Z-DTP2 exhibited a slightly higher activity than Z-DTP1 (data not shown; see also Table IV).

Cell apoptosis in cultures was measured at the times indicated by the use of propidium iodide (PI) nuclear staining and flow cytometry (FC) preformed essentially as described previously (Riccardi and Nicoletti (2006) Nature Protocols 1, 1458-1461) in order to identify cells with a sub-$G_1$ DNA content (i.e. apoptotic cells) (FIGS. 10A, 10B, 10C, 10D and 10E). For these assays, cells ($4 \times 10^5$ cells/ml) were cultured in 24-well plates for 72 or 144 hrs as indicated in FIGS. 10A, 10B, 10C, 10D and 10E, then washed twice in 1× phosphate buffer saline (PBS) and fixed with 70% ice-cold ethanol for 16 hrs at −20° C., after which they were subjected to centrifugation and subsequently resuspended in 1×PBS containing 100 µg/mL of RNAase A. After this step, the cells were incubated at room temperature for 30 min and subjected to centrifugation, then resuspended in 50 µg/mL of PI, and incubated for another 45 min at 4° C. in the dark. Flow cytometry (FC) was finally performed using a FACsCalibur automated system, and the data were analyzed using the FlowJo software.

In order to determine the basis for the different sensitivity of tumour cell lines to Z-DTP-induced killing, we measured levels of Gadd45β expression in a panel of 29 tumour cell lines or different tissues of origin by using quantitative real-time polymerase chain reaction (qRT-PCT) and correlated these levels with the degree of susceptibility of these cell lines to the cytotoxic activity of Z-DTPs. For these analyses, which are shown in FIG. 12, the breast cancer and HEK-293T cell lines were cultured in 75 cm$^2$ flasks ($5 \times 10^6$ cells/flask) in complete DMEM medium, whereas all the other cell lines were cultured in wells of 6-well plates at $5 \times 10^5$ cells/well in complete RPMI-1640 medium as described above. Total RNA was extracted with Trizol and purified using the PureLike RNA mini-kit (Invitrogen). 1 µg of RNA was added as template to reverse-transcriptase (RT) reactions performed using the GeneAmp RNA PCR Kit (Applied Biosystems). qRT-PCRs were carried out with the resulting cDNAs in triplicate using SYBR Green PCR Master Mix (Applied Biosystems), the Gadd45β-specific primers listed in Table VII and an ABI 7900 real-time PCR machine. Experimental Ct values were normalized to β-actin, and relative mRNA expression calculated versus a reference sample (i.e. mRNA from HEK-293T cells). The sensitivity of cancer cell lines to Z-DTP-induced killing was analyzed as described above by performing [$^3$H]thymidine incorporation assays after treatment of the cells with 10 µM of Z-DTP2 for 144 hrs. Also shown in FIG. 12 is the correlation plot of mRNA Gadd45β expression versus the percentage of cell survival after treatment with Z-DTP2. The significance of the correlation coefficient between the 2 parameters' domain was calculated by Pearson correlation, which quantifies the association between two variables, using the GraphPad software.

Figure 11:
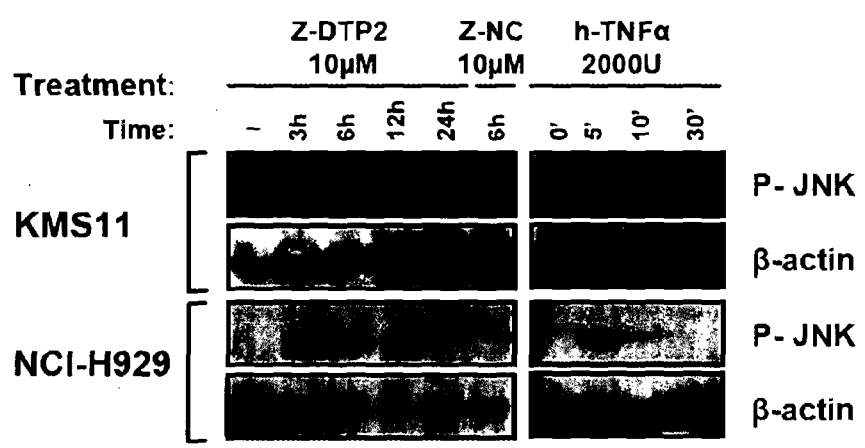
FIG. 11. Z-DTP2 treatment causes strong JNK activation in multiple myeloma cell lines. KMS11 and NCI-H929 cells were treated with 10 μM of Z-DTP2 or Z-DNC, as shown, and JNK activation was monitored at the indicated times by western blotting using an anti-phospho (P)-JNK-specific antibody. Increased JNK phosphorylation (a marker of JNK activation) is only seen after treatment with Z-DTP2, but not after treatment with Z-protected negative control peptide (Z-DNC). TNFα stimulation (2,000 U/ml) was used as positive control for JNK activation. Importantly, similar effects of Z-DTP2 were seen on MKK7 activation (data not shown). Moreover, as seen with the biological activity of Gadd45β (see references: De Smaele, et al. (2001) Nature 414:306-313; Papa, S et al., (2004) Nat. Cell Biol. 6, 146-153; Papa, et al. 2007 J. Biol. Chem. 282:19029-19041; Papa, et al. (2008) J. Clin. Invest. 118:191-1923), the effects of Z-DTPs in multiple myeloma cell lines were specific for the MKK7/JNK pathway, as no effects were observed with these compounds on the activation of the IKK/NF-κB, ERK and p38 pathways in these cell lines (data not shown).

In order to determine whether Z-DTP-induced killing of cancer cell lines was due to the induction of cytotoxic JNK signalling, we monitored JNK activation after treatment of two representative, sensitive multiple myeloma cell lines (i.e. the KMS11 and NCI-H929 cell lines) with Z-DTP2 (FIG. 11). To this end, we used Western blots analyses for an assessment of JNK phosphorylation—an indicator of JNK activation. The KMS11 and NCI-H929 multiple myeloma cell lines were cultured in 6-well plates at $5 \times 10^5$ cells/well in complete RPMI-1640 medium as described above, and treated with 10 µM of Z-DTP2 or of the negative control tetrapeptide, Z-DNC, for 3, 6, 12 or 24 hrs (FIG. 11). After tetrapeptide treatment, cell lysates were prepared essentially as described in Example 4 and Western blots were performed using an anti-phospho(P)-JNK-specific antibody. The methodology used for Western blot analyses is described in the references by De Smaele, et al. (2001) Nature 414:306-313; Papa, S et al., (2004) Nat. Cell Biol. 6, 146-153; Papa, et al. 2007 J. Biol. Chem. 282:19029-19041; Papa, et al. (2008) J. Clin. Invest. 118:191-1923. β-actin levels were determined using a β-actin-specific antibody and served as loading control (FIG. 11). TNFα stimulation (2,000 U/ml) of KMS11 and NCI-H929 cells was carried out for 5, 10 or 30 min and used as positive control for JNK activation (FIG. 11). These analyses revealed that JNK activation is only caused by treatment with Z-DTP2, but not by treatment with Z-DNC. Similar effects of Z-DTP2 were seen on MKK7 activation (data not shown). Importantly, as seen with the biological activity of Gadd45β (see references: De Smaele, et al. (2001) Nature 414:306-313; Papa, S et al., (2004) Nat. Cell Biol. 6, 146-153; Papa, et al. 2007 J. Biol. Chem. 282:19029-19041; Papa, et al. (2008) J. Clin. Invest. 118:191-1923), the effects of Z-DTP2 in multiple myeloma cells were specific for the MKK7/JNK pathway, as this compounds exhibited no effect on the activation of the IKK/NF-κB, ERK and p38 pathways (data not shown).

Results

Figure 7:
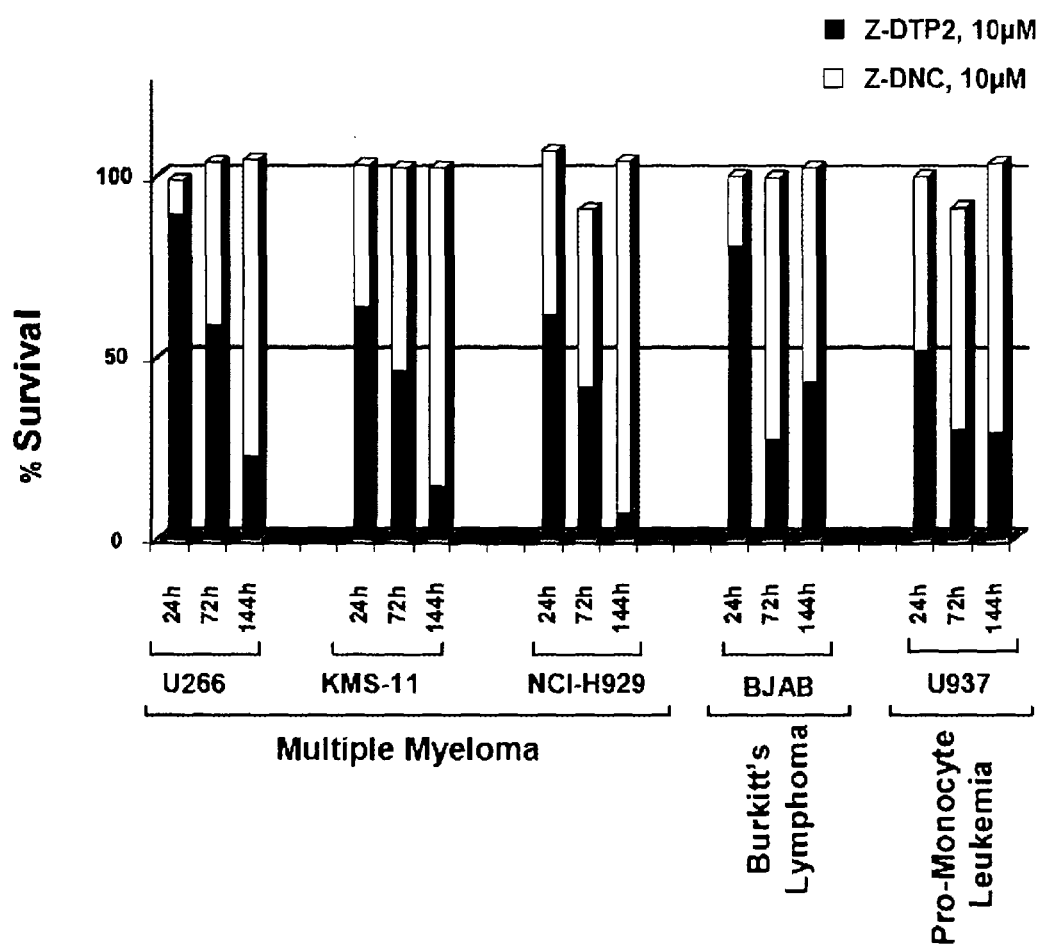
FIG. 7. (A, B, C) [$^3$H]thymidine incorporation assays, showing that Z-protected derivatives of DTP2 (Z-DTP2), but not the acetyl derivatives of DTP2 (Ac-DTP2) or the Z-protected derivatives of the L-isomers of DTP2 (Z-LTP2) have significant tumoricidal activity in tumour cell lines. Data are expressed as percentage of survival/proliferation of tumour cells after treatment with either 10 μM of Z-DTP2 (A), Ac-DTP2 (B) or Z-LTP2 (C) (filled columns), or with Z-DNC (A), Ac-DNC (B) and Z-LNC (C) (empty columns) relative to the survival/proliferation of untreated cells. Time points are indicated. Shown are 3 out of the 8 susceptible multiple myeloma cell lines tested (i.e. U266, KMS-11, NCI-H929), and the Burkitt's lymphoma (BJAB) and pro-monocytic leukaemia (U937) cell lines. These data establish the high cytotoxic activity of Z-DTP2 (A) compared to the inactivity of Ac-DTP2 (B) and the low activity of Z-LTP2 (C) (see also FIGS. 8A, 8B, and 8C and Table IV; additional multiple myeloma lines). (B) The absence of Ac-DTP2's tumoricidal activity in multiple myeloma cell lines correlated with the low cellular permeability of this compound, as established in CaCO2 assays (data not shown). The viability of multiple myeloma cell lines after treatment with other, less effective DTPs' derivatives (also designed to improve DTPs' cellular uptake), including those bearing a methyl (Me), acetyl (Ac), myristyl (Myr), 3-methoxy, 4-hydroxy-benzoyl, benzoyl, 6Cl-benzyloxycarbonyl (6Cl-Z), and/or fluorenylmethyloxycarbonyl (Fmoc) group, is not shown. (C) Although Z-LTPs' in vitro potency and cellular uptake were comparable to those of Z-DTPs (see FIG. 3C; also data not shown), Z-LTP2 shows low activity in multiple myeloma cells, due to low stability in biological fluids (see FIG. 4).
Figure 7:
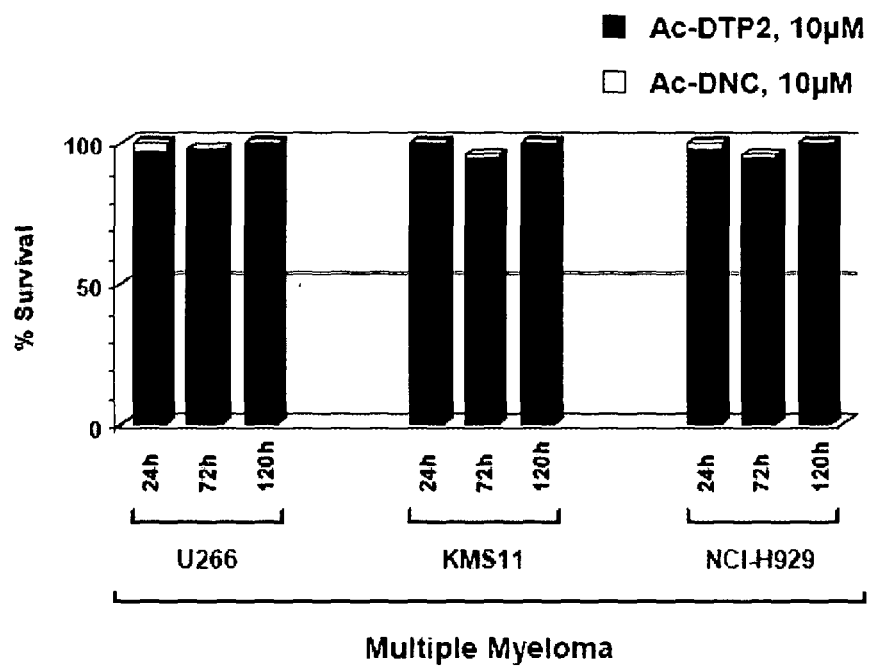
Figure 7:
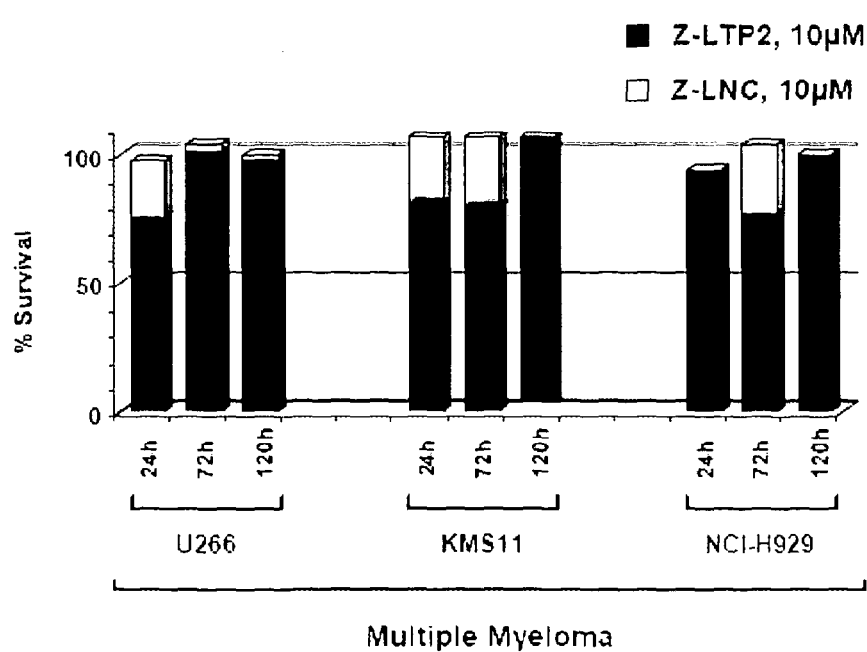
Figure 8:
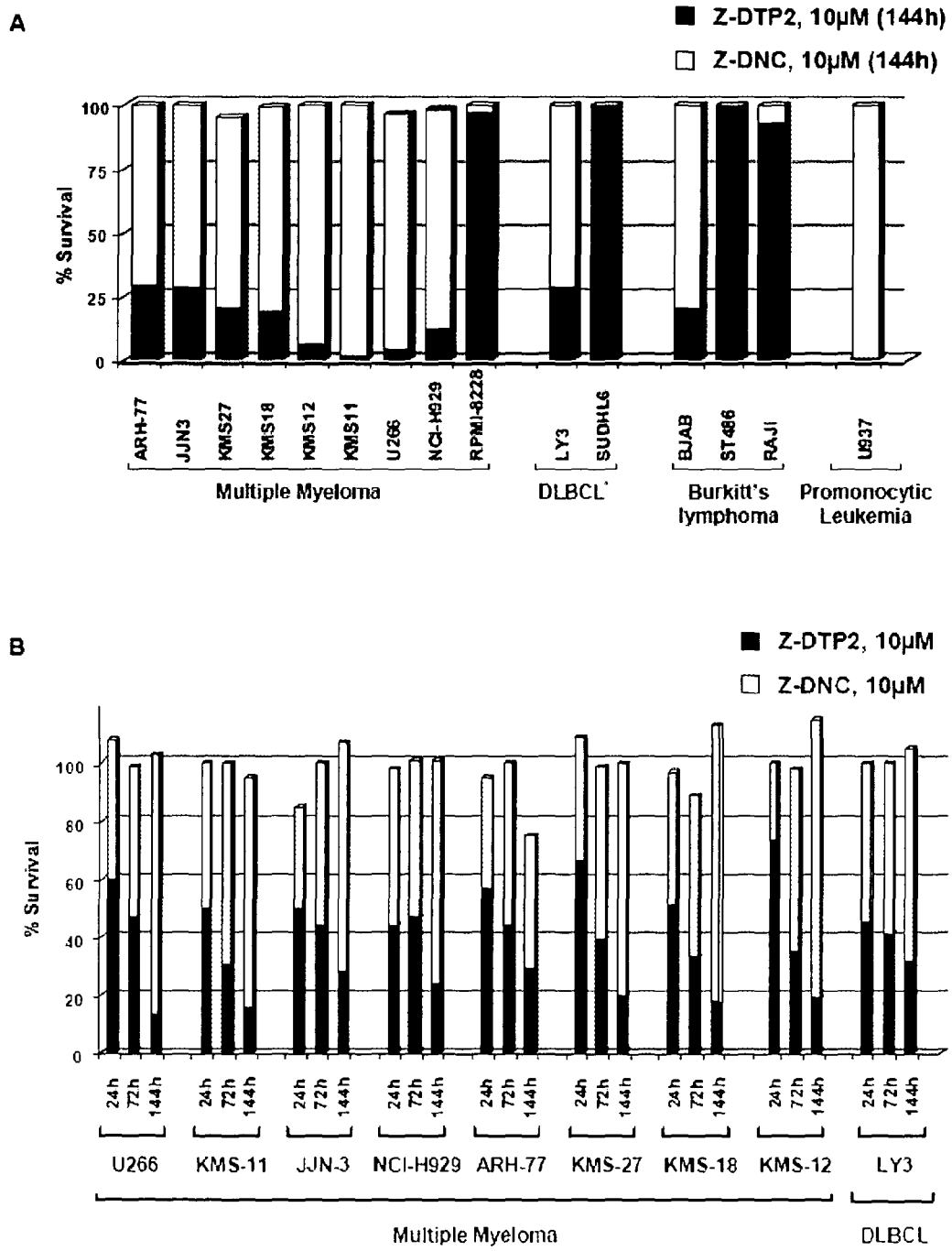
FIG. 8. Z-DTPs' proapoptotic activity is selective for tumour cell lines with constitutive NF-κB activity. (A, B, C) [$^3$H]Thymidine incorporation assays, performed as described in FIG. 7, showing cell survival in a panel of tumour cell lines after treatment with 10 μM Z-DTPs or Z-DNC for the following times: 144 hrs (A); 24 hrs, 72 hrs or 144 hrs (B, C), as indicated. (A) Shown is the potent tumoricidal activity of Z-DTP2 in 8 out of 9 multiple myeloma cell lines, 1 out of 2 diffuse large B-cell lymphoma (DLBCL; LY3) cell lines, 1 out of 1 promonocytic leukemia cell line (U937), and in 1 out of 6 Burkitt's lymphoma cell lines (BJAB) that were tested (see also FIG. 9). Interestingly, Z-DTP2 showed cytotoxic activity only in the DLBCL cell line of the activated-B-cell (ABC)-like subtype (i.e. LY3), and not in that of the germinal center B-cell (GCB)-like (i.e. SUDHL6) subtype, which does not feature constitutive NF-κB activation (Ngo V N, et al. Nature 441(7089):106-10; see also FIG. 12, levels of Gadd45β expression). They also show activity in multiple myeloma cells lines, virtually all of which feature constitutive NF-κB activation. Tumoricidal activity of Z-DTP2 (B) and Z-DTP1 (C) in multiple myeloma and DLBCL cell lines after treatment with 10 μM of Z-DTP1, Z-DTP2 and Z-DNC for the times indicated (i.e. 24, 72 or 144 hrs, as shown). Results were confirmed in trypan blue exclusion assays (data not shown) and propidium iodide (PI) assays (see FIG. 10; also data not shown).
Figure 8:
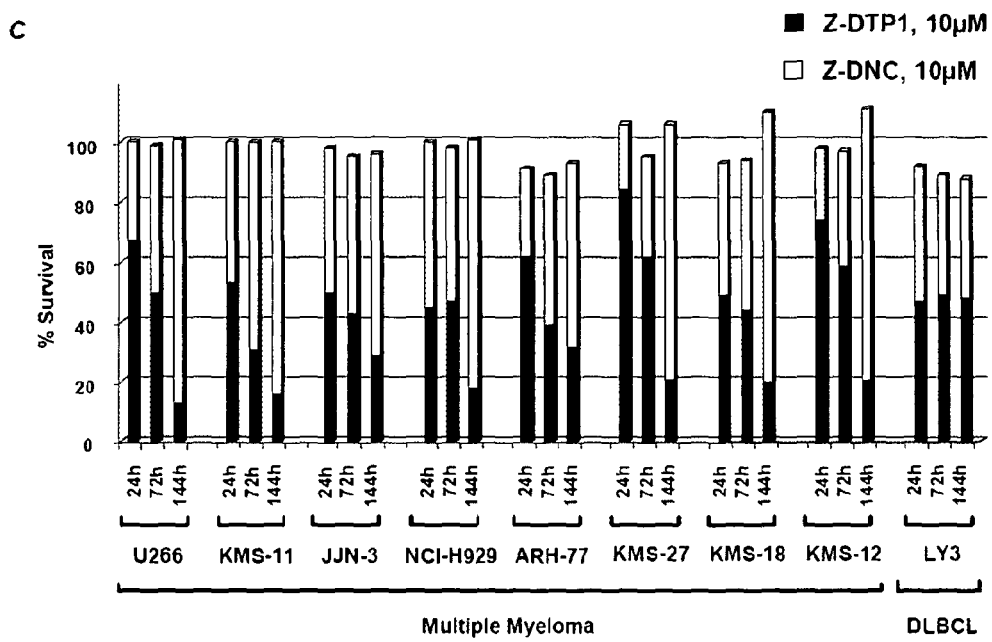
Figure 12:
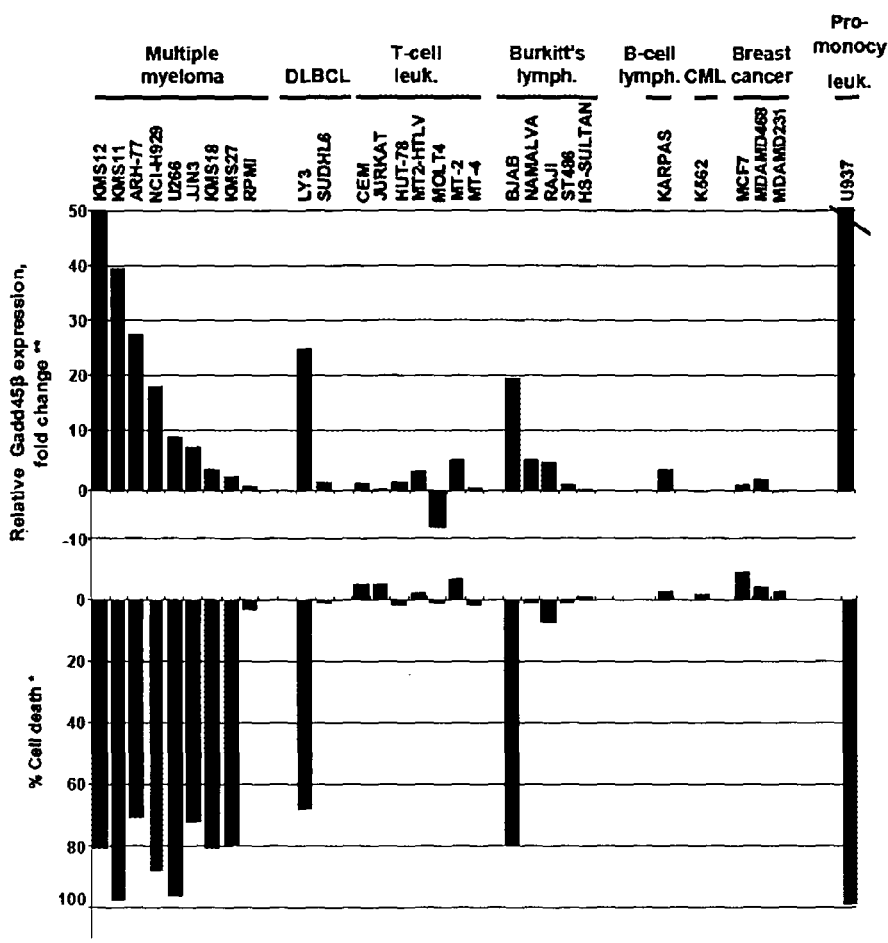
FIG. 12. Strong correlation in tumour cell lines between cell sensitivity to Z-DTP-induced killing and levels of Gadd45β expression. (A) The top panel shows the expression of Gadd45β in a panel of 29 cancer cell lines (qRT-PCR; red columns); whereas the bottom panel shows the percentage of cell death in the same cell lines after treatment with 10 μM of Z-DTP2 for 144 hrs ([$^3$H]thymidine incorporation; black columns). (B) Shown is the correlation plot of Gadd45β expression versus the percentage of cell survival after treatment with Z-DTP2 for the same experiment shown in (A). The significance of the correlation coefficient between the 2 parameters' domain is very high (p<0.01) (Pearson correlation, which quantifies the association between two variables, calculated using the GraphPad software). These data confirm the high target specificity of Z-DTPs in cells. Values in (A) (top panel) were normalized to β-actin.
Figure 12:
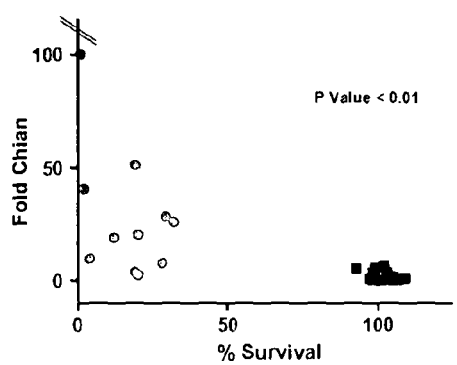

FIGS. 7A, 7B and 7C show that Z-protected derivatives of DTP2 (Z-DTP2), but not of acetly derivatives (Ac-DTP2) or of L-isomers of Z-DTP2 (Z-LTP2), nor the negative control tetrapeptides, Z-DNC, Ac-DNC and Z-LNC, markedly inhibit the proliferation of three representative multiple myeloma cell lines out of the 8 susceptible multiple myeloma cell lines tested (i.e. U266, KMS-11, and NCI-H929), of the Burkitt's lymphoma cell line, BJAB, and of the pro-monocytic leukemia cell line, U937 (see also FIGS. 8 and 12, and Table IV; additional multiple myeloma lines). The cells were cultured with 10 µM of either Z-DTP2 or Z-DNC (FIG. 7A), Ac-DTP2 or Ac-DNC (FIG. 7B), and Z-LTP2 or Z-LNC (FIG. 7C) as indicated. [$^3$H]-tTdR incorporation (measuring DNA synthesis) of treated cells was measured and compared to that of cells cultured with media alone. The data are expressed as the percentage of c.p.m. observed with tumour cells after treatment with Z-DTP2, Ac-DTP2 or Z-LTP2 (filled columns), or with Z-DNC, Ac-DNC or Z-LNC (empty columns) relative to the c.p.m. measured with cells cultured with medium alone (untreated cells). A marked inhibition of cell proliferation was observed in multiple myeloma and other tumour cell lines treated with Z-DTP2, but not in those treated with Z-DNC. In FIG. 7B, the absence of Ac-DTP2's tumoricidal activity in multiple myeloma cell lines correlated with the low cellular permeability of this compound, as established in CaCO2 assays (data not shown). The viability of multiple myeloma cell lines after treatment with other, less effective DTP derivatives (also designed to improve DTPs' cellular uptake), including those bearing a methyl (Me), acetyl (Ac), myristyl (Myr), 3-methoxy,4-hydroxy-benzoyl, benzoyl, 6Cl-benzyloxycarbonyl (6Cl-Z), and/or fluorenylmethyloxycarbonyl (Fmoc) group, is not shown. Although Z-LTPs' in vitro potency and cellular uptake were comparable to those of Z-DTPs (see FIG. 3C; also data not shown), Z-LTP2 showed low activity in multiple myeloma cells (FIG. 7C), due to low stability in biological fluids (see FIG. 4). A similar inhibition of cell proliferation was observed in the tumour cell lines treated with Z-DTP1, but not in those treated with Ac-DTP1 or Z-LTP1 (data not shown)—despite that (as also seen with DTP2 derivatives) these two latter compunds exhibited comparable potency to Z-DTP1 in vitro (see FIGS. 3C and 4). Together, these data establish the high cytotoxic activity of Z-DTPs (FIG. 7A and data not shown) compared to the inactivity of Ac-DTPs (FIG. 7B and data not shown) and the low activity of Z-LTPs (FIG. 7C and data not shown).

In FIGS. 8A, 8B and 8C, we examined the effects of D-tetrapeptide treatment on the proliferation of a larger panel of multiple myeloma cell lines (i.e. U266, KMS-11, JJN-3, NCI-H929, ARH-77, KMS-27, KMS-18, KMS-12, and RPMI-8226). Other tumour cell lines tested include the diffuse large B-cell lymphoma cell lines, LY-3 and SUDHL6, the Burkitt's lymphoma cell lines, BJAB, ST486 and RAJI, and the pro-monocytic leukemia cell line, U937. The cells were treated with 10 µM of either Z-DTP2, Z-DTP1 or Z-DNC, as shown, for the times indicated (i.e. 24, 72 or 144 hrs). [$^3$H]Thymidine incorporation of treated cells was measured as in FIG. 7 and compared to that of cells cultured with media alone. The data are expressed as the percentage of c.p.m. observed with tumour cells treated with Z-DTP2 or Z-DTP1 (filled columns), or with Z-DNC (empty columns) relative to the c.p.m. measured with untreated cells. FIG. 8A shows that Z-DTP2, but not Z-DNC, markedly inhibits the survival/proliferation of 8 out of 9 multiple myeloma cell lines tested (i.e. U266, KMS-11, JJN-3, and NCI-H929, ARH-77, KMS-27, KMS-18, KMS-12), of the Burkitt's lymphoma cell line, BJAB, of the diffuse large B-cell lymphoma (DLBCL) cell line, LY-3, and of the pro-monocytic leukemia cell line, U937 (see also FIG. 12). Notably, Z-DTP2 showed cytotoxic activity only in the DLBCL cell line of the activated-B-cell (ABC)-like subtype (i.e. LY3), which depends on NF-κB for survival, and not in that of the germinal center B-cell (GCB)-like (i.e. SUDHL6) subtype, which does not feature constitutive NF-κB activation (Ngo V N, et al. Nature 441(7089):106-10; see also FIG. 12). It also showed potent cytotoxic activity of Z-DTPs in the vast majority of the multiple cell lines tested—all of which depend on NF-κB for survival. As shown in FIGS. 8B and 8C, the inhibitory effects of Z-DPT1 and Z-DTP2 on tumour cell proliferation increased with time—maximal inhibition of proliferation was observed after tetrapeptide treatment for 144 hrs, albeit these effects were already apparent after treatment for 24 hrs. These data are in agreement with those obtained by cell counting in trypan blue exclusion assays (data not shown) and in PI nuclear staining assays for DNA content (see FIGS. 10A, 10B, 10C, 10D and 10E); also data not shown). Together, these and other data show that Z-DTPs' cytotoxic activity is selective for tumour cells exhibiting constitutive NF-κB activity (see also FIG. 12; also data not shown).

Figure 9:
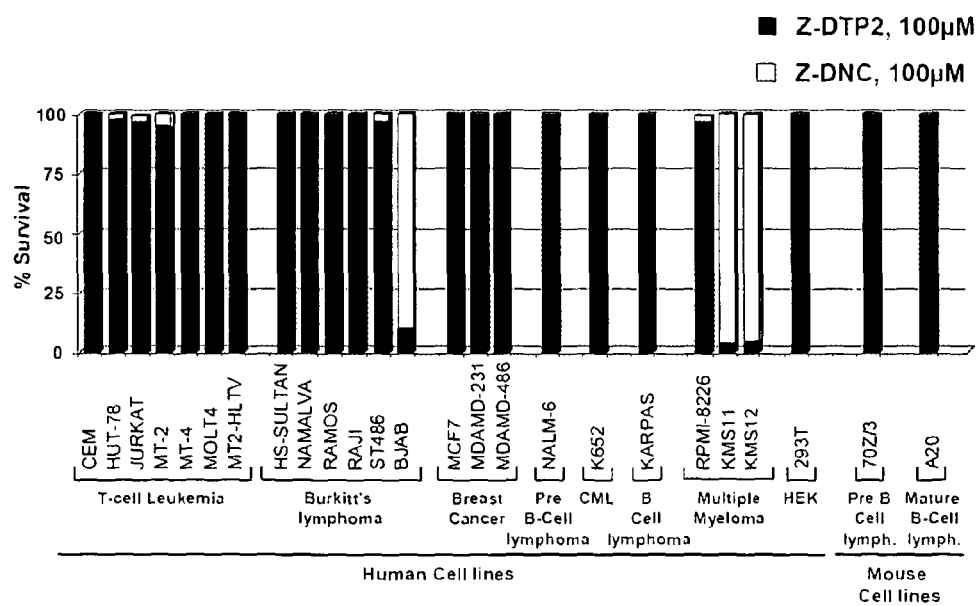
FIG. 9. [$^3$H]Thymidine incorporation assays showing absence of Z-DTP2 cytotoxicity in a panel of 22 resistant tumour cell lines after treatment with Z-DTP2 for 144 hours, even when this compound was used at very high concentrations—that is 100 μM. Z-DNC, Z-protected D-negative control. Also shown are the sensitive cell lines BJAB (Burkitt's lymphoma), KMS-11 and KMS-12 (multiple myeloma). Notably, there was a strong correlation in these cell lines between sensitivity to Z-DTP2-induced killing and levels of endogenous Gadd45β expression (see FIGS. 12A and 12B).
Figure 10:
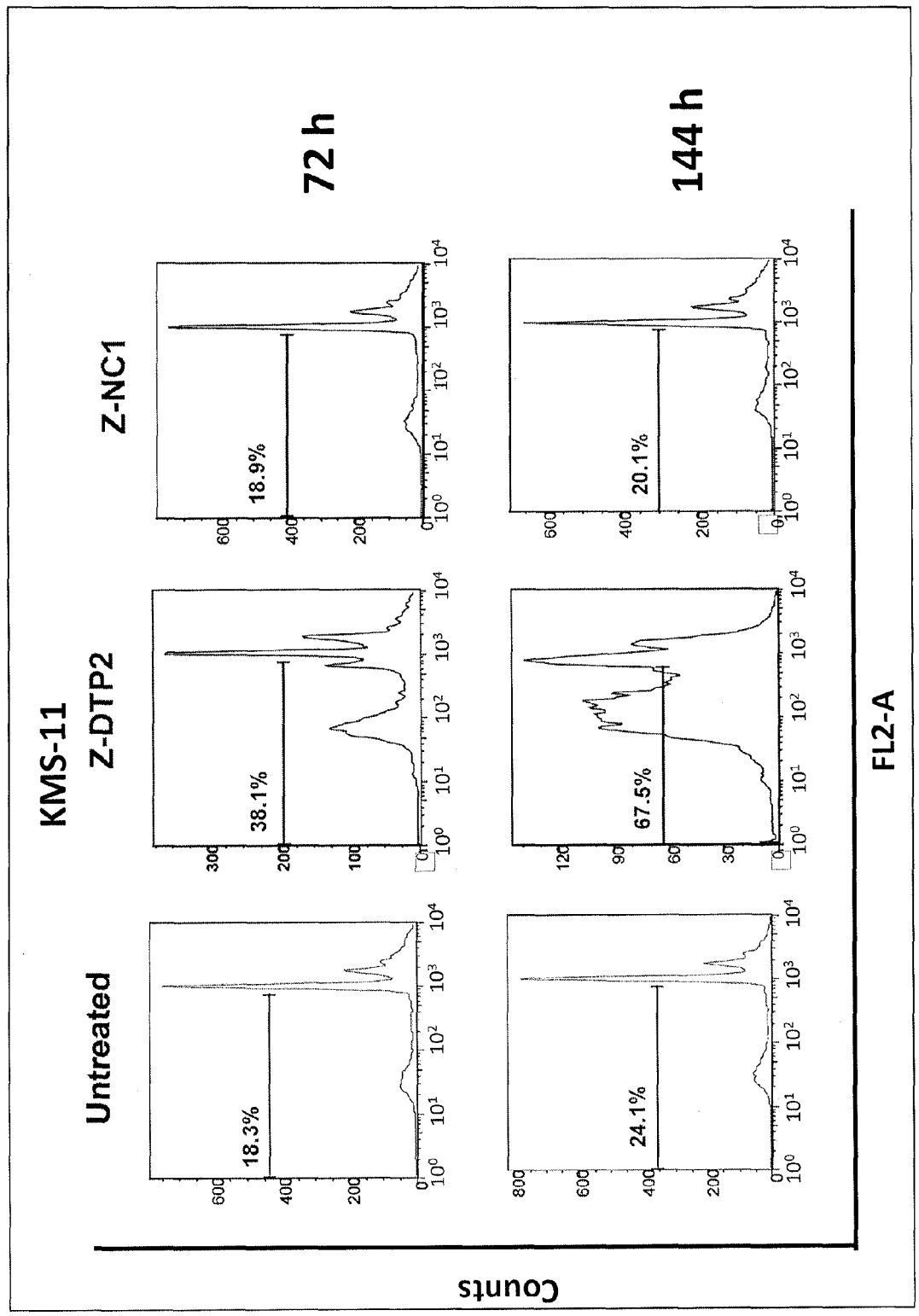
FIGS. 10A, 10B, 10C, 10D and 10E. Z-DTP2-induced killing in multiple myeloma cell lines is due to apoptosis. Propidium iodide (PI) nuclear staining assays showing the induction of apoptosis (i.e. sub-$G_1$ DNA content; see FL2-A) in the representative multiple myeloma cell lines, NCI-H929 (Figure A) KMS-11, (Figure B), ARH-77, (Figure C) JJN-3, (Figure D) and U266, (Figure E) after treatment with 10 μM of Z-DTP2 or Z-DNC1, as shown, for 72 or 144 hrs. Also shown is the DNA content of untreated cells cultured under the same conditions. Percentages of apoptotic cells are depicted in the histograms.
Figure 10:
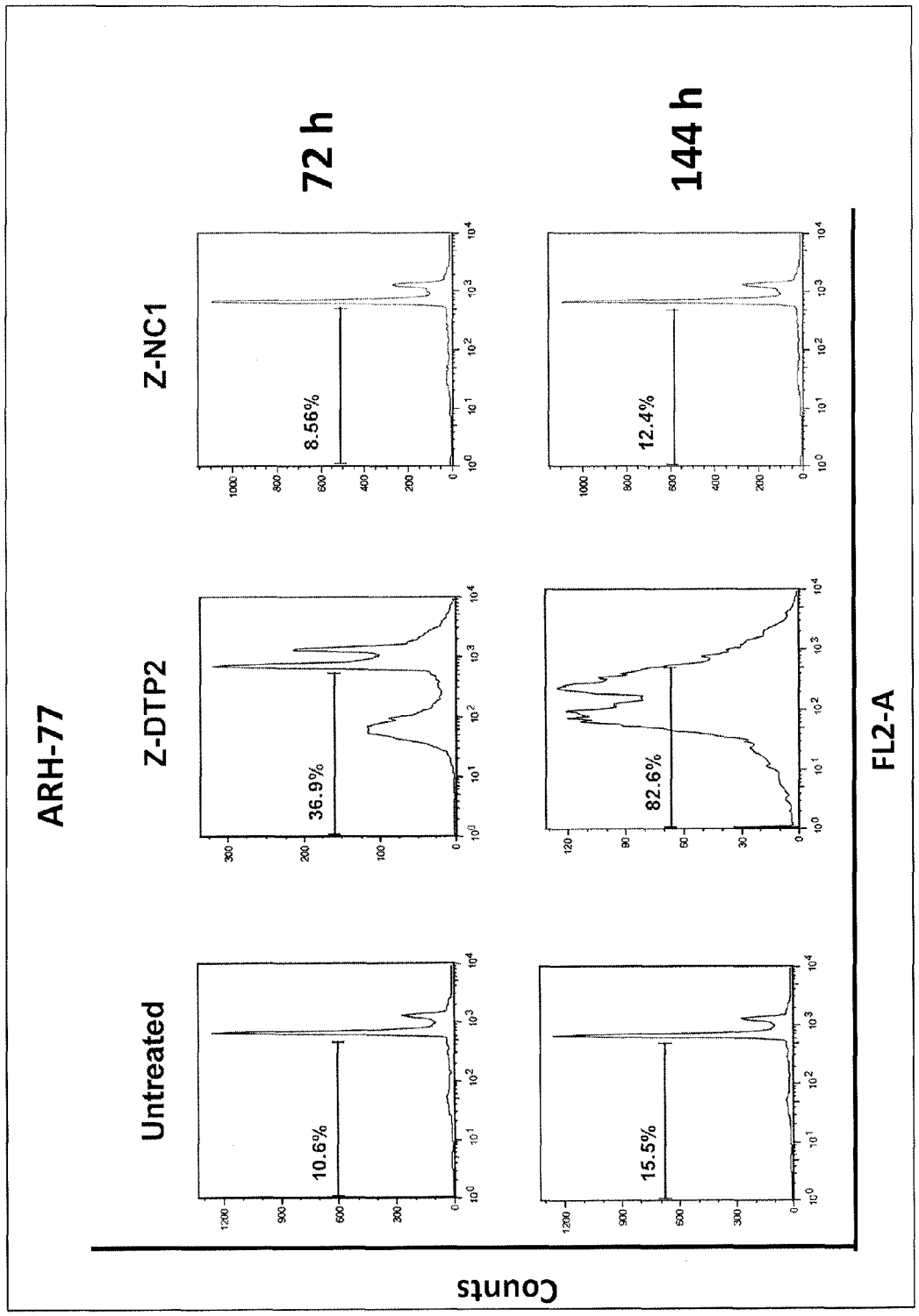
Figure 10:
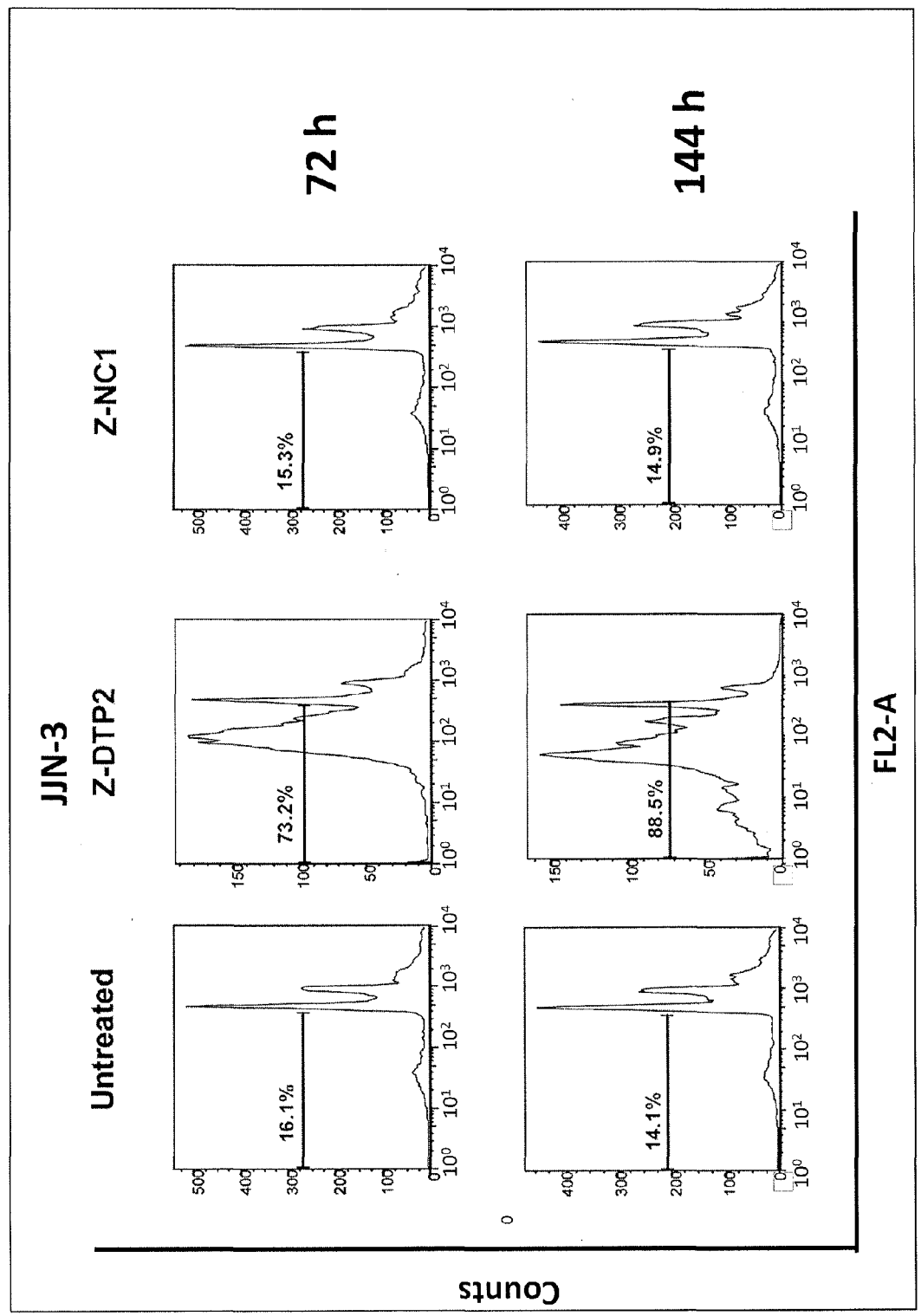
Figure 10:
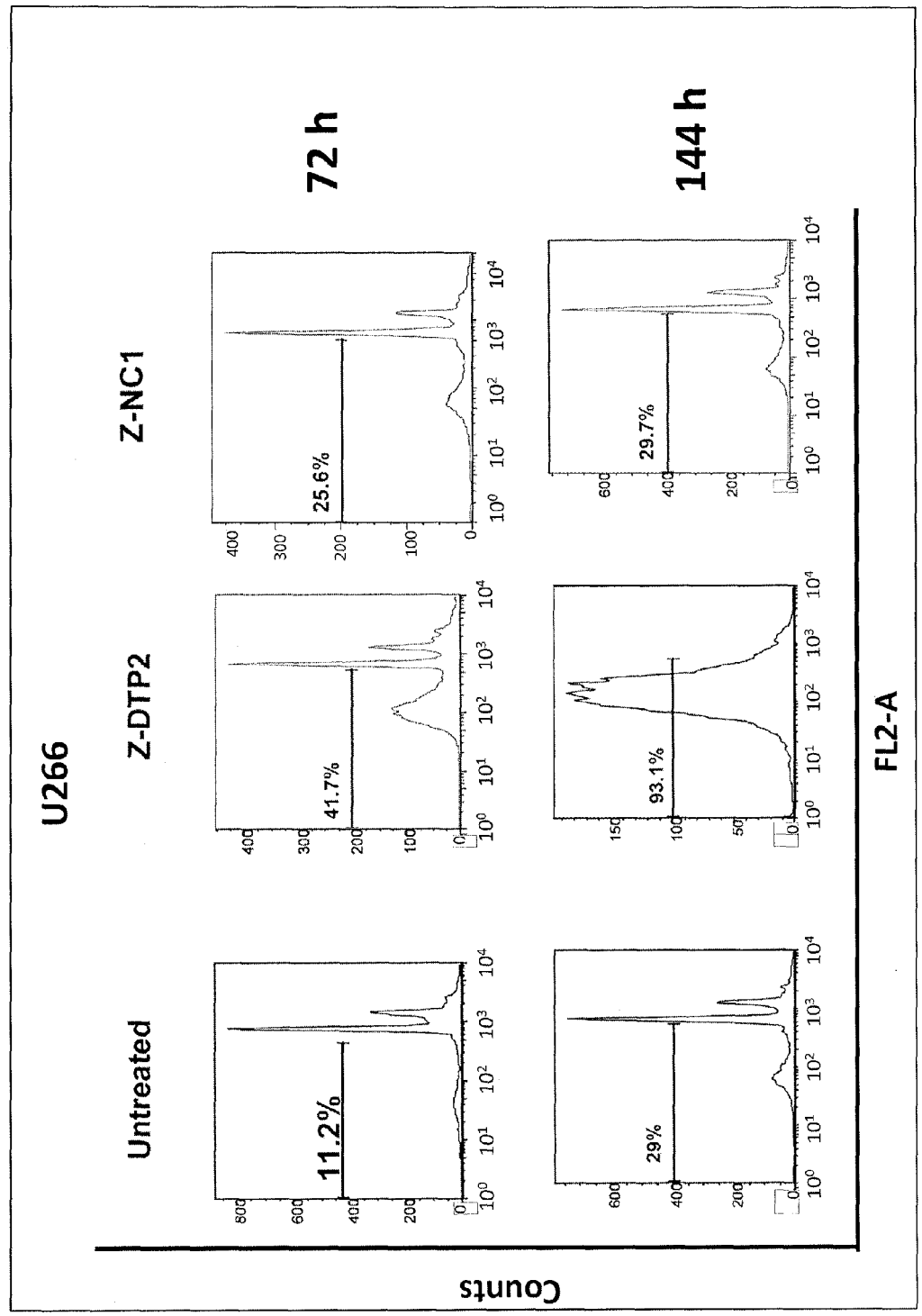

The specificity of the cytotoxic activity of Z-DTPs was further corroborated by the [$^3$H]thymidine proliferation assays shown in FIG. 9. This Figure shows the absence of Z-DTP2-induced cytotoxicity in a panel of 22 resistant tumour cell lines after treatment for 144 hours, even when this compound was used at very high concentrations—that is 100 μM. The [$^3$H]thymidine proliferation assays shown in FIG. 9 were performed as described in FIG. 8.

As it can be seen in FIG. 9, Z-DTP2 exhibited no cytotoxicity in the T-cell leukaemia and lymphoma cell lines, JURKAT, HUT-78, MT-2, MT-4, MOLT4, MT2-HTLV-I, and CEM, the Burkitt's lymphoma cell lines BJAB, ST486, RAJI, RAMOS, Namalwa, and HS-SULTAN, the breast cancer cell lines MCF7, MD-MDA-231, and MD-MDA-486, the pre-B-cell lymphoma cell lines NALM-6 and 70Z/3, the B-cell lymphoma cell lines KARPAS and A20, the chronic myelogenic leukemia cell line K652, the human embryonic kidney cell line HEK-293T, and the multiple myeloma cell line RPMI-8226 (see also FIG. 12). Also shown in FIG. 9 are the sensitive cell lines BJAB (Burkitt's lymphoma), KMS-11 and KMS-12 (multiple myeloma). Notably, there was a strong correlation in these cell lines also between sensitivity to Z-DTP2-induced killing and levels of endogenous Gadd45β expression (see FIG. 12). Of note, the RPMI-8226 cell line—the only multiple myeloma cell line tested that is resistant to Z-/mDTP-induced killing (FIGS. 8A and 9)—displayed very low levels of Gadd45β (see FIG. 12), further confirming that the cytotoxic activity of DTPs in cancer is dependent on the levels of constitutive Gadd45β expression.

In FIGS. 10A, 10B, 10C, 10D and 10 E, the embedded panels show the percentage of cells exhibiting propidium iodide (PI) staining indicative of a sub-$G_1$ amount of DNA (i.e. cells which are either dead or dying by apoptosis), after treatment for the indicated times (i.e. 72 or 144 hrs) with either culture medium alone (untreated) or culture medium delivering a 10 μM final concentration of either Z-DTP2 or Z-NC1. The percentages of apoptotic cells are depicted in the histograms. Shown are the five representative sensitive multiple myeloma cell lines, NCI-H929, (see FIG. 10A) KMS-11, (see FIG. 10B), ARH-77, (see FIG. 10C), JJN-3, (see FIG. 10D) and U266 (see FIG. 10E). As it can be seen, Z-DTP2-induced killing of multiple myeloma cells is due to the triggering of apoptosis, and the portion of apoptotic cells seen after cell exposure to this compound increases with the time of treatment.

FIG. 11 shows that Z-DTP2 treatment causes strong activation of JNK in multiple myeloma cell lines. The two representative sensitive multiple myeloma cell lines, KMS11 and NCI-H929, were treated with 10 μM of Z-DTP2 or Z-DNC, as shown. JNK activation was monitored at the indicated times by western blotting using an anti-phospho (P)-JNK-specific antibody. It can be seen that JNK phosphorylation (a marker of JNK activation) only increases after treatment with Z-DTP2, but not after treatment with Z-protected negative control peptide (Z-DNC). Indeed, Z-DTP2 caused an even stronger activation of JNK than TNFα stimulation did (2,000 U/ml)—our positive control. Similar effects of Z-DTP2 were seen on MKK7 activation and using kinase assays to monitor JNK and MKK7 activities (data not shown). Notably, as seen with the biological activity of Gadd45β (see references: De Smaele, et al. (2001) Nature 414:306-313; Papa, S et al. (2004) Nat. Cell Biol. 6, 146-153; Papa, et al. (2007) J. Biol. Chem. 282: 19029-19041; Papa, et al. (2008) J. Clin. Invest. 118:191-1923), the effects of Z-DTP2, as well as of Z-DTP1 and mDTP3 (data not shown), in multiple myeloma cells were specific for the MKK7/JNK pathway, as no effects were observed with these compounds on the IKK/NF-κB, ERK and p38 pathways (data not shown). Importantly, Z-DTPs' treatment failed to activate JNK in the multiple myeloma cell line, RPMI-8226, which is resistant to Z-DTP-induced killing (see FIGS. 8A and 9). These and other data (see also FIG. 20) support the view that Z-DTPs inducing apoptosis in tumour cell lines by activating JNK cytotoxic signaling.

Crucially, the data presented in FIGS. 12A and 12B show that the sensitivity of cancer cell lines to Z-DTP-induced killing correlates with a very high degree of statistical significance with levels of endogenus Gadd45β expression (p<0.01). Gadd45β mRNA expression was assessed in a panel of 29 cancer cell lines by using qRT-PCR assays (FIG. 12A, top panel, red columns). Values were normalized to β-actin. Viability/proliferation in the same cancer cell lines was determined by performing [$^3$H]thymidine incorporation after treatment with 10 μM of Z-DTP2 for 144 hrs. These results are shown in the bottom panel of FIG. 12A (black columns). The values reported here represent the percentage of c.p.m. measured with cells treated with Z-DTP2 relative to the c.p.m. measured with untreated cells. FIG. 12B shows the correlation plot of Gadd45β expression versus the percentage of cell survival/proliferation observed after treatment with Z-DTP2 for the same experiment shown in FIG. 12A. As it can be seen, the significance of the correlation coefficient between the 2 parameters' domain is very high (p<0.01) (Pearson correlation, which quantifies the association between two variables, calculated using the GraphPad software). This is a key issue for the development of a successful therapy in man. These data demonstrate the high target specificity of the Z-DTPs in cells for Gadd45β. In further support of this conclusion, sh-RNA-mediated silencing of Gadd45β induces apoptosis in multiple myeloma cells, whereas sh-RNA-mediated silencing of MKK7 MKK7 renders these cells completely resistant to Z-DTP-induced killing (see FIGS. 16, 17, 18, and 20). Together, these data also show that should DTP-based therapy enter the clinic, it will be possible to predict patient responder populations via simple and cost-effective qRT-PCR analysis. Accordingly, it follows that primary cell from multiple myeloma patients can be analyzed for levels of Gadd45β expression, and patients with high levels of this expression can be deemed as those who will receive the most benefit from treatment with the compounds of the invention. Hence, an important aspect of the invention is a theranostic aspect—that is the application of a clinically useful assay to predict DTPs' therapy response in patients.

Example 9

IC$_{50}$s In Vitro and in Cells of a Panel of Z-DTPs' Derivatives

Figure 13:
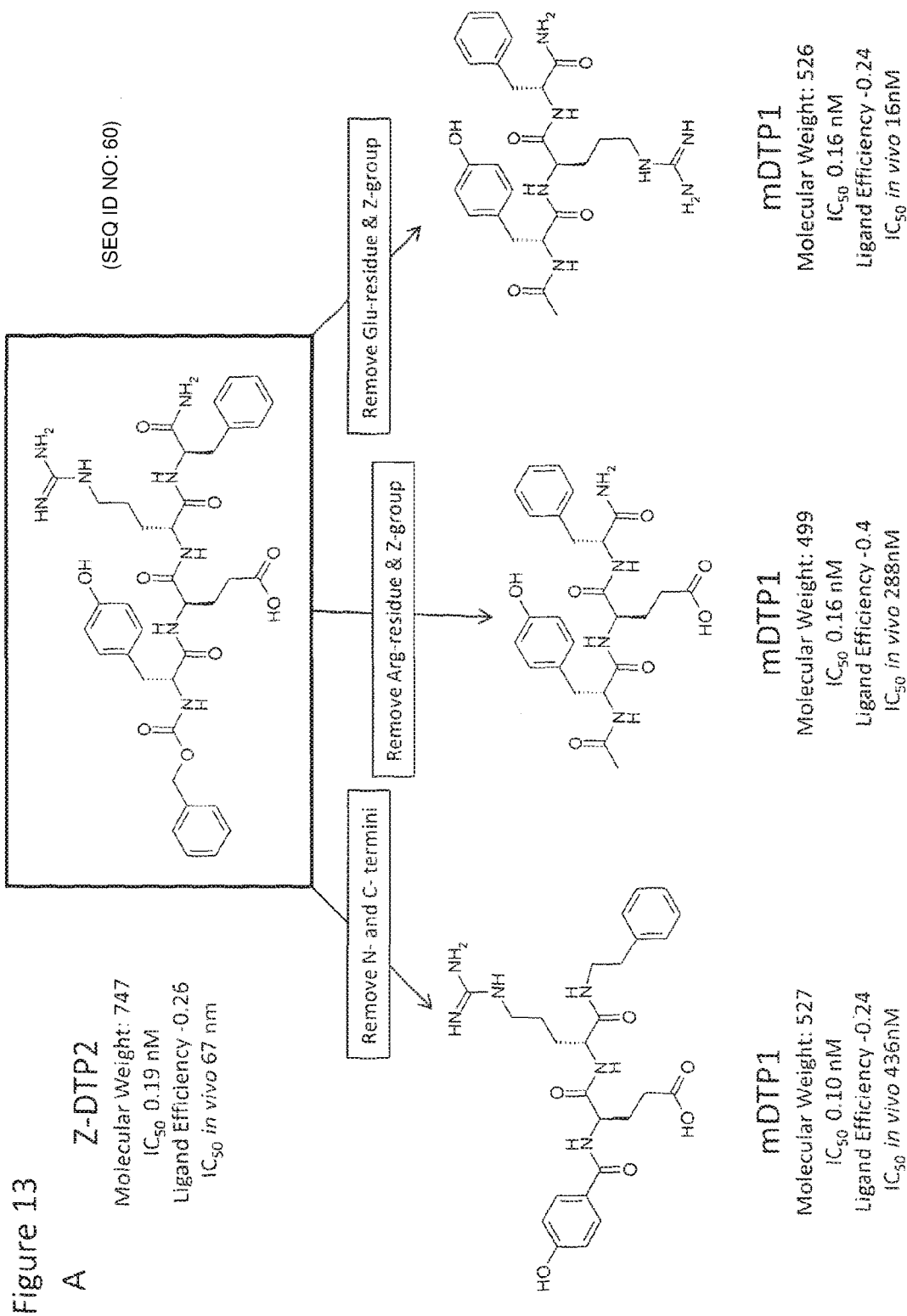
FIG. 13. Chemical structures of relevant compounds disclosed in this patent and description of possible pharmacophores and strategies for their assessment. (A) Shown are the chemical structures of the parent compound Z-DTP2 (Z-D-Tyr-D-Glu-D-Arg-D-Phe-NH$_2$) [SEQ ID NO.: 1] and of the Z-DTP2 derivatives, mDTP1 (p-hydroxy-benzoic-acid-D-Glu-D-Arg-phenetylamine), mDTP2 (Ac-D-Tyr-D-Glu-D-Phe-NH$_2$), and mDTP3 (Ac-D-Tyr-D-Arg-D-Phe-NH$_2$). These modified Z-DTP2 compounds (hereafter termed mDTPs) were tested for activity both in vitro (ELISA) and in cells (killing assays). The molecular weights (MW), IC$_{50}$s in vitro and in cells and ligand efficiency of Z-DPT2 and of these representative modified compounds are also reported (see also Table V). (B) Outlined are the main steps of the strategy achieved to identify the possible pharmacophore of the bioactive compounds (Geeson M P. 2008 J Med Chem. 51:817-834). Most of the proposed changes have already been explored: N-terminal groups (see Table III); Tyr to cyclohexylalanine, Phe to cyclohexylalanine exchange, removal of the internal Glu and/or Arg, exchange of Glu to Asp, ester prodrugs on Asp side chain (see Table V); Tyr to Phe swap, exchange Arg to His, Lys or Pro (see Table VI). Together, the data show that the bioactive pharmacophore can be described as follows: a tyrosine or a similar aromatic ring with H-bond donor/acceptors needed on position $Y_1$; at least one alpha-amino acid needed on position $Y_2$ and/or $Y_3$, preferably with a basic group to improve cellular uptake. Proline, asparagines, or leucine at position $Y_2$ with or without arginine on position $Y_3$ also allow the retention of bioactivity. A distance greater than about 7 Angstrom between the two aromatic rings (i.e. a distance greater than that imposed by one alpha-amino acid) causes a reduction in bioactivity; an aromatic ring is needed at position $Y_4$, with or without H-bond donor/acceptor groups for retention of bioactivity (Table VI).
Figure 13:
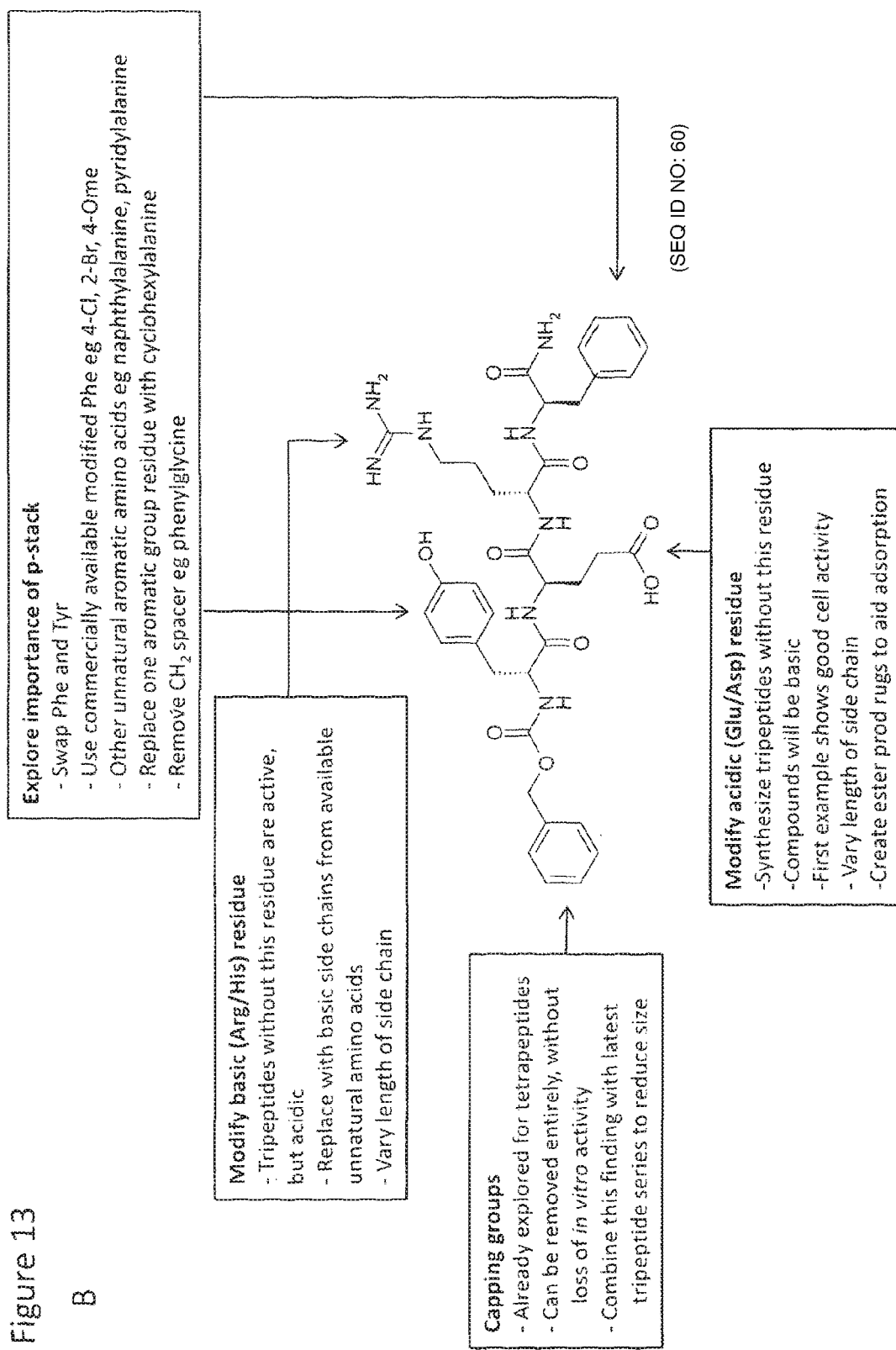

We have developed an extensive plan of lead optimization to deliver a safe and effective new therapy for treating cancer and other diseases and disorder, using our current leads as starting points. Z-DTP2 already shows high stability, high solubility, sub-nM activity in vitro, and good activity in multiple myeloma cells (primary and cell lines) and other cancer cells, with high target specificity and no toxicity in normal cells (see FIGS. 3C, 4, 8, 9, 12, 14 and 15; see also Table IV; data not shown). It also exhibits excellent starting DMPK and safety profiles in vivo (single i.v. bolus dose in mice) (see Tables VIII and IX). We have applied rational molecular design to produce DTP derivatives with improved ADMET properties whilst retaining high bioactivity (Geeson M P. 2008 J Med Chem. 51:817-834). In this approach, we have modified size (MW), lipophilicity (Log P), and ionization state (molecular charge)—the key bulky properties of molecules that influence ADMET properties—using our model pharmacophore to preserve structural elements responsible for bioactivity in vitro (see FIG. 13). As described in this Example, our most recent derivatives (e.g. mDTP3 and mDTP4) retain high potency in vitro, but show improved killing activity in multiple myeloma cells, with substantially reduced MW (~500 vs>700), hence increased ligand efficiencies (FIG. 13). We have also applied additional means of improving peptides' cellular activity and PK values, including cyclization, addition of blocking groups to internalize vulnerable amides, and/or replacement with nonamide linkages.

Materials and Methods 33 compounds were designed on the basis of the lead tetrapeptide sequences: Tyr-Glu-Arg-Phe and Tyr-Asp-His-Phe derived from the library screening (see FIG. 3). All compounds—except for compounds 2, 3, 4, 5, 6, 7, 10, 11, 12, 13, 14, 15, and 16 (see Table V)—were prepared by a solid phase method following classical Fmoc/tBu chemistry (as described in the reference by Fields G B, Noble R L. *Solid phase peptide synthesis utilizing 9-fluorenylmethoxycarbonil amino acids. Int J Pept Protein Res* 1990; 35:161-214). Only amino acids in the D-configuration were used to assemble, the peptides shown in Table V. N-terminal acetylation was carried out by treatment with 10% acetic anhydride in dimethylformammide (DMF) containing 5% DIEA (di-isopropyl-ethylamine). Where necessary, the Z group was introduced by on-resin treatment with Z-OSu (Benzyloxycarbonyl-N-hydroxysuccinimide) 0.5 M in DMF/5% DIEA. Compounds were cleaved from the resin using TFA (trifluoroacetic acid) and scavengers treatment, then were purified to homogeneity by preparative reverse phase (RP)-PLC. The synthesis of compounds 2, 3, 4, 5, 6, 7, 10, 11, 12, 13, 14, 15, and 16 (Table V) was outsourced. Compound identity and purity was assessed by using LC-MS and NMR analyses. $X_1$ was benzoic acid, $X_2$ was benzylic acid, $Y_1$ was aniline, $Y_2$ was benzylamine, and $Y_3$ was phenetylamine. The compounds were all dissolved in DMSO at the stock concentration of 5 mM, and aliquots were then serially diluted in buffer to achieve the concentrations indicated for the ELISA competition assays. Proteins were prepared as reported in Tornatore L., et al. (2008). *J Mol Biol;* 378:97-111.

The ELISA competition binding assays were performed as reported in the reference by Tornatore L., et al. (2008). *J Mol Biol;* 378:97-111 (see also the Methods described in Examples 2 and 3), using peptides at increasing concentrations, ranging between 0.01 nM and 10 nM. Briefly, GST-MKK7 was immobilized at 42 nM onto wells of 96-well microtiter plates. Competing compounds were preincubated with biotin-hGadd45β (21 nM) and then incubated with the coated kinase. For each compound, the $IC_{50}$ in vitro was calculated as the concentration resulting in a 50% reduction of Gadd45β binding to MKK7 relative to the binding observed in the absence of competitors.

We investigated the effects of each compound on the viability/proliferation of the DTP derivatives in the two representative, sensitive multiple myeloma cell lines, KMS12 and KMS-11. [$^3$H]Thymidine incorporation assays in KMS11 and KMS12 multiple myeloma cells lines were performed as described for Examples 6 and 8 (FIGS. 7A, 7B, 7C, 8A, 8B, and 8C, and Table IV. Briefly, cells in 96-wells plate were cultured and treated separately with the indicated compound in wells of in 96-wells plates using increasing compound concentrations, ranging between 0.1 nM and 10 μM. Cell cultures and compound treatments were also carried out as described for FIGS. 7A, 7B, 7C, 8A, 8B, and 8C, and Table IV. [$^3$H]Thymidine upake, measuring cell viability/proliferation, was determined after treatment with the compounds for 1, 3, o 6 days as indicated. At these times, the $IC_{50}$s of each compound were calculated as described in Example 6 by determining the concentration resulting in a 50% inhibition of cell survival/proliferation relative to the survival/proliferation observed with untreated cells.

The $IC_{50}$s in vitro (ELISA) and in cells (KMS-11 and KMS-12 cells) of the 33 compounds described in this Example are reported in Table V.

Results

Shown in Table V are the $IC_{50}$ values in vitro and in cells of a panel of tetra- and tripeptides designed on the basis of the consensus sequences, Tyr-Glu-Arg-Phe and Tyr-Asp-His-Phe, derived from the library screening and lead optimization chemistry.

These compounds were screened in vitro using an ELISA competition assay where the displacement of the binding of biotin-Gadd45β to coated GST-MKK7 was determined by testing the activities of the compounds at different concentrations. In vivo $IC_{50}$s for a group of selected compounds were determined using a [$^3$H]thymidine incorporation assays in KMS-11 and KMS-12 myeloma cells lines to assess the tumouricidal activities of the compounds. $IC_{50}$s of the indicated compounds in cells were determined after a treatment for 1, 3 or 6 days. Z denotes a benzyloxycarbonyl group. As it can be seen in Table V, the most active compounds in cells were compound 9, denoted as Z-DTP2 ($IC_{50}$=10 nM in KMS-11 cells; $IC_{50}$=66 nM in KMS-12) and compound 17, denoted as mDTP3 ($IC_{50}$=25 nM in KMS-11 cells; $IC_{50}$=16 nM in KMS-12).

The 33 compounds described in this Example were all screened in vitro, in ELISA competition assays, for their ability to disrupt the Gadd45β/MKK7 interaction (Table V). Most of these compounds-except for compounds 18, 20, 21, 22, 32, and 33-were also screened in cells, using a [$^3$H] thymidine incorporation assays in KMS-11 and/or KMS-12 multiple myeloma cells lines, and their $IC_{50}$s in these cells determined at day 1, 3 and 6. As it can be seen in Table V, compounds 1, 2, 3, 4, 5, 6, 7, 9, 15 and 17 were tested in both cell lines. Compounds 15 and 19 were only tested in KMS-12 cells. Compounds 10, 11, 12, 13, 14, 23, 24, 25, 26, 27, 28, 29, 30, and 31 were only tested in the KMS-11 cell line. Compounds 18, 20, 21, 22, 32, and 33 were not tested in cells due to their relatively low activity in vitro.

Table V shows that the $IC_{50}$s in vitro of the compounds tested ranged between 100 μM (see compound 7, $X_2$-Asp-His-$Y_3$; compound 15, $X_2$-Glu-Arg-$Y_3$; and compound 19, Z-Tyr-Arg-Phe) and >10 nM (see compounds 24, 27, 30, 31, 32, and 33). As it can be seen, the activities of the compounds that were in vitro were often reflected on their activities in cells, although some of the compounds active in vitro had relatively low activity in cells, plausibly due to their poor cellular uptake, e.g. compare compound 15 (showing an in vitro $IC_{50}$=100 μM, and an $IC_{50}$=263 nM in KMS-11 cells) to compound 9 (Z-DTP2; showing an in vitro $IC_{50}$=190 μM and an $IC_{50}$=10 nM in KMS-11 cells). The data in cells also show that the presence of a Z group at the N-terminus and/or of basic side chains resulted in a higher activity in cells, due to increased cellular uptake. For examples of the relevance of the basic side chain, compare the $IC_{50}$s in cells of compound 19 (Z-Tyr-Arg-Phe-$NH_2$; $IC_{50}$=81 nM in KMS-12 cells at day 3) to that of compound 8 (Z-Tyr-Asp-Phe-$NH_2$; $IC_{50}$>10 μM in KMS-11 cells at day 3) (i.e. Arg to Asp exchange), or to that of compound 16 (Z-Tyr-Glu-Phe-$NH_2$; $IC_{50}$=3.0 nM in KMS-11 cells at day 3) (i.e. Arg to Glu exchange); also note the comparable, low IC$_{50}$s in vitro of these three compounds—all of which are in the sub-nM range (Table V). For examples of the relevance of the Z group, compare the IC$_{50}$s in U266, KMS-11, and NCI-H929 cells of Z-DTP2 (FIG. 7A) to that of Ac-DTP2 (FIG. 7B); see also the similar IC$_{50}$s in vitro of these two compounds (FIGS. 3C and 4; data not shown). The data also show that compounds without aromatic rings at both ends (e.g. compounds 20 and 21) are inactive both in vitro and in cells (Table V), indicating that such aromatic rings are absolutely required for bioactivity. Interestingly, the presence of 2 tyrosines at the N-terminus also resulted in loss of activity (Table V).

Example 10

IC$_{50}$s In Vitro of a Panel of Additional Z-DTPs' Derivatives

Material and Methods

A panel of 18 additional compounds was designed on the basis of the lead tripeptide sequence, Tyr-Arg-Phe (i.e. mDTP3), in order to investigate the relevance to bioactivity of: 1) the distance between the two aromatic rings; 2) the properties of the amino acid in the central position; 3) the occurrence the acetyl group at the N-terminus; 4) and the presence of substituents of the aromatic rings (see Table VI). All compounds were prepared by a solid phase method following classical Fmoc/tBu chemistry (as described in the reference by Fields G B, Noble R L. *Solid phase peptide synthesis utilizing 9-fluorenylmethoxy-carbonil amino acids. Int. J. Pept. Protein Res.* 1990; 35:161-214). N-terminal acetylation was carried out by treatment with 10% acetic anhydride in dimethylformammide (DMF) containing 5% DIEA (di-isopropyl-ethylamine).

Compounds were cleaved from the resin by using TFA (trifluoroacetic acid) and scavengers treatment, then were purified to homogeneity by preparative reverse phase (RP)-PLC. Compound identity and purity were assessed by LC-MS and NMR analyses. Compounds were purified using RP-HPLC, then all were dissolved in DMSO at the stock concentration of 5 mM and stored until they were used. Aliquots were then serially diluted in buffer to achieve the concentrations indicated in the ELISA competition assays. ELISA competition binding assays were performed as reported in the reference by Tornatore L., et al. (2008). *J Mol Biol;* 378:97-111 (see also the Methods in Examples 2 and 3), using peptides at increasing concentrations, ranging between 0.01 nM and 10 nM. Briefly, GST-MKK7 was immobilized at 42 nM onto wells of 96-well microtiter plates. Competing compounds were preincubated with biotin-hGadd45β (21 nM) and then incubated with the coated kinase. For each compound, the IC$_{50}$ in vitro was calculated as the concentration resulting in a 50% reduction of Gadd45β binding to MKK7 relative to the binding observed in the absence of competitors.

Results

Table VI shows the IC$_{50}$ values of a panel of 18 tripeptides and dipeptides designed on the basis of mDTP3 (Ac-D-Tyr-D-Arg-D-Phe). Compounds were designed to investigate the influence on bioactivity of the following parameters: 1) the distance between the two aromatic rings at the N- and C-termini (see compounds A1, A1 bis, A3, A6, A7, and A8); 2) the properties of the amino acid in the central position (see compounds B2, B13, B16, B16 bis, O5, and O5 bis); 3) the presence or absence of a hydroxyl group on the aromatic ring of the residues at positions 1 and 3 (see compounds A9, O1, O3, O5, O5 bis, O6, O7, and O8); the occurrence of an acetyl group at the N-terminus (see compounds A9 and O7; B16 and B16 bis; O1 and O8; O3 and O6; O5 and O5 bis).

The 18 additional compounds were tested for activity in vitro using ELISA completions assays and increasing compound concentrations, ranging from 0.01 nM to 100 nM. As it can be seen in Table VI, all the dipeptides tested were inactive regardless of the occurrence of a Phe or Tyr amino acid at either the N-terminus or the C-terminus (see compounds A1, A1 bis, A7 and A8). The introduction of a spacers longer than an alpha-amino acid in the central position of the tripeptides also resulted in loss of activity in vitro (see compounds A3 and A6, carrying a β-alanine and an ε-caproic acid in the middle position, respectively). This was not true for tetrapeptides where positions Y$_2$ and Y$_3$ were occupied by Asp/Glu or His/Arg—compare the IC$_{50}$s in vitro of compound 9 (i.e. Z-DTP2) to those of compound 16 (i.e. mDTP2), and those of compound 1 (i.e. Z-DTP1) to those of compound 8 (i.e. Z-Tyr-Asp-Phe-NH$_2$). This is because Z-DPT2 and Z-DTP1, which contain an exta-amino acid between the two active aromatic groups, retained high potency in vitro (see IC$_{50}$s in Table V). Remarkably, as shown in Table VI, the removal of the hydroxyl group on the N-terminal tyrosine also resulted in the complete loss of bioactivity in vitro (see compounds A9, O1, O5, O5 bis, O7, and O8) regardless of the presence of an acetyl group. Significantly, this observation points to an important contribution of the hydroxyl group to the interaction of the active compounds with the target proteins. Indeed, this group is likely involved in the formation of a H-bond or a polar interaction. In contrast, the occurrence of a hydroxyl group on the aromatic ring at the C-terminus did not affect activity of the compounds (see compounds A9, O1, O3, O5, O5 bis, O6, O7 and O8). Likewise, replacing arginine with another basic amino acid, such as histidine or lysine, or with proline did not alter bioactivity in vitro (see compounds B2, B13, B16, B16 bis, O5, and O5 bis), suggesting a minor role for the side chain of this residue in the ability of the compounds to disrupt the Gadd45β/MKK7 interaction.

Example 11

Lentiviral Infections Establishing the Essential Role of Gadd45β in Multiple Myeloma Cell Survival Material and Methods To determine the role of Gadd45β and MKK7 in the survival of multiple myeloma cell lines, we investigated the effects of down-regulating the expression of Gadd45β or MKK7 in these cells (see FIGS. 16A, 16B, 16C, 17A, 17B, 18A, 18B, 18C, 19A, 19B, and 19C). To this end, we performed infection with lentiviruses expressing Gadd45β- and MKK7-targeting sh-RNAs, which result in the silencing of the Gadd45β and MKK7 genes, respectively. The DNA sequences encoding the targeting small hairpin (sh)-RNAs are listed in Table VII. The targeting sh-RNA sequences (i.e. sh-Gadd45β-1, sh-Gadd45β-2, sh-Gadd45β-3, sh-MKK7-1, and sh-MKK7-2) and the non-specific control sequences, sh-NS-1 and sh-NS-2, were introduced between the BamHI and HpaI restriction sites of the lentiviral vector, LentiLox3.7 (see the reference by Yang et all 2006 PNAS 103, 10397-10402). The production of high-titer lentiviral preparation in HEK-293T cells were performed using essentially the same conditions described in the references by Pham et all 2004 Cell 116, 529-542 and by Yang et all 2006 PNAS 103, 10397-10402. For introduction of the Gadd45β- and MKK7-targeting sh-RNA sequences and the non-specific control sh-RNA sequences, the five representative Z-DTP-sensitive multiple myeloma cell lines, ARH-77, NCI-H929, U266, KMS11 and KMS12, and the Z-DTP-resistant multiple myeloma cell line, RPMI-8226, were infected with LentiLox3.7 lentiviruses, as reported in published protocols essentially as described in the reference by Yang et all 2006 PNAS 103, 10397-10402. 5 days after infection, eGFP multiple myeloma cells were sorted using a BD FACSAria™ II cell sorter, then left to rest for 2 days before beginning the analyses of cell survival and cell proliferation. The viability of the infected multiple myeloma cells was monitored over a period of 8 days by performing flow cytometry-measuring the expression of enhanced green fluorescent protein (eGFP) (labelling infected cells)—and cell counting (FIGS. 16A, 16B, 16C, 17A, 17B). Apoptosis (FIGS. 18A, 18B, and 18C) and cell cycle distribution (FIGS. 19A, 19B, and 19C) were measured by performing PI nuclear staining assays as described in Riccardi C. and Nicoletti I 2006 Nature Protocols 1, 1458-1461 (see also the Methods described in Example 8).

Results

FIGS. 16A, 16B, and 16C show that the sh-RNA-mediated silencing of Gadd45β expression results in the rapid incution of cell death, leading to reduced proliferation, in the representative Z-DTP-sensitive multiple myeloma cell lines ARH-77 (FIG. 16A) and NCI-H929 (FIG. 16B), but not in the Z-DTP-resistant multiple myeloma cell line, RPMI-8226 (FIG. 16C). In the experiment shown in FIGS. 16A, 16B, and 16C, multiple myeloma cell lines were infected with lentivirus expressing either Gadd45β -specific sh-RNAs (sh-Gadd45β-1, sh-Gadd45β-2, or sh-Gadd45β-3), MKK7-specific sh-RNAs (sh-MKK7-1 or sh-MKK7-2), or non-specific sh-RNAs (sh-NS-1 or sh-NS-2), and viability of infected cells was monitored over a period of 8 days by using flow cytometry—revealing cells expressing enhanced green fluorescent protein (eGFP), that is infected cells—and cell counting. Shown is the percent survival of eGFP$^+$ (that is lentivirus-infected) multiple myeloma cells at the times indicated relative to the viability of eGFP$^+$ multiple myeloma cells in the same culture at day 0. Cells were infected with pLentiLox.3.7 lentiviruses expressing the indicated sh-RNAs and eGFP, using standard methods (as reported in Yang H et al., Proc Natl Acad Sci USA. 2006 Jul. 5; 103(27):10397-402). 5 days later, eGFP$^+$ cells were sorted using a BD FACSAria™ II cell sorter, then left to rest for 2 days before beginning the analyses of cell viability. This time (that is the start of the viability analyses) is denoted in FIGS. 16A, 16B, and 16C as day 0. The data show that the inhibition of Gadd45β expression, but not the inhibition of MKK7 expression, rapidly causes cell death in multiple myeloma cell lines that are sensitive to Z-DTP-induced toxicity (that is the ARH-77 and NCI-H929 cell lines) (FIGS. 16A and 16B, respectively), but not in the RPMI-8226 multiple myeloma cell line (FIG. 16C), which is resistant to this toxicity. These data further establish the target specificity of Z-DTPs for the Gadd45β/MKK7 complex in multiple myeloma cells (see also FIGS. 7, 8, 9, and 12; killing and qRT-PCR assays). Indeed, in further agreement with this conclusion, the kinetics of the inhibition of multiple myeloma cell proliferation observed after the silencing of Gadd45β were very similar to those observed after treatment of these cells with Z-DTPs (see FIGS. 7A, 8B, and 8C). The data also demonstrate the essential role that Gadd45β plays in multiple myeloma cell survival, thus further validating Gadd45β as a therapeutic target in multiple myeloma.

FIGS. 17A and 17B showing that the sh-RNA-mediated silencing of Gadd45β, but not that of MKK7, has potent inhibitory activity on the survival/proliferation only of multiple myeloma cell lines that are susceptible to Z-DTPs-induced killing (e.g. the ARH-77 and NCI-H929 cell lines; see also FIGS. 7 and 8, sensitivity to Z-DTP-induced killing). In striking contrast, the viability of the Z-DTP-resistant multiple myeloma cell line, RPMI-8226, was completely unaffected by sh-RNA-mediated Gadd45β inhibition. Cell proliferation/survival in FIGS. 17A and 17B were determined by the use of [$^3$H]Thymidine incorporation assays, performed as described in Examples 6 and 8. Shown in FIG. 17A is the viability of the three representative multiple myeloma cell lines, RPMI-8226, NCI-H929 and ARH-77, after the silencing of Gadd45β or MKK7. FIG. 17B shows the viability/proliferation of the multiple myeloma cell line, ARH-77, after the silencing of Gadd45β or MKK7 using three different Gadd45β-specific sh-RNAs (sh-Gadd45β-1, sh-Gadd45β-2, or sh-Gadd45β-3), two different MKK7-specific sh-RNAs (sh-MKK7-1 or sh-MKK7-2), and two different non-specific sh-RNAs (sh-NS-1 or sh-NS-2). Multiple myeloma cell lines were infected with the indicated sh-RNA-expressing pLentiLox.3.7 lentivirus, then eGFP$^+$ multiple myeloma cells (that is cells infected with lentivirus) were sorted using a BD FACSAria™ II cell sorter as in FIG. 16. The [$^3$H]thymidine incorporation assays depicted in FIGS. 17A and 17B were performed 10 days after cell sorting, corresponding to day 8 in FIG. 16. Shown is the percent [$^3$H]thymidine incorporation (that is c.p.m.), a measure of cell proliferation, at day 8 (that is 10 days after cell sorting) relative to the [$^3$H]thymidine incorporation occurring in the same cells at day 0 (that is 2 days after cell sorting). These data further establish the target specificity of Z-DTPs for the Gadd45β/MKK7 complex in multiple myeloma cells (see also FIGS. 7, 8, 9, 12, and 16), and confirm the essential role that Gadd45β plays in multiple myeloma cell survival. Together, they also further validate Gadd45β as therapeutic target in multiple myeloma.

Figure 16:
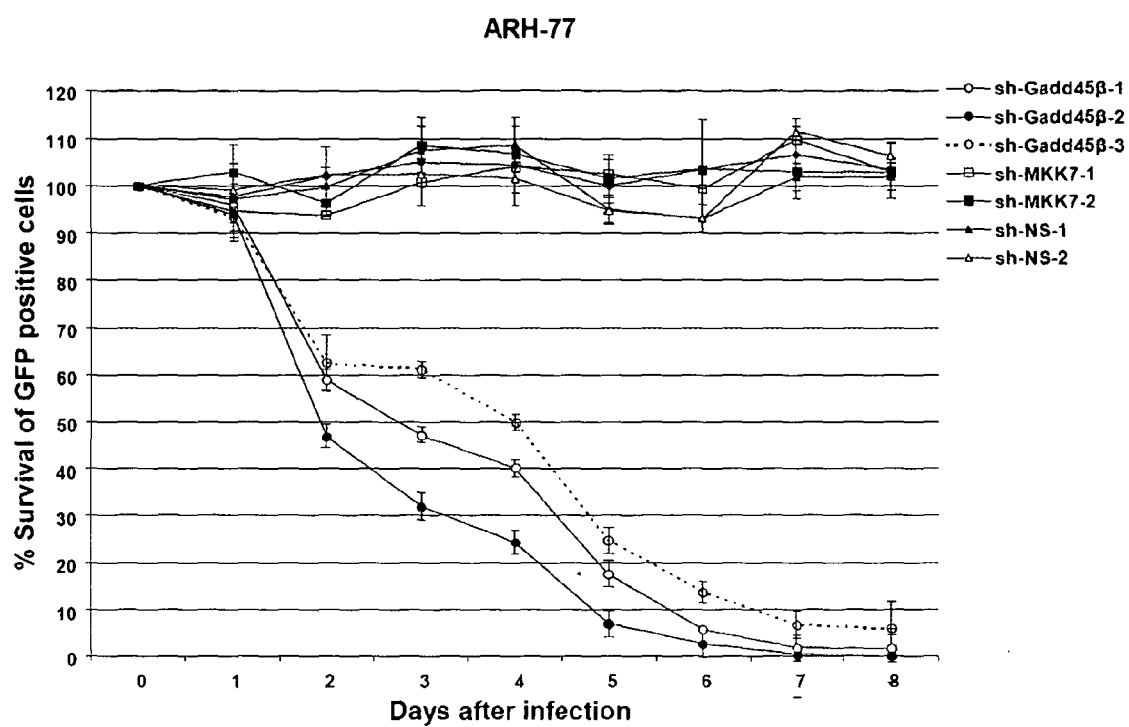
FIG. 16. Induction of cell death in representative multiple myeloma cell lines after sh-RNA-mediated silencing of Gadd45β expression. (A, B, C) The Z-DTP-sensitive multiple myelom cell lines ARH-77 (A) and NCI-H929 (B) and the Z-DTP-resistant multiple myeloma cell line, RPMI-8226 (C), were infected with lentivirus-expressing either Gadd45β-specific sh-RNAs (i.e sh-Gadd45β-1, sh-Gadd45β-2, or sh-Gadd45β-3), MKK7-specific sh-RNAs (i.e. sh-MKK7-1 or sh-MKK7-2), or non-specific sh-RNAs (i.e. sh-NS-1 or sh-NS-2), and the viability of infected cells was monitored over a period of 8 days by using flow cytometry—revealing cells expressing enhanced green fluorescent protein (eGFP), that is infected cells—and cell counting. Shown is the percent survival of eGFP$^+$ (that is infected) multiple myeloma cells at the times indicated relative to the viability of eGFP$^+$ multiple myeloma cells in the same culture at day 0. (A, B, C) Cells were infected with pLentiLox.3.7 lentiviruses expressing the indicated sh-RNAs as well as eGFP, using standard methods (as reported in the reference by Yang H et al., Proc Natl Acad Sci USA. 2006 Jul. 5; 103(27):10397-402). 5 days later, eGFP$^+$ cells were sorted using a BD FACSAria™ II cell sorter, then left to rest for 2 days before beginning the analyses of cell viability. This time (that is the start of the viability analyses) is denoted in the graphs as day 0. The data show that the inhibition of Gadd45β expression causes rapid cell death in multiple myeloma cell lines that are sensitive to Z-DTP-induced toxicity (that is the ARH-77, NCI-H929 cell lines) (A, B), but not in the RPMI-8226 multiple myeloma cell line (C), which is resistant to this toxicity. These data further establish the target specificity of Z-DTPs for the Gadd45β/MKK7 complex in multiple myeloma cells (see also FIGS. 7, 8, 9, and 12; killing and qRT-PCR assays). They also demonstrate the essential role that Gadd45β plays in multiple myeloma cell survival, thus further validating Gadd45β as a therapeutic target in multiple myeloma.
Figure 16:
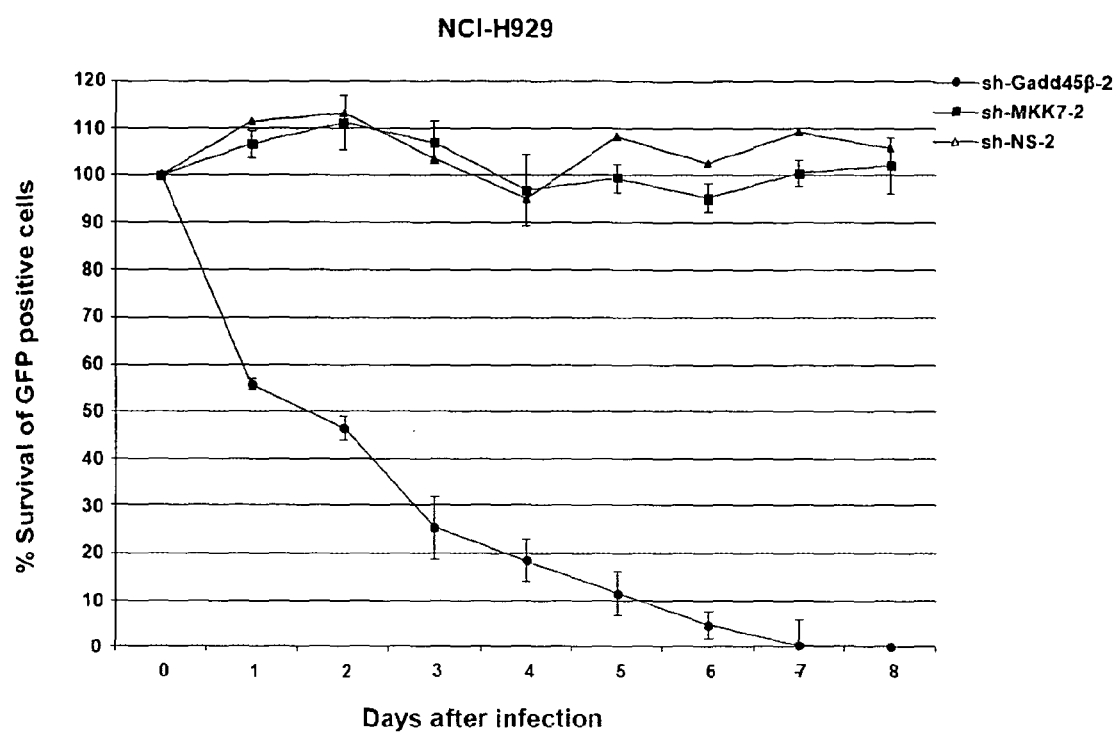
Figure 16:
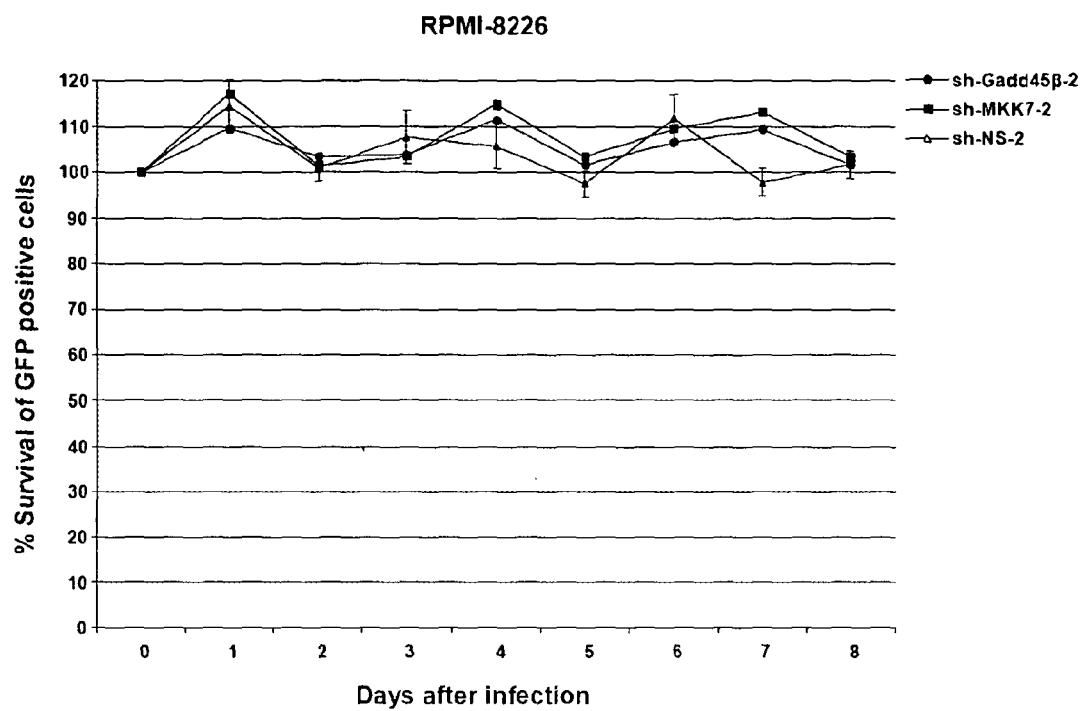
Figure 17:
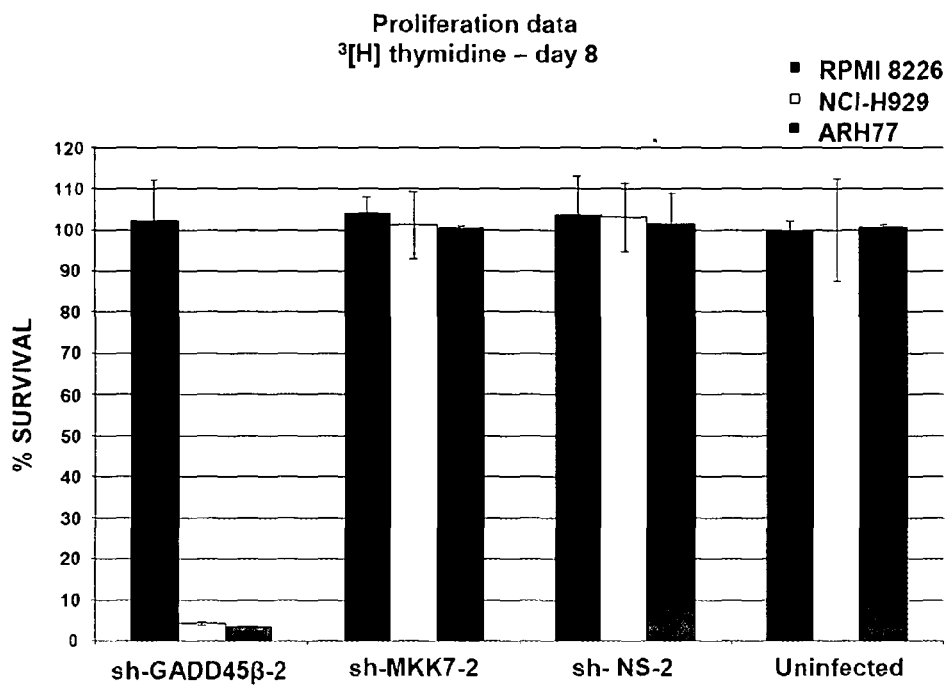
FIG. 17. (A, B) [$^3$H]Thymidine incorporation assays showing that the sh-RNA-mediated silencing of Gadd45β, but not that of MKK7, has potent tumouricidal activity in multiple myeloma cell lines that are susceptible to Z-DTPs-induced killing (that is the ARH-77 and NCI-H929 cell lines; see also FIGS. 7A, 7B, 7C and 8, sensitivity to Z-DTP-induced killing). Viability of the Z-DTP-resistant multiple myeloma cell line, RPMI-8226, is instead unaffected by sh-RNA-mediated Gadd45β inhibition. (A) Shown is the viability of the three representative multiple myeloma cell lines, RPMI-8226, NCI-H929 and ARH-77, after the silencing of Gadd45β or MKK7. (B) Shown is the viability of the multiple myeloma cell line, ARH-77, after the silencing of Gadd45β or MKK7 using three different Gadd45β-specific sh-RNAs (i.e. sh-Gadd45β-1, sh-Gadd45β-2, or sh-Gadd45β-3), two different MKK7-specific sh-RNAs (i.e. sh-MKK7-1 or sh-MKK7-2), and two different non-specific sh-RNAs (i.e. sh-NS-1 or sh-NS-2). (A, B) Multiple myeloma cell lines were infected with the indicated sh-RNA-expressing pLentiLox.3.7 lentivirus, then eGFP$^+$ multiple myeloma cells (that is cells infected with lentivirus) were sorted using a BD FACSAria™ II cell sorter as in FIG. 16. [$^3$H]Thymidine incorporation assays were performed 10 days after cell sorting, corresponding to day 8 in FIG. 16. Shown is the percent of [$^3$H]thymidine incorporation (that is c.p.m.), a measure of cell proliferation, at day 8 (that is 10 days after cell sorting) relative to the [$^3$H]thymidine incorporation occurring in the same cells at day 0 (that is 2 days after cell sorting). These data further establish the target specificity of Z-DTPs for the Gadd45β/MKK7 complex in multiple myeloma cells (see also FIGS. 7, 8, 9 and 12, Z-DTP-induced killing and Gadd45β expression.
Figure 17:
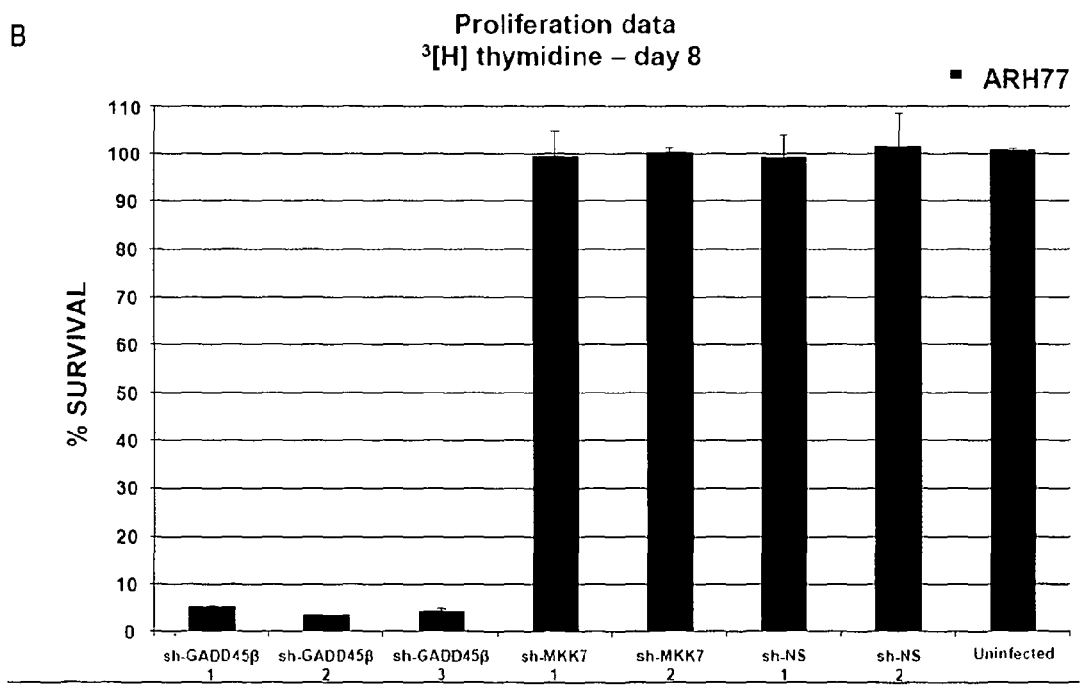
Figure 18:
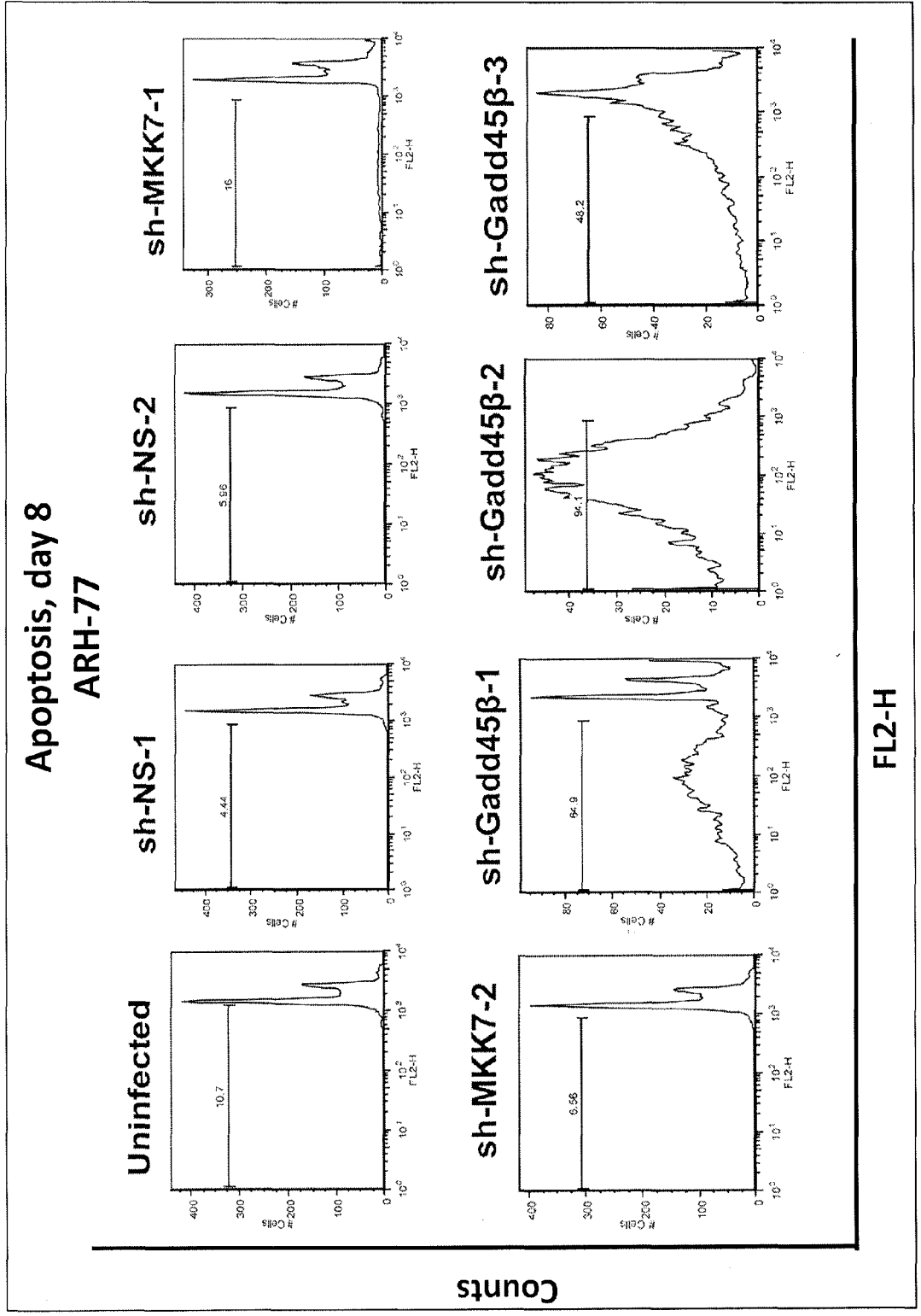
FIG. 18. (A, B, C) PI nuclear staining assays showing that the sh-RNA-mediated silencing of Gadd45β induces apoptosis in the Z-DTP-sensitive multiple myeloma cell lines, ARH-77 (FIG. 18A) and NCI-H929 (FIG. 18B), but not in the Z-DTP-resistant multiple myeloma cell line, RPMI-8226 (FIG. 18C) (see also FIGS. 16 and 17, sh-RNA-mediated silencing.
Figure 18:
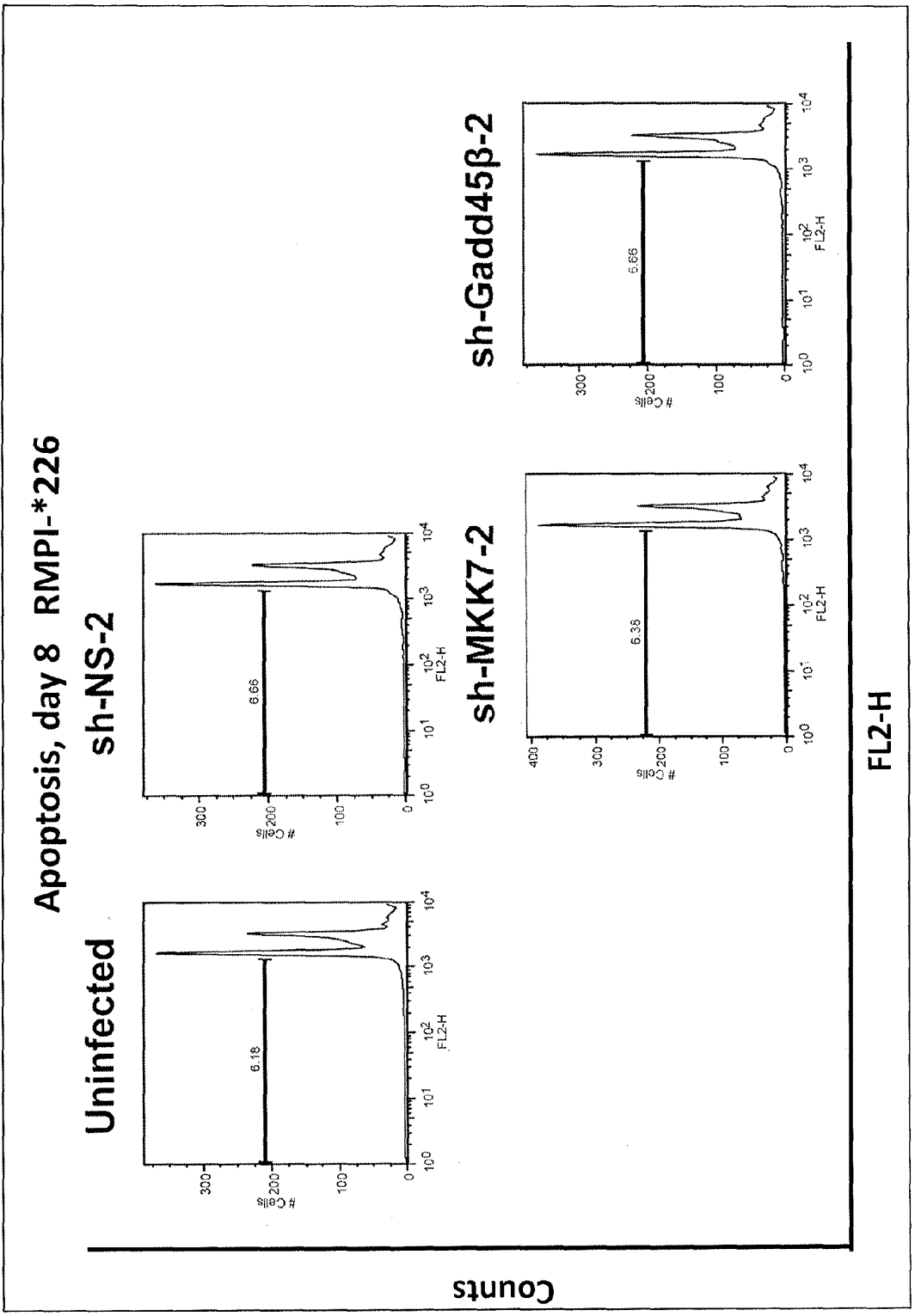

FIGS. 18A, 18B, and 18C show that the sh-RNA-mediated silencing of Gadd45β effectively induces apoptosis in the Z-DTP-sensitive multiple myeloma cell lines, ARH-77 (FIG. 18A) and NCI-H929 (FIG. 18B), but not in the Z-DTP-resistant multiple myeloma cell line, RPMI-8226 (FIG. 18C) (see also FIGS. 16 and 17, sh-RNA-mediated silencing; FIGS. 7, 8, and 12, multiple myeloma cell line sensitivity to Z-DTP-induced killing and levels of Gadd45β expression). Apoptosis induction in FIGS. 18A, 18B, and 18C was determined by the use of PI nuclear staining assays, performed as described in Example 8. These data demonstrate that the inhibition of multiple myeloma cell survival/proliferation caused by the down-regulation of Gadd45β expression observed in FIGS. 16 and 17 was due to the induction of programmed cell death mediated by the apoptosis pathway. Notably, no significant induction of apoptosis was observed in the same multiple myeloma cell lines in the absence of lentiviral infection (uninfected) or after expression of MKK7-specific sh-RNAs (sh-MKK7-1 and sh-MKK7-2) or non-specific sh-RNAs (sh-NS-1 and sh-NS-2) (FIGS. 18A, 18B, and 18C). Multiple myeloma cell lines were infected with sh-RNA-expressing pLentiLox.3.7 lentiviruses, and eGFP$^+$ multiple myeloma cells (that is cells infected with lentivirus) were sorted using a BD FACSAria™ II cell sorter as in FIG. 16. PI nuclear staining assays were performed 10 days after cell sorting, corresponding to day 8 in FIG. 16. The percentages of apoptotic cells (that is cells exhibiting sub-G$_1$ DNA content) are depicted in the histograms. Importantly, the levels of apoptosis induced by the different Gadd45β-specific sh-RNAs (that is sh-Gadd45β-1, sh-Gadd45β-2, and sh-Gadd45β-3) correlated with the levels of Gadd45β downregulation induced by each of these Gadd45β-specific sh-RNAs (FIG. 18A; also data not shown). The data in FIGS. 18A, 18B, and 18C further establish the target specificity of Z-DTPs for the Gadd45β/MKK7 complex in multiple myeloma cells (see also FIGS. 7, 8 and 9, killing assays with Z-DTPs; FIG. 12, statistically significant correlation between Gadd45β expression and cancer cell sensitivity to Z-DTP-induced killing; FIGS. 16 and 17, induction of multiple myeloma cell line killing by the downregulation of Gadd45β, but not of MKK7), and confirm the essential role that Gadd45β plays in multiple myeloma cell survival. Together, they further validate Gadd45β as therapeutic target in multiple myeloma.

Figure 19:
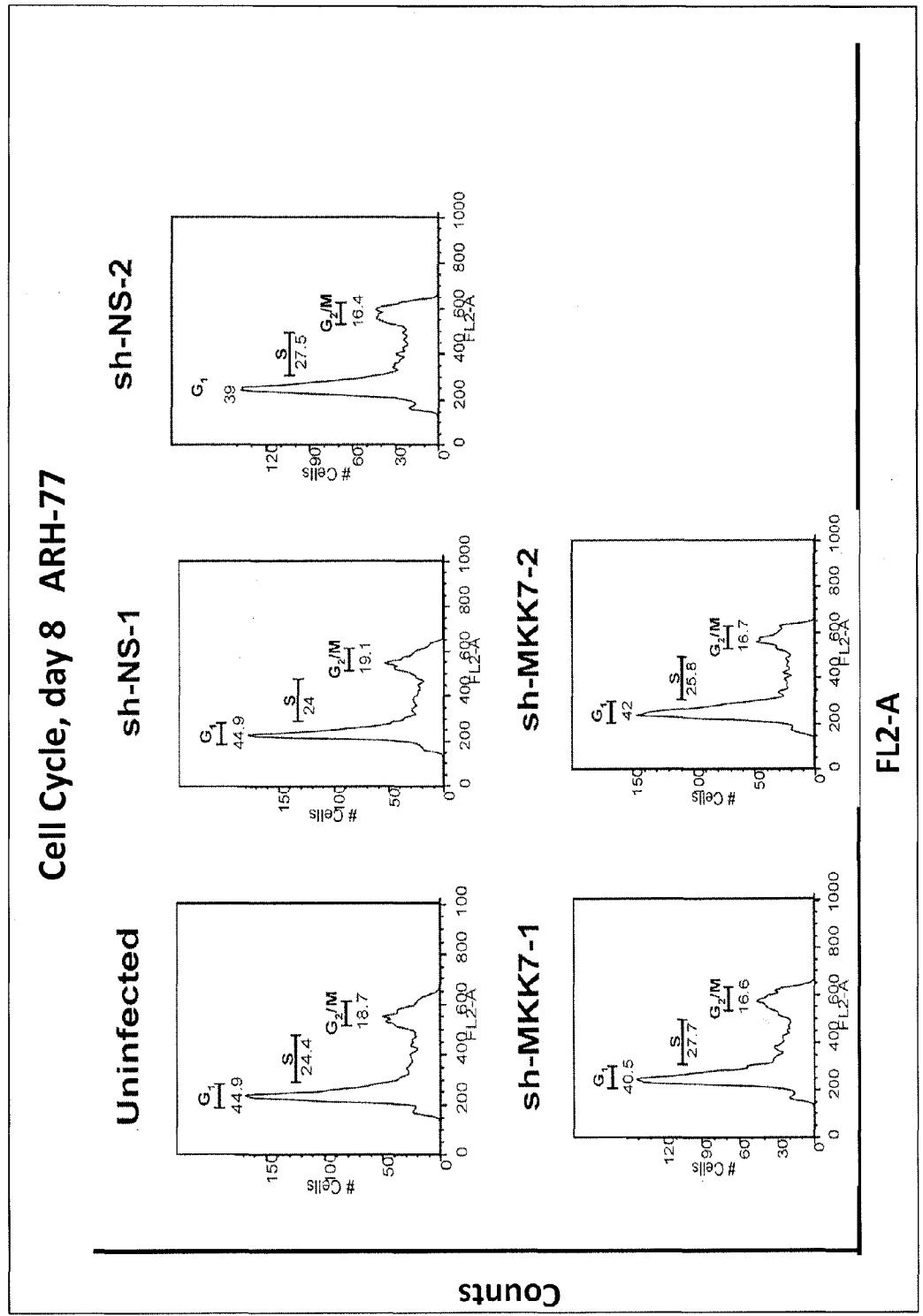
FIG. 19. (A, B, C) PI nuclear staining assays showing that the sh-RNA-mediated silencing of either MKK7 or Gadd45β does not affect cell-cycle distribution in multiple myeloma cell lines. The representative lentivirus-infected multiple myeloma cell lines shown—that is ARH-77 (FIG. 19A), NCI-H929 (FIG. 19B), and RPMI-8226 (FIG. 19C)—are from the same experiment exhibited in FIG. 18. Differently from the data shown in FIGS. 18A, B and C (in which PI staining profiles are represented in a logarithmic scale, which highlights apoptosis), PI staining (that is FL2-A) in this figure is represented in a linear scale, which highlights cell-cycle distribution. The percentages of multiple myeloma cells in the different phases of the cell cycle (that is $G_1$, S, and $G_2$/M) are depicted in the histograms.
Figure 19:
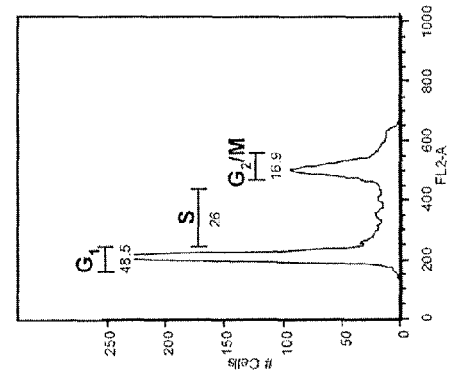
Figure 19:
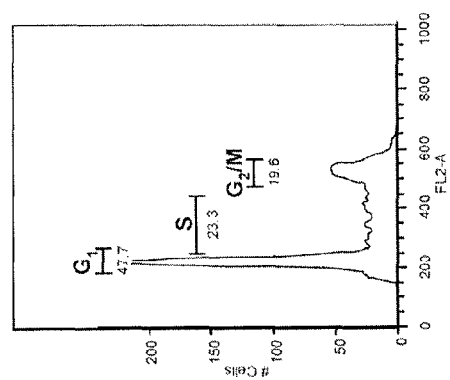
Figure 19:
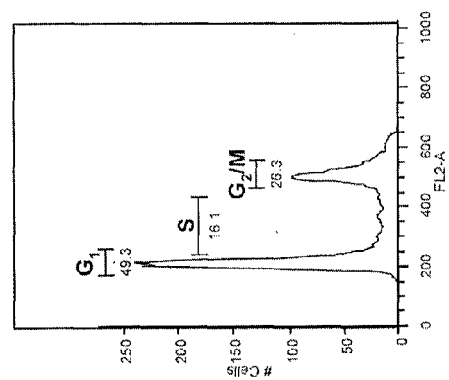
Figure 19:
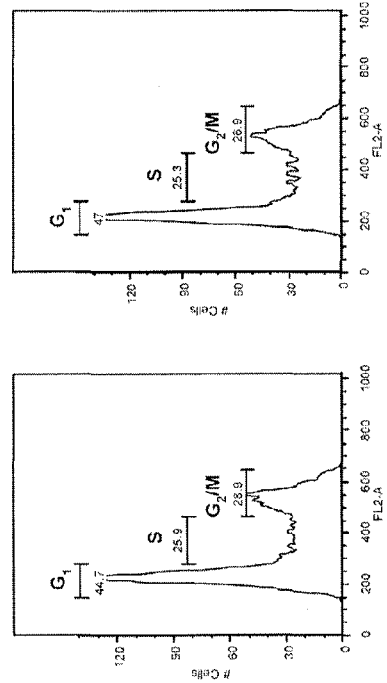

FIGS. 19A, 19B, and 19C show that the sh-RNA-mediated silencing of either MKK7 or Gadd45β does not affect cell-cycle distribution in multiple myeloma cell lines. The representative lentivirus-infected multiple myeloma cell lines shown—that is ARH-77 (FIG. 19A), NCI-H929 (FIG. 19B), and RPMI-8226 (FIG. 19C)—are from the same experiment exhibited in FIGS. 18A, 18B and 18 C. The cell cycle analyses shown in FIGS. 19A, 19B, and 19C were performed by the use of PI nuclear staining assays, carried out as described in Example 8 (see also FIGS. 18A, B and C). Differently from the data shown in FIGS. 18A, B and C (in which PI staining profiles are represented in a logarithmic scale, which highlights apoptosis), PI staining (that is FL2-A) in this Figures is represented in a linear scale, which highlights cell-cycle distribution. The percentages of multiple myeloma cells in the different phases of the cell cycle (that is $G_1$, S, and $G_2/M$) are depicted in the histograms. Cell-cycle analyses could not be performed with Gadd45β-specific sh-RNAs in the case of the ARH-77 (FIG. 19A) and NCI-H929 (FIG. 19B) multiple myeloma cell lines, due to the induction of massive apoptosis after expression of these sh-RNAs (see FIGS. 18A and 18B). Nevertheless, as it can be seen in FIG. 19A, Gadd4513 down-regulation had not effect on cell-cycle distribution in Z-DTP-resistant cell line, RPMI-8229.

Example 12

The Downregulation of MKK7 Expression Renders Normally Sensitive Multiple Myeloma Cell Lines Completely Refractory to Z-DTP-Induced Killing Materials and Methods To assess the target specificity of Z-/mDTPs for the Gadd45β/MKK7 complex, we investigated the effects of down-regulating the expression of MKK7 on the sensitivity of susceptible multiple myeloma cell lines to Z-/mDTP-induced killing (FIGS. 20A, 20B, and 20C). To this end, we infected the representative multiple myeloma cell line, ARH-77, with lentiviruses expressing MKK7-specific sh-RNAs, which result in the silencing of the MKK7 gene, or of control non-specific sh-RNAs. The DNA sequences encoding the targeting small hairpin (sh)-RNAs are listed in Table VII. The MKK7-targeting sh-RNA sequences and the non-specific control sequences were introduced between the BamHI and HpaI restriction sites of the lentiviral vector, LentiLox3.7, as described in Example 11 (see the reference by Yang et all 2006 PNAS 103, 10397-10402. The production of hig-titer lentiviral preparation in HEK-293T cells were performed using essentially the same conditions described in the reference by Yang et all 2006 PNAS 103, 10397-10402. For introduction of the MKK7-targeting and the non-specific control sh-RNA sequences, the representative Z-DTP-sensitive multiple myeloma cell line, ARH-77, was infected with LentiLox3.7 lentiviruses expressing either MKK7-specific sh-RNAs (sh-MKK7) or non-specific sh-RNAs (sh-NS), as reported in published protocols essentially as described in the reference by Yang et all 2006 PNAS 103, 10397-10402. 5 days after infection, eGFP ARH-77 cells were sorted using a BD FACSAria™ II cell sorter. Then, 10 days after cell sorting, lentivirus-infected multiple myeloma ARH-77 cells were treated with either Z-DTP1, Z-DTP2, mDTP3 or Z-NC for 72 hrs at 37° C., or were cultured under the same conditions in the absence of peptide treatment, as described in Example 8. The treatments with Z-DTP1, Z-DTP2, mDTP3 and Z-NC were carried out at the following final peptide concentrations: 0.01 μM, 0.03 μM, 0.1 μM, 0.3 μM, 1 μM, 3 μM, and 10 μM. After these treatments, ARH-77 survival/proliferation was determined by performing [$^3$H]thymidine incorporation assays as described in Examples 6 and 8. The results from these experiments were expressed as the percentages of survival/proliferation (i.e. c.p.m.) observed in lentivirus-infected multiple myeloma cells treated with Z-DTP1, Z-DTP2, mDTP3 or Z-NC relative to the survival/proliferation of the respective lentivirus-infected cells in the absence of peptide treatment. The mean concentrations of Z-DTP1, Z-DTP2, mDTP3, and Z-DNC resulting in 50% ($IC_{50}$) inhibition of cell survival/proliferation were determined by performing [$^3$H]thymidine incorporation assays and were calculated as described in Example 6. The results from these experiments are shown in FIGS. 20A, 20B, and 20C.

Results

FIGS. 20A, 20B, and 20C show that the sh-RNA-mediated silencing of MKK7 renders the representative Z-/mDTP-sensitive cell line, ARH-77, completely resistant to Z-/mDTP-induced killing. The [$^3$H]thymidine incorporation assays depicted in these Figures show the $IC_{50}$s of D-isomer negative control tetrapeptide (Z-DNC) (FIGS. 20A, 20B, and 20C), Z-DTP1 (FIG. 20A), Z-DTP2 (FIG. 20B), and mDTP3 (FIG. 20C) in ARH-77 multiple myeloma cells expressing either MKK7-specific (sh-MKK7) or non-specific sh-RNAs (sh-NS). Treatments of ARH-77 cells were carried out with different concentrations of these peptides and cell viability/proliferation analyzed by [$^3$H] thymidine incorporation assays after 3 days. It can be seen that sh-NS-expressing ARH-77 cells are highly sensitive to Z-/mDTP-induced killing—shown by the $IC_{50}$ values of 1.4 μM (Z-DTP1; FIG. 20A), 302 nM (Z-DTP2; FIG. 20B), and 303 nM (mDTP3; FIG. 20C)—similar to what is seen in the uninfected, parental ARH-77 cells (see Table IV). In striking contrast, however, sh-MKK7-expressing ARH-77 cells became completely resistant to Z-/mDTP-induced killing— shown by the $IC_{50}$ values >10 μM of Z-DTP1, Z-DTP2, and mDTP3—similar to what is seen in Z-DNC-treated ARH-77 cells (FIGS. 20A, 20B, and 20C). $IC_{50}$s were calculated as described in Example 6, using increasing concentrations of Z-DNC (FIGS. 20A, 20B, and 20C), Z-DTP1 (FIG. 20A), Z-DTP2 (FIG. 20B), and mDTP3 (FIG. 20C), ranging from 0.01 to 10 μM. Reported in the graphs are the percentages of the counts per minute (c.p.m.), a measure of cell survival/proliferation, obtained with treated cells relative to the c.p.m. values obtained with untreated cells. Similar data were obtained with additional Z-/mDTP-sensitive multiple myeloma cell lines, including the U266, KMS-11, and KMS-12 cell lines (data not shown). These data (i.e. the loss of Z-/mDTP sensitivity in susceptible multiple myeloma cell by the silencing of MKK7), together with the data shown in FIG. 12 (i.e. the strong correlation between Gadd45β expression and cancer cell sensitivity to Z-DTP-induced killing), conclusively demonstrate the very high target specificity of Z-/mDTPs for the Gadd45β/MKK7 complex in multiple myeloma cells.

Example 13

Z-DTPs Retain Strong and Specific Cytotoxic Activity in Primary Multiple Myeloma Cells from Patients Materials and Methods To confirm that Z-/mDTPs retain cytotoxic activity in primary multiple myeloma cells, we examined the effects of Z-DTP1 and Z-DTP2 on the survival of multiple myeloma cells isolated from patients with a clinical diagnosis of multiple myeloma. To this end, multiple myeloma cells were purified from bone marrow (BM) aspirates of multiple myeloma patients by negative selection, using CD138-conjugated magnetic beads, essentially as described in the reference by Hideshima T. et all 2006, Blood 107: 4053-4062. The purity of multiple myeloma cells was confirmed by flow cytometric, using and CD138 and anti-CD45 antibodies, also essentially in accordance with the procedure described in the reference by Hideshima T. et all 2006, Blood 107: 4053-4062. Purified CD138$^+$ BM cells were then cultured at a concentration of 4×10$^5$ cells/ml in wells of 96-well plates and treated with either 1 μM or 10 μM of Z-DTP1, Z-DTP2 or Z-DNC for 48 hrs. Cell viability was measured by cell counting using trypan blue exclusion assays (FIGS. 14A, 14B, 14C, 14D, and 14E).

In order to determine the in vitro therapeutic index of Z-/mDTPs, viability and proliferation assays were also performed with primary untransformed cells of both human and mouse origin, after treatment with either 10 μM or 100 μM of Z-DTP1, Z-DTP2 and Z-DNC. To this end, bone marrow stromal cells (BMSCs) peripheral blood mononuclear cells (PBMNCs) and mesenkymal stem cells (MSCs) were purified from healthy individuals after Ficoll-Hypaque density separation, in accordance with the protocols reported in the reference by Piva R. et all 2008 Blood 111: 2765-2775). BMSCs, PBMNCs, and MSCs cells were then treated for the times indicated and with the peptide concentrations specified in FIGS. 15A and 15B. To further establish the specificity of the cytotoxic activity of Z-/mDTPs for cancer cells, we also used primary B and T lymphocytes purified from the spleen and lymph nodes of mice, respectively, essentially as described in the reference by Shirakawa et al 2010 Cell Mol immunology 1-12. B and T cells were then activated by simulation with 1 ng/mL of LPS for 16 hrs and subsequently treated with 100 μM of Z-DTP1, Z-DTP2 or Z-DNC for 72 hrs as shown in FIG. 15B.

Results

FIGS. 14A, 14B, 14C, 14D, and 14E show that Z-DTP1 and Z-DTP2, but not Z-DNC, exhibit strong cytotoxic activity in primary multiple myeloma cells isolated from 5 representative patients. Each panel depicts the data obtained with multiple myeloma cells from a different patient—that is patient 1 (FIG. 14A), patient 2 (FIG. 14B), patient 3 (FIG. 14C), patient 4 (FIG. 14D), and patient 5 (FIG. 14E). Treatments with Z-DTP2, Z-DTP1 and Z-DNC were at the concentrations indicated (i.e. 1 μM or 10 μM), for 48 hrs. Assays were performed using trypan blue exclusion. Values represent the percent of live cells after treatment with Z-DTP2, Z-DTP1 or Z-DNC relative to the viability of untreated control cells. Strong cytotoxic activity—comparable to that of Z-DTP2 and Z-DTP1—was also observed in primary myeloma cells from patients with mDTP3, under similar experimental conditions (data not shown). These findings demonstrate that Z-/mDTPs retain activity in primary multiple myeloma cells and indicate that Z-/mDTP-based therapy can be used in patients to treat multiple myeloma.

Figure 14:
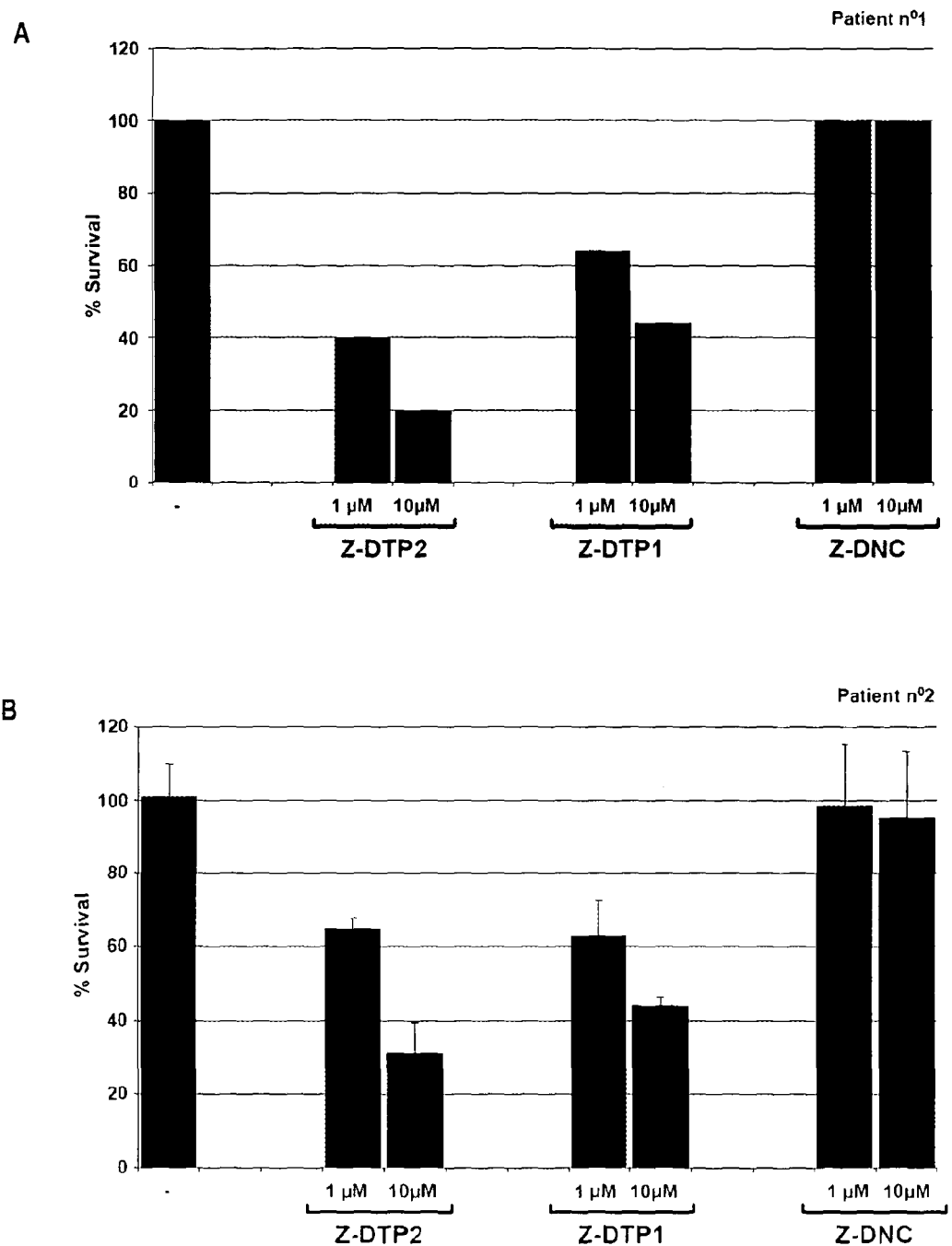
FIG. 14. (A, B, C, D, E) Cytotoxic activity of Z-DTPs in primary multiple myeloma cells isolated from 5 representative patients. Each panel depicts the data obtained with cells from a different patient—that is patient 1 (A), patient 2 (B), patient 3 (C), patient 4 (D), and patient 5 (E). (A, B, C, D, E) Treatments with Z-DTP2, Z-DTP1 and Z-DNC were at the concentrations indicated, for 48 hrs. Also shown are the untreated cells from each patient (−). Assays were performed using trypan blue exclusion and cell counting. Values represent the percentage of live cells observed after treatment with Z-DTP2, Z-DTP1 or Z-DNC relative to the viability of untreated control cells.
Figure 14:
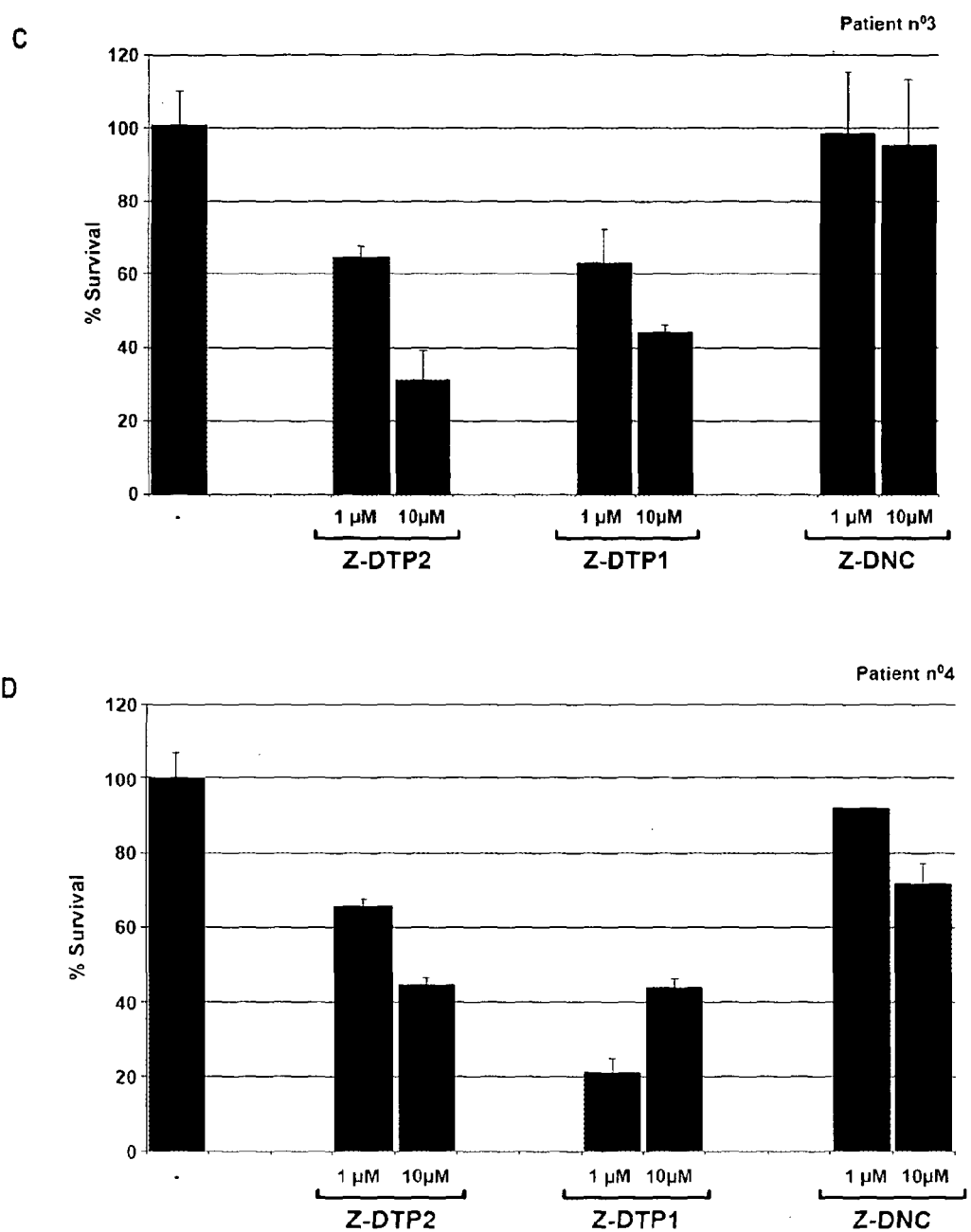
Figure 14:
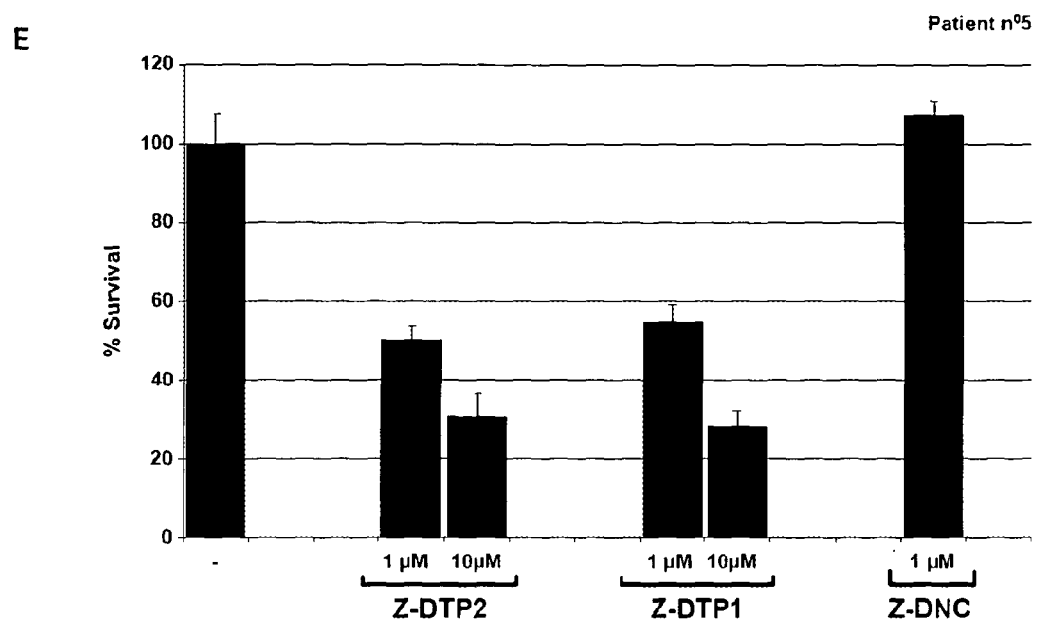
Figure 15:
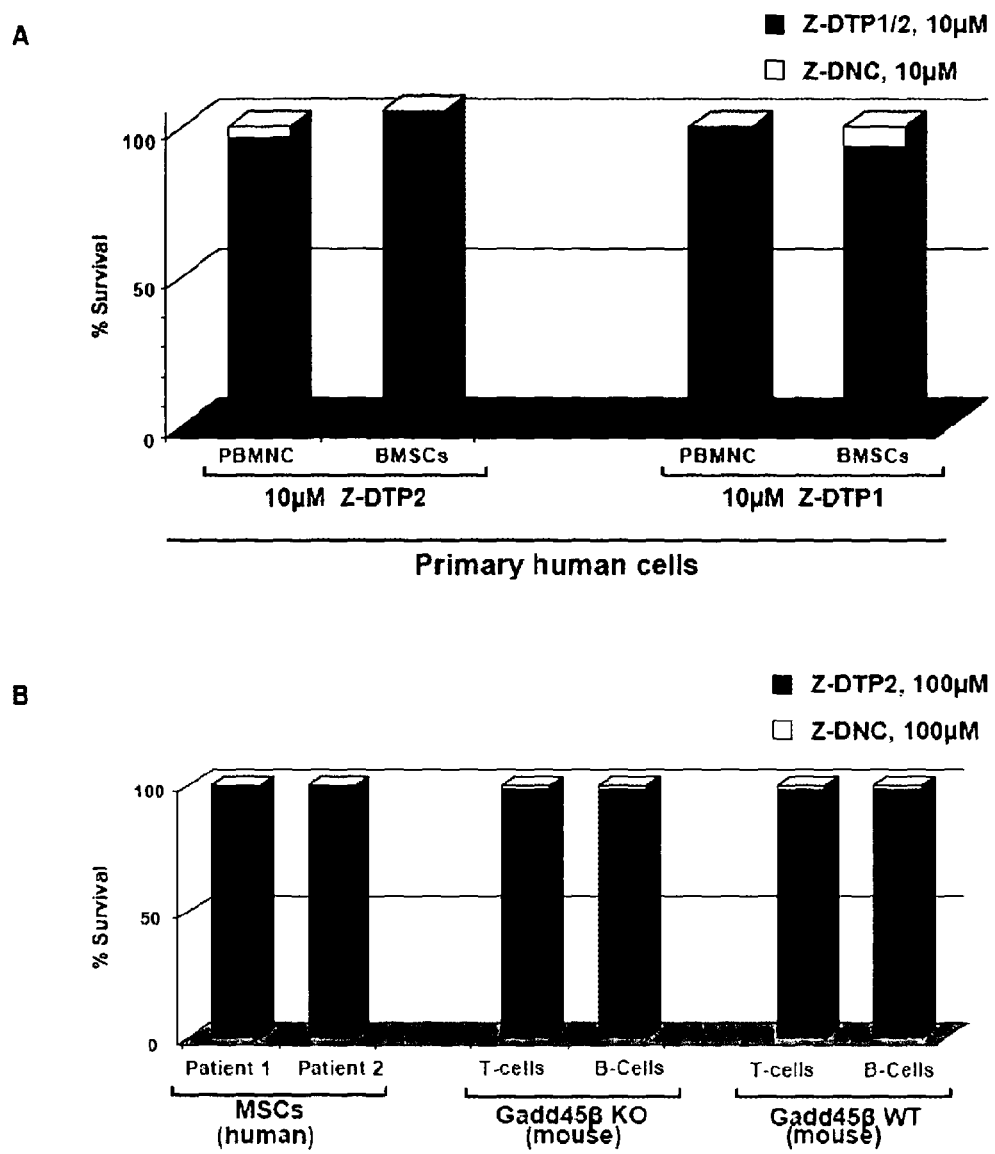
FIG. 15. Absence of cytotoxic activity of Z-DTPs in primary untransformed cells from multiple myeloma-free individuals, including bone marrow stromal cells (BMSCs) (A), peripheral blood mononuclear cells (PBMNCs) (A), and mesenkymal stem cells (MSCs) (B), or in purified primary B- and T-lymphocytes from mice (B). Treatments with Z-DTP2, Z-DTP1 and Z-DNC were at the concentrations indicated, for either: 48 hrs (BMSCs, PBMNCs) (A), 72 hrs (murine B and T cells) (B), or 144 hrs MSCs (B). Assays were performed using trypan blue exclusion and cell counting (A) or [$^3$H]thymidine incorporation (B).

FIGS. 15A and 15B show that Z-DTP1 and Z-DTP2 exhibit no toxicity to normal primary cells of either mouse or human origin, even when used at very high concentrations—that is 100 μM. The primary cells tested included normal bone marrow stromal cells (BMSCs) (FIG. 15A), peripheral blood mononuclear cells (PBMNCs) (FIG. 15A), and mesenkymal stem cells (MSCs) (FIG. 15B), isolated from multiple myeloma-free individuals, and purified primary B and T lymphocytes isolated from mice (FIG. 15B). Treatments with Z-DTP2, Z-DTP1 and Z-DNC were at the concentrations indicated, for either: 48 hrs (BMSCs, PBMNCs) (FIG. 15A), 72 hrs (murine B and T cells) (FIG. 15B), or 144 hrs MSCs (FIG. 15B). Assays were performed by using trypan blue exclusion (FIG. 15A) or [$^3$H]thymidine incorporation (FIG. 15B). The data presented in FIGS. 14 and 15 indicate that Z-DTPs have a high in vitro therapeutic indices (i.e. lack of toxicity in normal cell versus a high toxicity in cancer cells). Indeed, Z-DTP1 and Z-DTP2, but not Z-DNC, show strong tumoricidal activity in multiple myeloma cells from patients (FIG. 14), but exhibit no toxicity in primary normal cells from healthy individuals or mice (FIG. 15A), even when used at very high concentrations such as 100 μM (see FIG. 15B). These data demonstrate that Z-DTPs do not have indiscriminated cytotoxic effects in cells—rather their cytotoxic effects are specific for cancer cells and/or cells featuring high levels of Gadd45β expression or activity and/or constitutive high expression or activity of NF-κB.

The high activity of Z-/mDTPs in multiple myeloma and other cancer cells, combined with their lack of toxicity in primary normal cells, including primary human BMSCs, MSCs, PBMNCs and mouse B and T lymphocytes, even when used at high concentrations (ie 100 μM), demonstrate that the compounds of the invention have excellent in vitro therapeutic indices (see FIG. 9, lack of toxicity in cell lines that do not depend on NF-κB for survival; FIG. 12, correlation between Gadd45β expression and cancer cell sensitivity to Z-DTPs; FIGS. 14 and 15, killing assays in primary cells)—a key advantage of our invention over existing therapies. The compounds of the invention also lack toxicity in tumour cell lines such as T-cell leukemia, Burkitt's lymphoma and many others, which do not depend on NF-κB for survival (even when used at 100 μM; see FIG. 9), showing that their activity has inherent specificity for cells with constitutively active NF-κB. Furthermore, in a large panel of tumour cell lines of different tissues of origin, there is a highly statistically significant correlation between levels of Gadd45β expression and sensitivity to Z-/mDTP-induced killing (p<0.01; FIG. 12), thereby establishing the high specificity of the Z-/mDTPs' cytotoxic action for Gadd45β. Crucially, the sh-RNA-mediated mediated down-regulation of Gadd45β causes apoptosis in Z-/mDTP-sensitive multiple myeloma cell lines (e.g. ARH-77 and NCIH929) with kinetics similar to those seen with Z-/mDTPs, but not in Z-/mDTP-resistant multiple myeloma cell lines (e.g. RPMI-8226), and the sh-RNA-mediated mediated down-regulation of MKK7 causes results in a loss of sensitivity to Z-/mDTP-induced killing in susceptible multiple myeloma cell lines (e.g. ARH-77) (see FIG. 20). Together, our data show that the cytotoxic activity of Z-/mDTPs is restricted to tumour cells featuring constitutively active NF-κB and/or high levels of Gadd45β expression or activity—Z-/mDTPs exhibit cytoxicity at nM levels in sensitive multiple myeloma cell lines, but have no toxicity in resistant tumour lines that do not depend on NF-κB for survival or that exhibit low levels of Gadd45β expression, even when used at 100 μM. Moreover, in contrast to mice lacking core components of the IKK/NF-κB pathway, gadd45β$^{-/-}$ mice are viable and seemingly healthy (Papa et all 2008 J Clin Invest 118, 1911-1923), indicating that (unlike full proteasome/NF-κB blockade) complete Gadd45β inactivation is well tolerated in vivo (Papa et all 2008 J Clin Invest 118, 1911-1923). Together, these findings indicate that Z-/mDTP-based therapy will be safe and specific (see FIGS. 9 and 15, lack of toxicity in NF-κB-independent tumour cell lines and normal primary cells; FIG. 12, correlation between Gadd45β expression and cancer cell sensitivity to Z-/mDTP-induced killing; FIG. 14, Z-/mDTP-induced killing of primary multiple myeloma cells).

Proteasome inhibitors (PIs), such bortezomib, and other multiple myeloma therapies also kill multiple myeloma cells by activating JNK (Chauhan et al 2008 Blood 111, 1654-1664), but cannot cure due to low therapeutic indices (Lauback et al 2009 Leukemia 23, 2222-2232; Ludwing et al 2010 Oncologist 15, 6-25 and www.cancecare.on.ca/). Targeting the discrete functions of NF-κB in multiple myeloma survival via Gadd45β will enable to dissociate NF-κB's functions in immunity, inflammation and survival, so provide a safer, more specific therapy that can be tolerated at doses required to cure. Z-/mDTPs define an entirely new class of therapeutic agents targeting a novel pathway in multiple myeloma, and potentially other cancers and diseases or disorder that depend on NF-κB for survival.

Example 14

Binding Properties of mDTP3 to Gadd45β and MKK7 Proteins in Isolation and as Part of a Gadd45β/MKK7 Complex By way of example, binding experiments were performed with mDTP3 to Gadd45β, the kinase domain of MKK7 (MKK7$_{KD}$) and to the Gadd45β/MKK7 complex using the Surface Plasmon Resonance technique.

Materials and Methods

To determine how DTPs bind to the Gadd45β/MKK7 complex, experiments were performed with a Biacore3000 SPR instrument (GE Healthcare, Milan, Italy), using 4-channels CM5 sensorchips (GE Healthcare, Milan, Italy). Full length human Gadd45β was prepared and purified as described in the reference by Tornatore L., et al. (2008). J Mol Biol; 378:97-111. The constitutively active kinase domain of MKK7, spanning residues 101 to 405, and carrying the S287D and T291D mutations (MKK7$_{KD}$), was expressed in *E. Coli* as a fusion protein of His6. The protein was purified to homogeneity by two subsequent steps of affinity chromatography (Ni-NTA support) and gel filtration (Superdex G75), and then characterized by SDS-PAGE, LC-MS to verify identity and purity, and by Circular Dichroism to assess folding.

MKK7$_{KD}$ was immobilized on the Biacore sensorchip via classical EDC/NHS coupling chemistry at pH 5 (protein pI, ~9) at a flow rate of 5 μL/min. An immobilization level of about 8000 Response Units was achieved. Gadd45β, which is an intrinsically acidic protein with a pI of about 4.5, was immobilized at pH 3.5 (6000 RU immobilization levels) on a separate channel. The residual reactive groups on both the Gadd45β and MKK7$_{KD}$ channels were finally inactivated by treatment with ethanolamine. On another channel the same procedure of activation with EDC/NHS and inactivation with ethanolamine was performed. This channel was used as reference and the signal deriving from it was considered as blank, and values were accordingly subtracted from the experimental channels detecting Gadd45β or MKK7$_{KD}$ proteins to remove non-specific binding to the chip surface. To determine whether the two proteins were effectively immobilized, we performed repeated injections of Gadd45β (20-200 nM) and MKK7$_{KD}$ (1-25 nM) at increasing protein concentrations (3 min contact time; 60 μL). Regeneration was achieved using either 1M NaCl injections (1 min, MKK7$_{KD}$-derivatized channel) or 20 mM NaOH (30 sec, Gadd45β-derivatized channel).

Increasing concentrations of the tripeptide mDTP3 (Ac-D-Tyr-D-Arg-D-Phe-NH$_2$) were finally injected over the chip at concentrations ranging between 1 nM and 10 μM. In a separate experiment, mDTP3 was injected during the dissociation phase of either Gadd45β from immobilized MKK7$_{KD}$ or of MKK7$_{KD}$ from immobilized Gadd45β. The results from these analyses are reported in FIGS. 21A, 21B, 21C, and 21D.

Results

Figure 21:
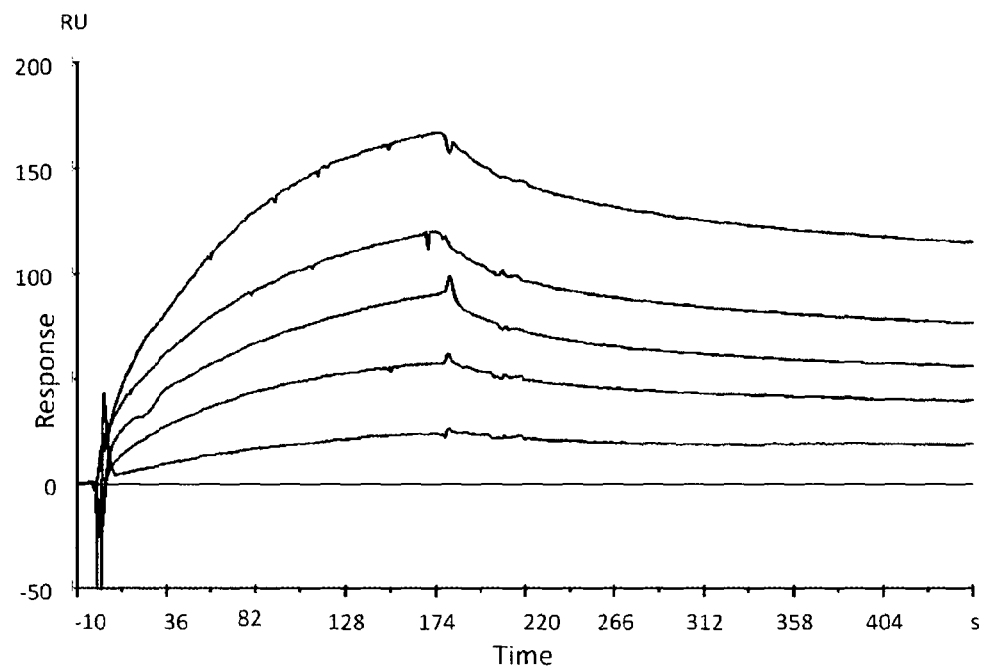
FIG. 21. (A, B, C, D) The compounds of the invention do not bind to either Gadd45β or MKK7 in isolation; rather they require for binding the formation of a Gadd45β/MKK7 complex, as determined in biacore assays. (A) Shown is the binding of Gadd45β to the kinase domain of MKK7 ($MKK7_{KD}$) immobilized on a chip. Different concentrations of Gadd45β (ranging from 20 to 200 nM) were injected onto the chip where $MKK7_{KD}$ had been previously immobilized. The dose-dependent binding of Gadd45β to $MKK7_{KD}$ and the dissociation curves of the Gadd45β/$MKK7_{KD}$ complex were recorded and an equilibrium dissociation constant ($K_D$) value of 4.0±0.7 nM was determined by averaging the values determined by the kinetic parameters of each individual curve. Briefly, the termodinamic parameter of equilibrium dissociation constant ($K_D$) was calculated considering the association ($k_a$) and dissociation phases ($k_d$) corresponding to an increase or decrease in the SPR signal (expressed as response units, RU) respectively. (B) Binding of $MKK7_{KD}$ to Gadd45β, when Gadd45β was immobilized on the chip. Here the $K_D$ values were determined by injecting $MKK7_{KD}$ at different concentrations (ranging from 1 to 25 nM) onto a chip with immobilized Gadd45β. As in (A), the dose-response curves were recorded at all the tested concentrations of $MKK7_{KD}$. From these analyses a $K_D$ value of 3.4±0.6 nM was obtained—which is very similar to the $K_D$ value obtained in (A). (C) The injection of mDTP3 onto a chip containing either Gadd45β or $MKK7_{KD}$ is shown. To determine whether mDTP3 binds to Gadd45β and/or to $MKK7_{KD}$, a solution containing mDTP3 at a concentration ranging from 1 nM and 10 μM was injected onto a chip derivatized with either one or the other protein. As it can be see, no binding of mDTP3 to either Gadd45β or MKK7 was recorded even at the highest concentration of mDTP3 used (i.e. 10 μM). (D) Shown is the binding of mDTP3 to a preformed Gadd45β/MKK7 complex. A 100 nM concentration of Gadd45β was injected onto the chip derivatized with $MKK7_{KD}$ (60 μL; contact time of 3 min). Gadd45β proteins were allowed to dissociate for about 10 min and when approximately 50% of Gadd45β was still bound to $MKK7_{KD}$, mDTP3 was injected at the concentration of either 10 nM, 100 nM, or 1 μM. As it can be seen, when it was used at a concentration equivalent to or lower than 100 nM, mDTP3 induced a rapid dissociation of the Gadd45β/$MKK7_{KD}$ complex. As it can also be seen, Gadd45β/$MKK7_{KD}$ complex formation was rapidly recovered after mDTP3 was washed away. At higher concentrations (e.g. 1 μM), however, mDTP3 afforded dose-response binding and dissociation curves, indicating that it was binding to either Gadd45β and/or to $MKK7_{KD}$ or to a complex of the two proteins. These data support the view that the DTPs do not bind to Gadd45β or MKK7 proteins in isolation; rather they bind to one and/or the other protein or to a complex of the two proteins only when the two proteins come in contact with each other.
Figure 21:
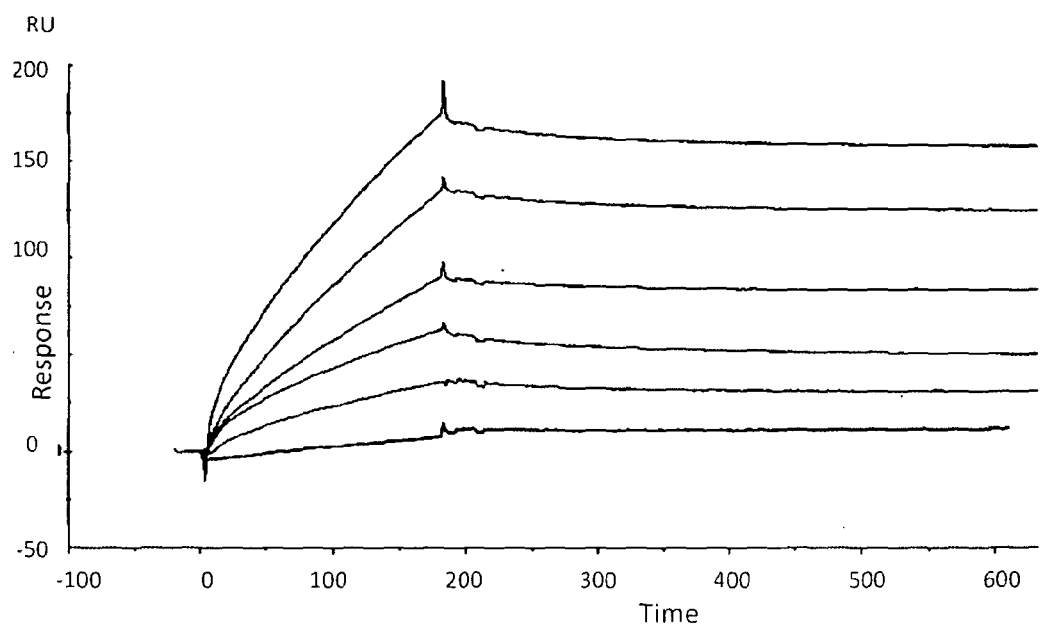
Figure 21:
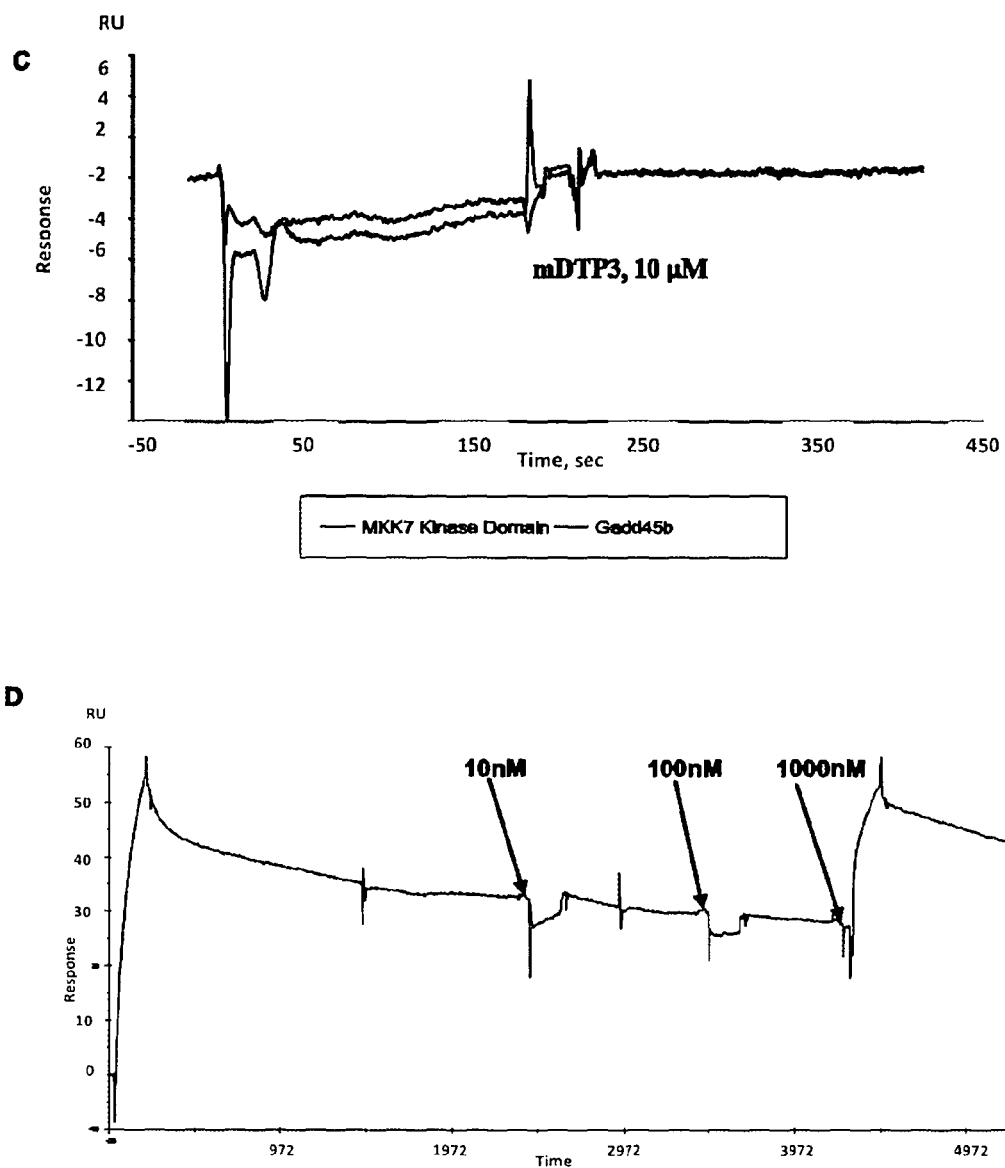

As it can be seen in FIG. 21A, the binding of Gadd45β to immobilized MKK7$_{KD}$ was very effective. Dose-response association and dissociation curves were observed at all the concentration used. The dissociation constant $K_D$ of the Gadd45β/MKK7$_{KD}$ interaction was estimated by averaging the values calculated over each of the different curves and determined to be 4.0±0.7 nM (see FIG. 21A). Similarly, repeated injections of MKK7$_{KD}$ on the Gadd45β channel provided dose-response association and dissociation curves (FIG. 21B) from which a $K_D$ of 3.4±0.6 nM was derived.

To determine whether mDTP3 binds to MKK7$_{KD}$ and/or to Gadd45β, samples of the peptide (i.e. mDTP3) were injected over the Gadd45β and MKK7$_{KD}$-derivatized channels. Surprisingly, as it can be seen in FIG. 21C, the data show that this peptide does not bind to either Gadd45β or MKK7$_{KD}$ in isolation. Strikingly, however, when mDTP3 was injected during the dissociation phase of Gadd45β from MKK7$_{KD}$ (FIG. 21D) or the dissociation phase of MKK$_{KD}$ from Gadd45β (data not shown), binding was observed and dose-response association and dissociation curves could be recorded. FIG. 21D shows that when mDTP3 was injected at the low concentrations of either 10 nM or 100 nM, this peptide induced a rapid dissociation of the Gadd45β/MKK7$_{KD}$ complex. As it can also be seen, Gadd45β/MKK7$_{KD}$ complex formation was rapidly recovered after the peptide was washed away. FIG. 21D also shows that when mDTP3 was injected at higher concentrations (e.g. 1 μM), dose-response binding and dissociation curves were recorded, indicating that mDTP3 was binding to either Gadd45β and/or to MKK7$_{KD}$ or to a complex of the two proteins. Together, these data demonstrate that mDTP3 is unable to bind to either Gadd45β or MKK7$_{KD}$ in isolation, even when used at high concentrations, rather its binding to either Gadd45β, MKK7$_{KD}$, or a surface created by interaction of the two proteins requires formation of a Gadd45β/MKK7 complex. These data are important, as they show that our therapeutic target is the interface between two proteins (i.e. Gadd45β and MKK7)—which provides potential for high target selectivity in cells, a key advantage of our invention over existing therapies.

Example 15

In Vivo Pharmacokinetical (DMPK) Profiles of Z-DTP2 and mDTP3

To assess the suitability of Z-DTP2 and mDTP3 for therapeutic use in vivo, we performed pharmacokinetical analyses in mice.

Materials and Methods
Mouse Pharmacokinetics Study:
Protocol Summary:

Z-DTP2 and Z-mDTP3 were administered intravenously to mice. Blood samples were collected at up to 7 time points after intravenous (i.v.) injection of the compounds over 8 hrs, and plasma was analysed by LC-MS/MS to determine the concentration of the compounds at each time point.

Experimental Procedure:

Three male CD1 mice, 25-30 grams each, were dosed per administration route per time-point, per compound. The test compound was administered intravenously (at a typical dose level of 10 mg of compound per kg of body weight). Animals were given free access to food throughout the study.

At the following time points, the animals were anaesthetised, blood was collected in heparinised tubes, and the animals were sacrificed:

i.v. dosing: 0.08, 0.25, 0.5, 1, 2, 4 and 8 hrs post-dosing

Sample Preparation:

Blood samples were centrifuged to obtain the plasma, which was then transferred to a separate labelled container. Aliquots from the individual time points for the three animals were analysed singly. Proteins were precipitated by adding three volumes of methanol and centrifuging for 30 min at 4° C. Aliquots of 100 μl of the resulting supernatants were diluted with 200 μl of HPLC grade water in wells of a 96-well plate.

Quantitative Analysis:

Standard curves were prepared in blank plasma matrices and treated in an identical manner to the samples. The plasma samples were quantified by LC-MS/MS, and the concentration of each compound in the plasma were reported in μg/mL.

Pharmacokinetic Analysis:

Pharmacokinetic parameters were calculated employing non-compartmental model analysis, as described in the web site http://www.pharsight.com/main.php Bioanalysis:
Protocol Summary:

The test compound concentration in plasma samples was measured by LC-MS/MS. The data were quantified using a five-point standard curve over a range of 3-3000 ng/mL.

Experimental Procedure:

Proteins were precipitated from 50 μL aliquots of the individual plasma samples by adding 150 μL methanol. Following protein precipitation, plasma samples were centrifuged for 30 min at 4° C. Aliquots of 100 μL of the resulting supernatant were diluted with 200 μL of HPLC grade water in a 96 well plate. The test compound was then quantified by LC-MS/MS from a five-point standard curve prepared by spiking plasma with varying concentrations of test compound dissolved in DMSO over a final concentration range of 3-3000 ng/mL (final DMSO concentration 1%) and treated in an identical manner to the test samples as described above.

Results

Pharmacokinetical studies in male CD1 mice show that both Z-DTP2 and mDTP3 have in vivo DMPK profiles suitable for administration via intravenous (i.v.) infusion (see Tables VIII, IX [A], and IX [B]), in the absence of acute toxicity in mice. Table VIII reports the values of the most important in vivo pharmacokinetical parameters obtained with Z-DTP2 and mDTP3, including half-life in plasma ($T_{1/2}$), steady state (Vss) and terminal (Vβ) Volumes of distribution, and total clearance (tot CL), area under the plasma concentration versus time curve (AUC), and concentration at time point 0 ($C_0$). Values were calculated from the data of plasma concentration versus time curves based on the non-compartmental and compartimental methods of analysis (Groulx A. 2006 ScianNew 9: 1-5 and DiStefano 3rd 1982 Am J Physiol Regul Integr Comp Physiol 243: 1-6) (data not shown). Each parameter shown represents the average of experimental values obtained from three different pools of male CD1 mice following a single intravenous (i.v.) injection of the compounds at a dose of 10 mg per kg of body weight. Three male CD1 mice (25-30 gr of body weight) were dosed via i.v. administration of either Z-DTP2 or mDTP3. Blood samples were collected at 7 time points as shown (i.e. at 0.08, 0.25, 0.5, 1, 2, 4 and 8 hrs after injection) and the plasma was analysed by liquid chromatography mass spectrometry (LC-MS) to determinate the blood concentrations of the two compounds at each time point. The plots of the plasma concentration versus time profile were extrapolated for both Z-DTP2 and mDTP3. The results show that Z-DTP2 and mDTP3 both follow a multiphasic disposition after intravenous injection (data not shown). Indeed, the concentration-versus-time curves of the intravenously administered compounds display a distinct bio-exponential profile with a steep initial distribution phase and a long terminal $T_{1/2}$ (data not shown).

The main pharmacokinetical parameters extrapolated from the data of plasma concentration-time curves (i.e. $C_0$, AUC to last, T½, Vβ, Vss, and CL) are crucial for calculating the dosing levels and regiment of administration, required to achieve the desired systemic steady state concentrations of a drug (i.e. the therapeutic systemic concentrations). As it can be seen in Table VIII, Z-DTP2 and mDTP3 exhibit half-lives in vivo of approximately 2 hrs and of approximately 1 hr and 20 min, respectively.

Interestingly, Z-DTP2 and mDTP3 both show an initial distributive half-life of approximately 5 min, which could suggest rapid tissue/cellular uptake, but alternatively could suggest binding to plasma proteins. Most importantly, both compounds exhibit very slow elimination from the tissues, which is reflected by a terminal half-life of approximately 8 hrs (Table VIII and data not shown) (http://www.pharsight.com/main.php and http://www.meds.com/leukemia/idamycin/adriamycin.html and Kupperman et al 2010 Cancer Res 70 1970-1980). The data also show that Z-DTP2 and mDTP3 both follow a general linear pharmacokinetic system (Berezhkovskiy (2007) J Pharm Sci. 96, 1638-52), as indicated by the finding that their values of total volume distribution are higher then those of steady state volume distribution (i.e. Vβ>Vss).

Both the terminal and steady state volume distributions as well as the terminal half-lives of the two compounds synergistically contribute to establish the quantity of drug required in the body for a constant rate of infusion.

Importantly, Z-DTP2 and mDTP3 show values of total clearance in the range of 66 to 90 mL/min/kg and of 22 to 27 mL/min/kg, respectively, suggesting slow metabolic and biliary excretion rates for both compounds (Table VIII and data not shown).

Tables IX [A] and IX [B] show the predicted dosing for in vivo administration of Z-DTP2 and mDTP3, respectively, required to achieve systemic therapeutic concentrations of the two compounds. The values report the dosing expressed in mg/hr required to obtained the desired steady state plasma concentrations of 1, 5 or 10 µM for either Z-DTP (Table IX [A]) or mDTP3 (Table IX [B]). Significantly, despite having a comparable half-life as well as a comparable terminal half-life to Z-DTP2, mDTP3 exhibits a total clearance value that is 3 times lower then that of Z-DTP2 (Table VIII and data not shown). Of note, even a small difference in this crucial pharmacokinetical parameter may significantly affect the dosing size and regimen required to achieve the desired steady state plasma concentration of a compound, as seen with the difference in the dosings predicted for Z-DTP2 and mDTP3 (Tables IX [A] and IX [B], respectively). Indeed, Tables IX [A] and IX [B] (modelling analyses) show that in order to achieve a steady state plasma concentration of 1, 5, or 10 µM, the dosing required for mDTP3 is significantly lower than that required for Z-DTP2. Thus, based on these pharmacokinetic results and on the $IC_{50}$ values determined for the two compounds in multiple myeloma cell lines (see Table IV) in order to achieve a steady state plasma concentration of up to 10 µM it will be necessary to administer Z-DTP2 and mDTP3 via continuous i.v. infusion at a rate of 0.976 mg/hr and 0.218 mg/hr, respectively (Tables IX [A] and IX [B]).

Of note, Z-/mDTP synthesis, is concise and straightforward, hence cost-effective even for chronic use. Thus, even with low $T_{1/2}$, Z-/mDTP therapy by infusion will be acceptable in hospitalized patients already on chemotherapy. The compounds of the invention are also highly soluble and have high specificity and good safety profiles, so can be delivered at high doses, in low volumes to maximize therapeutic effects, as successfully exploited by existing peptide therapies.

Tables

TABLE I

| Amino acid sequence (single-letter code) | SEQ ID NO: | MW | % Inhibition of Gadd45β-MKK7 binding |
|---|---|---|---|
| Fmoc(βAla)$_2$-QX$_2$X$_3$X$_4$-NH$_2$ | 156 | — | 0 |
| Fmoc(βAla)$_2$-SX$_2$X$_3$X$_4$-NH$_2$ | 157 | — | 4 |
| Fmoc(βAla)$_2$-RX$_2$X$_3$X$_4$-NH$_2$ | 158 | — | 45 |
| Fmoc(βAla)$_2$-AX$_2$X$_3$X$_4$-NH$_2$ | 159 | — | 56 |
| Fmoc(βAla)$_2$-YX$_2$X$_3$X$_4$-NH$_2$ | 160 | — | 100 |
| Fmoc(βAla)$_2$-PX$_2$X$_3$X$_4$-NH$_2$ | 161 | — | 48 |
| Fmoc(βAla)$_2$-MX$_2$X$_3$X$_4$-NH$_2$ | 162 | — | 36 |
| Fmoc(βAla)$_2$-CX$_2$X$_3$X$_4$-NH$_2$ | 163 | — | 49 |
| Fmoc(βAla)$_2$-FX$_2$X$_3$X$_4$-NH$_2$ | 164 | — | 58 |
| Fmoc(βAla)$_2$-LX$_2$X$_3$X$_4$-NH$_2$ | 166 | — | 55 |
| Fmoc(βAla)$_2$-HX$_2$X$_3$X$_4$-NH$_2$ | 167 | — | 56 |
| Fmoc(βAla)$_2$-DX$_2$X$_3$X$_4$-NH$_2$ | 168 | — | 55 |
| Fmoc(βAla)$_2$-YDHQ-NH$_2$ | 165 | — | 26 |
| Fmoc(βAla)$_2$-YSX$_3$X$_4$-NH$_2$ | 169 | — | 16 |
| Fmoc(βAla)$_2$-YRX$_3$X$_4$-NH$_2$ | 170 | — | 28 |
| Fmoc(βAla)$_2$-YAX$_3$X$_4$-NH$_2$ | 171 | — | 20 |
| Fmoc(βAla)$_2$-YYX$_3$X$_4$-NH$_2$ | 172 | — | 52 |
| Fmoc(βAla)$_2$-YPX$_3$X$_4$-NH$_2$ | 173 | — | 42 |
| Fmoc(βAla)$_2$-YMX$_3$X$_4$-NH$_2$ | 174 | — | 54 |
| Fmoc(βAla)$_2$-YCX$_3$X$_4$-NH$_2$ | 175 | — | 27 |
| Fmoc(βAla)$_2$-YFX$_3$X$_4$-NH$_2$ | 176 | — | 39 |
| Fmoc(βAla)$_2$-YLX$_3$X$_4$-NH$_2$ | 177 | — | 52 |
| Fmoc(βAla)$_2$-YHX$_3$X$_4$-NH$_2$ | 178 | — | 53 |
| Fmoc(βAla)$_2$-YDX$_3$X$_4$-NH$_2$ | 179 | — | 96 |
| Fmoc(βAla)$_2$-YDQX$_4$-NH$_2$ | 180 | — | 19 |
| Fmoc(βAla)$_2$-YDSX$_4$-NH$_2$ | 181 | — | 11 |
| Fmoc(βAla)$_2$-YDRX$_4$-NH$_2$ | 182 | — | 93 |
| Fmoc(βAla)$_2$-YDAX$_4$-NH$_2$ | 183 | — | 0 |
| Fmoc(βAla)$_2$-YDYX$_4$-NH$_2$ | 184 | — | 25 |
| Fmoc(βAla)$_2$-YDPX$_4$-NH$_2$ | 185 | — | 25 |
| Fmoc(βAla)$_2$-YDMX$_4$-NH$_2$ | 186 | — | 13 |
| Fmoc(βAla)$_2$-YDCX$_4$-NH$_2$ | 187 | — | 6 |
| Fmoc(βAla)$_2$-YDFX$_4$-NH$_2$ | 188 | — | 37 |
| Fmoc(βAla)$_2$-YDLX$_4$-NH$_2$ | 189 | — | 30 |
| Fmoc(βAla)$_2$-YDHX$_4$-NH$_2$ | 190 | — | 99 |
| Fmoc(βAla)$_2$-YDDX$_4$-NH$_2$ | 191 | — | 37 |
| Fmoc(βAla)$_2$-YDHQ-NH$_2$ | 192 | 925.94 | 0 |
| Fmoc(βAla)$_2$-YDHS-NH$_2$ | 193 | 884.88 | 0 |
| Fmoc(βAla)$_2$-YDHR-NH$_2$ | 194 | 953.99 | 2 |
| Fmoc(βAla)$_2$-YDHA-NH$_2$ | 195 | 868.89 | 15 |
| Fmoc(βAla)$_2$-YDHY-NH$_2$ | 196 | 960.98 | 63 |
| Fmoc(βAla)$_2$-YDHP-NH$_2$ | 197 | 894.92 | 16 |
| Fmoc(βAla)$_2$-YDHM-NH$_2$ | 198 | 928.99 | 14 |
| Fmoc(βAla)$_2$-YDHC-NH$_2$ | 199 | 900.95 | 44 |
| Fmoc(βAla)$_2$-YDHF-NH$_2$ (Fmoc-LTP1) | 200 | 944.98 | 99 |
| Fmoc(βAla)$_2$-YDHL-NH$_2$ | 201 | 910.96 | 33 |
| Fmoc(βAla)$_2$-YDHH-NH$_2$ | 202 | 934.94 | 40 |
| Fmoc(βAla)$_2$-YDHD-NH$_2$ | 203 | 912.89 | 0 |

TABLE II

Modified pure peptides

| Amino acid sequence (single-letter code) | SEQ ID NO: | MW | % Inhibition of Gadd45β-MKK7 binding |
|---|---|---|---|
| Ac-YDHF-NH$_2$ (Ac-LTP1) | 61 | 621 | 94 |
| Ac-YEHF-NH$_2$ | 41 | 636 | 52 |
| Ac-WDHF-NH$_2$ | 85 | 645 | 28 |
| Ac-WEHF-NH$_2$ | 43 | 659 | 36 |
| Ac-YDRF-NH$_2$ | 42 | 640 | 45 |
| Ac-YDKF-NH$_2$ | 208 | 612 | 35 |
| Ac-YEKF-NH$_2$ | 40 | 626 | 64 |
| Ac-YERF-NH$_2$ (Ac-LTP2) | 27 | 654 | 93 |
| Ac-WEKF-NH$_2$ | 44 | 649 | 65 |
| Ac-WERF-NH$_2$ | 86 | 678 | 29 |
| Ac-WDKF-NH$_2$ | 46 | 659 | 26 |
| Ac-WDRF-NH$_2$ | 87 | 663 | 46 |
| Ac-YDHW-NH$_2$ | 88 | 661 | 58 |
| Ac-YEHW-NH$_2$ | 90 | 675 | 64 |
| Ac-WDHW-NH$_2$ | 91 | 683.7 | 50 |
| Ac-WEHW-NH$_2$ | 92 | 698 | 75 |
| Ac-YDRW-NH$_2$ | 93 | 679 | 43 |
| Ac-YDKW-NH$_2$ | 94 | 622 | 23 |
| Ac-YEKW-NH$_2$ | 95 | 666 | 27 |
| Ac-YERW-NH$_2$ | 96 | 694 | 59 |
| Ac-WEKW-NH$_2$ | 97 | 689 | 65 |
| Ac-WERW-NH$_2$ | 98 | 717 | 69 |
| Ac-WDKW-NH$_2$ | 99 | 674 | 69 |
| Ac-WDRW-NH$_2$ | 100 | 702 | 93 |
| Ac-YDHQ-NH$_2$ | 101 | 602 | 99 |

TABLE III

Modified peptides

| Amino acid sequence (single-letter code) | SEQ ID NO: | MW | % Inhibition of Gadd45β-MKK7 binding |
|---|---|---|---|
| Ac-YEHF-NH$_2$ | 41 | 636 | 23 |
| Ac-YDRF-NH$_2$ | 42 | 642 | 19 |
| Ac-AERF-NH$_2$ | 102 | 563 | 7 |
| Ac-YARF-NH$_2$ | 103 | 597 | 17 |
| Ac-YEAF-NH$_2$ | 104 | 570 | 13 |

TABLE III-continued

Modified peptides

| Amino acid sequence (single-letter code) | SEQ ID NO: | MW | % Inhibition of Gadd45β-MKK7 binding |
|---|---|---|---|
| Ac-YERA-NH$_2$ | 105 | 579 | 28 |
| Ac-PERF-NH$_2$ | 106 | 589 | 24 |
| Ac-YPRF-NH2 | 108 | 623 | 13 |
| Ac-YEPF-NH$_2$ | 107 | 596 | 13 |
| Ac-YERP-NH$_2$ | 109 | 605 | 0 |
| Z-YERF-NH$_2$ (Z-LTP2) | 60 | 747 | 78 |
| Z-YDHF-NH$_2$ (Z-LTP1) | 61 | 714 | 84 |
| Z-YDHQ-NH$_2$ | 101 | 695 | 13 |
| Z-YD(OMe)HF-NH$_2$ | 62 | 729 | 84 |
| Z-YD(OMe)HQ-NH$_2$ | 111 | 710 | 3 |
| 2Cl-Z-YERF-NH$_2$ | 112 | 783 | 38 |
| 2Cl-Z-YDHF-NH$_2$ | 113 | 749 | 38 |
| 2Cl-Z-YDHQ-NH$_2$ | 114 | 730 | 40 |
| Myr-YERF-NH$_2$ | 70 | 823 | 37 |
| Myr-YDHF-NH$_2$ | 71 | 790 | 26 |
| Myr-YDHQ-NH$_2$ | | 771 | 28 |
| Benzoic acid-YERF-NH$_2$ | 112 | 718 | 24 |
| Benzoic acid-YDHF-NH$_2$ | | 684 | 0 |
| Benzoic acid-YDHQ-NH$_2$ | 110 | 665 | 1 |
| 3-OH—4MeO-Benzoid acid-YERF-NH$_2$ | 63 | 763 | 86 |
| 3-OH—4MeO-Benzoid acid-YDHF-NH$_2$ | 64 | 732 | 81 |
| 3-OH—4MeO-Benzoid acid-YDHQ-NH$_2$ | 115 | 713 | 7 |
| Fmoc-YERF-NH$_2$ | 66 | 835 | 60 |
| Fmoc-YDHF-NH$_2$ | 69 | 802 | 58 |
| Fmoc-YDFQ-NH$_2$ | 116 | 783 | 19 |
| Ac-YERFLys(Z)-NH$_2$ | 204 | 917 | 6 |
| Ac-YDHFLys(Z)-NH$_2$ | 205 | 884 | 8 |
| Ac-YDHQLys(Z)-NH$_2$ | 206 | 865 | 2 |

TABLE IV

| | IC$_{50}$s of Z-DTP1 | | | IC$_{50}$s of Z-DTP2 | | |
|---|---|---|---|---|---|---|
| MM cell lines | Day 1 | Day 3 | Day 6 | Day 1 | Day 3 | Day 6 |
| KMS12 | 6.0 µM | 537 nM | 316 nM | 1.3 µM | 144 nM | 67 nm |
| KMS11 | 4.26 µM | 51.3 nM | 10.1 nM | 2.88 µM | 25.7 nM | 10 nM |
| ARH-77 | >10 µM | 950 nM | 2.2 µM | >10 µM | 218 nM | 1.2 µM |
| NCI | 5.25 µM | 4.07 µM | 776 nM | 5.25 µM | 2.35 µM | 501 nM |
| U266 | 6.3 µM | 81.3 nM | 40.7 nM | 6.02 µM | 67.7 nM | 40.7 nM |
| JJN3 | 10 µM | 1.1 µM | 350 nM | 10 µM | 1 µM | 223 nM |
| KMS18 | 7.9 µM | 6.2 µM | 3.7 µM | 9.8 µM | 3.4 µM | 3.0 µM |
| KMS27 | >10 µM | >10 µM | 4.9 µM | >10 µM | 1.6 µM | 4.5 µM |

TABLE V

| | Amino acid sequence (three-letter code) | IC$_{50}$ ELISA | IC$_{50}$ [H$^3$] thymidine incorporation assay in KMS12 | | | IC$_{50}$ [H$^3$] thymidine incorporation assay in KMS11 | | |
|---|---|---|---|---|---|---|---|---|
| | | | Day 1 | Day 3 | Day 6 | Day 1 | Day 3 | Day 6 |
| 1 | Z-Tyr-Asp-His-Phe-NH$_2$ (Z-DTP1) SEQ ID NO: 61 | 220 pM | 6.0 µM | 537 nM | 316 nM | 4.26 µM | 51.3 nM | 10.1 nM |
| 2 | X$_1$-Asp-His-Y$_1$ | >1 nM | >10 µM | >10 µM | >10 µM | >10 µM | >10 µM | >10 µM |
| 3 | X$_1$-Asp-His-Y$_2$ | >1 nM | >10 µM | >10 µM | >10 µM | >10 µM | >10 µM | >10 µM |
| 4 | X$_1$-Asp-His-Y$_3$ | 500 pM | >10 µM | >10 µM | >10 µM | >10 µM | >10 µM | >10 µM |
| 5 | X$_2$-Asp-His-Y$_1$ | 316 pM | >10 µM | >10 µM | >10 µM | >10 µM | >10 µM | >10 µM |
| 6 | X$_2$-Asp-His-Y$_2$ | 250 pM | >10 µM | >10 µM | >10 µM | >10 µM | >10 µM | >10 µM |
| 7 | X$_2$-Asp-His-Y$_3$ (mDTP4) | 100 pM | 8.5 µM | 380 nM | 199 nM | 2.5 µM | 1.17 µM | 549 nM |
| 8 | Z-Tyr-Asp-Phe-NH$_2$ | 162 pM | — | — | — | >10 µM | >10 µM | >10 µM |
| 9 | Z-Tyr-Glu-Arg-Phe-NH$_2$ (Z-DTP2) SEQ ID NO: 60 | 190 pM | 1.3 µM | 141 nM | 66 nM | 2.9 µM | 25.7 nM | 10 nM |
| 10 | X$_1$-Glu-Arg-Y$_1$ | 500 pM | — | — | — | >10 µM | >10 µM | >10 µM |
| 11 | X$_1$-Glu-Arg-Y$_2$ | 500 pM | — | — | — | >10 µM | >10 µM | >10 µM |
| 12 | X$_1$-Glu-Arg-Y$_3$ | 301 pM | — | — | — | >10 µM | >10 µM | >10 µM |
| 13 | X$_2$-Glu-Arg-Y$_1$ | >1 nM | — | — | — | >10 µM | >10 µM | >10 µM |
| 14 | X$_2$-Glu-Arg-Y$_2$ | >1 nM | — | — | — | >10 µM | >10 µM | >10 µM |
| 15 | X$_2$-Glu-Arg-Y$_3$ (mDTP1) | 100 pM | 6.0 µM | 301 nM | 436 nM | 2.8 µM | 562 nM | 263 nM |
| 16 | Z-Tyr-Glu-Phe-NH$_2$ (mDTP2) | 158 pM | 6.5 µM | 3 µM | 288 nM | | | |
| 17 | Ac-Tyr-Arg-Phe-NH$_2$ (mDTP3) | 157 pM | 354 nM | 81 nM | 16 nM | 1 µM | 89 µM | 25 nM |
| 18 | Ac-Tyr-Tyr-Arg-Phe-NH$_2$ SEQ ID NO: 117 | >5 nM | — | — | — | — | — | — |
| 19 | Z-Tyr-Arg-Phe-NH$_2$ | 100 pM | 354 nM | 81 nM | 20 nM | — | — | — |
| 20 | Ac-Cha-Arg-Phe-NH$_2$ | >5 nM | — | — | — | — | — | — |
| 21 | Ac-Tyr-Arg-Cha | >5 nM | — | — | — | — | — | — |

TABLE V-continued

| Amino acid sequence (three-letter code) | IC$_{50}$ ELISA | IC$_{50}$ [H$^3$] thymidine incorporation assay in KMS12 Day 1 | Day 3 | Day 6 | IC$_{50}$ [H$^3$] thymidine incorporation assay in KMS11 Day 1 | Day 3 | Day 6 |
|---|---|---|---|---|---|---|---|
| 22 Z-Tyr-Tyr-Glu-Arg-Phe-NH$_2$ SEQ ID NO: 118 | >5 nM | — | — | — | — | — | — |
| 23 Ac-Tyr-Gln-Arg-Phe-NH$_2$ (Elisa) SEQ ID NO: 57 Z-Tyr-Gln-Arg-Phe-NH$_2$ ([H$^3$] assay) SEQ ID NO: 121 | 5 nM | — | — | — | >10 µM | >10 µM | >10 µM |
| 24 Ac-Tyr-Met-Arg-Phe-NH$_2$ (Elisa) SEQ ID NO: 59 Z-Tyr-Met-Arg-Phe-NH$_2$ ([H$^3$] assay) SEQ ID NO: 122 | >10 nM | — | — | — | >10 µM | >10 µM | >10 µM |
| 25 Ac-Tyr-Asn-Arg-Phe-NH$_2$ (Elisa) SEQ ID NO: 123 Z-Tyr-Asn-Arg-Phe-NH$_2$ ([H$^3$] assay) SEQ ID NO: 124 | 10 nM | — | — | — | >10 µM | >10 µM | >10 µM |
| 26 Ac-Tyr-Leu-Arg-Phe-NH$_2$ (Elisa) SEQ ID NO: 125 Z-Tyr-Leu-Arg-Phe-NH$_2$ ([H$^3$] assay) SEQ ID NO: 126 | 5 nM | — | — | — | >10 µM | >10 µM | >10 µM |
| 27 Ac-Tyr-Gln-Phe-NH$_2$ (Elisa) Z-Tyr-Gln-Phe-NH$_2$ ([H$^3$] assay) | >10 nM | — | — | — | >10 µM | >10 µM | >10 µM |
| 28 Ac-Tyr-Leu-Phe-NH$_2$ (Elisa) Z-Tyr-Leu-Phe-NH$_2$ ([H$^3$] assay) | 1.8 nM | — | — | — | >10 µM | >10 µM | >10 µM |
| 29 Ac-Tyr-Asn-Phe-NH$_2$ (Elisa) Z-Tyr-Asn-Phe-NH$_2$ ([H$^3$] assay) | 1.9 nM | — | — | — | >10 µM | >10 µM | >10 µM |
| 30 AC-Tyr-Met-Phe-NH$_2$ (Elisa) Z-Tyr-Met-Phe-NH$_2$ ([H$^3$] assay) | >10 nM | — | — | — | >10 µM | >10 µM | >10 µM |
| 31 Ac-Tyr-Gln-Phe-NH$_2$ (Elisa) ZTyr-Gln-Phe-NH$_2$ ([H$^3$] assay) | >10 nM | — | — | — | >10 µM | >10 µM | >10 µM |
| 32 Z-Tyr-Asp-His-Gln-NH$_2$ SEQ ID NO: 127 | >10 nM | — | — | — | — | — | — |
| 33 Z-Tyr-Tyr-Asp-His Gln-NH$_2$ SEQ ID NO: 128 | >10 nM | — | — | — | — | — | — |

TABLE VI

| Compounds | | |
|---|---|---|
| ID | Amino acid sequence (single-letter code) | IC$_{50}$ Elisa |
| A1 | Ac-YF-NH$_2$ | >100 nM |
| A1 bis | Ac-FF-NH$_2$ | >100 nM |
| A3 | Ac-YbetaAla-F-NH$_2$ | >100 nM |
| A6 | Ac-Y-eCaprioic-F-NH$_2$ | >100 nM |
| A7 | Ac-YY-NH$_2$ | >100 nM |
| A8 | Ac-FY-NH$_2$ | >100 nM |
| A9 | Ac-FRF-NH$_2$ | >100 nM |
| B2 | Ac-YKF-NH$_2$ | 0.851 nM |
| B13 | Ac-YPF-NH$_2$ | 0.645 nM |
| B16 | Ac-YHF-NH$_2$ | 0.690 nM |
| B16 bis | H-YHF-NH$_2$ | 0.645 nM |
| O1 | Ac-FRY-NH$_2$ | >100 nM |
| O3 | Ac-YRY-NH$_2$ | 0.758 nM |
| O5 | H-FHY-NH$_2$ | >100 nM |
| O6 | H-YRY-NH$_2$ | 0.750 nM |
| O5 bis | Ac-FHY-NH$_2$ | >100 nM |
| O7 | H-FRF-NH$_2$ | >100 nM |
| O8 | H-FRY-NH$_2$ | >100 nM |

TABLE VII

RNA interference

| Gene | Targeting Sequences | Forward | Reverse |
|---|---|---|---|
| ns-1 | CAGTCGCGTTTGCGACTGG SEQ ID NO: 129 | TCAGTCGCGTTTGCGACTGGTTCAAGAGACCAGTCGCAAACGCGACTGTTTTTTC SEQ ID NO: 130 | TCGAGAAAAAACAGTCGCGTTTGCGACTGGTCTCTTGAACCAGTCGCAAACGCGACTGA SEQ ID NO: 131 |
| ns-2 | AAGTATGGTGAGCACGCGT SEQ ID NO: 132 | TAAGTATGGTGAGCACGCGTTTCAAGAGAACGCGTGCTCACCATACTTTTTTTTC SEQ ID NO: 133 | TCGAGAAAAAAAGTATGGTGAGCACGCGTTCTCTTGAAACGCGTGCTCACCATACTTA SEQ ID NO: 134 |
| Gadd45β-1 | CCAAGTTGATGAATGTGGA SEQ ID NO: 135 | TCCACTGTCTTCCCTTCCTATTCAAGAGATAGGAAGGGAAGACAGTGGTTTTTC SEQ ID NO: 136 | GAAAAAACCAAGTTGATGAATGTGGATCTCTTGAATCCACATTCATCAACTTGGA SEQ ID NO: 137 |
| Gadd45β-2 | CAGAAGATGCAGACGGTGA SEQ ID NO: 138 | TCAGAAGATGCAGACGGTGATTCAAGAGATCACCGTCTGCATCTTCTGTTTTTTC SEQ ID NO: 139 | TCGAGAAAAAACAGAAGATGCAGACGGTGATCTCTTGAATCACCGTCTGCATCTTCTGA SEQ ID NO: 140 |
| Gadd45β-3 | CAAATCCACTTCACGCTCA SEQ ID NO: 141 | TCAAATCCACTTCACGCTCATTCAAGAGATGAGCGTGAAGTGGATTTGTTTTTTC SEQ ID NO: 142 | TCGAGAAAAAACAAATCCACTTCACGCTCATCTCTTGAATGAGCGTGAAGTGGATTTGA SEQ ID NO: 143 |
| MKK7-1 | GATCACAGGAAGAGACCAA SEQ ID NO: 144 | TGATCACAGGAAGAGACCAATTCAAGAGATTGGTCTCTTCCTGTGATCTCTTTTTTC SEQ ID NO: 145 | TCGAGAAAAAAGATCACAGGAAGAGACCAATCTCTTGAATTGGTCTCTTCCTGTGATCA SEQ ID NO: 146 |
| MKK7-2 | GCATTGAGATTGACCAGAA SEQ ID NO: 147 | TGCATTGAGATTGACCAGAATTCAAGAGATTCTGGTCAATCTCAATGCTTTTTTC SEQ ID NO: 148 | TCGAGAAAAAAGCATTGAGATTGACCAGAATCTCTTGAATTCTGGTCAATCTCAATGCA SEQ ID NO: 149 | qRT-PCR Primers

| Gene | Forward | Reverse |
|---|---|---|
| hGadd45β | CTCCTTAATGTCACGCACGAT SEQ ID NO: 150 | GTCCGTGTGAGGGTTCTGTA SEQ ID NO: 151 |
| hATCB | CATGTACGTTGCTATCCAGGC SEQ ID NO: 152 | CTCCTTAATGTCACGCACGAT SEQ ID NO: 153 |

TABLE VIII

| Pharmacokinetic parameters | Z-DTP2 | mDTP3 |
|---|---|---|
| $C_0$ (μg/mL) | 8.738 | 29.065 |
| $T_{max}$ (hr) | NA | NA |
| AUC to Last (g-hr/mL) | 2.085 | 6.432 |
| $T_{1/2}$ (hr) | 2.085 | 1.262 |
| Vβ (ml) | 393.600 | 75.625 |
| Total CL (mL/hr) | 130.762 | 44.181 |
| Total CL (mL/min/kg) | 78.114 | 27.131 |
| Last Time point | 8.0 | 6.667 |
| MRTINF (hr) | 0.973 | 0.281 |
| Vss (mL) | 125.898 | 12.609 |

TABLE IX [A]

| | Z-DTP2 | | |
|---|---|---|---|
| | Dose level | | |
| | 1 | 2 | 3 |
| Desidered steady state plasma level (CPss) (μM) | 1 | 5 | 10 |
| Desidered steady state plasma level (CPss) (mg/L) | 0.746 | 3.73 | 7.46 |
| KO (kel × V × Cp) mg/hr | 0.0976 | 0.4879 | 0.9758 |

Note:
kel/$t_{1/2}$ = 0.693/2.08 = 0.332327 hr$^{-1}$

TABLE IX [B]

| | mDTP3 | | |
|---|---|---|---|
| | Dose level | | |
| | 1 | 2 | 3 |
| Desidered steady state plasma level (CPss) (µM) | 1 | 5 | 10 |

TABLE IX [B]-continued

| | mDTP3 | | |
|---|---|---|---|
| | Dose level | | |
| | 1 | 2 | 3 |
| Desidered steady state plasma level (CPss) (mg/L) | 0.525 | 2.625 | 5.25 |
| KO (kel × V × Cp) mg/hr | 0.022 | 0.109 | 0.218 |

Note:
$kel/t_{1/2} = 0.693/2.08 = 0.332327 \text{ hr}^{-1}$

The invention claimed is:

1. A compound according to Formula I

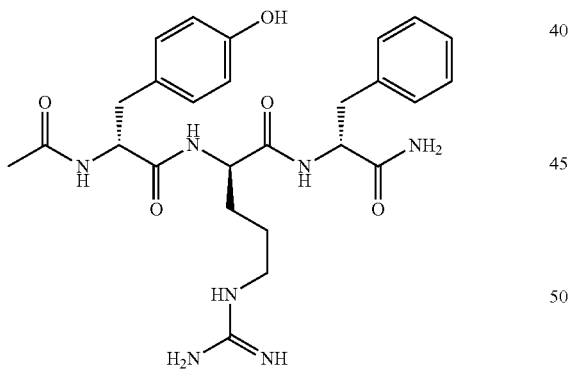

Formula I or a pharmaceutically acceptable salt thereof.

2. A pharmaceutical composition comprising the compound of claim 1 and a pharmaceutically acceptable excipient.

* * * * *

UNITED STATES PATENT AND TRADEMARK OFFICE
CERTIFICATE OF CORRECTION

| | |
|---|---|
| PATENT NO. | : 9,518,083 B2 |
| APPLICATION NO. | : 14/618613 |
| DATED | : December 13, 2016 |
| INVENTOR(S) | : Guido Franzoso et al. |

It is certified that error appears in the above-identified patent and that said Letters Patent is hereby corrected as shown below:

In the Specification

On Column 1, Line 3, after the "Title", insert the following:
--STATEMENT REGARDING FEDERALLY SPONSORED RESEARCH OR DEVELOPMENT
"This invention was made with government support under R01 CA098583, and R01 CA084040 awarded by the National Institutes of Health. The Government has certain rights in the invention".--

Signed and Sealed this
Eighth Day of April, 2025

Coke Morgan Stewart
*Acting Director of the United States Patent and Trademark Office*